US009102719B2

(12) United States Patent
Combs et al.

(10) Patent No.: US 9,102,719 B2
(45) Date of Patent: Aug. 11, 2015

(54) SOGA POLYNUCLEOTIDES AND POLYPEPTIDES AND USES THEREOF

(71) Applicant: University of North Carolina at Chapel Hill, Chapel Hill, NC (US)

(72) Inventors: Terry P. Combs, Chapel Hill, NC (US); James A. Swenberg, Pittsboro, NC (US)

(73) Assignee: The University of North Carolina at Chapel Hill, Chapel Hill, NC (US)

(*) Notice: Subject to any disclaimer, the term of this patent is extended or adjusted under 35 U.S.C. 154(b) by 0 days.

(21) Appl. No.: 14/019,925

(22) Filed: Sep. 6, 2013

(65) Prior Publication Data

US 2014/0134174 A1 May 15, 2014

Related U.S. Application Data

(62) Division of application No. 13/376,239, filed as application No. PCT/US2010/037472 on Jun. 4, 2010, now Pat. No. 8,530,174.

(60) Provisional application No. 61/184,392, filed on Jun. 5, 2009.

(51) Int. Cl.

| | |
|---|---|
| ***C07K 16/18*** | (2006.01) |
| ***G01N 33/66*** | (2006.01) |
| ***C07K 14/47*** | (2006.01) |
| ***C07K 14/575*** | (2006.01) |
| *A61K 38/00* | (2006.01) |

(52) U.S. Cl.

CPC ............ *C07K 16/18* (2013.01); *C07K 14/4713* (2013.01); *C07K 14/575* (2013.01); *G01N 33/66* (2013.01); *A61K 38/00* (2013.01)

(58) Field of Classification Search

None

See application file for complete search history.

(56) References Cited

U.S. PATENT DOCUMENTS

| | | | |
|---|---|---|---|
| 6,982,362 | B1 | 1/2006 | Inoue et al. |
| 7,442,513 | B2 | 10/2008 | Worley |
| 2005/0204410 | A1 | 9/2005 | Karow et al. |

FOREIGN PATENT DOCUMENTS

| | | | |
|---|---|---|---|
| WO | WO 2008/016356 | A2 | 2/2008 |
| WO | WO 2008/021290 | A2 | 2/2008 |
| WO | WO 2008/093464 | A1 | 8/2008 |

OTHER PUBLICATIONS

"Human brain cerrebellum-specific protein SEO:5967", retrieved from EBI accession No. GSP:AUN04626, Feb. 3, 2011.
"Novel human cDNA sequence #2466", retrieved from EBI accession No. GSN:ADQ67493, Oct. 7, 2004.
"Psoriasis associated human gene SEQ ID No. 5247", retrieved from EBI accession No. GSN:ARY64380, Aug. 21, 2008.
"Psoriasis associated human protein SEQ ID No. 5248", retrieved from EBI accession No. GSP:ARY64381, Aug. 21, 2008.
"RecName: Full=Uncharacterized protein C20orf117", retrieved from EBI accession No. UNIPROT:094964, May 26, 2009.
Brajenovic et al. (2004), J. Biol. Chem. 279 (13), 12804-12811.
European Search Report Corresponding to European Application No. 10 78 4183.5; Dated: Nov. 28, 2012; 7 Pages.
Genbank Accession No. NP542194.1, hypothetical protein LOC140710 isoform 1 [*Homo sapiens*] (2 pages) May 7, 2006.
International Application No. PCT/US2010/037472, filed Jun. 4, 2010, international preliminary report on patentability mailed Dec. 15, 2011.
European Office Action Corresponding to European Application No. 10 78 4183.5; Dated: Mar. 11, 2015; 5 Pages.

*Primary Examiner* — Doug Schultz

(74) *Attorney, Agent, or Firm* — Myers Bigel Sibley & Sajovec, P.A.

(57) ABSTRACT

The present invention relates to the identification of polynucleotides and polypeptides involved in insulin and adiponectin signaling and regulation of glucose production. The invention further relates to the use of the identified polynucleotides and polypeptides, and inhibitors of the polynucleotides and polypeptides, in the regulation of glucose production and the monitoring and treatment of metabolic disorders such as diabetes.

14 Claims, 19 Drawing Sheets

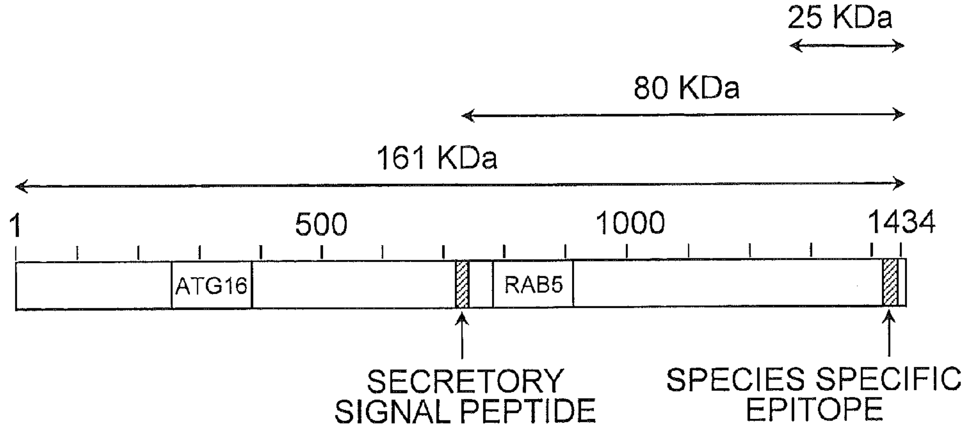

FIG. 10A

```
   1 MLDCGPGGLVRELEELRSENDYLKDEIEELRAEMLEMRDVYMEEDVYQLQYRLR
  55 KAERRSLRAAQTGQVDGELIRGLEQDVKVSKDISMRLHKELEVVEKKRMRLEEE
 109 NEGLRQRLIETELAKQVLQTELDRPREHSLKKRGTRSLGKTDKKPTAQEDSADL
 163 KCQLHFAKEESALMCKKLTKLAKENDSMKEELLKYRSLYGDLDAALSAEELADA
 217 PHSRETELKVHLKLVEEEANLLSRRIVELEVENRGLRAEMDDMKDHGGGGGPEA
 271 RLAFSSLGGECGESLAELRRHLQFVEEEAELLRRSSAELEDQNKLLLNELAKYR
 325 SEHELDVTLSEDSCSVLSEPSQEELAAAKLQIGELSGKVKKLQYENRVLLSNLQ
 379 RCDLASCQSTRPMLETDAEAGDSAQCVPAPLGETLEPHAARLCRAREAEALPGL
 433 REQAALVSKAIDVLVADANGFSVGLRLCLDNECADLRLHEAPDNSEGPRDAKLI
 487 HAILVRLSVLQQELNAFTRKADVALGSSGKEQPEPFPALPALGSQGPAKEIMLS
 541 KDLGSDFQPPDFRDLLEWEPRIREAFRTGDLESKPDPSRNFRPYRAEDNDSYAS
 595 EIKDLQLVLAEAHDSLRGLQEQLSQERQLRKEEADSFNQKMVQLKEDQQRALLR
 649 REFELQSLSLQRRLEQKFWSQEKNILVQESQQFKHNFLLLFMKLRWFLKRWRQG
 703 KVLPSEEDDFLEVNSMKELYLLMEEEEMNAQHSDNKACTGESWTQNTPNECIKT
 757 LADMKVTLKELCWLLQDERRGLTELQQQFAKAKATWETERAELKGHASQMELKA
 811 GKGASERPGPDWKAALQREREEQQHLLAESYSAVMELTRQLQLSERHWSQEKLQ
 865 LVERLQGEKQQVEQQVKELQNRLSQLQKAAEPWVLKHSDMEKQDNSWKEARSEK
 919 THDKEGVSEAELGGTGLKRTKSVSSMSEFESLLDCSPYLAGGDARNKKLPNGPA
 973 FAFVSTEPVEPEKDAKEKAGLSTRDCSHIGSLACQEPAGRQMQRSYTAPDKTGI
1027 RVYYSPPVARRLGVPVVHDKEGKILIEPGFLFTTAKPKESAEADGLAESSYSRW
1081 LCNFSRQRLDGGSGASTSGSGPAFPALHDFEMSGNMSDDMKEITNCVRQAMRSG
1135 SLERKVKNTSSQTVGVATVGTQTIRTVSVGLQTDPPRSSLHSKSWSPRSSSLVS
1189 VRSKQISSSLDKVHSRIERPCCSPKYGSPKLQRRSVSKLDSTKDRSLWNLHQGK
1243 QNGSAWARSTTTRDSPVLRNINDGLSSLFSVVEHSGSTESVWKLGMSEARTKPE
1297 PPKYGIVQEFFRNVCGRAPSPTTAAGEESCKKPEPLSPASYHQPEGVSRILNKK
1351 AAKAGGSEEVRPTMLSQVGKDGILRDGDGSLILPSEDAVCDCSAQSLASCFIRP
1405 SRNTIRHSPSKCRLHPSESGWGGEERAAPQ
```

FIG. 10B

SOGA POLYNUCLEOTIDES AND POLYPEPTIDES AND USES THEREOF

RELATED APPLICATIONS

This application is a continuation of U.S. application Ser. No. 13/376,239; filed Dec. 5, 2011, now U.S. Pat. No. 8,530,174, which is a 35 U.S.C. §371 national phase application of PCT Application PCT/US2010/037472, filed Jun. 4, 2010, which claims the benefit under 35 U.S.C. §119(e) of U.S. Provisional Patent Application Ser. No. 61/184,392, filed Jun. 5, 2009. The entire contents of each of these applications is incorporated herein by reference.

STATEMENT OF FEDERAL SUPPORT

This invention was made, in part, with government support under grant numbers DK075573, DK056350, and ES010126 from the National Institutes of Health. The United States government has certain rights to this invention.

FIELD OF THE INVENTION

The present invention relates to the identification of polynucleotides and polypeptides involved in insulin and adiponectin signaling and regulation of glucose production. The invention further relates to the use of the identified polynucleotides and polypeptides, and inhibitors of the polynucleotides and polypeptides, in the regulation of glucose production and the monitoring and treatment of metabolic disorders such as diabetes.

BACKGROUND OF THE INVENTION

Adipose tissue exerts a powerful effect on glucose metabolism by regulating the concentration of circulating adiponectin (Goldfine et al., *Lancet* 362:1431 (2003)). High adiponectin in the lean state is linked to elevated insulin sensitivity whereas low adiponectin in the obese state is linked to insulin resistance and diabetes (Arita et al., *Biochem. Biophys. Res. Commun.* 257:79 (1999); Hotta et al., *Artererioscler. Thromb. Vasc. Biol.* 20:1595 (2000); Maeda et al., *Diabetes* 50:2094 (2001); Weyer et al., *J. Clin. Endocrinol. Metab.* 2001, 86:1930 (2001)). Endogenous glucose production is elevated in diabetes (Wahren et al., *Annu. Rev. Nutr.* 27:329 (2007)). Studies in mice and liver cells show that adiponectin lowers glucose production by increasing the insulin sensitivity of the liver (Berg et al., *Nat. Med.* 7:947 (2001); Combs et al., *J. Clin. Invest.* 108:1875 (2001); Combs et al., *Endocrinology* 145:367 (2004)).

The signal transduction pathway of adiponectin is currently linked to (a) adiponectin receptors that bind to the full-length or the carboxy-terminal 'globular' fragment of adiponectin, (b) binding of the intracellular domains of adiponectin receptors 1 and 2 to the adaptor APPL1 and (c) the activation of AMPK, a signaling intermediate that reduces the gene expression of rate limiting enzymes for glucose production (Combs et al., *J. Clin. Invest.* 108:1875-(2001); Combs et al., *Endocrinology* 145:367 (2004); Tomas et al., *Proc. Natl. Acad. Sci. USA* 99:16309 (2002); Yamauchi et al., *Nat. Med.* et al., *J. Biol. Chem.* 281:2654 (2006); Andreelli et al., *Endocrinology* 147:2432 (2006); Mao et al., *Nat. Cell Biol.* 8:516 (2006); Brooks et al., *J. Biol. Chem.* 282:35069 (2007); Yoon et al., *Exp. Mol. Med.* 41:577 (2009); Wang et al., *J. Biol. Chem.* 282:7991 (2007)). However, the inhibition of glucose production by this pathway is not completely clear.

Glucose production depends on autophagy, a regulated mechanism of intracellular degradation that is inhibited by insulin (Amherdt et al., *J. Clin. Invest.* 54:188 (1974)). Autophagy provides the biochemical intermediates for glucose production through the hydrolysis of proteins, glycogen and triglycerides (Mortimore et al., *Annu. Rev. Nutr.* 7:539 (1987); Kotoulas et al., *Pathol. Res. Pract.* 202:631 (2006); Singh et al., *Nature* 458:1131 (2009)). Insulin inhibition of autophagy in isolated hepatocytes is linked to the activation of mTOR (Blommaart et al., *J. Biol. Chem.* 270:2320 (1995); Kanazawa et al., *J. Biol. Chem.* 279:8452 (2004)). Hence, reports that AMPK, an essential mediator of adiponectin action, inhibits mTOR and stimulates autophagy are perplexing (Shaw et al., *Cancer Cell* 6:91 (2004); Meley et al., *J. Biol. Chem.* 281:34870 (2006); Xu et al., *Cell Death Differ.* 14:1948 (2007); Liang et al., *Nat. Cell Biol.* 9:218-(2007); Meijer et al., *Autophagy* 3:238 (2007); Cheng et al., *J. Biol. Chem.* 279:15719 (2004); Hoyer-Hansen et al., *Mol. Cell.* 25:193 (2007)).

The present invention addresses previous shortcomings in the art by providing a novel polynucleotide and polypeptide that connects insulin, adiponectin, and glucose production and that can be used for diagnostic and therapeutic methods.

SUMMARY OF THE INVENTION

The present invention is based, in part, on the identification of a novel polypeptide named Suppressor of Glucose by Autophagy (SOGA), also known as Target of Adiponectin (TOA), and the role it plays in insulin and adiponectin signaling and glucose production. The invention is based further on the use of this polypeptide, polynucleotides encoding the polypeptide, and inhibitors thereof, in the regulation of glucose production and the monitoring and treatment of metabolic disorders related to glucose levels, such as diabetes.

Accordingly, as one aspect, the invention provides an isolated polynucleotide selected from the group consisting of:

(a) a polynucleotide comprising a nucleotide sequence at least 70% (e.g., 75%, 80%, 85%, 90%, 95%, 97%, 98%, 99%, 100%) identical to a nucleotide sequence selected from the group consisting of SEQ ID NOS:1 and 3 and encoding a functional SOGA polypeptide;

(b) a polynucleotide that hybridizes to a nucleotide sequence selected from the group consisting of SEQ ID NOS:1 and 3 under stringent hybridization conditions and encodes a functional SOGA polypeptide;

(c) a polynucleotide encoding a functional SOGA polypeptide comprising an amino acid sequence at least 70% (e.g., 75%, 80%, 85%, 90%, 95%, 97%, 98%, 99%, 100%) identical to an amino acid sequence selected from the group consisting of SEQ ID NOS:2 and 4; and (d) a functional fragment of any of (a) to (c).

The invention further relates to vectors and cells comprising the polynucleotides of the invention, and methods of recombinantly expressing the polypeptides of the invention.

Another aspect of the invention relates to isolated SOGA polypeptides or functional fragments thereof encoded by the isolated polynucleotides of the invention. Functional fragments include, without limitation, C-terminal fragments of about 80 kDa and about 25 kDa. In some embodiments, the polypeptide is part of a fusion protein.

A further aspect of the invention relates to agents that inhibit the expression and/or activity of SOGA polypeptides or polynucleotides, including antibodies, antisense oligonucleotides, ribozymes, siRNAs, and small molecules.

An additional aspect of the invention relates to pharmaceutical compositions comprising the polypeptides, polynucleotides, or inhibitory agents of the invention.

A further aspect of the invention relates to non-human animals genetically modified to express the polypeptide of the invention or to inhibit expression of the polypeptide of the invention.

Another aspect of the invention relates to methods of decreasing glucose production in a cell or decreasing autophagy in a cell, comprising contacting the cell with the polypeptides or polynucleotides of the invention.

A further aspect of the invention relates to methods of decreasing blood glucose levels in a subject or of increasing insulin sensitivity in a subject, comprising delivering to the subject the polypeptides or polynucleotides of the invention.

Another aspect of the invention relates to methods of increasing glucose production in a cell or increasing autophagy in a cell, comprising contacting the cell with an agent that decreases the expression and/or activity of the polypeptides or polynucleotides of the invention.

Another aspect of the invention relates to methods of increasing blood glucose levels in a subject or of decreasing insulin sensitivity in a subject, comprising delivering to the subject an agent that decreases the activity of the polypeptides or polynucleotides of the invention.

An additional aspect of the invention relates to a method of measuring the response of a subject to a treatment for diabetes, comprising determining the circulating level of the polypeptides of the invention in the subject after administration of the treatment and comparing it to the circulating level of the polypeptide in the subject before administration of the treatment.

Another aspect of the invention relates to a method of predicting the clinical outcome of a diabetes treatment in a subject, comprising determining the circulating level of the polypeptide of the invention in the subject after administration of the treatment and comparing it to the circulating level of the polypeptide in the subject before administration of the treatment.

Another aspect of the invention relates to a method of identifying an agent that binds to the polypeptides of the invention, comprising contacting the polypeptide or a functional fragment thereof with a test agent under conditions whereby binding between the polypeptide or a functional fragment thereof and the test agent can occur; and detecting binding between the polypeptide or a functional fragment thereof and the test agent.

An additional aspect of the invention relates to a method of identifying an agent that modulates the activity of polypeptides of the invention, comprising contacting the polypeptide or a functional fragment thereof with a test agent under conditions whereby modulation of the activity of the polypeptide or a functional fragment thereof can occur; and detecting modulation of the activity of the polypeptide or a functional fragment thereof upon contact with the test agent as compared to activity of the polypeptide or a functional fragment thereof in the absence of contact with the test agent.

A further aspect of the invention relates to a kit comprising a reagent for determining the expression and/or activity of the polypeptides and/or polynucleotide of the invention.

BRIEF DESCRIPTION OF THE DRAWINGS

FIGS. 10A-10B show the sequence (SEQ ID NO:2) and predicted functional domains of SOGA.

DETAILED DESCRIPTION OF THE INVENTION

Figure 1:
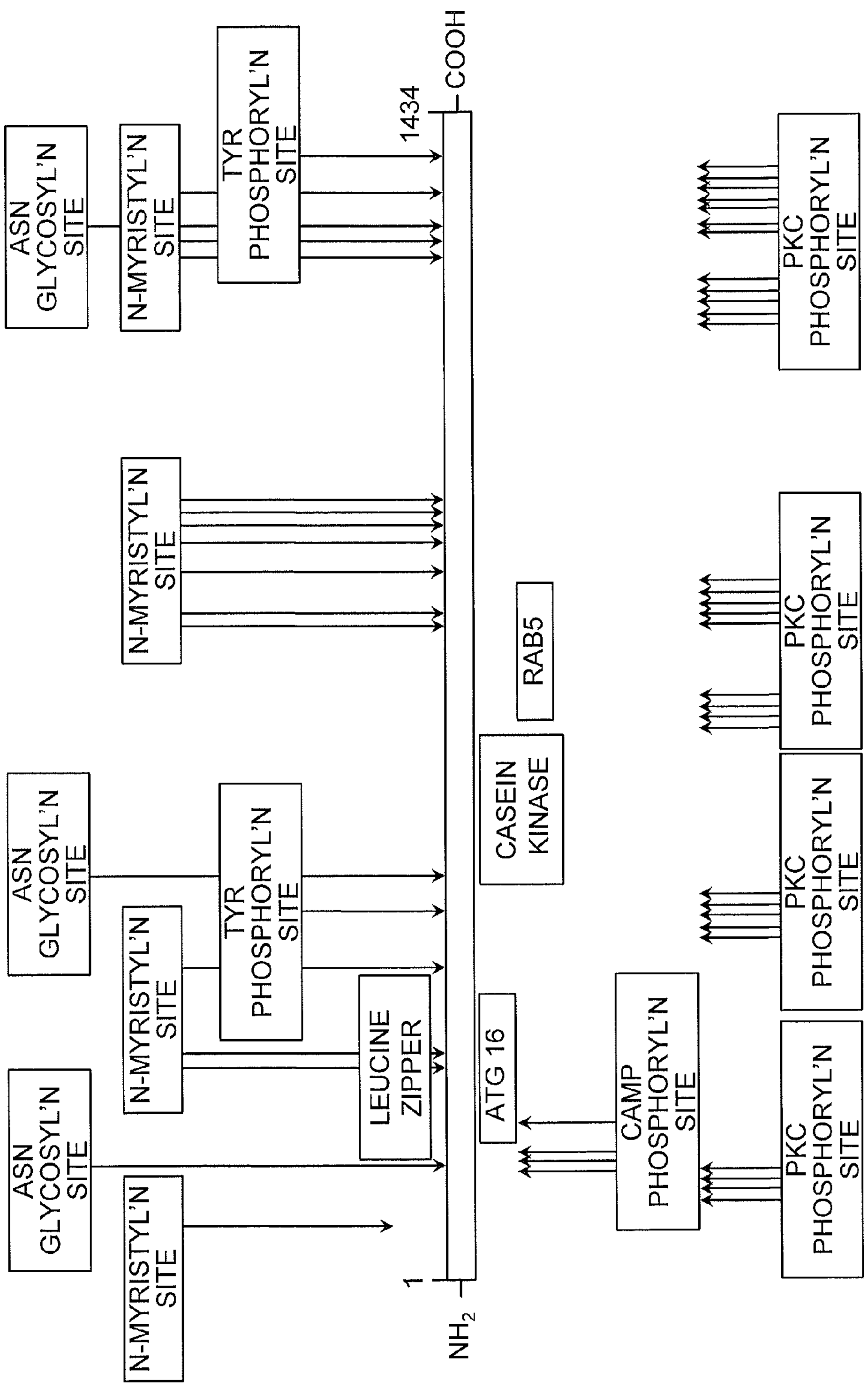
FIG. 1 shows an amino acid sequence analysis of SOGA for conserved functional domains.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. §1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. *Current Protocols in Molecular Biology* (Green Publishing Associates, Inc. and John Wiley & Sons, Inc., New York).

I. DEFINITIONS

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in the ability to inhibit glucose production of at least about 50% or more as compared to the activity of a polypeptide consisting of the recited sequence.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject (e.g., in the case of diabetes, reduction in glucose levels or increase in insulin sensitivity). Those skilled in the art will appreciate that the therapeutic effects need not be complete or curative, as long as some benefit is provided to the subject.

By the terms "treat," "treating," or "treatment of," it is intended that the severity of the subject's condition is reduced or at least partially improved or modified and that some alleviation, mitigation or decrease in at least one clinical symptom is achieved.

The term "control sample," as used herein, refers to a tissue or cell sample that is used to compare the level of expression and/or activity of a SOGA polypeptide to the level of expression and/or activity in a sample of interest. The control sample may be, for example, from a normal (i.e., non-diseased) portion of the same tissue or cell type in the subject, from a different tissue or cell type in the subject, from a matched individual, or may be a standard derived from the average of measurements taken from a population of subjects. In another embodiment, the control sample may be from the disease tissue of the subject, e.g., at the time of diagnosis, prior to treatment, or after a stage of treatment.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "isolated" can refer to a nucleic acid or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose. In certain embodiments, the polypeptide is at least about 50% pure, e.g., at least about 60%, 70%, 80%, 90%, 95%, 96%, 97%, 98%, or 99% or more pure.

An isolated cell refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

The term "fragment," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, 250, 300, 400, 500, or more consecutive nucleotides of a nucleic acid according to the invention. In some embodiments, such fragments can comprise, consist essentially of, and/or consist of oligonucleotides having a length of less than about 8, 10, 12, 15, 20, 25, 30, 35, 40, 45, 50, 75, 100, 150, 200, 250, 300, 400, or 500 consecutive nucleotides of a nucleic acid according to the invention.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, 300, 400, 500, or more consecutive amino acids of a polypeptide or amino acid sequence according to the invention. In some embodiments, such fragments can comprise, consist essentially of, and/or consist of peptides having a length of less than about 8, 10, 12, 15, 20, 25, 30, 35, 40, 45, 50, 75, 100, 150, 200, 250, 300, 400, or 500 consecutive nucleotides of a nucleic acid according to the invention.

The term "functional SOGA polypeptide," as applied herein, refers to a polypeptide that substantially retains at least one biological activity normally associated with the naturally occurring SOGA polypeptide (e.g., the ability to inhibit glucose production, protein binding, ligand or receptor binding). In particular embodiments, the "functional" polypeptide substantially retains all of the activities possessed by the naturally occurring polypeptide. By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as protein binding and suppression of glucose production can be measured using assays that are well known in the art and as described herein. In certain embodiments, the "activity" of a SOGA polypeptide is defined as the ability to inhibit glucose production in a population of isolated hepatocytes (either primary hepatocytes or a hepatocyte cell line).

The term "functional fragment," as applied to a polypeptide, refers to a fragment that substantially retains at least one biological activity of the full length polypeptide, e.g., the ability to inhibit glucose production. By "substantially retains" biological activity, it is meant that the fragment retains at least about 20%, 30%, 40%, 50%, 60%, 75%, 85%, 90%, 95%, 97%, 98%, 99%, or more, of the biological activity of the full length polypeptide (and can even have a higher level of activity than the full length polypeptide). A "non-functional" fragment is one that exhibits little or essentially no detectable biological activity normally associated with the polypeptide (e.g., at most, only an insignificant amount, e.g., less than about 10% or even 5%).

The term "functional fragment," as applied to a polynucleotide, refers to a polynucleotide that encodes a functional fragment of a polypeptide.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and adenovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311, filed Mar. 15, 1990).

In some embodiments, a polynucleotide of this invention can be delivered to a cell in vivo by lipofection. Synthetic cationic lipids designed to limit the difficulties and dangers encountered with liposome-mediated transfection can be used to prepare liposomes for in vivo transfection of a nucleotide sequence of this invention (Felgner et al., *Proc. Natl. Acad. Sci. USA* 84:7413 (1987); Mackey, et al., *Proc. Natl. Acad. Sci. U.S.A.* 85:8027 (1988); and Ulmer et al., *Science* 259:1745 (1993)). The use of cationic lipids may promote encapsulation of negatively charged nucleic acids, and also promote fusion with negatively charged cell membranes (Felgner et al., *Science* 337:387 (1989)). Particularly useful lipid compounds and compositions for transfer of nucleic acids are described in International Patent Publications WO95/18863 and WO96/17823, and in U.S. Pat. No. 5,459,127. The use of lipofection to introduce exogenous nucleotide sequences into specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules can be coupled to liposomes chemically.

In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931).

It is also possible to introduce a vector in vivo as naked nucleic acid (see U.S. Pat. Nos. 5,693,622, 5,589,466 and 5,580,859). Receptor-mediated nucleic acid delivery approaches can also be used (Curie) et al., *Hum. Gene Ther.* 3:147 (1992); Wu et al., *J. Biol. Chem.* 262:4429 (1987)).

The term "transfection" or "transduction" means the uptake of exogenous or heterologous nucleic acid (RNA and/or DNA) by a cell, A cell has been "transfected" or "transduced" with an exogenous or heterologous nucleic acid when such nucleic acid has been introduced or delivered inside the cell. A cell has been "transformed" by exogenous or heterologous nucleic acid when the transfected or transduced nucleic acid imparts a phenotypic change in the cell and/or a change in an activity or function of the cell. The transforming nucleic acid can be integrated (covalently linked) into chromosomal DNA making up the genome of the cell or it can be present as a stable plasmid.

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

II. SOGA POLYNUCLEOTIDES AND POLYPEPTIDES

In one aspect, the invention relates to an isolated polynucleotide encoding a SOGA polypeptide or a functional fragment thereof. In one embodiment, the SOGA polypeptide is a mammalian SOGA polypeptide, e.g., human or mouse. The cDNA, polypeptide, and genomic sequences of mouse SOGA have been deposited in GenBank under Accession No. FJ977045 and are disclosed herein as SEQ ID NOS:1, 2, and 10, respectively. The cDNA, polypeptide, and genomic sequences of human SOGA are disclosed herein as SEQ ID NOS:3, 4, and 11, respectively. The polynucleotide can comprise cDNA sequences, genomic sequences, synthetic sequences, or combinations thereof.

```
Mouse SOGA cDNA Sequence
                                                        (SEQ ID NO: 1)
agttgggcctggagctggcgctgagcagcgacgccgagtctgcggcgggcggcccggcgg    60

ggacccgcaccgggcagccgccccagccagcgcagtcggggcagcagcctccgcggcctc   120

ccgcctccccggatgagccgtcggtggccgcatcgtcggtgggcagcagccgcttgcaat   180

tcagcgcctcgctagccttctccgacctcaccgaggagatgctggactgtgggcccggag   240

gcttggtgcgggagctggaagagctgcgttccgagaacgactatctcaaggatgagattg   300

aggagctacgggctgagatgctggagatgcgggatgtctacatggaggaagacgtgtatc   360

agctgcagtaccgactgcgtaaggctgagcgccgcagcctccgcgctgcccagacaggcc   420

aggttgatggggaactcatccgaggtctggaacaggacgtcaaggtctctaaggacatct   480

ccatgcggcttcacaaggagctggaggtggtggagaagaagcggatgaggctggaggagg   540

agaacgaggggcttcgacagaggctcattgagacagagctggccaagcaggtgctacaga   600

cggagctggatcgtcccagagagcattccttgaagaaaagaggaacccggtctctgggga   660

agacagataagaagcctactgcacaggaggatagtgcagacctgaagtgccagctgcatt   720

ttgcaaaggaggagtcggccctcatgtgcaagaagctcaccaagttggctaaggagaacg   780
```

-continued

```
acagcatgaaggaggagctgctcaagtacagatcgctctatggggacctggatgcagccc    840
tgtcggcagaggagctggcggatgctccgcactcccgtgagactgagctgaaggtgcacc    900
tgaagctggtggaggaggaggccaacctgctgagccggcgcatagtggagctggaggtgg    960
agaaccgtggcctgcgagccgagatggacgacatgaaggaccacgggggtggcgggggtc   1020
ccgaggccaggctggccttctcttctctgggtggtgagtgcggggacagcctagccgagt   1080
tgcggcgccacctgcagttcgtggaagaggaggctgagctgctgaggcgctcctcagctg   1140
agctggaggaccagaacaagttgctgctgaacgagctggccaaataccgctcggagcacg   1200
agctggacgtgacgctgtcggaggacagctgctccgtgctcagcgagccctcgcaggagg   1260
agctggcagccgccaagctgcagatcggcgagctcagcggcaaggtcaagaagctgcagt   1320
atgagaaccgcgtgctcctctccaatctgcagcgctgtgacctggcctcctgccagagca   1380
cacgccccatgctggagacggacgctgaggctggggactctgcgcagtgcgtgcctgccc   1440
ctctgggtgagacgctggagccccacgccgcccggctgtgcagggcccgtgaagccgagg   1500
cgctgcccggcctacgggagcaggccgctttggtcagcaaggccatcgacgtcctggtgg   1560
ctgatgccaatggcttctcagtcggcctccgcctgtgcctggacaatgagtgtgctgact   1620
tgcgactgcacgaggcgcctgacaacagcgagggccccagggatgccaagctcatccacg   1680
ccatcctggtgcggctgagtgtgttgcaacaggagctgaacgccttcacccgcaaggcag   1740
atgtggccttggggagctctggcaaggagcagcctgagcccttccctgctctgcctgcct   1800
tgggctcccagggccctgctaaggagatcatgctgtccaaagaccttggctctgacttcc   1860
agccacctgacttcagagacctgcttgagtgggagcccaggatccgagaggccttccgta   1920
ccggggacttggagtccaagcctgaccctagtcggaacttcaggccctaccgagctgaag   1980
ataacgattcttatgcctctgagatcaaggatcttcagctggtcctggccgaggcccacg   2040
acagcctccggggcttgcaagagcagctgtcccaggagcggcagctccggaaggaggagg   2100
ctgacagcttcaaccagaaaatggtccagctgaaggaagaccagcagagggcgctgctga   2160
gacgggagtttgagctgcagagtctgagcctccagcggcgactggagcagaagttctgga   2220
gccaagagaagaacatcctggtgcaggagtcccagcagttcaagcacaactttctgctgc   2280
tcttcatgaagctccggtggttcctgaagcgctggcggcagggcaaggttctgcccagcg   2340
aagaggatgacttcctggaggtgaacagcatgaaggaactgtacctgctgatggaggaag   2400
aggagatgaacgcccagcactcggataacaaggcctgcacaggggagagctggacccaga   2460
acacgcctaatgagtgcatcaagaccctggccgacatgaaggtcaccctgaaggagctgt   2520
gctggctgctccaggacgagcgtcggggtctgactgaacttcagcagcagttcgcaaagg   2580
ccaaggccacctgggagacagagcgtgcagagctcaagggccacgcctcgcagatggagc   2640
tgaaggctgggaagggtgccagtgagaggcccgggcctgactggaaggctgcactgcaga   2700
gagagcgggaggagcagcaacacctcctggcagagtcctacagcgccgtcatggagctga   2760
cgaggcagctgcagctgagcgagcgccactggagccaggagaagctgcagctggtggagc   2820
ggctgcagggagaaaagcagcaggtggagcagcaggtgaaggagctgcagaaccgcctca   2880
gtcagttgcagaaggctgccgagccctgggtcctgaagcactcagacatggagaagcaag   2940
acaacagctggaaagaggcacgaagtgagaagacccatgacaaggagggtgtctctgaag   3000
ctgagctcgggggaactggcttaaagaggaccaaatcagtctcctccatgtctgagtttg   3060
aaagtttgctcgactgctccccgtaccttgctggcggggatgcccggaacaagaagctgc   3120
ccaacggccctgcttttgcctttgtgagtactgagccagtggagcctgagaaagacgcca   3180
aggagaaggcggggctttccacccgggactgtagccacattggtagcttggcctgtcagg   3240
```

-continued aacctgcagggagacagatgcagcgcagctacacggctccagacaagacgggaatccgag 3300 tctactatagtccgccagtggctcggcgcctgggtgtccctgtggtccatgacaaggagg 3360 gcaagatcctcattgagccaggcttcctcttcactaccgccaagcccaaggagtcagccg 3420 aggctgacgggctggccgagagctcctacagccggtggctttgcaatttctcccggcagc 3480 ggctggatggaggatccggggccagcacctcgggttccggacctgctttccccgccttgc 3540 atgactttgagatgtcgggcaacatgagtgacgacatgaaggagatcaccaactgcgtgc 3600 ggcaggccatgcgctccggctctctggagaggaaggtaaagaacacatccagccagacgg 3660 taggcgtggccaccgtgggcacccagaccattcggacggtcagtgtaggtcttcagaccg 3720 acccaccccgcagcagcctccacagcaagagctggtcaccccgcagctcctcgcttgtgt 3780 ctgtgcgcagcaagcagatctcttcctccctggacaaggtccattctcgcattgagcggc 3840 catgttgctcgcccaagtacggctcacccaagctccagagacgatcggtgtccaagctgg 3900 atagcaccaaggaccgcagcctgtggaacctgcaccagggcaagcaaaatggctccgcct 3960 gggctcgctccaccaccacacgggatagccctgtactgaggaacatcaatgatgggcttt 4020 ctagcctctttagtgtggtggagcactctgggagcaccgagtctgtgtggaaactgggca 4080 tgtctgaggcccgaaccaaacctgagcctcccaagtatggcattgttcaggagttcttcc 4140 ggaacgtgtgtggccgggcaccgagccccactactgcagcaggcgaggaaagctgcaaga 4200 aaccagagcccctttcgccagccagctaccatcaacccgagggtgtatccaggatcctga 4260 acaagaaggcggccaaggcaggtggtagcgaagaggtcagacccaccatgctgtcccagg 4320 tggggaaggatggcatccttcgggatggagatggatccttgatccttcccagtgaggatg 4380 ccgtatgtgactgtagcgcccagtcacttgcctcctgcttcatccggccatcccgcaaca 4440 ccatccggcactctccttccaagtgcaggctgcacccttcagagtcaggctggggcgggg 4500 aggagagggcagctccccagtgagtccctgagcaaccaagcacccacctcaagcagccca 4560 gaccctggagatgaggcaagggctcgtgtcctcagcctcagtccatccaggaggaatggc 4620 agctgtgccactgccacagaagagctttcacattaaggtaaagcaaggtgtcttgctgac 4680 tgctgggcagtgacctctgatttccaggggaagaca 4716

Mouse SOGA Polypeptide Sequence (SEQ ID NO: 2)

MLDCGPGGLVRELEELRSENDYLKDEIEELRAEMLEMRDVYMEEDVYQLQYRLRKAERRS 60

LRAAQTGQVDGELIRGLEQDVKVSKDISMRLHKELEVVEKKRMRLEEENEGLRQRLIETE 120

LAKQVLQTELDRPREHSLKKRGTRSLGKTDKKPTAQEDSADLKCQLHFAKEESALMCKKL 180

TKLAKENDSMKEELLKYRSLYGDLDAALSAEELADAPHSRETELKVHLKLVEEEANLLSR 240

RIVELEVENRGLRAEMDDMKDHGGGGGPEARLAFSSLGGECGESLAELRRHLQFVEEEAE 300

LLRRSSAELEDQNKLLLNELAKYRSEHELDVTLSEDSCSVLSEPSQEELAAAKLQIGELS 360

GKVKKLQYENRVLLSNLQRCDLASCQSTRPMLETDAEAGDSAQCVPAPLGETLEPHAARL 420

CRAREAEALPGLREQAALVSKAIDVLVADANGFSVGLRLCLDNECADLRLHEAPDNSEGP 480

RDAKLIHAILVRLSVLQQELNAFTRKADVALGSSGKEQPEPFPALPALGSQGPAKEIMLS 540

KDLGSDKQPPDERDLLEWEPRIREAFRTGDLESKPDPSRMFRPYRAEDNDSYASEIKDLQ 600

LVLAEAHDSLRGLQEQLSQERQLRKEEADSFNQKMVQLKEDQQRALLRREFELQSLSLQR 660

RLEQKFWSQEKNILVQESQQFKHNFLLLFMKLRWFLKRWRQGKVLPSEEDDFLSVNSMKE 720

LYLLMEEEEMNAQHSDNKACTGESWTQNTPNECIKTLADMKVTLKELCWLLQDERRGLTE 780

LQQQFAKAKATWETERAELKGHASQMELKAGKGASERPGPDWKAALQREREEQOHLLAES 840

YSAVMELTRQLQLSERHWSQEKLQLVERLQGEKQQVEQQVKELQNRLSQLQKAAEPWVLK 900

-continued

HSDMEKQDNSWKEARSEKTHDKEGVSEAELGGTGLKRTKSVSSMSEFESLLDCSPYLAGG 960

DARNKKLPNGPAFAFVSTEPVEPEKDAKEKAGLSTRDCSMIGSLACQEPAGRQMQRSYTA 1020

PDKTGIRVYYSPPVARRLGVPVVHDKEGKILIEPGFLFTTAKPKESAEADGLASSSYSRW 1080

LCNFSRQRLDGGSGASTSGSGPAFPALHDFEMSGNMSDDMKEITNCVRQAMRSGSLERKV 1140

KNTSSQTVGVATVGTQTIRTVSVGLQTDPPRSSLHSKSWSPRSSSLVSVRSKQISSSLDK 1200

VHSRIERPCCSPKYGSPKLQRRSVSKLDSTKDRSLWNLHQGKQNGSAWARSTTTRDSPVL 1260

RNINDGLSSLFSVVEHSGSTESVWKLGMSEARTKPEPPKYGIVQEFFRNVCGRAPSPTTA 1320

AGEESCKKPEPLSPASYHQPEGVSRILNKKAAKAGGSEEVRPTMLSQVGKDGILRDGDGS 1380

LILPSEDAVCDCSAQSLASCFIRPSRNTIRHSPSKCRLHPSESGWGGEERAAPQ 1434

Human SOGA cDNA Sequence (SEQ ID NO: 3)

cgctgagcagcgacgccgagtccgcggccgggggcccggcgggggtccgtacggggcagc 60 cggcccagcccgcgccctccgcgcagcagcccccgcggccgcccgcctccccggacgagc 120 cgtcggtggccgcgtcgtcggtgggcagcagccgcttgccgctcagcgcctcgcttgcct 180 tctccgacctcaccgaggagatgctggactgcgggcccagcggcttggtgcgggagctgg 240 aggacctgcgctcggagaacgactatctcaaggacgagattgaggagctgcgggccgaga 300 tgctcgagatgcgggacgtctatatggaggaggacgtgtatcagctgcagtaccggctgc 360 gcaaagccgagcgccgcagtctccgtgccgcccagaccggccaggtggacggcgagctta 420 tccgtggtctggagcaggatgtcaaggtctctaaggacatctccatgcggctgcataagg 480 agctcgaggtggtggagaagaaacgggcgcggctggaggaggagaacgaagagcttcgtc 540 agcggctcatcgagactgagctggctaagcaggtgctgcagacggagctggagcgaccga 600 gagaccattccttgaagaaaagaggaacccgctccctggggaaggccgataagaagactt 660 tggtgcaggaggacagtgcagacctgaagtgccagttgcactttgcaaaggaggagtcag 720 ccctcatgtgcaagaagctcactaagcttgccaaggagaatgacagcatgaaggaggagc 780 tgctgaagtaccgctcgctctatggggacctggacagcgcgctgtcagccgaggagctgg 840 ccgatgcccccactcgcgggagaccgagctgaaggtgcacctgaagctggtggaggagg 900 aagccaacctgctgagccgccgcatcgtggagctggaggtggagaaccgaggcctgcggg 960 ctgagatggacgacatgaaggatcatggaggtggctgtgggggtcctgaggcacgcctgg 1020 ccttctccgcgctgggtggcggagagtgcggggagagcttggcagagctgcggcgacacc 1080 tgcagtttgtcgaagaggaggccgagctgctgcggcgctcctctgccgagctcgaggacc 1140 agaacaagctgctgctgaacgagctggccaagttccgctcggagcacgagctggacgtgg 1200 cgctgtcggaggacagttgttctgtgctcagcgaaccttcacaggaggagctggcggccg 1260 ccaagctgcagatcggcgagctcagcggcaaggtcaagaagctgcagtacgagaaccgcg 1320 tgctcctctccaacctccagcgctgtgacctcgcctcctgccagagtacgcggcccatgc 1380 tggagacggacgccgaggccggggactctgcccagtgtgtgcctgctcccctgggcgaga 1440 cacacgagtcccatgcggtccgactctgcagagccagggaggccgaggtgctgcctgggc 1500 tgagagagcaggccgccctggtcagtaaggccatcgatgtcctggtggctgatgccaatg 1560 gcttcacggctggcctccggctgtgtctggacaacgagtgtgctgacttccggctgcatg 1620 aggcccccgacaacagcgagggccccagggacaccaagctcatccatgccatcctggtgc 1680 gcctgagcgtgctgcagcaggagctgaatgccttcacgcggaaggcagatgcagtcctcg 1740 ggtgctctgtcaaggaacagcaggagtccttctcatcactgcccccttgggctcccagg 1800 ggctctctaaggagattcttctggcaaaagaccttggctcagactttcagccacctgact 1860

-continued

```
tcagggacctgccggaatgggagcccaggatccgagaggctctccgcactggtgacttgg   1920
actctaagcccgaccccagccggagcttcaggccttaccgagctgaagacaatgattcct   1980
atgcctctgagatcaaggagctgcagctggtgctggctgaggcccacgacagcctccggg   2040
gcttgcaagagcagctctcccaggagcggcagctacgaaaggaggaggccgacaatttca   2100
accagaaaatggtccagctgaaggaggaccagcagagggcgctcctgaggcgggagtttg   2160
agctgcagagtctgagcctccagcggaggctggagcagaaattctggagccaggagaaga   2220
acatgctggtgcaggagtcccagcaattcaagcacaacttcctgctgctcttcatgaagc   2280
tcaggtggttcctcaagcgctggcggcagggcaaggttttgcccagcgaaggggatgact   2340
tcctcgaggtgaacagcatgaaggagctgtacttgctgatggaggaagaggagataaacg   2400
ctcagcattctgataacaaggcctgcacggggggacagctggacccagaacacgcccaatg   2460
agtacatcaagacactggccgacatgaaggtgacgctgaaggagctgtgctggctgctcc   2520
gggatgaacgccgtggtctgacggagcttcagcaacagtttgccaaggccaaggctacct   2580
gggagacagagcgggcagagctcaagggccatacctcccagatggagctgaagacaggga   2640
agggggccggggagcgggcagggcccgactggaaggcagccctacagcgggagcgtgagg   2700
agcagcagcacctcctagctgagtcctacagcgctgtcatggagctgactcggcagctgc   2760
agatcagtgagcgcaactggagccaggaaaagctgcagctggtggagcggctgcagggtg   2820
agaagcagcaggtggagcagcaggtgaaggagctgcagaaccgcctaagccagctgcaga   2880
aggctgccgacccctgggtcctgaagcactcggagctggagaagcaggacaacagctgga   2940
aggagacacgcagtgagaagatccacgacaaggaggctgtttccgaagttgagcttggag   3000
gaaatggtttaaagagaaccaaatctgtttcttccatgtctgagtttgaaagtttgctcg   3060
actgttccccttaccttgctggcggagatgcccggggcaagaagctgcctaacaaccctg   3120
cctttggctttgtgagctccgagccaggggatccagagaaagacaccaaggagaagcctg   3180
ggctctcgtcgagggactgcaaccacctgggtgccctggcctgccaggacccccccaggga   3240
ggcagatgcagcgcagctacacggctcctgacaagacgggcatccgagtctactatagtc   3300
cccggtggcccggcgcctcggagtccctgtggttcatgacaaagagggcaagatcatta   3360
tcgagcccggcttcctcttcaccacagccaagcccaaagagtcggccgaggctgatgggc   3420
tggctgagagctcctatggtcggtggctctgcaacttctcacggcagcgcctggacggag   3480
gctcagcgggcagcccctcggcggccgggcctggcttcccagcggccctgcatgactttg   3540
agatgtcaggcaacatgagtgatgacatgaaggagatcaccaactgtgtgcgccaggcca   3600
tgcgctccggctcactggagaggaaagtgaagagcacatccagccagacggtgggcctgg   3660
ccagtgtgggcacacagaccatccgcacggtcagcgtgggcctgcagaccgacccacccc   3720
gcagcagcctccatggcaaggcctggtcaccccgcagctcttcgctcgtgtctgtgcgca   3780
gcaagcagatctcctcctccctggacaaggtccattcgcgcatcgagcggccccgctgct   3840
cccccaagtatggctcaccaaagctccagaggcggtctgtgtccaagctggacagcagca   3900
aggaccgcagcctgtggaacctgcaccagggcaagcagaacggctcggcctgggcccgct   3960
ccaccaccacgcgggacagccctgtattgagaaacatcaacgatggactctccagcctct   4020
tcagtgtggtggagcactcagggagcacggagtctgtctggaaactaggcatgtctgaga   4080
cgcgcgccaagcccgagcctcccaagtacggcattgtgcaggaattcttccgtaatgtgt   4140
gtggccgggcaccgagccccacctcatcagcaggagaggagggcaccaagaagccagagc   4200
ccctctccccagccagctaccatcagccagagggtgtggccaggatcctgaacaagaagg   4260
cagccaagttgggcagcagtgaggaggtcagactcaccatgctcccccaggtggggaagg   4320
```

-continued

```
atggtgtcctccgggacggagatggagccgtggtccttcccaatgaggacgctgtttgtg   4380

actgtagtacccagtctctcacctcctgcttcgcccgatcgtcccgctctgccatccgcc   4440

actctccttccaagtgcaggctgcacccttcagagtccagctggggtggggaggagaggg   4500

cactcccccccagcgagtgacagagcagccaagctccccgcctcaaccagcccagcccct   4560

ggatagcagaagggaaccagcagagacgagacgaggtgaggcgaggggctgtgtcctcag   4620

cattgcctggccctggagggacagcagtgatgccactgccagaatgcagctttcacatca   4680

aggtaaagccgggtctcctgctggcccctgggtggtgagcttcgacttcccaggggaagg   4740

cagtgagtgggagagagaccaaacctgggcttcccaagcatccactgagagatctgtcaa   4800

gagccgatccctgggtcctaagagagagccttgcctggttctgcccatgccaccctcttg   4860

ga                                                             4862
```

Human SOGA Polypeptide Sequence

```
                                                          (SEQ ID NO: 4)
MLDCGPSGLVRELEELRSENDYLKDEIEELRAEMLEMRDVYMEEDVYQLQYRLRKAERRS     60

LRAAQTGQVDGELIRGLEQDVKVSKDISMRLHKELEVVEKKRARLEEENEELRQRLIETE    120

LAKQVLQTELERPREHSLKKRGTRSLGKADKKTLVQEDSADLKCQLHFAKEESALMCKKL    180

TKLAKENDSMKEELLKYRSLYGDLDSALSAEELADAPHSRETELKVHLKLVEEEANLLSR    240

RIVELEVENRGLRAEMDDMKDHGGGCGGPEARLAFSALGGGECGESLAELRRHLQFVEEE    300

AELLRRSSAELEDQNKLLLNELAKFRSEHELDVALSEDSCSVLSEPSQEELAAAKLQIGE    360

LSGKVKKLQYENRVLLSNLQRCDLASCQSTRPMLETDAEAGDSAQCVPAPLGETHESHAV    420

RLCRAREAEVLPGLREQAALVSKAIDVLVADANGFTAGLRLCLDNECADFRLHEAPDNSE    480

GPRDTKLIHAILVRLSVLQQELNAFTRKADAVLGCSVKEQQESFSSLPPLGSQGLSKEIL    540

LAKDLGSDFQPPDFRDLPEWEPRIREAFRTGDLDSKPDPSRSFRPYRAEDNDSYASEIKE    600

LQLVLAEAHDSLRGLQEQLSQERQLRKEEADNFNQKMVQLKEDQQRALLRREFELQSLSL    660

QRRLEQKFWSQEKNMLVQESQQFKHNELLLFMKLRWELKRWRQGKVLPSEGDDELEVNSM    720

KELYLLMEEEEINAQHSDNKACTGDSWTQNTPNEYIKTLADMKVTLKELCWLLRDERRGL    780

TELQQQFAKAKATWETERAELKGHTSQMELKTGKGAGERAGPDWKAALQREREEQQHLLA    840

ESYSAVMELTRQLQISERNWSQEKLQLVERLQGEKQQVEQQVKELQNRLSQLQKAADPWV    900

LKHSELEKQDNSWKETRSEKIHDKEAVSEVELGGNGLKRTKSVSSMSEFESLLDCSPYLA    960

GGDARGKKLPNNPAFGFVSSEPGDPEKDTKEKPGLSSRDCNHLGALACQDPPGRQMQRSY   1020

TAPDKTGIRVYYSPPVARRLGVPVVHDKEGKIIIEPGFLFTTAKPKESAEADGLAESSYG   1080

RWLCNFSRQRLDGGSAGSPSAAGPGFPAALHDFEMSGNMSDDMKEITNCVRQAMRSGSLE   1140

RKVKSTSSQTVGLASVGTQTIRTVSVGLQTDPPRSSLHGKAWSPRSSSLVSVRSKQISSS   1200

LDKVHSRIERPCCSPKYGSPKLQRRSVSKLDSSKDRSLWNLHQGKQNGSAWARSTTTRDS   1260

PVLRNINDGLSSLFSVVEHSGSTESVWKLGMSETRAKPEPPKYGIVQEFFRNVCGRAPSP   1320

TSSAGEEGTKKPEPLSPASYHQPEGVARILNKKAAKLGSSEEVRLTMLPQVGKDGVLRDG   1380

DGAVVLPNEDAVCDCSTQSLTSCFARSSRSAIRHSPSKCRLHPSESSWGGEERALPPSE    1439
```

One embodiment of the invention is an isolated polynucleotide selected from the group consisting of:

(a) a polynucleotide comprising a nucleotide sequence at least 70% (e.g., 75%, 80%, 85%, 90%, 95%, 97%, 98%, 99%, 100%) identical to a nucleotide sequence selected from the group consisting of SEQ ID NOS:1 and 3 and encoding a functional SOGA polypeptide;

(b) a polynucleotide that hybridizes to a nucleotide sequence selected from the group consisting of SEQ ID NOS:1 and 3 under stringent hybridization conditions and encodes a functional SOGA polypeptide;

(c) a polynucleotide encoding a functional SOGA polypeptide comprising an amino acid sequence at least 70% (e.g., 75%, 80%, 85%, 90%, 95%, 97%, 98%, 99%, 100%) identical to an amino acid sequence selected from the group consisting of SEQ ID NOS:2 and 4; and (d) a functional fragment of any of (a) to (c).

In another embodiment, the isolated polynucleotide is selected from the group consisting of:

(a) a polynucleotide comprising a nucleotide sequence selected from the group consisting of SEQ ID NOS:1 and 3 or a fragment thereof that encodes a functional SOGA polypeptide;

(b) a polynucleotide encoding a functional SOGA polypeptide comprising an amino acid sequence selected from the group consisting of SEQ ID NOS:2 and 4 or a functional fragment thereof; and (c) a polynucleotide comprising a nucleotide sequence that differs from the nucleotide sequences of (a) or (b) above due to the degeneracy of the genetic code.

In one aspect, the invention relates to SOGA polypeptides and functional fragments or homologs thereof. The SOGA polypeptide can be from any species expressing SOGA, such as mammalian SOGA, e.g., human or mouse SOGA. As used herein, the term "homolog" is used to refer to a polypeptide which differs from a naturally occurring polypeptide by minor modifications to the naturally occurring polypeptide, but which significantly retains a biological activity of the naturally occurring polypeptide. Minor modifications include, without limitation, changes in one or a few amino acid side chains, changes to one or a few amino acids (including deletions, insertions, and substitutions), changes in stereochemistry of one or a few atoms, and minor derivatizations, including, without limitation, methylation, glycosylation, phosphorylation, acetylation, myristoylation, prenylation, palmitation, amidation, and addition of glycosylphosphatidyl inositol. The term "substantially retains," as used herein, refers to a fragment, homolog, or other variant of a polypeptide that retains at least about 20% of the activity of the naturally occurring polypeptide (e.g., inhibition of glucose production), e.g., about 30%, 40%, 50% or more. SOGA activity can be measured as disclosed herein. Other biological activities may include enzyme activity, receptor binding, ligand binding, a cell signal transduction event, etc.

Functional fragments of SOGA polypeptide include any fragment that substantially retains at least one biological activity of full length SOGA polypeptide. In one embodiment, the functional fragment is a C-terminal fragment of SOGA. In certain embodiments, the C-terminal fragment begins immediately after the internal signal sequence of SOGA. In other embodiments, the functional fragment is a C-terminal fragment of about 80 kDa or 25 kDa.

In exemplary embodiments, the polypeptide comprises, consists essentially of, or consists of the amino acid sequence of the polypeptide disclosed herein and in the GenBank accession numbers listed above or a functional fragment thereof. In another embodiment, the isolated polypeptide comprises, consists essentially of or consists of an amino acid sequence that is at least 70% identical, e.g., at least 75%, 80%, 85%, 90%, 95%, 96%, 97%, 98%, or 99% identical to the disclosed amino acid sequence or a functional fragment thereof (and polynucleotide sequences encoding the same).

The polypeptide of the invention also include functional portions or fragments (and polynucleotide sequences encoding the same). The length of the fragment is not critical as long as it substantially retains at least one biological activity of the polypeptide. Illustrative fragments comprise at least about 4, 6, 8, 10, 12, 15, 20, 25, 30, 35, 40, 45, 50, 75, 100, 150, 200, 250, 300, 400, 500, or more contiguous amino acids of a SOGA polypeptide.

Likewise, those skilled in the art will appreciate that the present invention also encompasses fusion polypeptides (and polynucleotide sequences encoding the same) comprising a SOGA polypeptide or a functional fragment thereof. For example, it may be useful to express the polypeptide (or functional fragment) as a fusion protein that can be recognized by a commercially available antibody (e.g., FLAG motifs) or as a fusion protein that can otherwise be more easily purified (e.g., by addition of a poly-His tail). Additionally, fusion proteins that enhance the stability of the polypeptide may be produced, e.g., fusion proteins comprising maltose binding protein or glutathione-S-transferase. As another alternative, the fusion protein can comprise a reporter molecule. In other embodiments, the fusion protein can comprise a polypeptide that provides a function or activity that is the same as or different from the activity of the polypeptide, e.g., a targeting, binding, or enzymatic activity or function.

Likewise, it will be understood that the SOGA polypeptides specifically disclosed herein will typically tolerate substitutions in the amino acid sequence and substantially retain biological activity. To identify polypeptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the DNA sequence (or RNA sequence), according to the following codon table.

TABLE 1

| Amino Acid | | | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

In identifying amino acid sequences encoding polypeptides other than those specifically disclosed herein, the hydropathic index of amino acids may be considered. The importance of the hydropathic amino acid index in conferring interactive biologic function on a protein is generally understood in the art (see, Kyte and Doolittle, *J. Mol. Biol.* 157:105 (1982); incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, id.), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). Accordingly, the hydropathic index of the amino acid (or amino acid sequence) may be considered when modifying the polypeptides specifically disclosed herein.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Thus, the hydrophilicity of the amino acid (or amino acid sequence) may be considered when identifying additional polypeptides beyond those specifically disclosed herein.

In embodiments of the invention, the polynucleotide encoding the SOGA polypeptide (or functional fragment) will hybridize to the nucleic acid sequences specifically disclosed herein or fragments thereof under standard conditions as known by those skilled in the art and encode a functional polypeptide or functional fragment thereof.

For example, hybridization of such sequences may be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS, and 1×SSPE at 42° C.; and conditions represented by a wash stringency of 50% formamide with 5×Denhardt's solution, 0.5% SDS and 1×SSPE at 42° C., respectively) to the polynucleotide sequences encoding the SOGA polypeptides or functional fragments thereof specifically disclosed herein. See, e.g., Sambrook et al., Molecular Cloning: A Laboratory Manual 2nd Ed. (Cold Spring Harbor, N.Y., 1989).

In other embodiments, polynucleotide sequences encoding the SOGA polypeptides have at least about 70%, 80%, 85%, 90%, 95%, 96%, 97%, 98%, 99% or higher sequence identity with the nucleic acid sequences disclosed herein and in the GenBank accession numbers listed above or functional fragments thereof and encode a functional polypeptide or functional fragment thereof.

Further, it will be appreciated by those skilled in the art that there can be variability in the polynucleotides that encode the polypeptides (and fragments thereof) of the present invention due to the degeneracy of the genetic code. The degeneracy of the genetic code, which allows different nucleic acid sequences to code for the same polypeptide, is well known in the literature (See, e.g., Table 1).

Likewise, the polypeptides (and fragments thereof) of the invention include polypeptides that have at least about 70%, 80%, 85%, 90%, 95%, 96%, 97%, 98%, 99% or higher amino acid sequence identity with the disclosed polypeptide sequences.

As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.,* 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Those skilled in the art will appreciate that the isolated polynucleotides encoding the polypeptides of the invention will typically be associated with appropriate expression control sequences, e.g., transcription/translation control signals and polyadenylation signals.

It will further be appreciated that a variety of promoter/enhancer elements can be used depending on the level and tissue-specific expression desired. The promoter can be constitutive or inducible, depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

To illustrate, the polypeptide coding sequence can be operatively associated with a cytomegalovirus (CMV) major immediate-early promoter, an albumin promoter, an Elongation Factor 1-$\alpha$ (EF1-$\alpha$) promoter, a P$\gamma$K promoter, a MFG promoter, or a Rous sarcoma virus promoter.

Inducible promoter/enhancer elements include hormone-inducible and metal-inducible elements, and other promoters regulated by exogenously supplied compounds, including without limitation, the zinc-inducible metallothionein (MT) promoter; the dexamethasone (Dex)-inducible mouse mammary tumor virus (MMTV) promoter; the T7 polymerase promoter system (see WO 98/10088); the ecdysone insect promoter (No et al., *Proc. Natl. Acad. Sci. USA* 93:3346 (1996)); the tetracycline-repressible system (Gossen et al., *Proc. Natl. Acad. Sci. USA* 89:5547 (1992)); the tetracycline-inducible system (Gossen et al., *Science* 268:1766 (1995); see also Harvey et al., *Curr. Opin. Chem. Biol.* 2:512 (1998)); the RU486-inducible system (Wang et al., *Nat. Biotech.* 15:239 (1997); Wang et al., *Gene Ther.,* 4:432 (1997)); and the rapamycin-inducible system (Magari et al., *J. Clin. Invest.* 100: 2865 (1997)).

Other tissue-specific promoters or regulatory promoters include, but are not limited to, promoters that typically confer tissue-specificity in hepatocytes. These include, but are not limited to, promoters for albumin, hepatocyte nuclear factors, transthyretin, $\alpha_1$-antitrypsin, and the hepatitis B virus core promoter. In other embodiments, the promoters typically confer tissue specific in renal cells. These include, but are not limited to, promoters for ksp-cadherin, erythropoietin, $\gamma$-glutamyl transpeptidase, kidney androgen-regulated protein, vacuolar $H^+$-ATPase B1 subunit, and AQP2. In other embodiments, the promoters typically confer tissue specific in muscle cells, e.g., skeletal muscle and/or cardiac muscle. Skeletal muscle cell promoters include, but are not limited to, promoters for $\beta$-actin, Pitx3, creatine kinase, and myosin light chain. Cardiac muscle cell promoters include, but are not limited to, promoters for cardiac actin, cardiac troponin T, troponin C, myosin light chain-2, and $\alpha$-myosin heavy chain.

Moreover, specific initiation signals are generally required for efficient translation of inserted polypeptide coding sequences. These translational control sequences, which can include the ATG initiation codon and adjacent sequences, can be of a variety of origins, both natural and synthetic.

The present invention further provides cells comprising the isolated polynucleotides and polypeptides of the invention. The cell may be a cultured cell or a cell in vivo, e.g., for use in therapeutic methods, diagnostic methods, screening methods, methods for studying the biological action of SOGA polypeptides, in methods of producing the polypeptides, or in methods of maintaining or amplifying the polynucleotides of the invention, etc. In another embodiment, the cell is an ex vivo cell that has been isolated from a subject. The ex vivo cell may be modified and then reintroduced into the subject for diagnostic or therapeutic purposes.

In particular embodiments, the cell is an untransformed cell or a cell from a cell line of a gluconeogenic tissue, such as liver, kidney, skeletal muscle, or cardiac muscle.

The isolated polynucleotide can be incorporated into an expression vector. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a SOGA polypeptide or functional fragment thereof operatively associated with the promoter, and, optionally, a termination sequence including a stop signal for RNA polymerase and a polyadenylation signal for polyadenylase.

Non-limiting examples of promoters of this invention include CYC1, HIS3, GAL1, GAL4, GAL10, ADH1, PGK, PHO5, GAPDH, ADC1, TRP1, URA3, LEU2, ENO, TPI, and alkaline phosphatase promoters (useful for expression in *Saccharomyces*); AOX1 promoter (useful for expression in *Pichia*); $\beta$-lactamase, lac, ara, tet, trp, $IP_L$, $IP_R$, T7, tac, and trc promoters (useful for expression in *Escherichia coli*); light regulated-, seed specific-, pollen specific-, ovary specific-, pathogenesis or disease related-promoters, cauliflower mosaic virus 35S, CMV 35S minimal, cassaya vein mosaic virus (CsVMV), chlorophyll a/b binding protein, ribulose 1,5-bisphosphate carboxylase, shoot-specific promoters, root specific promoters, chitinase, stress inducible promoters, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells).

Further examples of animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, baculovirus IE1 promoter, elongation factor 1 alpha (EF1) promoter, phosphoglycerate kinase (PGK) promoter, ubiquitin (Ubc) promoter, an albumin promoter, the regulatory sequences of the mouse metallothionein-L promoter and transcriptional control regions, the ubiquitous promoters (HPRT, vimentin, $\alpha$-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis and/or disease-related promoters, and promoters that exhibit tissue specificity, such as the elastase I gene control region, which is active in pancreatic acinar cells; the insulin gene control region active in pancreatic beta cells, the immunoglobulin gene control region active in lymphoid cells, the mouse mammary tumor virus control region active in testicular, breast, lymphoid and mast cells; the albumin gene promoter, the Apo AI and Apo AII control regions active in liver, the alpha-fetoprotein gene control region active in liver, the alpha 1-antitrypsin gene control region active in the liver, the beta-globin gene control region active in myeloid cells, the myelin basic protein gene control region active in oligodendrocyte cells in the brain, the myosin light chain-2 gene control region active in skeletal muscle, and the gonadotropic releasing hormone gene control region active in the hypothalamus, the pyruvate kinase promoter, the villin promoter, the promoter of the fatty acid binding intestinal protein, the promoter of smooth muscle cell α-actin, and the like. In addition, any of these expression sequences of this invention can be modified by addition of enhancer and/or regulatory sequences and the like.

Enhancers that may be used in embodiments of the invention include but are not limited to: an SV40 enhancer, a cytomegalovirus (CMV) enhancer, an elongation factor I (EF1) enhancer, yeast enhancers, viral gene enhancers, and the like.

Termination control regions, i.e., terminator or polyadenylation sequences, may be derived from various genes native to the preferred hosts. In some embodiments of the invention, the termination control region may comprise or be derived from a synthetic sequence, a synthetic polyadenylation signal, an SV40 late polyadenylation signal, an SV40 polyadenylation signal, a bovine growth hormone (BGH) polyadenylation signal, viral terminator sequences, or the like.

It will be apparent to those skilled in the art that any suitable vector can be used to deliver the polynucleotide to a cell or subject. The vector can be delivered to cells in vivo. In other embodiments, the vector can be delivered to cells ex vivo, and then cells containing the vector are delivered to the subject. The choice of delivery vector can be made based on a number of factors known in the art, including age and species of the target host, in vitro versus in vivo delivery, level and persistence of expression desired, intended purpose (e.g., for therapy or screening), the target cell or organ, route of delivery, size of the isolated polynucleotide, safety concerns, and the like.

Suitable vectors include plasmid vectors, viral vectors (e.g., retrovirus, alphavirus; vaccinia virus; adenovirus, adeno-associated virus and other parvoviruses, lentivirus, poxvirus, or herpes simplex virus), lipid vectors, poly-lysine vectors, synthetic polyamino polymer vectors, and the like.

Any viral vector that is known in the art can be used in the present invention. Protocols for producing recombinant viral vectors and for using viral vectors for nucleic acid delivery can be found in Ausubel et al., Current Protocols in Molecular Biology (Green Publishing Associates, Inc. and John Wiley & Sons, Inc., New York) and other standard laboratory manuals (e.g., Vectors for Gene Therapy. In: *Current Protocols in Human Genetics*. John Wiley and Sons, Inc.: 1997).

Non-viral transfer methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, poly-lysine conjugates, and artificial viral envelopes.

In particular embodiments, plasmid vectors are used in the practice of the present invention. For example, naked plasmids can be introduced into muscle cells by injection into the tissue. Expression can extend over many months, although the number of positive cells is typically low (Wolff et al., *Science* 247:247 (1989)). Cationic lipids have been demonstrated to aid in introduction of nucleic acids into some cells in culture (Felgner and Ringold, *Nature* 337:387 (1989)). Injection of cationic lipid plasmid DNA complexes into the circulation of mice has been shown to result in expression of the DNA in lung (Brigham et al., *Am. J. Med. Sci.* 298:278 (1989)). One advantage of plasmid DNA is that it can be introduced into non-replicating cells.

In a representative embodiment, a nucleic acid molecule (e.g., a plasmid) can be entrapped in a lipid particle bearing positive charges on its surface and, optionally, tagged with antibodies against cell surface antigens of the target tissue (Mizuno et al., *No Shinkei Geka* 20:547 (1992); PCT publication WO 91/06309; Japanese patent application 1047381; and European patent publication EP-A-43075).

Liposomes that consist of amphiphilic cationic molecules are useful as non-viral vectors for nucleic acid delivery in vitro and in vivo (reviewed in Crystal, *Science* 270:404 (1995); Blaese et al., *Cancer Gene Ther.* 2:291 (1995); Behr et al., *Bioconjugate Chem.* 5:382 (1994); Remy et al., *Bioconjugate Chem.* 5:647 (1994); and Gao et al., *Gene Therapy* 2:710 (1995)). The positively charged liposomes are believed to complex with negatively charged nucleic acids via electrostatic interactions to form lipid:nucleic acid complexes. The lipid:nucleic acid complexes have several advantages as nucleic acid transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Felgner et al., *Proc. Natl. Acad. Sci. USA* 84:7413 (1987); Loeffler et al., *Meth. Enzymol.* 217:599 (1993); Felgner et al., *J. Biol. Chem.* 269:2550 (1994)).

Several groups have reported the use of amphiphilic cationic lipid:nucleic acid complexes for in vivo transfection both in animals and in humans (reviewed in Gao et al., *Gene Therapy* 2:710 (1995); Zhu et al., *Science* 261:209 (1993); and Thierry et al., *Proc. Natl. Acad. Sci. USA* 92:9742 (1995)). U.S. Pat. No. 6,410,049 describes a method of preparing cationic lipid:nucleic acid complexes that have a prolonged shelf life.

Expression vectors can be designed for expression of polypeptides in prokaryotic or eukaryotic cells. For example, polypeptides can be expressed in bacterial cells such as *E. coli*, insect cells (e.g., the baculovirus expression system), yeast cells, plant cells or mammalian cells. Some suitable host cells are discussed further in Goeddel, *Gene Expression Technology*: Methods in Enzymology 185, Academic Press, San Diego, Calif. (1990). Examples of bacterial vectors include pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, and pRIT5 (Pharmacia). Examples of vectors for expression in the yeast *S. cerevisiae* include pYepSec1 (Baldari et al., *EMBO J.* 6:229 (1987)), pMFa (Kurjan and Herskowitz, *Cell* 30:933 (1982)), pJRY88 (Schultz et al., *Gene* 54:113 (1987)), and pYES2 (Invitrogen Corporation, San Diego, Calif.). Baculovirus vectors available for expression of nucleic acids to produce proteins in cultured insect cells (e.g., Sf 9 cells) include the pAc series (Smith et al., *Mol. Cell. Biol.* 3:2156 (1983)) and the pVL series (Lucklow and Summers *Virology* 170:31 (1989)).

Examples of mammalian expression vectors include pWL-NEO, pSV2CAT, pOG44, pXT1, pSG (Stratagene) pSVK3, PBPV, pMSG, PSVL (Pharmacia), pCDM8 (Seed, *Nature* 329:840 (1987)) and pMT2PC (Kaufman et al., *EMBO J.* 6:187 (1987)). When used in mammalian cells, the expression vector's control functions are often provided by viral regulatory elements. For example, commonly used promoters are derived from polyoma, adenovirus 2, cytomegalovirus and Simian Virus 40.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

In addition to the regulatory control sequences discussed above, the recombinant expression vector can contain additional nucleotide sequences. For example, the recombinant expression vector can encode a selectable marker gene to identify host cells that have incorporated the vector.

Vector DNA can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA and RNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al., Molecular Cloning: A Laboratory Manual 2nd Ed. (Cold Spring Harbor, N.Y., 1989), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

Polypeptides and fragments of the invention can be modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

Another embodiment of the invention relates to homologs of the polypeptides of the invention that are peptidomimetic compounds that are designed based upon the amino acid sequences of the functional polypeptide fragments. Peptidomimetic compounds are synthetic compounds having a three-dimensional conformation (i.e., a "peptide motif") that is substantially the same as the three-dimensional conformation of a selected peptide. The peptide motif provides the peptidomimetic compound with biological activities qualitatively identical to that of the functional fragment from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbon A, dimethylene and ketomethylene bonds, are known in the art to be generally useful substitutes for peptide bonds in the construction of protease-resistant peptidomimetics.

III. INHIBITORS OF SOGA POLYPEPTIDES AND POLYNUCLEOTIDES

As one aspect, the invention provides agents that inhibit the expression and/or activity of SOGA polypeptides or polynucleotides. These agents can be used to inhibit or down-regulate the SOGA signaling pathway, e.g., in a cell or a subject.

In one embodiment of the invention, decreasing the expression and/or activity of a SOGA polypeptide comprises decreasing the level of a nucleic acid (DNA or RNA) encoding the polypeptide or the level of expression of the polypeptide from the nucleic acid. Numerous methods for reducing the level and/or expression of polynucleotides in vitro or in vivo are known. For example, the nucleotide sequences for the human and mouse SOGA polypeptides are disclosed herein. An antisense nucleotide sequence or nucleic acid encoding an antisense nucleotide sequence can be generated to any portion thereof in accordance with known techniques.

The term "antisense nucleotide sequence" or "antisense oligonucleotide" as used herein, refers to a nucleotide sequence that is complementary to a specified DNA or RNA sequence. Antisense oligonucleotides and nucleic acids that express the same can be made in accordance with conventional techniques. See, e.g., U.S. Pat. No. 5,023,243 to Tullis; U.S. Pat. No. 5,149,797 to Pederson et al. The antisense nucleotide sequence can be complementary to the entire nucleotide sequence encoding the polypeptide or a portion thereof of at least 10, 20, 40, 50, 75, 100, 150, 200, 300, or 500 contiguous bases or more and will reduce the level of polypeptide production.

Those skilled in the art will appreciate that it is not necessary that the antisense nucleotide sequence be fully complementary to the target sequence as long as the degree of sequence similarity is sufficient for the antisense nucleotide sequence to hybridize to its target and reduce production of the polypeptide. As is known in the art, a higher degree of sequence similarity is generally required for short antisense nucleotide sequences, whereas a greater degree of mismatched bases will be tolerated by longer antisense nucleotide sequences.

For example, hybridization of such nucleotide sequences can be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS, and 1×SSPE at 42° C.; and/or conditions represented by a wash stringency of 50% formamide with 5×Denhardt's solution, 0.5% SDS and 1×SSPE at 42° C., respectively) to the nucleotide sequences specifically disclosed herein. See, e.g., Sambrook et al., Molecular Cloning: A Laboratory Manual 2nd Ed. (Cold Spring Harbor, N.Y., 1989).

In other embodiments, antisense nucleotide sequences of the invention have at least about 70%, 80%, 90%, 95%, 97%, 98% or higher sequence similarity with the complement of the coding sequences specifically disclosed herein and will reduce the level of polypeptide production.

In other embodiments, the antisense nucleotide sequence can be directed against any coding sequence, the silencing of which results in a modulation of a SOGA polypeptide.

The length of the antisense nucleotide sequence (i.e., the number of nucleotides therein) is not critical as long as it binds selectively to the intended location and reduces transcription and/or translation of the target sequence, and can be determined in accordance with routine procedures. In general, the antisense nucleotide sequence will be from about eight, ten or twelve nucleotides in length up to about 20, 30, 50, 75 or 100 nucleotides, or longer, in length.

An antisense nucleotide sequence can be constructed using chemical synthesis and enzymatic ligation reactions by procedures known in the art. For example, an antisense nucleotide sequence can be chemically synthesized using naturally occurring nucleotides or various modified nucleotides designed to increase the biological stability of the molecules or to increase the physical stability of the duplex formed between the antisense and sense nucleotide sequences, e.g., phosphorothioate derivatives and acridine substituted nucleotides can be used. Examples of modified nucleotides which can be used to generate the antisense nucleotide sequence include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methyl inosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-m annosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleotide sequence can be produced using an expression vector into which a nucleic acid has been cloned in an antisense orientation (i.e., RNA transcribed from the inserted nucleic acid will be of an antisense orientation to a target nucleic acid of interest).

The antisense nucleotide sequences of the invention further include nucleotide sequences wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues can be modified as described. In another non-limiting example, the antisense nucleotide sequence is a nucleotide sequence in which one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides can be modified as described. See also, Furdon et al., *Nucleic Acids Res.* 17:9193 (1989); Agrawal et al., *Proc. Natl. Acad. Sci. USA* 87:1401 (1990); Baker et al., *Nucleic Acids Res.* 18:3537 (1990); Sproat et al., *Nucleic Acids Res.* 17:3373 (1989); Walder and Walder, *Proc. Natl. Acad. Sci. USA* 85:5011 (1988); incorporated by reference herein in their entireties for their teaching of methods of making antisense molecules, including those containing modified nucleotide bases).

Triple helix base-pairing methods can also be employed to inhibit production of SOGA polypeptides. Triple helix pairing is believed to work by inhibiting the ability of the double helix to open sufficiently for the binding of polymerases, transcription factors, or regulatory molecules. Recent therapeutic advances using triplex DNA have been described in the literature (e.g., Gee et al., (1994) In: Huber et al., Molecular and Immunologic Approaches, Futura Publishing Co., Mt. Kisco, N.Y.).

Small Interference (si) RNA, also known as RNA interference (RNAi) molecules, provides another approach for modulating the expression of SOGA polypeptides. The siRNA can be directed against polynucleotide sequences encoding the SOGA polypeptides or any other sequence that results in modulation of the expression of SOGA polypeptides.

siRNA is a mechanism of post-transcriptional gene silencing in which double-stranded RNA (dsRNA) corresponding to a coding sequence of interest is introduced into a cell or an organism, resulting in degradation of the corresponding mRNA. The mechanism by which siRNA achieves gene silencing has been reviewed in Sharp et al., *Genes Dev.* 15:485 (2001); and Hammond et al., *Nature Rev. Gen.* 2:110 (2001)). The siRNA effect persists for multiple cell divisions before gene expression is regained. siRNA is therefore a powerful method for making targeted knockouts or "knockdowns" at the RNA level. siRNA has proven successful in human cells, including human embryonic kidney and HeLa cells (see, e.g., Elbashir et al., *Nature* 411:494 (2001)). In one embodiment, silencing can be induced in mammalian cells by enforcing endogenous expression of RNA hairpins (see Paddison et al., *Proc. Natl. Acad. Sci. USA* 99:1443 (2002)). In another embodiment, transfection of small (21-23 nt) dsRNA specifically inhibits nucleic acid expression (reviewed in Caplen, *Trends Biotechnol.* 20:49 (2002)).

siRNA technology utilizes standard molecular biology methods. dsRNA corresponding to all or a part of a target coding sequence to be inactivated can be produced by standard methods, e.g., by simultaneous transcription of both strands of a template DNA (corresponding to the target sequence) with T7 RNA polymerase. Kits for production of dsRNA for use in siRNA are available commercially, e.g., from New England Biolabs, Inc. Methods of transfection of dsRNA or plasmids engineered to make dsRNA are routine in the art.

MicroRNA (miRNA), single stranded RNA molecules of about 21-23 nucleotides in length, can be used in a similar fashion to siRNA to modulate gene expression (see U.S. Pat. No. 7,217,807).

Silencing effects similar to those produced by siRNA have been reported in mammalian cells with transfection of a mRNA-cDNA hybrid construct (Lin et al., *Biochem. Biophys. Res. Commun.* 281:639 (2001)), providing yet another strategy for silencing a coding sequence of interest.

The expression of SOGA polypeptides can also be inhibited using ribozymes. Ribozymes are RNA-protein complexes that cleave nucleic acids in a site-specific fashion. Ribozymes have specific catalytic domains that possess endonuclease activity (Kim et al., *Proc. Natl. Acad. Sci. USA* 84:8788 (1987); Gerlach et al., *Nature* 328:802 (1987); Forster and Symons, *Cell* 49:211 (1987)). For example, a large number of ribozymes accelerate phosphoester transfer reactions with a high degree of specificity, often cleaving only one of several phosphoesters in an oligonucleotide substrate (Michel and Westhof, *J. Mol. Biol.* 216:585 (1990); Reinhold-Hurek and Shub, *Nature* 357:173 (1992)). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, *Nature* 338:217 (1989)). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., *Proc. Natl. Acad. Sci. USA* 88:10591 (1991); Sarver et al., *Science* 247: 1222 (1990); Sioud et al., *J. Mol. Biol.* 223:831 (1992)).

In another embodiment of the invention, decreasing the expression and/or activity of SOGA polypeptides comprises decreasing the activity of the polypeptide. Polypeptide activity can be modulated by interaction with an antibody or antibody fragment. The antibody or antibody fragment can bind to the polypeptide or to any other polypeptide of interest, as long as the binding between the antibody or the antibody fragment and the target polypeptide results in modulation of the activity of the SOGA polypeptide.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep, camel, or human, or can be a chimeric antibody. See, e.g., Walker et al., *Molec. Immunol.* 26:403 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980.

Antibody fragments included within the scope of the present invention include, for example, Fab, Fab', $F(ab')_2$, and Fv fragments; domain antibodies, diabodies; vaccibodies, linear antibodies; single-chain antibody molecules; and multispecific antibodies formed from antibody fragments. Such fragments can be produced by known techniques. For example, $F(ab')_2$ fragments can be produced by pepsin digestion of the antibody molecule, and Fab fragments can be generated by reducing the disulfide bridges of the $F(ab')_2$ fragments. Alternatively, Fab expression libraries can be constructed to allow rapid and easy identification of monoclonal Fab fragments with the desired specificity (Huse et al., *Science* 254:1275 (1989)).

Antibodies of the invention may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework (FR) regions (i.e., the sequences between the CDR regions) are those of a human immunoglobulin consensus sequence. The humanized antibody optimally also will comprise at least a portion of an immunoglobulin constant region (Fc), typically that of a human immunoglobulin (Jones et al., *Nature* 321:522 (1986); Riechmann et al., *Nature,* 332:323 (1988); and Presta, *Curr. Op. Struct. Biol.* 2:593 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can essentially be performed following the method of Winter and co-workers (Jones et al., *Nature* 321:522 (1986); Riechmann et al., *Nature* 332:323 (1988); Verhoeyen et al., *Science* 239: 1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues (e.g., all of the CDRs or a portion thereof) and possibly some FR residues are substituted by residues from analogous sites in rodent antibodies.

Human antibodies can also be produced using various techniques known in the art, including phage display libraries (Hoogenboom and Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., *J. Immunol.* 147:86 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779 (1992); Lonberg et al., *Nature* 368:856 (1994); Morrison, *Nature* 368:812 (1994); Fishwild et al., *Nature Biotechnol.* 14:845 (1996); Neuberger, *Nature Biotechnol,* 14:826 (1996); Lonberg and Huszar, *Intern. Rev. Immunol.* 13:65 (1995).

Polyclonal antibodies used to carry out the present invention can be produced by immunizing a suitable animal (e.g., rabbit, goat, etc.) with an antigen to which a monoclonal antibody to the target binds, collecting immune serum from the animal, and separating the polyclonal antibodies from the immune serum, in accordance with known procedures.

Monoclonal antibodies used to carry out the present invention can be produced in a hybridoma cell line according to the technique of Kohler and Milstein, *Nature* 265:495 (1975). For example, a solution containing the appropriate antigen can be injected into a Mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., Huse, *Science* 246:1275 (1989).

Antibodies specific to the target polypeptide can also be obtained by phage display techniques known in the art.

Various immunoassays can be used for screening to identify antibodies having the desired specificity for the polypeptides of this invention. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). A two-site, monoclonal-based immunoassay utilizing monoclonal antibodies reactive to two non-interfering epitopes on the polypeptides or peptides of this invention can be used as well as a competitive binding assay.

Antibodies can be conjugated to a solid support (e.g., beads, plates, slides or wells formed from materials such as latex or polystyrene) in accordance with known techniques. Antibodies can likewise be conjugated to detectable groups such as radiolabels (e.g., $^{35}S$, $^{125}I$, $^{131}I$), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

In one embodiment, the activity of SOGA polypeptides is inhibited using aptamers. Recently, small structured single-stranded RNAs, also known as RNA aptamers, have emerged as viable alternatives to small-molecule and antibody-based therapy (Que-Gewirth et al., *Gene Ther.* 14:283 (2007); Ireson et al., *Mol. Cancer. Ther.* 5:2957 (2006)). RNA aptamers specifically bind target proteins with high affinity, are quite stable, lack immunogenicity, and elicit biological responses. Aptamers are evolved by means of an iterative selection method called SELEX (systematic evolution of ligands by exponential enrichment) to specifically recognize and tightly bind their targets by means of well-defined complementary three-dimensional structures.

RNA aptamers represent a unique emerging class of therapeutic agents (Que-Gewirth et al., *Gene Ther.* 14:283 (2007); Ireson et al., *Mol. Cancer. Ther.* 5:2957 (2006)). They are relatively short (12-30 nucleotide) single-stranded RNA oligonucleotides that assume a stable three-dimensional shape to tightly and specifically bind selected protein targets to elicit a biological response. In contrast to antisense oligonucleotides, RNA aptamers can effectively target extracellular targets. Like antibodies, aptamers possess binding affinities in the low nanomolar to picomolar range. In addition, aptamers are heat stable, lack immunogenicity, and possess minimal interbatch variability. Chemical modifications, such as amino or fluoro substitutions at the 2' position of pyrimidines, may reduce degradation by nucleases. The biodistribution and clearance of aptamers can also be altered by chemical addition of moieties such as polyethylene glycol and cholesterol. Further, SELEX allows selection from libraries consisting of up to $10^{15}$ ligands to generate high-affinity oligonucleotide ligands to purified biochemical targets.

In another embodiment, the method of decreasing the activity of a SOGA polypeptide comprises delivering to a cell or to a subject an agent that decreases the activity of a SOGA polypeptide, the agent administered in an amount effective to modulate the activity of the polypeptide. The agent can interact directly with the SOGA polypeptide to decrease the activity of the polypeptide. Alternatively, the agent can interact with any other polypeptide, nucleic acid or other molecule if such interaction results in a decrease of the activity of the SOGA.

The term "agent" as used herein is intended to be interpreted broadly and encompasses organic and inorganic molecules. Organic compounds include, but are not limited to, small molecules, polypeptides, lipids, carbohydrates, coenzymes, aptamers, and nucleic acid molecules (e.g., gene delivery vectors, antisense oligonucleotides, siRNA, all as described above).

Polypeptides include, but are not limited to, antibodies (described in more detail above) and enzymes. Nucleic acids include, but are not limited to, DNA, RNA and DNA-RNA chimeric molecules. Suitable RNA molecules include siRNA, antisense RNA molecules and ribozymes (all of which are described in more detail above). The nucleic acid can further encode any polypeptide such that administration of the nucleic acid and production of the polypeptide results in a decrease of the activity of a SOGA polypeptide.

The agent can further be an agent that is identified by any of the screening methods described below.

In one embodiment of the invention, the agent is a modulator of the insulin and/or adiponectin signaling pathways that directly or indirectly inhibits SOGA expression and/or activity. For example, the agent can be an activator of AMPK such as AICAR(N1-(β-D-ribofuranosyl)-5-aminoimidazole-4-carboxamide). In another embodiment, the agent can be a PI3 kinase inhibitor such as LY294002. In a further embodiment, the agent can be an inhibitor of adiponectin such as rapamycin.

IV. INHIBITION OF GLUCOSE PRODUCTION

Increases in SOGA polypeptide levels and/or activity result in the inhibition of glucose production in cells. Thus, the SOGA polypeptides and polynucleotides of the invention can be used in methods in which a decrease in glucose production is desired for research, diagnostic, and/or therapeutic proposes. These methods can be carried using techniques to increase the expression and/or activity of SOGA polypeptides in a cell, in a tissue, and/or in a subject.

One aspect of the invention relates to a method of decreasing glucose production in a cell, comprising contacting said cell with a polynucleotide, polypeptide, or fusion protein of the invention in an amount effective to decrease glucose production in the cell.

Another aspect of the invention relates to a method of decreasing autophagy in a cell, comprising contacting said cell with a polynucleotide, polypeptide, or fusion protein of the invention in an amount effective to decrease autophagy in said cell.

The cells to be contacted can be in vitro, ex vivo, or in vivo (e.g., in an animal model of disease or a patient). Cells can be contacted with a polynucleotide or polypeptide of the invention by any means known in the art and as described herein.

A further aspect of the invention relates to a method of decreasing blood glucose levels in a subject, comprising delivering to said subject a polynucleotide, polypeptide, or fusion protein of the invention in an amount effective to decrease the blood glucose levels in said subject.

Another aspect of the invention relates to a method of increasing insulin sensitivity in a subject, comprising delivering to said subject a polynucleotide, polypeptide, or fusion protein of the invention in an amount effective to increase insulin sensitivity in said subject.

In one embodiment, the subject is one that is in need of decreased glucose levels and/or increased insulin sensitivity. The subject can currently have or be at risk for a carbohydrate-related metabolic disorder such as diabetes mellitus (Type I or Type II), alcoholic ketoacidosis, diabetic ketoacidosis, nonketotic hyperosmolar syndrome, and new onset diabetes (NOD), such as in cancer patients undergoing chemotherapy, immunosuppressed patients, post-operative patients, and trauma patients. In certain embodiments, the methods of the invention encompass methods of treating a subject having a carbohydrate-related metabolic disorder such as diabetes, comprising delivering to said subject a polynucleotide, polypeptide, or fusion protein of the invention in an amount effective to treat the disorder.

In one embodiment, increasing the expression and/or activity of a SOGA polypeptide comprises delivering a nucleic acid encoding the polypeptide or a fragment or homolog thereof to the cell or tissue or subject. In another embodiment, increasing the expression and/or activity of a SOGA polypeptide comprises delivering the polypeptide itself or a fragment or homolog thereof to the cell or tissue or subject.

In one embodiment, the methods comprise delivering to the subject an isolated SOGA polypeptide. In exemplary embodiments, the polypeptide comprises, consists essentially of, or consists of the amino acid sequence of the polypeptide disclosed herein or a functional fragment thereof. In another embodiment, the isolated polypeptide comprises, consists essentially of, or consists of an amino acid sequence that is at least 70% identical, e.g., at least 75%, 80%, 85%, 90%, 95%, 96%, 97%, 98%, or 99% identical to the disclosed amino acid sequence or a functional fragment thereof (and polynucleotide sequences encoding the same).

In one embodiment, the polynucleotides, polypeptides, or homologs thereof of the invention are administered directly to the subject. Generally, the compounds of the invention will be suspended in a pharmaceutically-acceptable carrier (e.g., physiological saline) and administered orally or by intravenous infusion, or injected subcutaneously, intramuscularly, intrathecally, intraperitoneally, intrarectally, intravaginally, intranasally, intragastrically, intratracheally, or intrapulmonarily. They can be delivered directly to a site involved in gluconeogenesis, such as the liver, kidney, and/or muscle. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100.0 μg/kg. Wide variations in the needed dosage are to be expected in view of the variety of polypeptides and fragments available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-; 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

According to certain embodiments, the polynucleotides or vectors can be targeted to specific cells or tissues in vivo. Targeting delivery vehicles, including liposomes and viral vector systems are known in the art. For example, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., *Biochemistry* 25:5500 (1986); Ho et al., *J. Biol. Chem.*, 262:13979 (1987); Ho et al., *J. Biol. Chem.* 262:13973 (1987); and U.S. Pat. No. 4,957,735 to Huang et al., each of which is incorporated herein by reference in its entirety). Enveloped viral vectors can be modified to deliver a nucleic acid molecule to a target cell by modifying or substituting an envelope protein such that the virus infects a specific cell type. In adenoviral vectors, the gene encoding the attachment fibers can be modified to encode a protein domain that binds to a cell-specific receptor. Herpesvirus vectors naturally target the cells of the central and peripheral nervous system. Alternatively, the route of administration can be used to target a specific cell or tissue. For example, intracoronary administration of an adenoviral vector has been shown to be effective for the delivery of a gene to cardiac myocytes (Maurice et al., *J. Clin. Invest.* 104:21 (1999)). Intravenous delivery of cholesterol-containing cationic liposomes has been shown to preferentially target pulmonary tissues (Liu et al., *Nature Biotechnol.* 15:167 (1997)), and effectively mediate transfer and expression of genes in vivo. Other examples of successful targeted in vivo delivery of nucleic acid molecules are known in the art. Finally, a recombinant nucleic acid molecule can be selectively (i.e., preferentially, substantially exclusively) expressed in a target cell by selecting a transcription control sequence, and preferably, a promoter, which is selectively induced in the target cell and remains substantially inactive in non-target cells.

The polypeptides and polynucleotides of the present invention can optionally be delivered in conjunction with other therapeutic agents. The additional therapeutic agents can be delivered concurrently with the polypeptides and polynucleotides of the invention. As used herein, the word "concurrently" means sufficiently close in time to produce a combined effect (that is, concurrently can be simultaneously, or it can be two or more events occurring within a short time period before or after each other). In one embodiment, the polypeptides and polynucleotides of the invention are administered in conjunction with anti-diabetic agents, including without limitation, (1) PPARγ agonists such as glitazones (e.g., ciglitazone, darglitazone, englitazone, isaglitazone (MCC-555), pioglitazone, rosiglitazone, troglitazone, BRL49653, CLX-0921, 5-BTZD, GW-0207, LG-100641, and LY-300512; (2) biguanides such as buformin, metformin, and phenformin; (3) protein tyrosine phosphatase-1B (PTP-1B) inhibitors such as ISIS 113715; (4) sulfonylureas such as acetohexamide, chlorpropamide, diabinese, glibenclamide, glypizide, glyburide, glimepiride, gliclazide, glipentide, gliquidone, glisolamide, tolazamide, and tolbutamide; (5) meglitinides such as repaglinide and nateglinide; (6) alpha glucoside hydrolase inhibitors such as acarbose, adiposine, camiglibose, emiglitate, miglitol, voglibose, pradimicin-Q, salbostatin, CKD-711, MDL-25,637, MDL-73,945, and MOR 14; (7) alpha-amylase inhibitors such as tendamistat, trestatin, and Al-3688; (8) insulin secretagogues such as linogliride and A4166; (9) fatty acid oxidation inhibitors such as clomoxir and etomoxir; (10) adenosine A2 antagonists such as midaglizole, isaglidole, deriglidole, idazoxan, earoxan, and fluparoxan; (11) insulin or insulin mimetics such as biota, LP-100, novarapid, insulin detemir, insulin lispro, insulin glargine, insulin zinc suspension (lente and Ultralente), Lys-Pro insulin, GLP-1 (73-7) (insulintropin), and GLP-1 (7-36)-$NH_2$); (12) non-thiazolidinediones such as JT-501 and farglitazar (GW-2570/GI-262579); (13) PPARα/γ dual agonists such as BVT-142, CLX-0940, GW-1536, GW1929, GW-2433, KRP-297, L-796449, LR-90, MK-0767, SB 219994, muraglitazar and reglitazar (JTT-501); (14) other insulin sensitizing drugs; (15) VPAC2 receptor agonists; (16) GLK modulators such as those disclosed in WO 03/015774; (17) retinoid modulators such as those disclosed in WO 03/000249; (18) GSK 3 beta/GSK 3 inhibitors such as 4-[2-(2-bromophenyl)-4-(4-fluorophenyl-1H-imidazol-5-yl]pyridine; (19) glycogen phosphorylase (HGLPa) inhibitors such as those disclosed in WO 03/037864; (20) ATP consumption promoters such as those disclosed in WO 03/007990; (21) TRB3 inhibitors, (22) vanilloid receptor ligands such as those disclosed in WO 03/049702, (23) hypoglycemic agents such as those disclosed in WO 03/015781 and WO 03/040114; and (24) Insulin-responsive DNA binding protein-1 (IRDBP-1) as disclosed in WO 03/057827.

V. STIMULATION OF GLUCOSE PRODUCTION

Decreases in SOGA polypeptide levels and/or activity result in the stimulation of glucose production in cells. Thus, inhibitors of the SOGA polypeptides and polynucleotides of the invention can be used in methods in which an increase in glucose production is desired for research, diagnostic, and/or therapeutic proposes. These methods can be carried using techniques to decrease the expression and/or activity of SOGA polypeptides in a cell, in a tissue, and/or in a subject.

One aspect of the invention relates to a method of increasing glucose production in a cell, comprising contacting said cell with an agent that decreases the activity of a polynucleotide or polypeptide of the invention in an amount effective to increase glucose production in the cell.

Another aspect of the invention relates to a method of increasing autophagy in a cell, comprising contacting said cell with an agent that decreases the activity of a polynucleotide or polypeptide of the invention in an amount effective to increase autophagy in said cell.

The cells to be contacted can be in vitro, ex vivo, or in vivo (e.g., in an animal model of disease or a patient). Cells can be contacted with an agent by any means known in the art and as described herein.

A further aspect of the invention relates to a method of increasing blood glucose levels in a subject, comprising delivering to said subject an agent that decreases the activity of a polynucleotide or polypeptide of the invention in an amount effective to increase the blood glucose levels in said subject.

Another aspect of the invention relates to a method of decreasing insulin sensitivity in a subject, comprising delivering to said subject an agent that decreases the activity of a polynucleotide or polypeptide of the invention in an amount effective to decrease insulin sensitivity in said subject.

In one embodiment, the subject is one that is in need of increased glucose levels and/or decreased insulin sensitivity. The subject can currently have or be at risk for a carbohydrate-related metabolic disorder such as hypoglycemia, e.g., as a result of sepsis, malaria, or injection of insulin.

Agents that can be used in the methods of the invention include, without limitation, an antisense oligonucleotide, ribozyme, or siRNA that targets a SOGA polynucleotide, an antibody or antibody fragment that binds to a SOGA polypeptide, agents that modulate the insulin and/or adiponectin signaling pathways, and agents identified by the screening methods described below.

The agents of the present invention can optionally be delivered in conjunction with other therapeutic agents. The additional therapeutic agents can be delivered concurrently with the agents of the invention.

VI. MONITORING OF RESPONSIVENESS TO TREATMENT

The increased levels of SOGA polypeptide in response to administration of insulin and adiponectin provides the basis for monitoring responsiveness of a subject to anti-diabetic treatments. It is known that insulin treatment of diabetics is not effective 100% of the time and that certain drugs may induce adiponectin but do not necessarily lower glucose. Measuring the induction of SOGA in response to an anti-diabetic treatment may provide insight into the ability of a subject to respond to the treatment and can help identify subjects that are likely to respond or not respond to a particular treatment.

One aspect of the invention relates to a method of measuring the response of a subject to a treatment for diabetes, comprising determining the circulating level of a SOGA polypeptide or a functional fragment thereof in said subject after administration of the treatment and comparing it to the circulating level of the polypeptide or a functional fragment thereof in said subject before administration of the treatment.

Another aspect of the invention relates to a method of predicting the clinical outcome of a diabetes treatment in a subject, comprising determining the circulating level of a SOGA polypeptide or a functional fragment thereof in said subject after administration of the treatment and comparing it to the circulating level of the polypeptide or a functional fragment thereof in said subject before administration of the treatment.

In these methods, an increase in circulating levels of SOGA polypeptide or a functional fragment thereof subsequent to administration of an anti-diabetic treatment is indicative that the subject will respond to the treatment (e.g., the treatment will lower glucose levels). Conversely, if the circulating level of SOGA does not increase or increases less than a "normal"

amount, the subject may not respond favorably to the treatment. The magnitude of the increase in SOGA polypeptide (e.g., a "normal" increase as compared to a "less than normal" increase in SOGA) can be classified based on average numbers in a population of similar subjects.

In one embodiment, determining the level of a SOGA polypeptide comprises determining the level the polypeptide. Determining the level of a polypeptide can be carried out by any means known in the art and as described herein, such as Western blots, immunoblots, immunoprecipitation, immunohistochemistry, immunofluorescence, enzyme-linked immunosorbant assays, and radioimmunoassays. Assays for expression and/or activity can be carried out automatically or partially automatically in a machine or apparatus designed to perform such assays, e.g., using computer-assisted methods. The results of the assays can be stored in a computer database and analyzed to produce predictive results. In some embodiments, the data can be analyzed, e.g., by comparing intra-patient results over time or before and after treatment or comparing inter-patient results to determine baseline and/or abnormal values in a population.

In a further embodiment, determining the level of a SOGA polypeptide comprises determining the activity of the polypeptides. The activity may be any activity associated with the polypeptide, including, without limitation, inhibition of glucose production, enzyme activity, protein interaction, receptor binding, ligand binding, a cell signal transduction event, etc.

In one embodiment, determining the level of a SOGA polypeptide comprises determining the level of a nucleic acid encoding the polypeptide. Determining the level of a nucleic acid can be carried out by any means known in the art and as described herein, such as Northern blots, dot blots, PCR, RT-PCR, quantitative PCR, sequence analysis, gene microarray analysis, in situ hybridization, and detection of a reporter gene.

One aspect of the invention relates to kits useful for carrying out the methods of the invention. One embodiment relates to kits for determining the level of expression and/or activity of SOGA, e.g., to assess responsiveness to anti-diabetic treatment, comprising a reagent for determining the expression and/or activity of a SOGA polypeptide or a functional fragment thereof. The reagents may be nucleic acids (e.g., an oligonucleotide that specifically hybridizes to a nucleic acid encoding a SOGA polypeptide and can be used as a hybridization probe or an amplification primer), antibodies (e.g., one the specifically binds to a SOGA polypeptide), or other agents that specifically recognize the polynucleotides or polypeptides of the invention.

The reagents can be conjugated to a detectable tag or detectable label. Such a tag can be any suitable tag which allows for detection of the reagents and includes, but is not limited to, any composition or label detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

In addition, the reagents can be immobilized on a substrate. Such a substrate can include any suitable substrate for immobilization of a detection reagent such as would be used in any of the previously described methods of detection. Briefly, a substrate suitable for immobilization of a detection reagent includes any solid support, such as any solid organic, biopolymer or inorganic support that can form a bond with the detection reagent without significantly effecting the activity and/or ability of the detection reagent to detect the desired target molecule. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and NiO) and sand.

The kits may further comprise other components useful for detecting expression or activity, e.g., buffers, cells, culture medium, enzymes, labeling reagents, containers, etc.

In one embodiment, the kit comprises an array of reagents for determining expression and/or activity. The array can comprise a substrate having a plurality of addresses. At least one address of the plurality includes a capture probe that binds specifically to a polynucleotide or polypeptide of the invention. The array can have a density of at least, or less than, 10, 20 50, 100, 200, 500, 700, 1,000, 2,000, 5,000 or 10,000 or more addresses/$cm^2$, and ranges between. The substrate can be a two-dimensional substrate such as a glass slide, a wafer (e.g., silica or plastic), a mass spectroscopy plate, or a three-dimensional substrate such as a gel pad. Addresses in addition to addresses of the plurality can be disposed on the array.

In one embodiment, at least one address of the plurality includes a nucleic acid capture probe that hybridizes specifically to a polynucleotide of the invention, e.g., the sense or anti-sense strand. Each address of the subset can include a capture probe that hybridizes to a different region of a polynucleotide. An array can be generated by any of a variety of methods. Appropriate methods include, e.g., photolithographic methods (e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another embodiment, at least one address of the plurality includes a polypeptide capture probe that binds specifically to a polypeptide of the invention or fragment thereof. The polypeptide capture probe can be a naturally-occurring interaction partner of a SOGA polypeptide. In one embodiment, the polypeptide is an antibody, e.g., an antibody specific for a SOGA polypeptide, such as a polyclonal antibody, a monoclonal antibody, or a single-chain antibody.

VII. Screening Assays and Animal Models

The identification of polynucleotides and polypeptides that are involved in insulin and adiponectin signaling and glucose regulation provides targets that can be used to screen for agents that regulate glucose production as well as models for studying these pathways in vitro or in animals.

One aspect of the invention relates to a method of identifying an agent that binds to a SOGA polypeptide or a functional fragment thereof of the invention, comprising:

contacting the polypeptide or a functional fragment thereof with a test agent under conditions whereby binding between the polypeptide or a functional fragment thereof and the test agent can occur; and detecting binding between the polypeptide or a functional fragment thereof and the test agent.

Another aspect of the invention relates to a method of identifying an agent that modulates the activity of a SOGA polypeptide or a functional fragment thereof of the invention, comprising:

contacting the polypeptide or a functional fragment thereof with a test agent under conditions whereby modulation of the activity of the polypeptide or a functional fragment thereof can occur; and detecting modulation of the activity of the polypeptide or a functional fragment thereof upon contact with the test agent as compared to activity of the polypeptide or a functional fragment thereof in the absence of contact with the test agent.

In each aspect above, the assay may be a cell-based or cell-free assay. In one embodiment, the cell may be a primary cell, e.g., an endothelial cell or a tumor cell, such as a breast tumor cell. In another embodiment, the cell is from a cell line, e.g., a hepatocyte, kidney, or muscle cell line or a tumor cell line. The cell may be contacted with the agent in vitro (e.g., in a culture dish) or in an animal (e.g., a transgenic animal or an animal model). In one embodiment, the detected increase or decrease in expression and/or activity is statistically significant, e.g., at least $p<0.05$, e.g., $p<0.01$, 0.005, or 0.001. In another embodiment, the detected increase or decrease is at least about 10%, 20%, 30%, 40%, 50%, 60&, 70%, 80%, 90%, 100% or more.

Any desired end-point can be detected in a screening assay, e.g., binding to the polypeptide, gene or RNA, modulation of the activity of the polypeptide, modulation of glucose-related pathways, and/or interference with binding by a known regulator of a polynucleotide or polypeptide. Methods of detecting the foregoing activities are known in the art and include the methods disclosed herein.

Any agent of interest can be screened according to the present invention. Suitable test agents include organic and inorganic molecules. Suitable organic molecules can include but are not limited to small molecules (compounds less than about 1000 Daltons), polypeptides (including enzymes, antibodies, and Fab' fragments), carbohydrates, lipids, coenzymes, and nucleic acid molecules (including DNA, RNA, and chimerics and analogs thereof) and nucleotides and nucleotide analogs. In particular embodiments, the agent is an antisense nucleic acid, an siRNA, or a ribozyme that inhibits production of a SOGA polypeptide.

Further, the methods of the invention can be practiced to screen an agent library, e.g., a small molecule library, a combinatorial chemical compound library, a polypeptide library, a cDNA library, a library of antisense nucleic acids, and the like, or an arrayed collection of agents such as polypeptide and nucleic acid arrays.

In one representative embodiment, the invention provides methods of screening test agents to identify a test agent that binds to a SOGA polypeptide or functional fragment thereof. Agents that are identified as binding to the polypeptide or functional fragment can be subject to further screening (e.g., for modulation of glucose production) using the methods described herein or other suitable techniques.

Also provided are methods of screening agents to identify those that modulate the activity of a SOGA polypeptide or functional fragment thereof. The term "modulate" is intended to refer to agents that enhance (e.g., increase) or inhibit (e.g., reduce) the activity of the polypeptide (or functional fragment). For example, the interaction of the polypeptide or functional fragment with a binding partner can be evaluated. As another alternative, physical methods, such as NMR, can be used to assess biological function. Activity of the SOGA polypeptides or functional fragment can be evaluated by any method known in the art, including the methods disclosed herein.

Agents that are identified as modulators of activity can optionally be further screened using the methods described herein (e.g., for binding to the SOGA polypeptide or functional fragment thereof, polynucleotide or RNA, modulation of glucose, and the like). The agent can directly interact with the polypeptide or functional fragment, polynucleotide or mRNA and thereby modulate its activity. Alternatively, the agent can interact with any other polypeptide, nucleic acid or other molecule as long as the interaction results in a modulation of the activity of the SOGA polypeptide or functional fragment.

With respect to cell-free binding assays, test agents can be synthesized or otherwise affixed to a solid substrate, such as plastic pins, glass slides, plastic wells, and the like. For example, the test agents can be immobilized utilizing conjugation of biotin and streptavidin by techniques well known in the art. The test agents are contacted with the polypeptide or functional fragment thereof and washed. Bound polypeptide can be detected using standard techniques in the art (e.g., by radioactive or fluorescence labeling of the polypeptide or functional fragment, by ELISA methods, and the like).

Alternatively, the target can be immobilized to a solid substrate and the test agents contacted with the bound polypeptide or functional fragment thereof. Identifying those test agents that bind to and/or modulate the SOGA polypeptide or functional fragment can be carried out with routine techniques. For example, the test agents can be immobilized utilizing conjugation of biotin and streptavidin by techniques well known in the art. As another illustrative example, antibodies reactive with the polypeptide or functional fragment can be bound to the wells of the plate, and the polypeptide trapped in the wells by antibody conjugation. Preparations of test agents can be incubated in the polypeptide (or functional fragment)-presenting wells and the amount of complex trapped in the well can be quantitated.

In another representative embodiment, a fusion protein can be provided which comprises a domain that facilitates binding of the polypeptide to a matrix. For example, glutathione-S-transferase fusion proteins can be adsorbed onto glutathione sepharose beads (Sigma Chemical, St. Louis, Mo.) or glutathione derivatized microtiter plates, which are then combined with cell lysates (e.g., $^{35}S$-labeled) and the test agent, and the mixture incubated under conditions conducive to complex formation (e.g., at physiological conditions for salt and pH). Following incubation, the beads are washed to remove any unbound label, and the matrix immobilized and radiolabel detected directly, or in the supernatant after the complexes are dissociated. Alternatively, the complexes can be dissociated from the matrix, separated by SDS-PAGE, and the level of SOGA polypeptide or functional fragment thereof found in the bead fraction quantitated from the gel using standard electrophoretic techniques.

Another technique for agent screening provides for high throughput screening of agents having suitable binding affinity to the polypeptide of interest, as described in published PCT application WO84/03564. In this method, a large number of different small test agents are synthesized on a solid substrate, such as plastic pins or some other surface. The test agents are reacted with the SOGA polypeptide or functional fragment thereof and washed. Bound polypeptide is then detected by methods well known in the art. Purified polypeptide or a functional fragment can also be coated directly onto plates for use in the aforementioned drug screening techniques. Alternatively, non-neutralizing antibodies can be used to capture the peptide and immobilize it on a solid support.

With respect to cell-based assays, any suitable cell can be used, including bacteria, yeast, insect cells (e.g., with a baculovirus expression system), avian cells, mammalian cells, or plant cells. In exemplary embodiments, the assay is carried out in a cell line that naturally expresses the polynucleotide or produces the polypeptide, e.g., hepatocytes or renal cells. Further, in other embodiments, it is desirable to use nontransformed cells (e.g., primary cells) as transformation may alter the function of the polypeptide.

The screening assay can be used to detect agents that bind to or modulate the activity of the native SOGA polypeptide (e.g., polypeptide that is normally produced by the cell). Alternatively, the cell can be modified to express (e.g., overexpress) a recombinant SOGA polypeptide or functional fragment thereof. According to this embodiment, the cell can be transiently or stably transformed with a polynucleotide encoding the SOGA polypeptide or functional fragment, but is preferably stably transformed, for example, by stable integration into the genome of the organism or by expression from a stably maintained episome (e.g., Epstein Barr Virus derived episomes). In another embodiment, a polynucleotide encoding a reporter molecule can be linked to a regulatory element of the polynucleotide encoding a SOGA polypeptide and used to identify compounds that modulate expression of the polypeptide.

In a cell-based assay, the agent to be screened can interact directly with the SOGA polypeptide or functional fragment thereof (i.e., bind to it and modulate the activity thereof. Alternatively, the agent can be one that modulates polypeptide activity (or the activity of a functional fragment) at the nucleic acid level. To illustrate, the agent can modulate transcription of the gene (or transgene), modulate the accumulation of mRNA (e.g., by affecting the rate of transcription and/or turnover of the mRNA), and/or modulate the rate and/or amount of translation of the mRNA transcript.

As a further type of cell-based binding assay, the SOGA polypeptide or functional fragment thereof can be used as a "bait protein" in a two-hybrid or three-hybrid assay (see, e.g., U.S. Pat. No. 5,283,317; Zervos et al., *Cell* 72:223 (1993); Madura et al., *J. Biol. Chem.* 268:12046 (1993); Bartel et al., *Biotechniques* 14:920 (1993); Iwabuchi et al., *Oncogene* 8:1693 (1993); and PCT publication WO94/10300), to identify other polypeptides that bind to or interact with the polypeptide of the invention or functional fragment thereof.

The two-hybrid system is based on the modular nature of most transcription factors, which consist of separable DNA-binding and activation domains. Briefly, the assay utilizes two different DNA constructs. In one construct, the polynucleotide that encodes the SOGA polypeptide or functional fragment thereof is fused to a nucleic acid encoding the DNA binding domain of a known transcription factor (e.g., GAL-4). In the other construct, a DNA sequence, optionally from a library of DNA sequences, that encodes an unidentified protein ("prey" or "sample") is fused to a nucleic acid that codes for the activation domain of the known transcription factor. If the "bait" and the "prey" proteins are able to interact in vivo, forming a complex, the DNA-binding and activation domains of the transcription factor are brought into close proximity. This proximity allows transcription of a reporter sequence (e.g., LacZ), which is operably linked to a transcriptional regulatory site responsive to the transcription factor. Expression of the reporter can be detected and cell colonies containing the functional transcription factor can be isolated and used to obtain the nucleic acid encoding the polypeptide that exhibited binding to the SOGA polypeptide or functional fragment.

As another cell-based assay, the invention provides a method of screening an agent for modulation of glucose production. In particular embodiments, the cell comprises an isolated polynucleotide encoding the SOGA polypeptide or functional fragment thereof. According to this embodiment, it is preferred that the isolated polynucleotide encoding the polypeptide or functional fragment is stably incorporated into the cell (i.e., by stable integration into the genome of the organism or by expression from a stably maintained episome such as Epstein Barr Virus derived episomes).

Screening assays can also be carried out in vivo in animals. Thus, as still a further aspect, the invention provides a transgenic non-human animal comprising an isolated polynucleotide encoding a SOGA polypeptide or functional fragment thereof, which can be produced according to methods well-known in the art. The transgenic non-human animal can be from any species, including avians and non-human mammals. According to this aspect of the invention, suitable non-human mammals include mice, rats, rabbits, guinea pigs, goats, sheep, pigs, and cattle. Suitable avians include chickens, ducks, geese, quail, turkeys, and pheasants.

The polynucleotide encoding the polypeptide or functional fragment can be stably incorporated into cells within the transgenic animal (typically, by stable integration into the genome or by stably maintained episomal constructs). It is not necessary that every cell contain the transgene, and the animal can be a chimera of modified and unmodified cells, as long as a sufficient number of cells comprise and express the polynucleotide encoding the polypeptide or functional fragment so that the animal is a useful screening tool.

Exemplary methods of using the transgenic non-human animals of the invention for in vivo screening of agents that modulate glucose production and/or the activity of a SOGA polypeptide comprise administering a test agent to a transgenic non-human animal (e.g., a mammal such as a mouse) comprising an isolated polynucleotide encoding a SOGA polypeptide or functional fragment thereof stably incorporated into the genome and detecting whether the test agent modulates glucose levels and/or polypeptide activity (or the activity of a functional fragment). It is known in the art how to measure these responses in vivo.

Methods of making transgenic animals are known in the art. DNA or RNA constructs can be introduced into the germ line of an avian or mammal to make a transgenic animal. For example, one or several copies of the construct can be incorporated into the genome of an embryo by standard transgenic techniques.

In an exemplary embodiment, a transgenic non-human animal is produced by introducing a transgene into the germ line of the non-human animal. Transgenes can be introduced into embryonal target cells at various developmental stages. Different methods are used depending on the stage of development of the embryonal target cell. The specific line(s) of any animal used should, if possible, be selected for general good health, good embryo yields, good pronuclear visibility in the embryo, and good reproductive fitness.

Introduction of the transgene into the embryo can be accomplished by any of a variety of means known in the art such as microinjection, electroporation, lipofection, or a viral vector. For example, the transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg can be incubated in vitro for varying amounts of time, or reimplanted into the surrogate host, or both. One common method is to incubate the embryos in vitro for about 1-7 days, depending on the species, and then reimplant them into the surrogate host.

The progeny of the transgenically manipulated embryos can be tested for the presence of the construct by Southern blot analysis of a segment of tissue. An embryo having one or more copies of the exogenous cloned construct stably integrated into the genome can be used to establish a permanent transgenic animal line.

Transgenically altered animals can be assayed after birth for the incorporation of the construct into the genome of the offspring. This can be done by hybridizing a probe corresponding to the polynucleotide sequence coding for the polypeptide or a segment thereof onto chromosomal material from the progeny. Those progeny found to contain at least one copy of the construct in their genome are grown to maturity.

Methods of producing transgenic avians are also known in the art, see, e.g., U.S. Pat. No. 5,162,215.

In particular embodiments, to create an animal model in which the activity or expression of a SOGA polypeptide is decreased, it is desirable to inactivate, replace or knock-out the endogenous gene encoding the polypeptide by homologous recombination with a transgene using embryonic stem cells. In this context, a transgene is meant to refer to heterologous nucleic acid that upon insertion within or adjacent to the gene results in a decrease or inactivation of gene expression or polypeptide amount or activity.

A knock-out of a gene means an alteration in the sequence of a gene that results in a decrease of function of the gene, preferably such that the gene expression or polypeptide amount or activity is undetectable or insignificant. Knock-outs as used herein also include conditional knock-outs, where alteration of the gene can occur upon, for example, exposure of the animal to a substance that promotes gene alteration (e.g., tetracycline or ecdysone), introduction of an enzyme that promotes recombination at a gene site (e.g., Cre in the Cre-lox system), or other method for directing the gene alteration postnatally. Knock-out animals may be prepared using methods known to those of skill in the art. See, for example, Hogan, et al. (1986) Manipulating the Mouse Embryo: A Laboratory Manual, Cold Spring Harbor Laboratory Press, Cold Spring Harbor, N.Y.

A knock-out construct is a nucleic acid sequence, such as a DNA or RNA construct, which, when introduced into a cell, results in suppression (partial or complete) of expression of a polypeptide encoded by endogenous DNA in the cell; A knock-out construct as used herein may include a construct containing a first fragment from the 5' end of the gene encoding a SOGA polypeptide, a second fragment from the 3' end of the gene and a DNA fragment encoding a selectable marker positioned between the first and second fragments. It should be understood by the skilled artisan that any suitable 5' and 3' fragments of a gene may be used as long as the expression of the corresponding gene is partially or completely suppressed by insertion of the transgene. Suitable selectable markers include, but are not limited to, neomycin, puromycin and hygromycin. In addition, the construct may contain a marker, such as diphtheria toxin A or thymidine kinase, for increasing the frequency of obtaining correctly targeted cells. Suitable vectors include, but are not limited to, pBLUESCRIPT, pBR322, and pGEM7.

Alternatively, a knock-out construct may contain RNA molecules such as antisense RNA, siRNA, and the like to decrease the expression of a gene encoding a SOGA polypeptide. Typically, for stable expression the RNA molecule is placed under the control of a promoter. The promoter may be regulated, if deficiencies in the protein of interest may lead to a lethal phenotype, or the promoter may drive constitutive expression of the RNA molecule such that the gene of interest is silenced under all conditions of growth. While homologous recombination between the knock-out construct and the gene of interest may not be necessary when using an RNA molecule to decrease gene expression, it may be advantageous to target the knock-out construct to a particular location in the genome of the host organism so that unintended phenotypes are not generated by random insertion of the knock-out construct.

The knock-out construct may subsequently be incorporated into a viral or nonviral vector for delivery to the host animal or may be introduced into embryonic stem (ES) cells. ES cells are typically selected for their ability to integrate into and become part of the germ line of a developing embryo so as to create germ line transmission of the knock-out construct. Thus, any ES cell line that can do so is suitable for use herein. Suitable cell lines which may be used include, but are not limited to, the 129J ES cell line or the Jl ES cell line. The cells are cultured and prepared for DNA insertion using methods well-known to the skilled artisan (e.g., see Robertson (1987) In: Teratocarcinomas and Embryonic Stem Cells: A Practical Approach, E. J. Robertson, ed. IRL Press, Washington, D.C.; Bradley et al., *Curr. Topics Develop. Biol.* 20:357 (1986); Hogan et al., (1986) Manipulating the Mouse Embryo: A Laboratory Manual, Cold Spring Harbor Laboratory Press, Cold Spring Harbor, N.Y.).

Insertion of the knock-out construct into the ES cells may be accomplished using a variety of methods well-known in the art, including, for example, electroporation, microinjection, and calcium phosphate treatment. For insertion of the DNA or RNA sequence, the knock-out construct nucleic acids are added to the ES cells under appropriate conditions for the insertion method chosen. If the cells are to be electroporated, the ES cells and construct nucleic acids are exposed to an electric pulse using an electroporation machine (electroporator) and following the manufacturer's guidelines for use. After electroporation, the cells are allowed to recover under suitable incubation conditions. The cells are then screened for the presence of the knockout construct.

Each knock-out construct to be introduced into the cell is first typically linearized if the knock-out construct has been inserted into a vector. Linearization is accomplished by digesting the knock-out construct with a suitable restriction endonuclease selected to cut only within the vector sequence and not within the knock-out construct sequence.

Screening for cells which contain the knock-out construct (homologous recombinants) may be done using a variety of methods. For example, as described herein, cells can be processed as needed to render DNA in them available for hybridization with a nucleic acid probe designed to hybridize only to cells containing the construct. For example, cellular DNA can be probed with $^{32}P$-labeled DNA which locates outside the targeting fragment. This technique can be used to identify those cells with proper integration of the knock-out construct. The DNA can be extracted from the cells using standard methods (e.g., see, Sambrook et al., Molecular Cloning: A Laboratory Manual 2nd Ed, (Cold Spring Harbor, N.Y., 1989)). The DNA may then be analyzed by Southern blot with a probe or probes designed to hybridize in a specific pattern to genomic DNA digested with one or more particular restriction enzymes.

Once appropriate ES cells are identified, they are introduced into an embryo using standard methods. They can be introduced using microinjection, for example. Embryos at the proper stage of development for integration of the ES cell to occur are obtained, such as by perfusion of the uterus of pregnant females. For example, mouse embryos at 3-4 days development can be obtained and injected with ES cells using a micropipet. After introduction of the ES cell into the embryo, the embryo is introduced into the uterus of a pseudopregnant female mouse. The stage of the pseudopregnancy is selected to enhance the chance of successful implantation. In mice, 2-3 days pseudopregnant females are appropriate.

Germline transmission of the knockout construct may be determined using standard methods. Offspring resulting from implantation of embryos containing the ES cells described above are screened for the presence of the desired alteration (e.g., knock-out of the SOGA polypeptide). This may be done, for example, by obtaining DNA from offspring (e.g., tail DNA) to assess for the knock-out construct, using known methods (e.g., Southern analysis, dot blot analysis, PCR analysis). See, for example, Sambrook et al., Molecular Cloning: A Laboratory Manual 2nd Ed, (Cold Spring Harbor, N.Y., 1989). Offspring identified as chimeras may be crossed with one another to produce homozygous knock-out animals.

Mice are often used as animal models because they are easy to house, relatively inexpensive, and easy to breed. However, other knock-out animals may also be made in accordance with the present invention such as, but not limited to, monkeys, cattle, sheep, pigs, goats, horses, dogs, cats, guinea pigs, rabbits and rats. Accordingly, appropriate vectors and promoters well-known in the art may be selected and used to generate a transgenic animal deficient in expression of a SOGA polypeptide.

In another embodiment, animal models may be created using animals that are not transgenic. For example, animal models of diabetes or obesity are well known in the art and can be used to study the effects of regulators of glucose production.

VIII. PHARMACEUTICAL COMPOSITIONS

As a further aspect, the invention provides pharmaceutical formulations and methods of administering the same to achieve any of the diagnostic or therapeutic effects (e.g., inhibition or stimulation of glucose production) discussed above. The pharmaceutical formulation may comprise any of the reagents discussed above in a pharmaceutically acceptable carrier, e.g., a polynucleotide encoding a SOGA polypeptide or a fragment thereof or a vector or cell comprising the polynucleotide, a SOGA polypeptide or fragment thereof, an antibody against a SOGA polypeptide, an antisense oligonucleotide, an siRNA molecule, a ribozyme, an aptamer, a peptidomimetic, a small molecule, or any other agent that modulates the activity of a SOGA polypeptide, including agents identified by the screening methods described herein.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The agents of the invention can be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the agent (including the physiologically acceptable salts thereof) is typically admixed with, inter alia, an acceptable carrier. The carrier can be a solid or a liquid, or both, and is preferably formulated with the agent as a unit-dose formulation, for example, a tablet, which can contain from 0.01 or 0.5% to 95% or 99% by weight of the agent. One or more agents can be incorporated in the formulations of the invention, which can be prepared by any of the well-known techniques of pharmacy.

A further aspect of the invention is a method of treating subjects in vivo, comprising administering to a subject a pharmaceutical composition comprising an agent of the invention in a pharmaceutically acceptable carrier, wherein the pharmaceutical composition is administered in a therapeutically effective amount. Administration of the compounds of the present invention to a human subject or an animal in need thereof can be by any means known in the art for administering agents.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, kidney or muscle). The most suitable route in any given case will depend on the nature and severity of the condition being treated and on the nature of the particular agent which is being used.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the agent can be administered in solid dosage forms, such as capsules, tablets, and powders, or in liquid dosage forms, such as elixirs, syrups, and suspensions. Agents can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the agent in a flavored base, usually sucrose and acacia or tragacanth; and pastilles comprising the agent in an inert base such as gelatin and glycerin or sucrose and acacia.

Formulations of the present invention suitable for parenteral administration comprise sterile aqueous and non-aqueous injection solutions of the agent, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising an agent of the invention, in a unit dosage form in a sealed container. The agent or salt is provided in the form of a lyophilizate which is capable of being reconstituted with a suitable pharmaceutically acceptable carrier to form a liquid composition suitable for injection thereof into a subject. The unit dosage form typically comprises from about 1 mg to about 10 grams of the agent or salt. When the agent or salt is substantially water-insoluble, a sufficient amount of emulsifying agent which is pharmaceutically acceptable can be employed in sufficient quantity to emulsify the agent or salt in an aqueous carrier. One such useful emulsifying agent is phosphatidyl choline.

Formulations suitable for rectal administration are preferably presented as unit dose suppositories. These can be prepared by admixing the agent with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the agent. Suitable formulations comprise citrate or bis\tris buffer (pH 6) or ethanol/water and contain from 0.1 to 0.2M of the agent.

The agent can alternatively be formulated for nasal administration or otherwise administered to the lungs of a subject by any suitable means, e.g., administered by an aerosol suspension of respirable particles comprising the agent, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the agent can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the agent can likewise be produced with any solid particulate medicament aerosol generator, by techniques known in the pharmaceutical art.

Alternatively, one can administer the agent in a local rather than systemic manner, for example, in a depot or sustained-release formulation.

Further, the present invention provides liposomal formulations of the agents disclosed herein and salts thereof. The technology for forming liposomal suspensions is well known in the art. When the agent or salt thereof is an aqueous-soluble salt, using conventional liposome technology, the same can be incorporated into lipid vesicles. In such an instance, due to the water solubility of the agent or salt, the agent or salt will be substantially entrained within the hydrophilic center or core of the liposomes. The lipid layer employed can be of any conventional composition and can either contain cholesterol or can be cholesterol-free. When the agent or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the agents disclosed herein or salts thereof, can be lyophilized to produce a lyophilizate which can be reconstituted with a pharmaceutically acceptable carrier, such as water, to regenerate a liposomal suspension.

In the case of water-insoluble agent s, a pharmaceutical composition can be prepared containing the water-insoluble agent, such as for example, in an aqueous base emulsion. In such an instance, the composition will contain a sufficient amount of pharmaceutically acceptable emulsifying agent to emulsify the desired amount of the agent. Particularly useful emulsifying agents include phosphatidyl cholines and lecithin.

In particular embodiments, the agent is administered to the subject in a therapeutically effective amount, as that term is defined above. Dosages of pharmaceutically active agents can be determined by methods known in the art, see, e.g., *Remington's Pharmaceutical Sciences* (Maack Publishing Co., Easton, Pa.). The therapeutically effective dosage of any specific agent will vary somewhat from agent to agent, and patient to patient, and will depend upon the condition of the patient and the route of delivery. As a general proposition, a dosage from about 0.1 to about 50 mg/kg will have therapeutic efficacy, with all weights being calculated based upon the weight of the agent, including the cases where a salt is employed. Toxicity concerns at the higher level can restrict intravenous dosages to a lower level such as up to about 10 mg/kg, with all weights being calculated based upon the weight of the agent, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 μmol/kg to 50 μmol/kg, and more particularly to about 22 μmol/kg and to 33 μmol/kg of the agent for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, clucks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults. In other embodiments, the subject is an animal model of diabetes or other metabolic disorder.

The present invention is more particularly described in the following examples that are intended as illustrative only since numerous modifications and variations therein will be apparent to those skilled in the art.

EXAMPLE 1

Identification of SOGA

Type II diabetes is associated with high glucose production. Obesity increases glucose production by lowering circulating levels of the hormone adiponectin. Therefore, type II diabetes can be treated by stimulating the adiponectin signaling pathway. Adiponectin lowers circulating glucose by inhibiting glucose production from the liver. Adiponectin inhibits glucose production by activating AMP-activated kinase (AMPK). AMPK stimulates fatty acid (FA) oxidation. The inhibition of glucose production by a signaling intermediate that increases FA oxidation is counter-intuitive because ATP generated from FA oxidation fuels glucose production. Furthermore, AMPK stimulates autophagy, a regulated mechanism of intracellular degradation that provides the biochemical intermediates for glucose production through the hydrolysis of proteins, glycogen and triglycerides. This deadlock led to the hypothesis that adiponectin inhibits glucose production through a novel mediator. Insulin inhibition of glucose production in the liver is mediated by the suppression of lysosome activity. We treated rat hepatoma cells with full-length recombinant adiponectin and identified the proteins that were bound to APPL1 in a co-immunoprecipitation assay using proteomics analysis. APPL1 was previously identified in a yeast 2-hybrid screen using the intracellular region of the adiponectin receptor. Proteomics analysis revealed a gene we are calling SOGA (also called TOA (Target Of Adiponectin)) that encodes a 161 kDa protein containing (1) a leucine zipper motif that enables binding to the leucine zipper motif of APPL1 and (2) Atg16 and Rab5-binding motifs that enable participation in membrane assembly for autophagy. The hydrolysis of proteins and glycogen by autophagy increases glucose production by producing biochemical intermediates for gluconeogenesis and glycogenolysis. Northern blot analysis revealed that SOGA is ubiquitously expressed as a 3.0 and a 4.5 kb mRNA. Our current hypothesis is that adiponectin stimulation of SOGA (NCBI Accession: FJ977045) can suppress glucose production.

We verified the expression of SOGA in the liver and other tissues by RT-PCR and Northern blot analysis. There are no publications describing SOGA, its gene, mRNA or amino acid sequence. The open reading frame of murine SOGA is derived from 16 exons. SOGA cDNA encodes a 1434 amino acid protein that lacks transmembrane domains. SOGA contains a leucine zipper motif that we predict allows SOGA to bind to the leucine zipper motif of APPL1 in our co-immunoprecipitation experiment (FIG. 1). The predicted regions of interest in SOGA include (1) a leucine zipper motif, (2) ATG16 motifs, (3) a Rab5 motif, (4) a casein kinase domain, (5) multiple myristoylation and glycosylation sites and (6) multiple kinase specific phosphorylation sites (FIG. 1). Amino acid sequence alignment shows that murine SOGA is 91% identical to human SOGA. When substitutions for similar amino acids are taken into account, murine SOGA is 95% identical to human SOGA. SOGA is a highly conserved gene in mammals but absent in lower eukaryotes like yeast. Our current model is that adiponectin signaling triggers SOGA binding to APPL1, a proximal target of the adiponectin receptor. Based on conserved domain predictions, SOGA binding to APPL1 contributes to adiponectin inhibition of protein degradation and glucose production. This may be accomplished through the binding of SOGA to APPL1, the proteolytic cleavage of SOGA and the secretion of its 25 kDa fragment.

Figure 2:
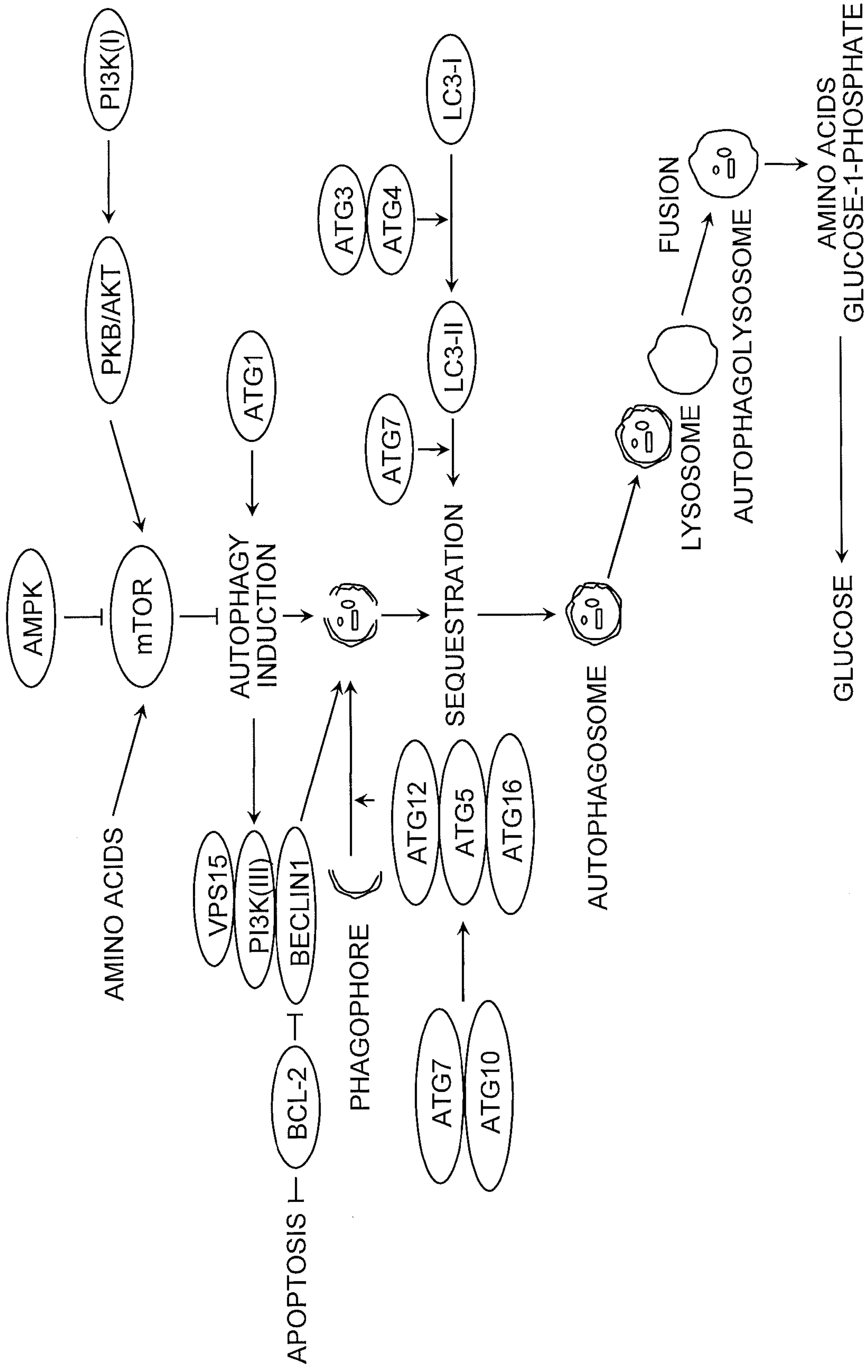
FIG. 2 shows the current model of autophagocytosis and the autophagy machinery showing mTOR and ATG16 in black.

The formation of the phagophore, a primary step in autophagy, can lead to the digestion of proteins and glycogen providing the biochemical intermediates for glucose production (FIG. 2). Atg16-Atg5-Atg12 forms a protein complex that is essential for the formation of an autophagosome. Atg12 is covalently conjugated to Atg5 by ubiquitination-like reactions that involve Atg7 and Atg10. Overexpression of Atg5 and Atg12 in yeast causes an increase in autophagy that is absent in mammalian cells, suggesting the existence of a novel protein in higher eukaryotes. Although 31 autophagy-related (Atg) proteins have been identified in yeast, SOGA is highly conserved in mammals but bears little homology to any gene product in yeast. Thus, the study of SOGA can lead to the elucidation of the mechanisms governing autophagy in mammals.

We predicted that SOGA plays a role in adiponectin's inhibition of glucose production based on its binding to APPL1 under adiponectin exposure and the conserved functional domains of SOGA which include (1) a leucine zipper motif that enables SOGA to bind to APPL1, (2) an ATG16 (autophagy 16) motif that enables SOGA to initiate autophagy through the formation of the phagophore, (3) Rab5 motif (a small GTPase) that enables the fusion of the autophagosome and lysosome, (4) casein kinase domain that enables a downstream signaling cascade, (5) myristoylation and glycosylation sites that enable anchoring and (6) multiple kinase-specific phosphorylation sites that enable the modulation of SOGA by kinases and phosphatases (FIG. 1). Further insight into SOGA can increase our understanding of nutrient metabolism and lead to new ways of preventing and treating diabetes.

Figure 3:
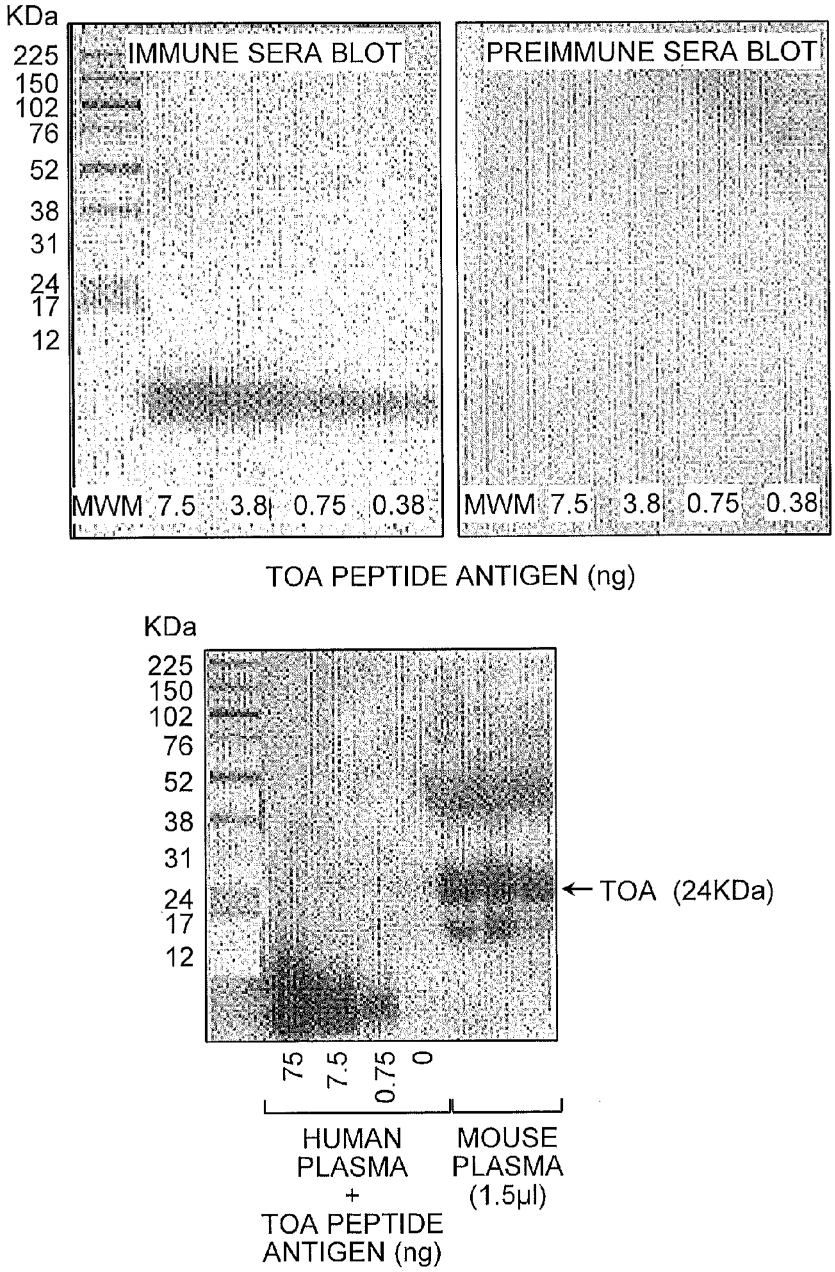
FIG. 3 shows proteolytic cleavage of SOGA yielding a circulating 25 kDa C-terminal fragment.
Figure 4:
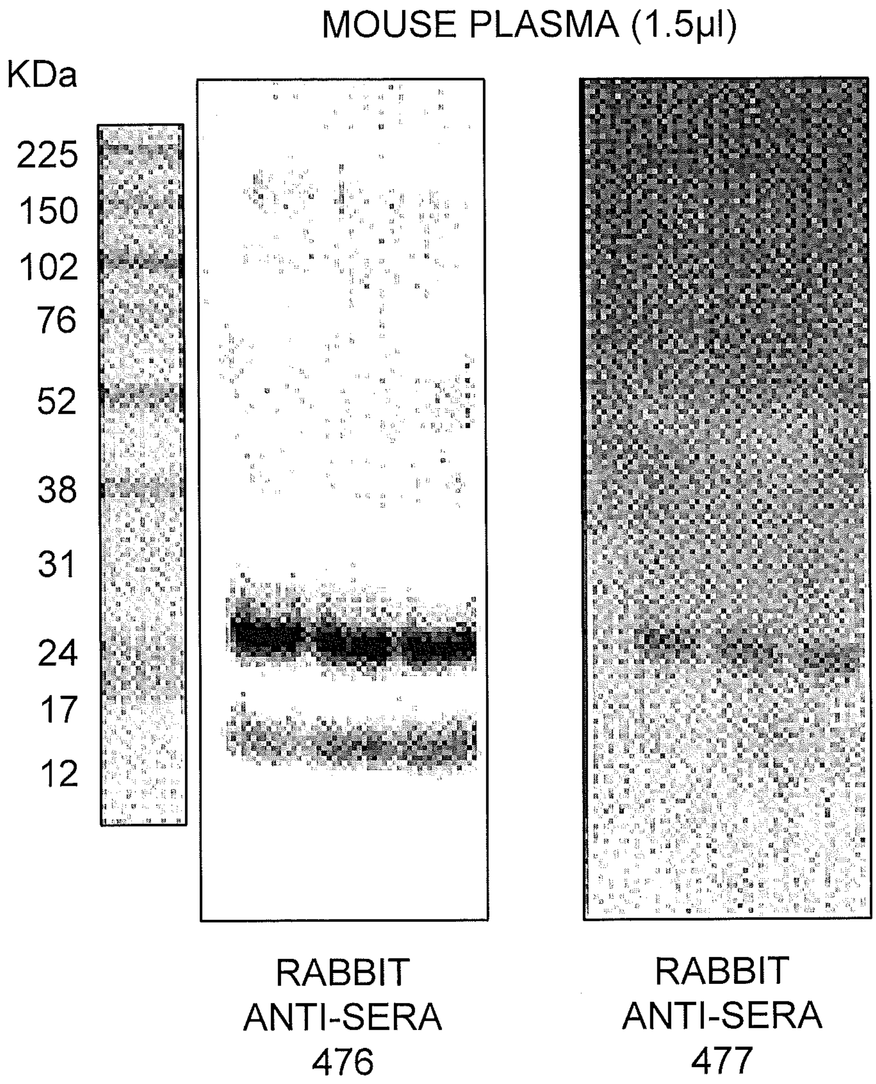
FIG. 4 shows that antisera from two different rabbits immunized with two different peptide antigens, 476 and 477, detected a 25 kDa band in mouse plasma.

Species specific (mouse) SOGA peptide antigen (476) was detected with immune but not pre-immune sera from New Zealand White rabbits (FIG. 3, left panel). The signal intensity is proportional to the peptide antigen concentration. Using our rabbit polyclonal antisera (476) that is specific for mouse SOGA, SOGA was detected in mouse plasma at 25 kDa but not in human plasma (FIG. 3, right panel). Antisera from two different rabbits immunized with two different peptide antigens, 476 and 477 specific for mouse SOGA, detected a 25 kDa band in mouse plasma (FIG. 4). Antigen peptides 476 and 477 correspond to overlapping amino acid sequences in mouse SOGA.

Figure 5:
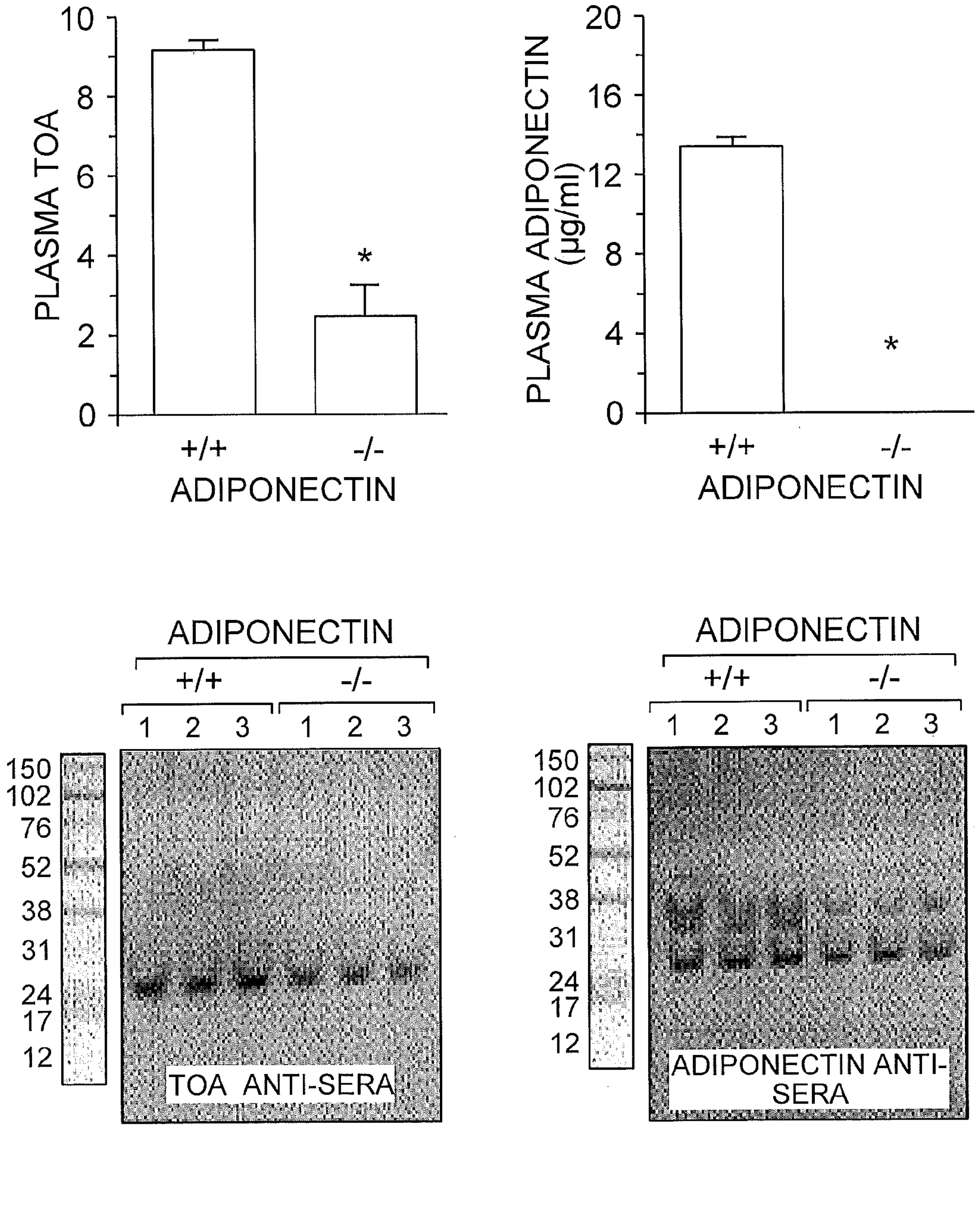
FIG. 5 shows that the concentration of SOGA in plasma corresponded with circulating levels of adiponectin.
Figure 6:
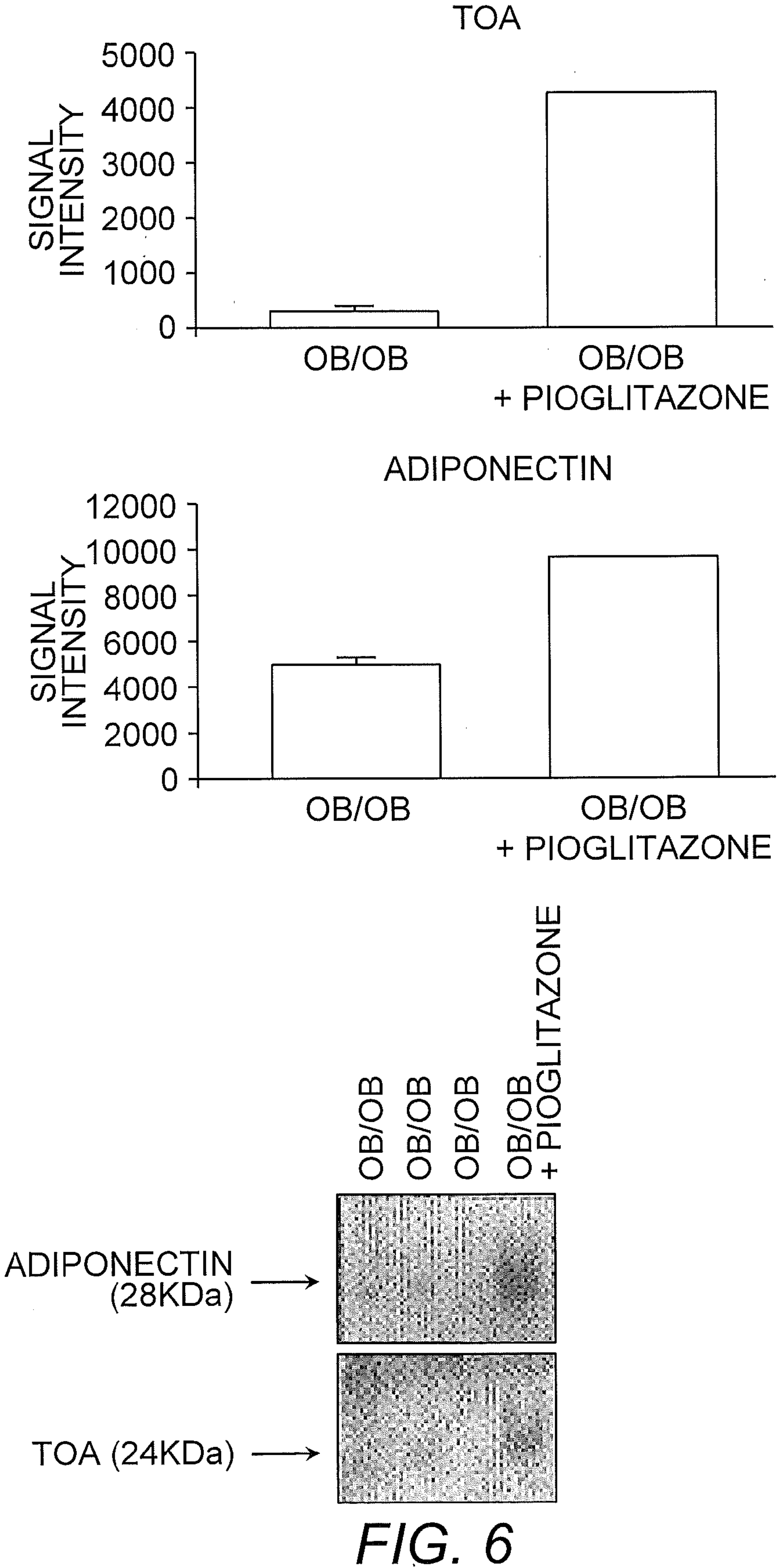
FIG. 6 shows western blot and densitometry of adiponectin and SOGA in ob/ob control mice and ob/ob mice treated with pioglitazone.
Figure 7:
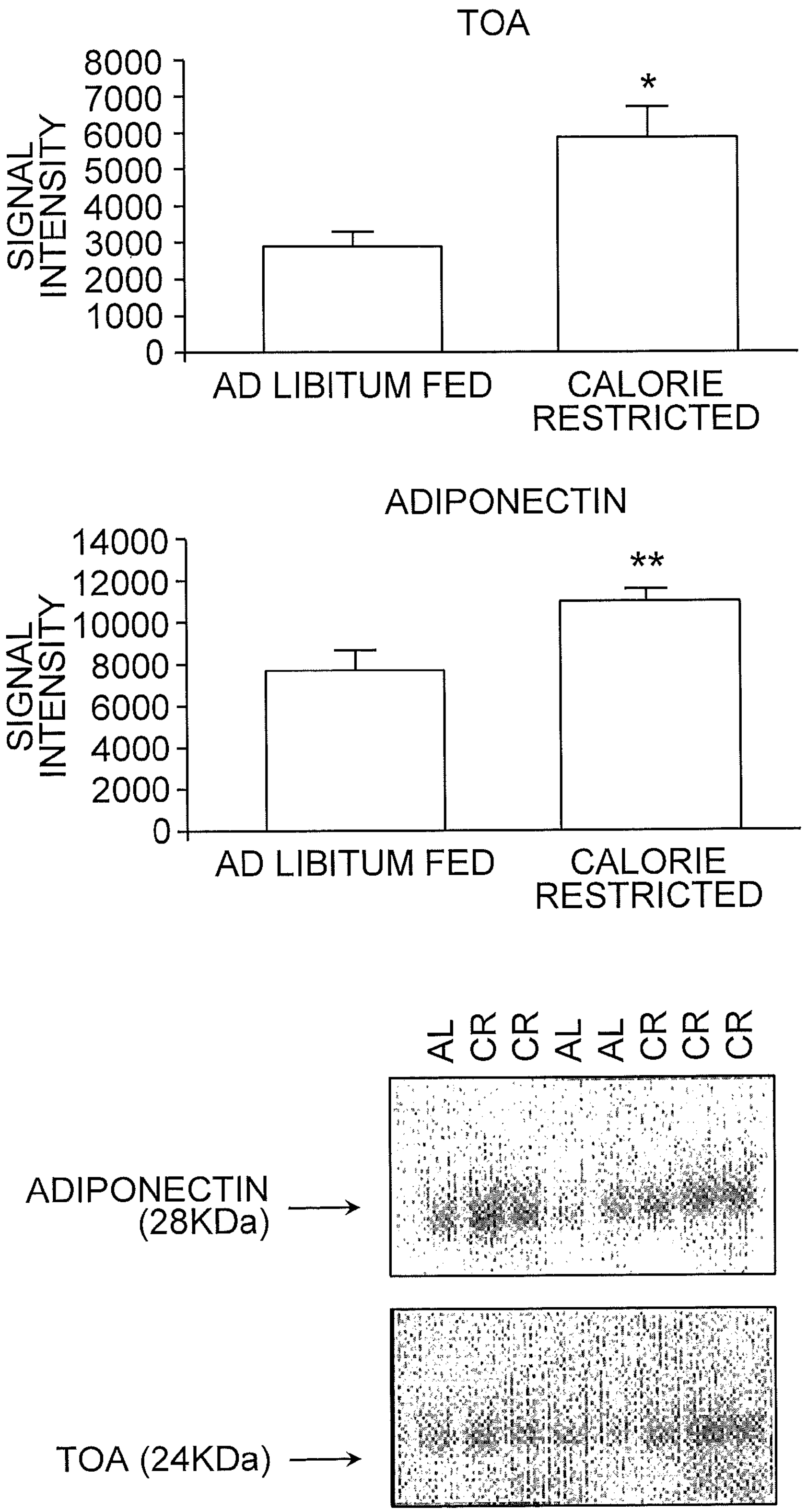
FIG. 7 shows western blot and densitometry of adiponectin and SOGA in ad libitum and calorie restricted fed C57B1 mice.
Figure 8:
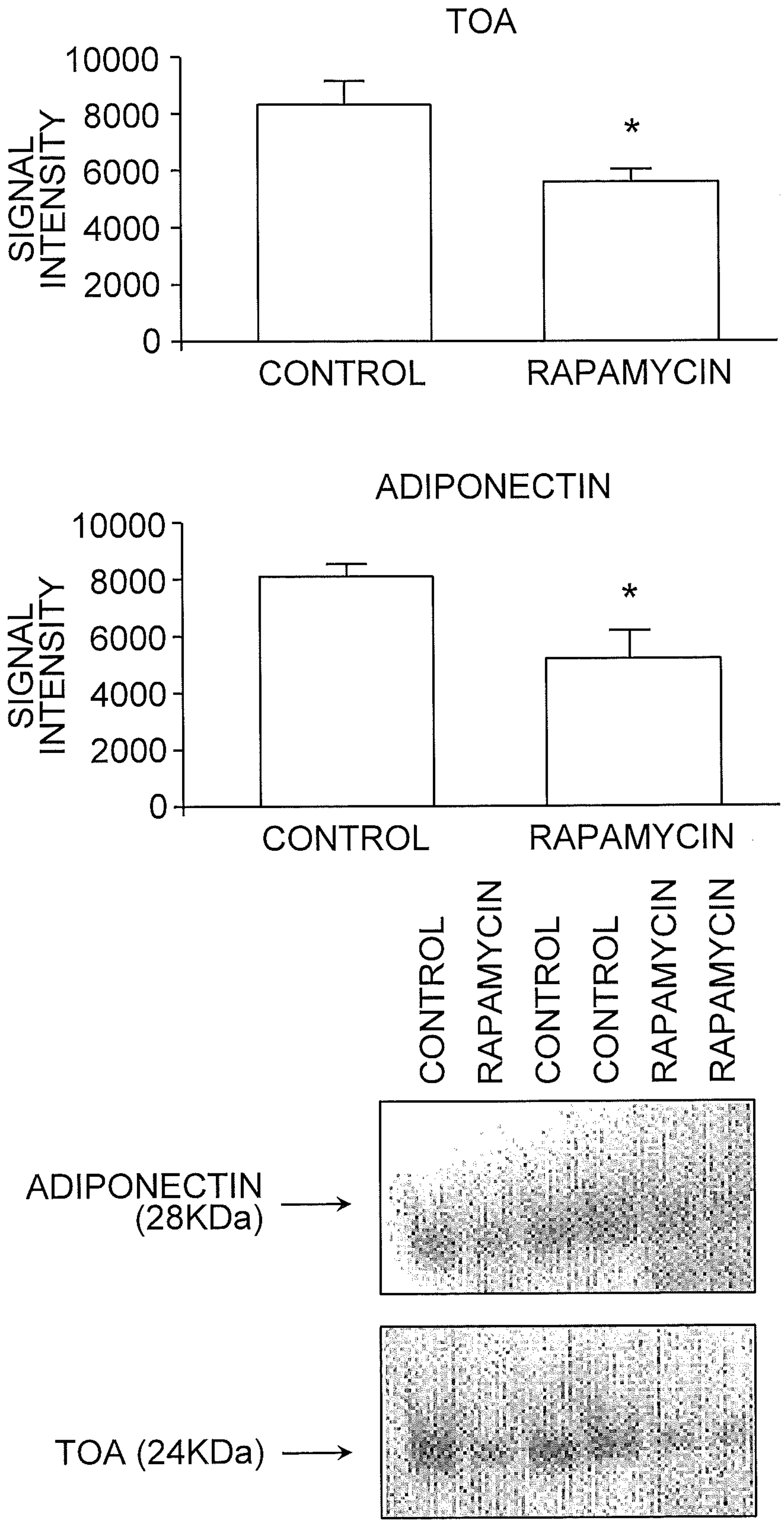
FIG. 8 shows western blot and densitometry of adiponectin and SOGA in rapamycin and control fed C57B1 mice.
Figure 9:
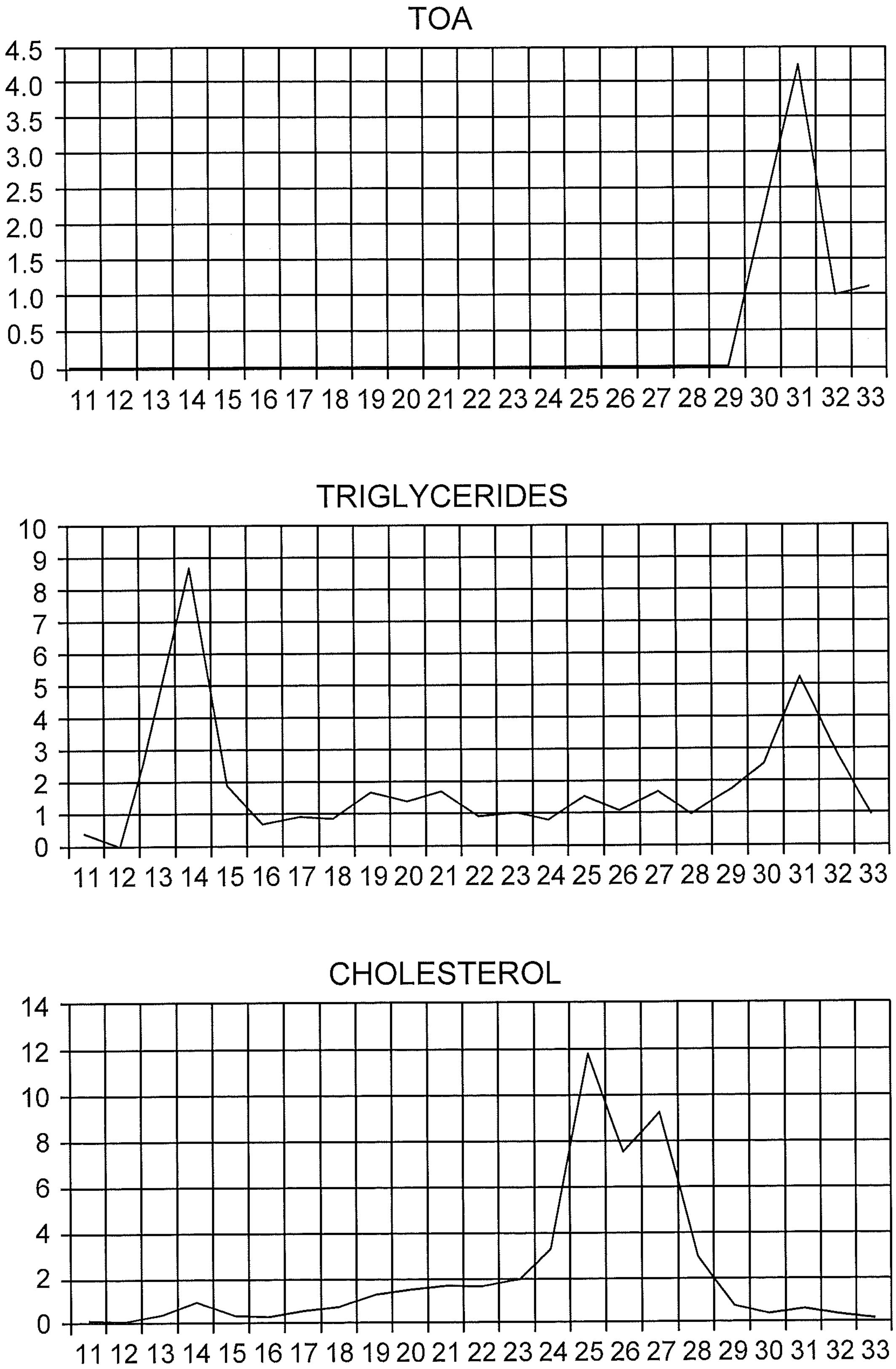
FIG. 9 shows FPLC fraction analysis of mouse plasma for SOGA.

The concentration of SOGA in plasma corresponded with circulating levels of adiponectin (FIG. 5). Plasma was sampled from young female C57B1 adiponectin null and wild-type mice. Western blot and densitometry of adiponectin and SOGA in ob/ob control mice and ob/ob mice treated with pioglitazone showed that adiponectin and SOGA were increased in ob/ob mice on pioglitazone compared to controls (FIG. 6). Western blot and densitometry of adiponectin and SOGA in ad libitum and calorie restricted fed C57 mice showed that adiponectin and SOGA were increased in calorie restricted mice compared to those fed ad libitum ($P<0.05$ for statistical significance) (FIG. 7). Western blot and densitometry of adiponectin and SOGA in rapamycin and control fed C57B1 mice revealed that SOGA was decreased in rapamycin fed mice compared to controls ($P<0.05$ for statistical significance) (FIG. 8). FPLC fraction analysis of mouse plasma for SOGA was performed (FIG. 9). Graphs show SOGA, triglyceride, and cholesterol levels in FPLC fractions 11-33.

In summary, SOGA (TOA) is a novel protein that we have identified through proteomics and a co-immunoprecipitation assay; it binds to APPL1 under adiponectin exposure. The SOGA gene contains Atg16 and Rab5-binding motifs that are indicative of autophagic activities; it is hypothesized that adiponectin stimulation of SOGA can suppress glucose production. SOGA peptide antigen was detected by immune sera from NZW rabbits; SOGA was detected at 25 kDa in mouse plasma but not human plasma. Two distinct antigens corresponding to overlapping segments of SOGA produced antisera that detected a 25 kDa SOGA. Circulating levels of SOGA were greatly suppressed in adiponectin null (−/−) mice. Adiponectin and SOGA were increased by pioglitazone, and calorie restriction, but were suppressed by rapamycin. FPLC analysis indicates that SOGA circulates below 100 kDa.

EXAMPLE 2

Experimental Methods

Mass Spectrometry.

McArdle rat hepatoma cells were exposed to adipocyte conditioned media with or without adiponectin (Brooks et al., *J. Biol. Chem.* 282:35069 (2007)). Cell lysates were digested with proteomics grade trypsin (Sigma) and filtered through YM-10 molecular weight cutoff filters (Millipore, Bedford, Mass.). Tryptic digests were injected into an LCQ-Deca Ion Trap mass spectrometer coupled to a Surveyor HPLC system (Thermo Fisher Scientific, Waltham, Mass.). The solvent, 50% methanol and 0.1% formic acid, was delivered to the spectrometer at 200 μL/min. Peptide masses were acquired in positive mode using electrospray ionization under the following source conditions: spray voltage was 5 kV, sheath gas was 40 (arbitrary units), auxiliary gas was 20 (arbitrary units), and heated capillary temperature was 350° C.

Cloning of Murine SOGA.

Total RNA was obtained from primary mouse hepatocytes using Triazol reagent (Invitrogen). mRNA was isolated using Oligotex mRNA Kit (Qiagen). Primers used to clone SOGA were designed using publically available genomic and mRNA sequence data based on the open reading frame of SOGA peptides detected by mass spectrometry. The 4.7 kb SOGA cDNA was isolated by annealing two PCR products using overlap extension. RNA ligase mediated RACE (Ambion) was used to clone the sequence from the 5'-end of SOGA mRNA. The cDNA for human SOGA was cloned by a similar method.

Antibody Production.

Human- and murine-specific polyclonal antisera were produced in three New Zealand White rabbits (Franklin Rabbitry, NC) using a human-specific peptide antigen STQSLTS CFARSSRSAIRHSPSKC (SEQ ID NO:5) and two partially overlapping murine-specific peptide antigens CSAQSLASCFIRPSRN (SEQ ID NO:6) and SAQSLASC*FIRPSRNPIRHSPSKC (SEQ ID NO:7), where $C^*$ represents acemidomethyl cysteine. Synthetic peptides were purified by HPLC and analyzed on the LCQ-Deca Ion Trap mass spectrometer to confirm their molecular weight. Antigenic peptides (10 mg) were dissolved in 0.1 M $NaH_2PO_4$ (pH 7.2)/0.05 M NaCl and conjugated to keyhole limpet hemocyanin (KLH; 4 mg) before injection. KLH conjugated peptides were dissolved in 3 ml of 0.03% trifluoroacetic acid and added to 3 ml complete Freund's adjuvant (Sigma). New Zealand White rabbits (Franklin Rabbitry, Wake Forest, N.C.) were injected intradermally using multiple injection sites. After 5 weeks, each animal was reinjected subcutaneously with KLH conjugated antigen in 1 ml of 50% incomplete Freund's adjuvant (Sigma). Four weeks later, 20 ml of blood were collected and rabbits were reimmunized. Injections and bleedings were performed at monthly intervals thereafter. The antibody production protocol was approved by UNC's Institutional Animal Care and Use Committee (IACUC).

Hepatocyte Studies.

Mouse livers were perfused with a Krebs-Ringer-HEPES buffer containing collagenase (Sigma-Aldrich). Livers were isolated and cells were dispersed by gentle shaking and filtered through sterile nylon gauze. Cells were washed twice with sterile phosphate-buffered saline and purified by centrifugation in 50% isotonic Percoll (Sigma-Aldrich). Cells were resuspended with Krebs-Ringer-HEPES+$Ca^{2+}$ buffer to a total volume of 10 ml. Viability was validated via trypan blue exclusion and routinely exceeded 90%. Freshly isolated mouse hepatocytes were plated at $10^5$ cells per well in 12-well culture plates coated with rat tail collagen I (BD Biosciences). Cells were maintained in Dulbecco's modified Eagle medium (DMEM; Caisson Laboratories), 25 mM glucose and 10% horse serum (HS). Adiponectin was provided from adipocyte conditioned media with or without adiponectin (Brooks et al., *J. Biol. Chem.* 282:35069 (2007)). SOGA siRNA, AICAR (500 μM) or LY293004 (10 nM) were introduced to the media 48 hours before the measurement of glucose production. siRNA sequences corresponding to base pairs 333-351 and 1988-2007 on the open reading frame of murine SOGA were selected using a rational design algorithm (Invitrogen). Transfection with a pool of 2 siRNAs targeting SOGA had a greater knockdown efficiency than transfecting with the individual siRNAs. Transfection was achieved by electroporation using the Mouse Hepatocyte Nucleofector Kit (LONZA) according to the manufacturer's protocol. In brief, freshly isolated mouse hepatocytes were diluted to $3\times10^6$ cells/tube in media without antibiotics and centrifuged at 2,000 rpm for 2 minutes. The supernatant was removed and the cells were resuspended in 100 μl of Nucleofector solution containing 100 nM of siRNA. The cell suspension was transferred to an electroporation cuvette which was placed in a Nucleofector I electroporation device and pulse charge was applied for 2 minutes using program T-28. Hepatocytes received 1.0 ml of media and were transferred to 12 well plates. SOGA expression, valine and glucose production were assayed 72 hours after siRNA transfection. Media was replaced with glucose-free DMEM containing MG-132 (10 μM), an inhibitor of the ubiquitin-proteasome pathway of protein degradation, for 6-8 hours to measure hepatocytes glucose production. Glucose was measured by colorimetric assay (Autokit Glucose CII) (Brooks et al., *J. Biol. Chem.* 282:35069 (2007)). Valine in the medium was measured by a UPLC (Waters) coupled TSQ-Quantum ultra triple quad mass analyzer (ThermoFinigan) in the Biomarkers Facility Core at UNC. Valine was measured in selected reaction monitoring mode (SRM) using the MS/MS transition of 118→72.

Lysosomal Activity.

Autophagic activity was estimated by lysosome and late autophagosome vacuole staining using LysoTracker Red DND 99 (Invitrogen), a membrane permeable fluorescent labeled basic amine with high affinity for the acidic interior of the lysosome and late autophagosome vacuole (Klionsky et al., *Autophagy* 4:151 (2008)). Cell medium was removed and replaced with GF/DMEM containing 50 nM LysoTracker Red. Cells were incubated for 30 min at 37° C. and the medium was replaced with GF/DMEM. Digital images were obtained at the Light Microscopy Facility at UNC with an Olympus IX81 Motorized Inverted Microscope, a 40×/1.30 Oil DIC lens, Camera pixel count: Hamamatsu C10600-10B 1344×1024 using the acquisition software Volocity 5.3.2 (Perkin Elmer). Fluorescence Filter Cubes Specifications (Semrock, Inc.) were TXRED-4040B for rhodamine and Texas Red: Exciter 562 nm±20, Dichroic R 530-585/T 601-800, Emitter 642±20. *Lysosome* and late autophagosome vacuole number was determined from digital images as isolated punctuate staining, greater than background staining intensity threshold, distinct from lipid droplets in clearly demarcated cells containing two nuclei. Spot recognition and enumeration according to the foregoing definition was determined by two individuals.

Mouse Studies.

Mice were housed in ventilated isolator cage systems in a pathogen-free barrier facility maintained at 23° C., 55% humidity on a 12-h light/12-h dark cycle. Mice received a standard chow diet consisting of 73% carbohydrate, 18% protein, 4% fat and 5% ash (Purina). Young (3-6 month old) female C57B1/6J calorie restricted (CR) and ad libitum fed (AL) mice were maintained as previously described (Combs et al., *Diabetes* 52:268 (2003)). Adjustments were made to ensure that CR mice received 70% of the ad libitum food intake. Blood samples were collected at 1300 from the tail tip using heparinized capillary tubes (Fisher) and stored at −20° C. Male ob/ob mice (FVB background strain) received a daily dose of pioglitazone at 0.6 mg/kg BW in 0.025% (w/w) carboxymethylcellulose by oral gavage for 4 days. Control mice received carboxymethylcellulose by oral gavage for 4 days. Blood was collected from the tail tip on day 5 and analyzed for glucose, adiponectin and 25 kDa SOGA. Immediately after the collection of blood samples, ob/ob mice were sacrificed by cervical dislocation for tissue collection. Northern blot analysis for SOGA mRNA and 18S RNA was performed using 20 μg of liver RNA. NOD mice were bred and housed as previously described (Wong et al., *J. Immunol.* 176:1637 (2006)). Where indicated, diabetic NOD mice were injected with 5 units of insulin (NPH Human Insulin, Isophane Suspension; 100 U/ml Novolin; Novo Nordisk) 24 hours prior to blood collection. Adiponectin transgenic mice were produced as previously described (Combs et al., *Endocrinology* 145:367 (2004)). Glucose was measured by colorimetric assay. Adiponectin and SOGA were measured by SDS-PAGE analysis using 1 μl of plasma. The total concentration of protein in plasma, measured by BCA assay (Pierce), did not differ between groups. Experimental procedures were approved by IACUC.

Human Studies.

Thirteen healthy women between the ages of 20-63, body mass indexes (in kg/m$^2$) between 20.2 and 31.9, were included for this study. Inclusion was contingent on a good, age-typical health status, as ascertained by physical examination and standard clinical laboratory tests such as complete blood count, blood chemistries, fasting glucose, insulin, lipid and liver function tests, liver lipid content and the presence of no known chronic disease including diabetes. Subjects were admitted to the Clinical and Translational Research Center of UNC and placed on a balanced weight maintenance diet for 10 days (Fischer et al., *Am. J. Clin. Nutr.* 85:1275 (2007)). Circulating SOGA and adiponectin were measured from plasma samples collected from an intravenous catheter following an overnight fast. The race-ethnicity distribution of the participants was white (63%), African American (27%), Asian (6%), and Native American (4%), which reflected the local population characteristics of the Raleigh-Durham-Chapel Hill area. Plasma adiponectin and SOGA were determined by SDS-PAGE using polyclonal antisera against human adiponectin and human SOGA, horseradish peroxidase linked secondary anti-rabbit IgG. Circulating adiponectin and SOGA levels were measured by enhanced chemiluminescence (ECL) signal intensity. Human studies were performed under an IRB approved protocol (CTRC-2645; Study: 07-1158).

Statistical Analysis.

Student's t test was used to identify significant differences when data within groups showed a normal distribution and Wilcoxon-Rank Sum test was used when data did not show a normal distribution. P values less than 0.05 were considered significant.

EXAMPLE 3

Identification of SOGA by Mass Spectrometry

Protein extracts from hepatoma cells exposed to adiponectin were digested with trypsin and analyzed by mass spectrometry. Mass spectrometry revealed a peptide, KVLPSEEDDFLEVNSM (SEQ ID NO:8), encoded by a gene located on chromosome 2 in mice (2qH1) and chromosome 20 in humans (20q11). Mouse liver RNA was used to clone the full length 4.7 kb SOGA cDNA (GENBANK ID: FJ977045). Northern blot analysis, using a probe recognizing the C-terminal end of SOGA, revealed a single dominant 4-5 kb band in the liver. The ORF of the cDNA clone predicts a 161 kDa protein that contains an internal secretory peptide sequence, FKHNFLLLFMKLRWFLKRWRQG (SEQ ID NO:9) (FIG. 10). On the basis of computational methods that incorporate signal peptide and cleavage site predictions, SOGA is cleaved between G at the end of the signal peptide and K at the beginning of at the peptide identified by mass spectrometry (Emanuelsson et al., *Nat. Protoc.* 2:953 (2007)).

FIG. 10A is a map showing the location of the conserved ATG16 and Rab5-binding motifs, the secretory signal peptide and the species-specific epitope in the predicted 161 kDa SOGA. The map also shows the predicted domains of the 80 kDa peptide detected in vitro and the 25 kDa peptide detected in plasma. FIG. 10B shows the amino acid sequence for murine SOGA (SEQ ID NO:2) showing the location of the Atg16 (232-375) and Rab5-binding (757-886) motifs underlined, the signal peptide (681-702) in bold, the tryptic peptide identified by mass spectrometry (703-718) shaded and the species specific domain (1392-1416) in a box. The position of the internal signal peptide explains why our antibodies, recognizing the species-specific epitope near the C-terminus of SOGA, detect an 80 kDa SOGA peptide rather than the 161 kDa SOGA protein.

EXAMPLE 4

Function of SOGA in Primary Hepatocytes

Figure 11A:
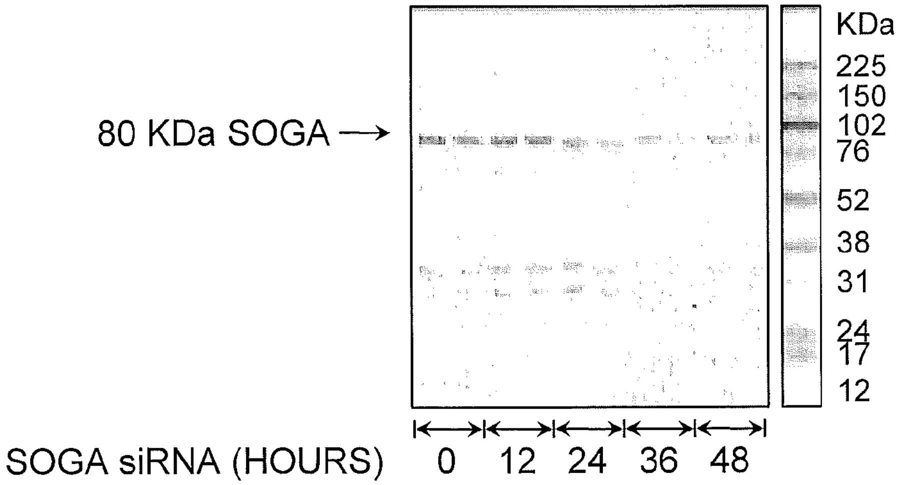
FIGS. 11A-11D show the function and regulation of SOGA in primary hepatocytes.
Figure 11B:
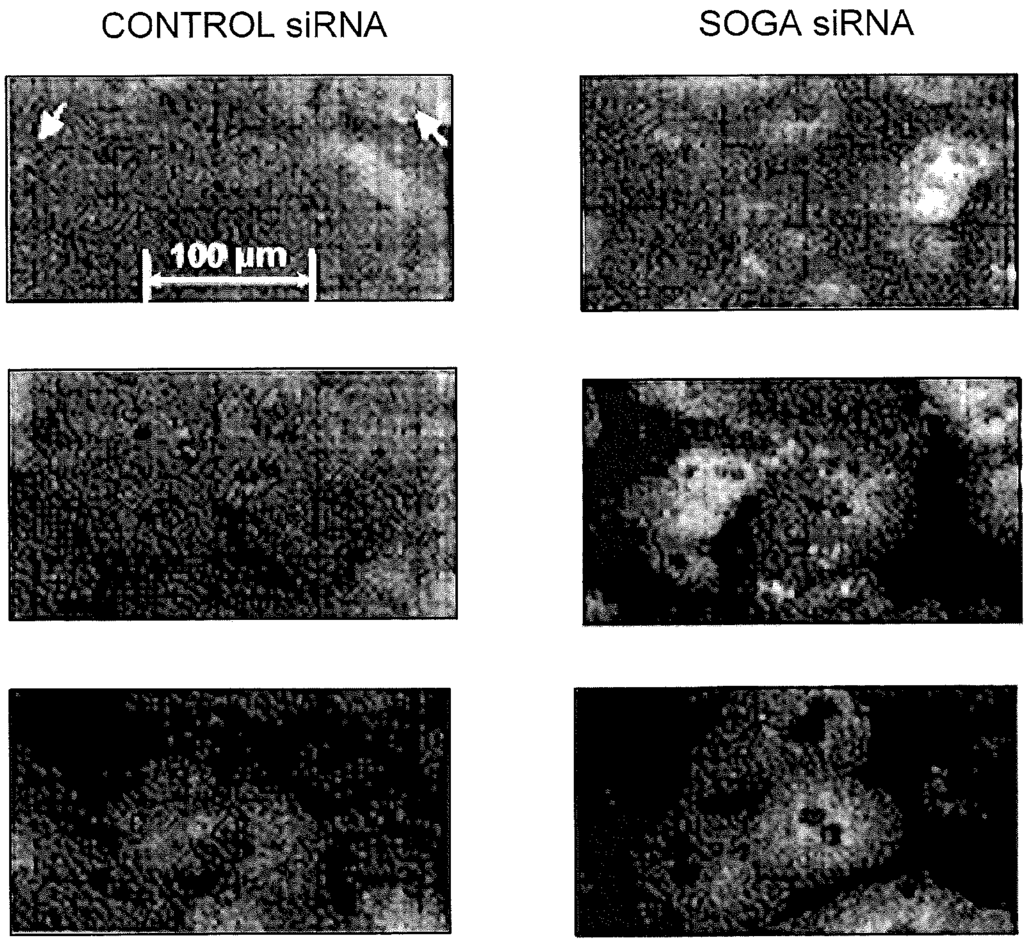
Figure 11C:
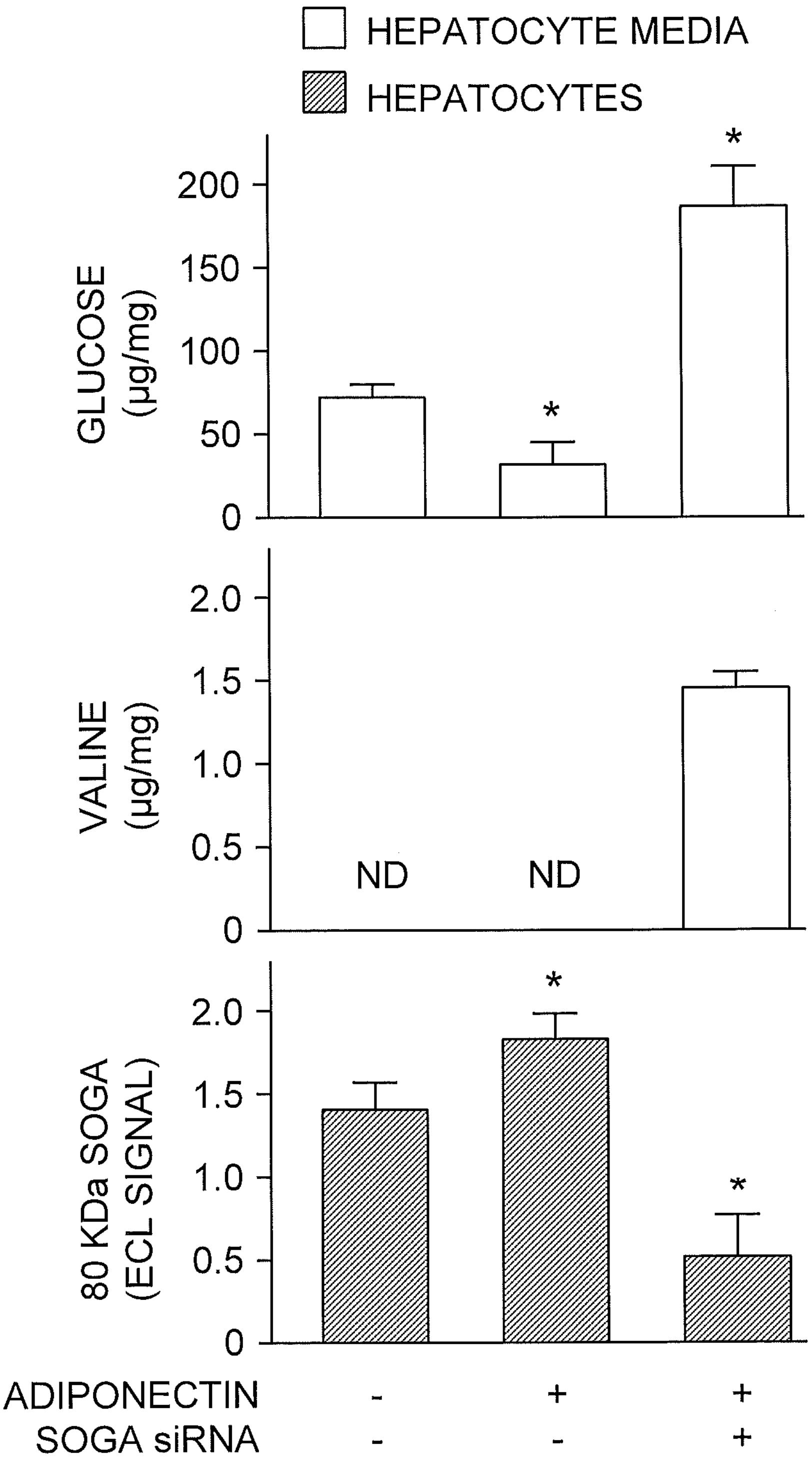

Consistent with the predicted position of the cleavage site, rabbit antisera recognizing the species-specific domain on the C-terminal region of murine SOGA recognized a single 80 kDa protein in isolated hepatocytes (FIG. 11A). FIG. 11A shows a representative SDS-PAGE of primary murine hepatocyte samples showing the knockdown of 80 kDa SOGA as a function of time after exposure to siRNA. siRNA suppression of SOGA caused a dramatic increase in lysosome and late autophagic vacuole number (2.0±0.2 per cell compared to 17.5±2.0 per cell where n=25-30 cells per group, $p<0.0001$) as indicated by isolated punctate acidotropic dye staining which provides correlative data on autophagy (FIG. 11B) (Klionsky et al., *Autophagy* 4:151 (2008)). FIG. 11B shows representative purified binucleate hepatocyte cultures transfected with control (left) or SOGA siRNA (right) stained with the lysosome-specific fluorescent dye LysoTracker Red. The hypothesis that SOGA inhibits autophagy is further supported by the reduction of total cell protein content 48 hours after siRNA suppression of SOGA (11.2±0.6 μg/well compared to 16.3±0.4 μg/well; n=4 per group; $p<0.05$). FIG. 2C depicts bar graphs showing the effects of adiponectin and SOGA siRNA on glucose and valine secretion in hepatocyte conditioned media (top and middle) and 80 kDa SOGA measured by densitometry of ECL (enhanced chemiluminescent signal) after SDS-PAGE (bottom). Adiponectin exposure caused a 40% increase of SOGA in primary hepatocytes and a 50% reduction in glucose production (FIG. 11C). siRNA suppression of SOGA blocked the inhibition of glucose production and stimulated valine secretion (FIG. 11C). The secretion of valine, an essential amino acid that cannot be metabolized, due to the absence of branched chain aminotransferase in hepatocytes, also suggests an increase in autophagy. These results support the hypothesis that the elevation of SOGA in response to adiponectin exposure is linked to the inhibition of autophagy.

EXAMPLE 5

Figure 11D:
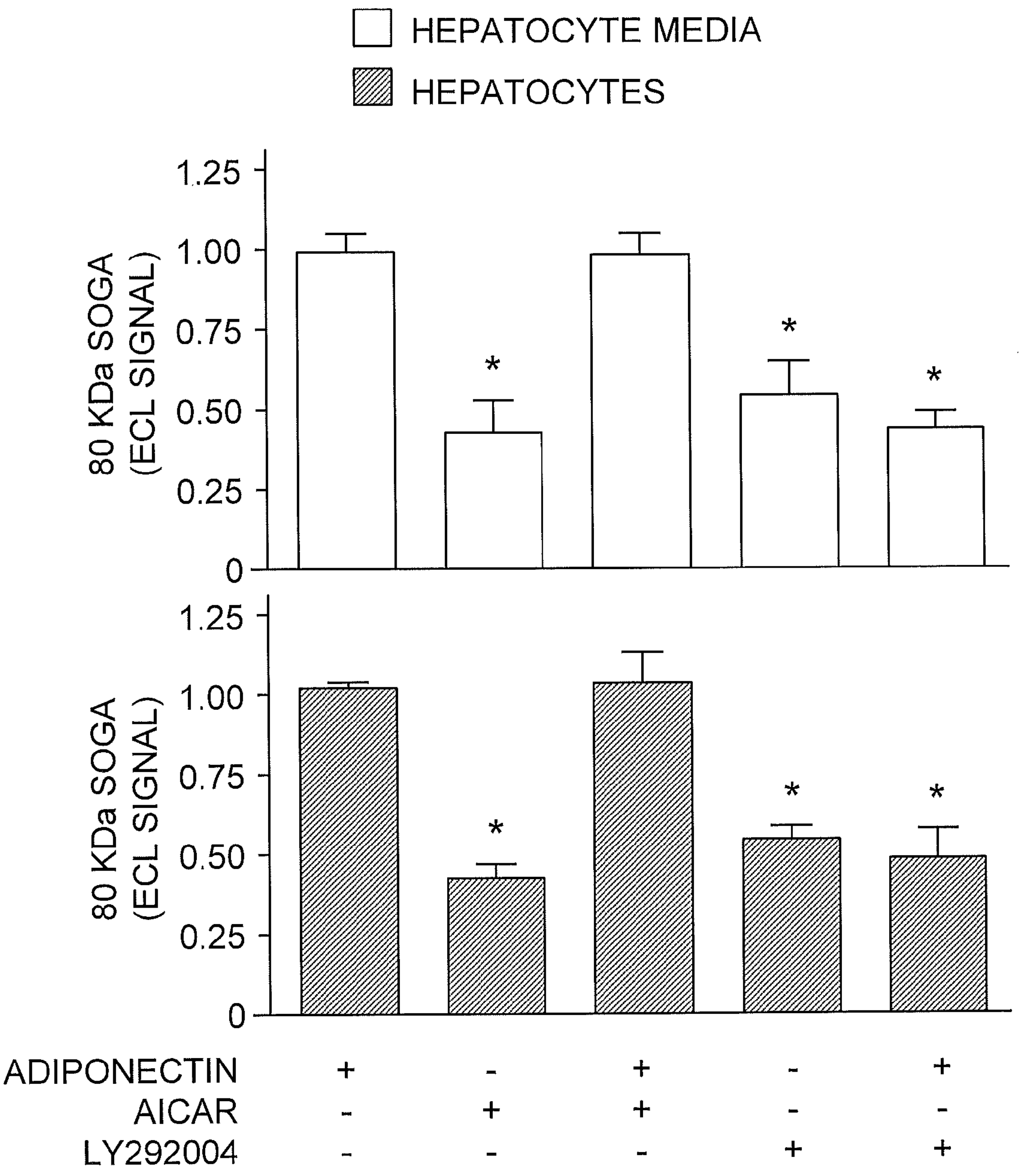

Regulation of SOGA in Primary Hepatocytes and the Correlation of Intracellular and Extracellular Levels of SOGA FIG. 11D depicts bar graphs showing the roles of AMPK and PI3K on adiponectin regulation of intracellular and extracellular SOGA levels. Primary hepatocytes were incubated in the presence or absence of 500 μM AICAR, a stimulator of AMPK, or 10 nM LY294002, a PI3K inhibitor. Bars represent mean values±SEM for n=4 per group where "*" indicates a significant difference compared to control (left bar) at $p<0.05$ by nonparametric Student's t-test. Grey and black bars indicate whether measurements were made in hepatocyte conditioned media or hepatocytes, respectively. The activation of AMPK by AICAR caused a decrease in SOGA that was blocked by adiponectin exposure (FIG. 11D). On the other hand, the inhibition of PI3K by LY294002 caused a decrease in SOGA that was not blocked by adiponectin (FIG. 11D). These observations suggest that adiponectin increases SOGA through the insulin signaling pathway through a mechanism that can be inhibited by AMPK. Consistent with the identification of an internal secretory signal peptide in SOGA, SDS-PAGE analysis revealed that the 80 kDa SOGA fragment is secreted in hepatocyte conditioned media. The reduction of intracellular SOGA by adiponectin and LY294002 was reflected in the levels of SOGA in hepatocyte conditioned media. These results suggested that extracellular levels of SOGA could be used as a biomarker of its intracellular activity.

EXAMPLE 6

Circulating SOGA in Mice and Humans

Figure 12A:
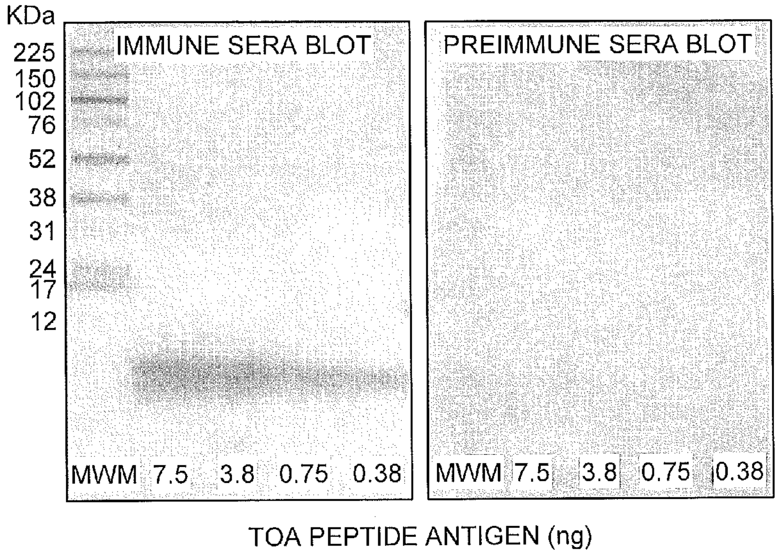
FIGS. 12A-12C show detection of circulating SOGA in mice.
Figure 12B:
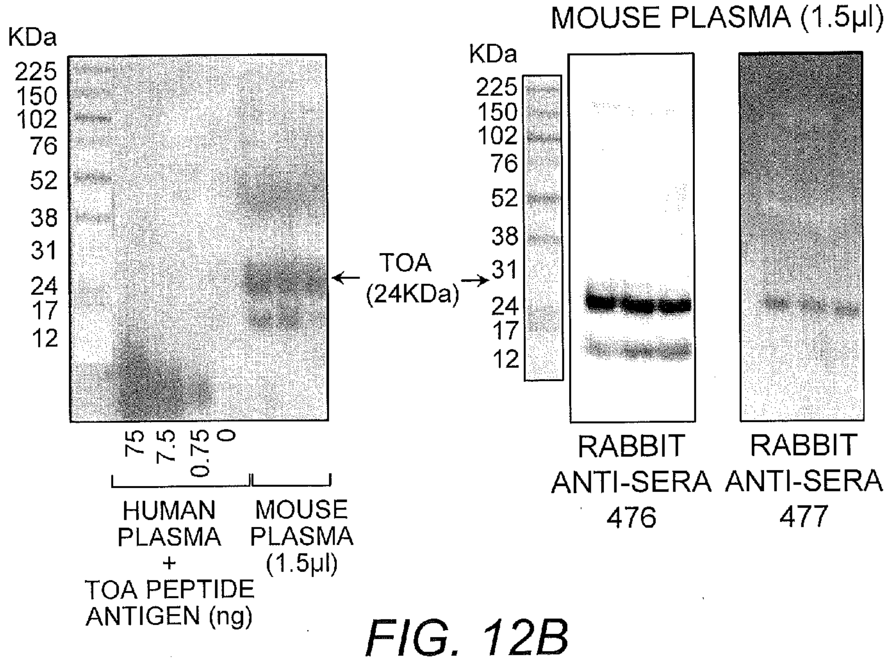
Figure 12C:
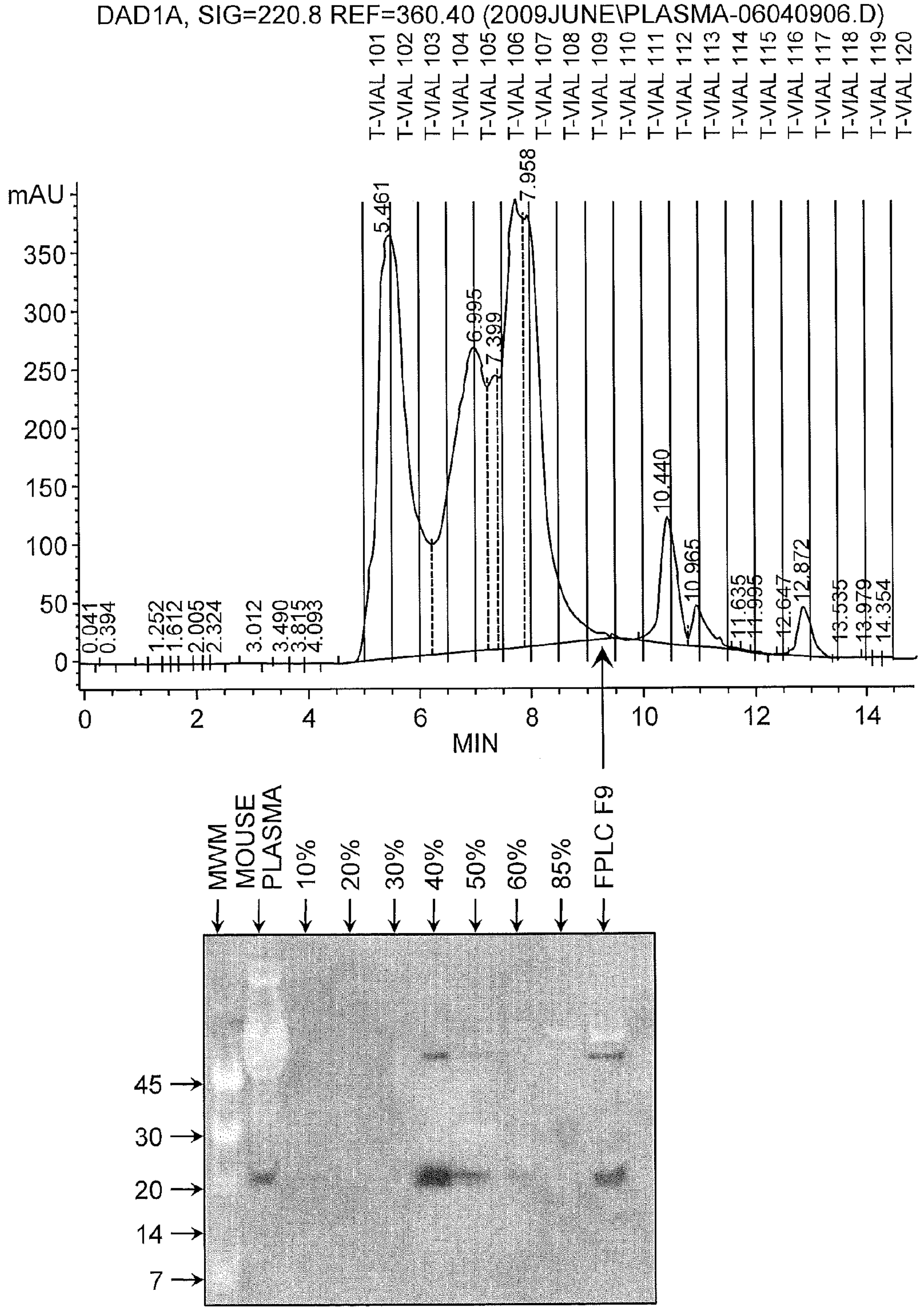

Antisera from 2 different rabbits immunized with two different peptide antigens, 476 and 477, detected a 25 kDa peptide in mouse plasma (FIG. 12A). SDS-PAGE shows the SOGA peptide antigen 476 was detected with immune but not pre-immune sera. The blot exposed to immune sera shows that the signal intensity is proportional to the peptide antigen concentration. FIG. 12B, left panel, shows that mouse-specific polyclonal antisera 476 detected a 25 kDa protein in mouse plasma but not human plasma. FIG. 12B, right panel, shows that antisera from two different rabbits immunized with two different peptide antigens, 476 and 477, detected a 25 kDa peptide in mouse plasma. Peptide antigens 476 and 477 correspond to overlapping amino acid sequences in the species specific epitope of SOGA. Peptide antigens used to produce rabbit antisera, SAQSLASCFIRPSRNPIRHSPSKC (SEQ ID NO:7) (antigen 476) and CSAQSLASCFIRPSRN (SEQ ID NO:6) (antigen 477), were analyzed by mass spectrometry to confirm their amino acid sequence. Rabbit antisera recognizing murine SOGA did not cross-react with any proteins in human plasma. FIG. 12C, top panel, shows a UV absorption plot for plasma proteins generated by HPLC. SDS-PAGE shows that 25 kDa SOGA eluted in fraction 9. For reference, the triglyceride peak (VLDL particle, −400 kDa) and the cholesterol peak (HDL particle, −200 kDa) were observed in fractions 1-2 and 5-6, respectively. HPLC analysis confirms that 25 kDa SOGA circulates as a monomer. FIG. 12C, bottom panel, presents SDS-PAGE showing SOGA precipitated out of HPLC fraction 9 in a 40% ammonium sulfate solution. Due to the presence of cysteine residues within the antigenic motif of SOGA, antibody detection of 25 kDa SOGA required the reduction of the sample with dithiothreitol. Based on the predicted sequence of 25 kDa fragment, the intramolecular disulfide bonds between cysteine residues on the carboxy-terminal end of SOGA should generate a fish hook conformation. Two observations indicate that 25 kDa SOGA circulates as a monomer. First, SOGA was detected at 25 kDa when plasma samples were reduced after SDS-PAGE. Second, by size exclusion chromatography of plasma proteins under native conditions, SOGA eluted at 25 kDa (FIG. 12C).

Figure 13A:
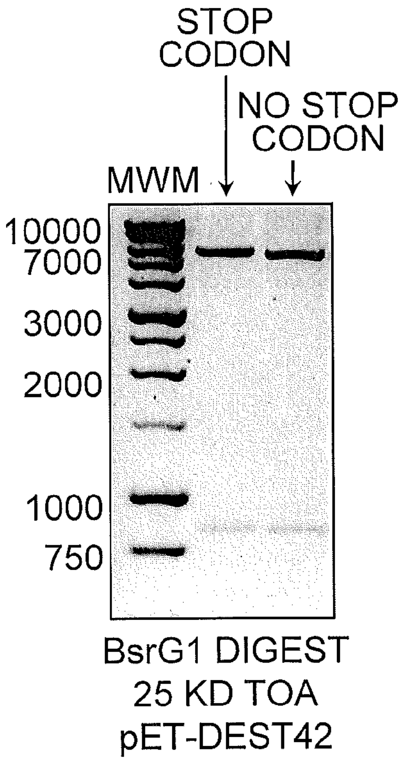
FIGS. 13A-13B show detection of recombinant SOGA.
Figure 13B:
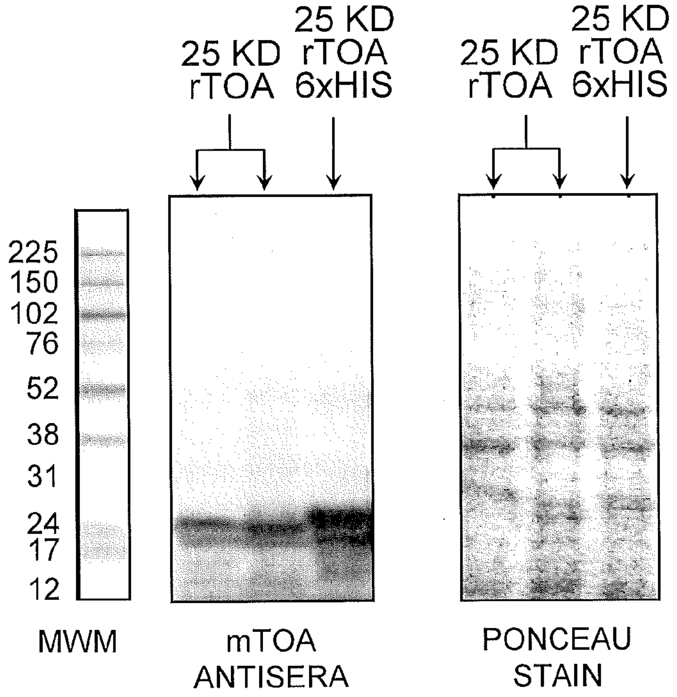

Recombinant 25 kDa SOGA was produced in *E. coli* and was detectable with the antibodies raised against full length SOGA. FIG. 13A shows a BsrG1 digest of murine 25 kDa SOGA clone in pET-DEST42 GATEWAY vector in 2% agarose. FIG. 13B shows a SDS-PAGE blot of recombinant 25 kDa murine SOGA, either without or with 6×His tag, produced in IPTG stimulated *E. coli* transformed with the pET-DEST42 GATEWAY vector. The left panel shows cross reactivity of our murine SOGA antisera with recombinant 25 kDa murine SOGA. The right panel shows a Ponceau red stained blot of total bacterial lysates after SDS-PAGE.

EXAMPLE 7

Correlation Between Circulating Adiponectin and SOGA

Figure 14A:
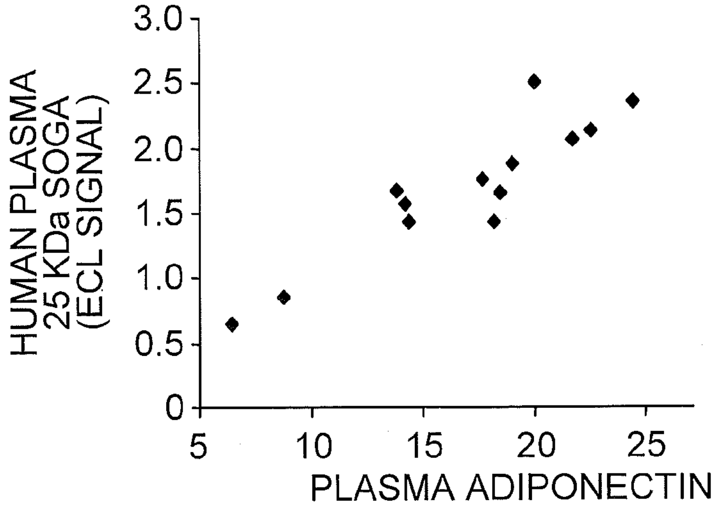
FIGS. 14A-14D show the circulating levels of adiponectin and SOGA in humans and mice.
Figure 14B:
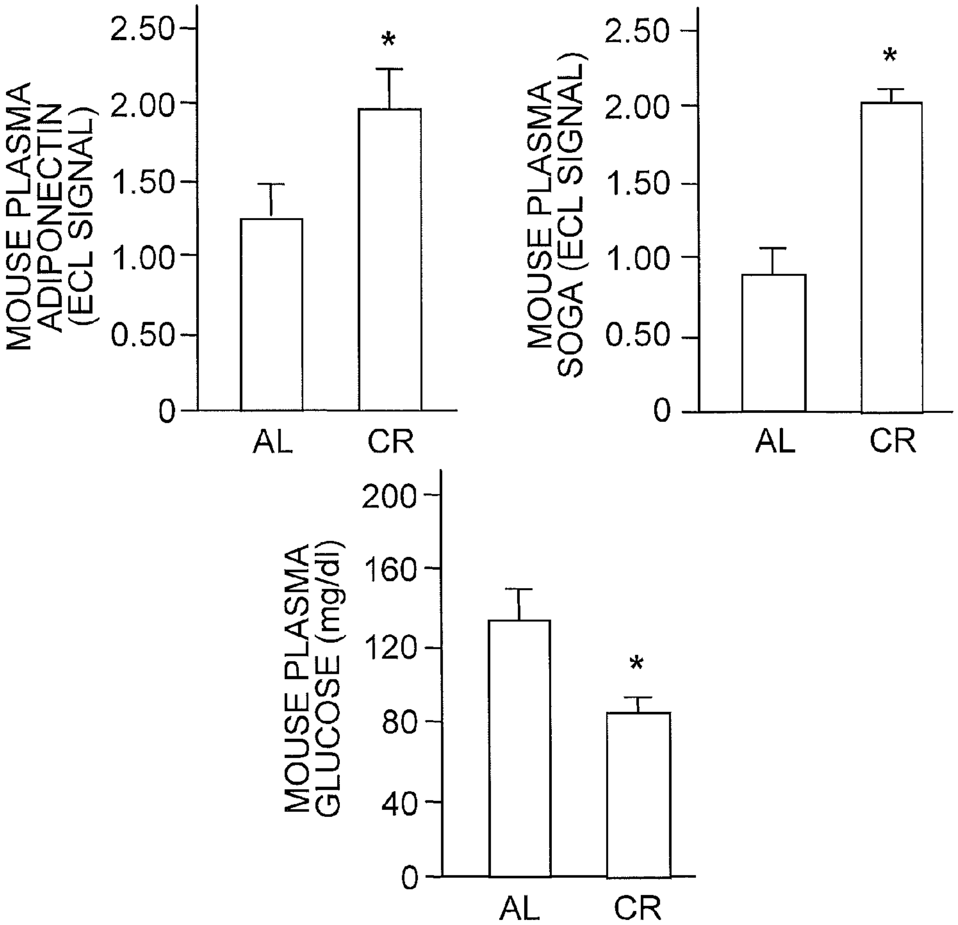
Figure 14D:
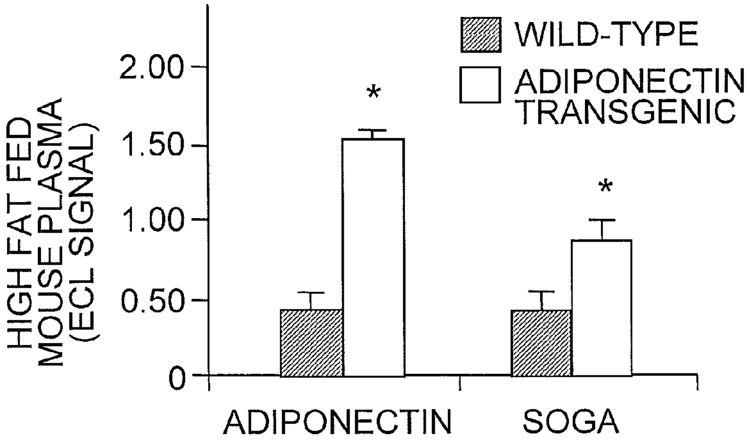
Figure 14C:
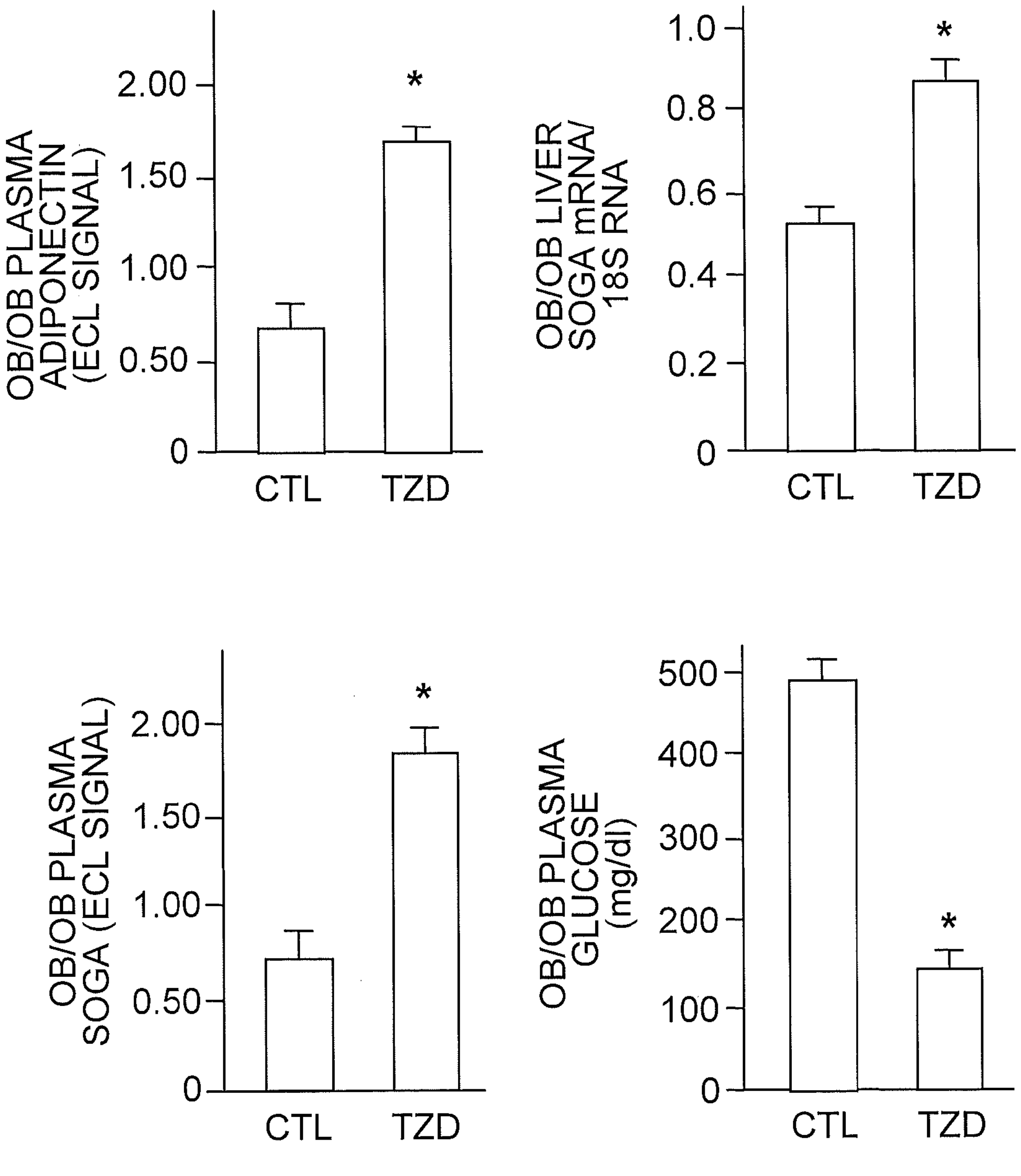

To further validate the link between adiponectin and SOGA in vivo, circulating levels of adiponectin and SOGA were measured in (a) healthy human volunteers, (b) wild-type mice after weight reduction by calorie restriction, and (c) pioglitazone treatment in ob/ob mice, a model of type II diabetes. FIG. 14A shows adiponectin and 25 kDa SOGA levels in human plasma from healthy female volunteers (ages 20-63; n=13). Plasma was collected after an overnight fast. Values represent averages from 2 plasma samples taken 10 minutes apart. A correlation coefficient ($R^2$) of 0.82 was found between SOGA and adiponectin. The analysis of human plasma from healthy fasting female volunteers (plasma insulin: 7.1±1.0 μU/ml) showed a positive correlation between circulating levels of adiponectin and SOGA ($R^2$=0.82) (FIG. 14A). FIG. 14B shows the effect of ad libitum (AL) versus 30% calorie restricted (CR) feeding on adiponectin, SOGA and glucose in wild-type mice. Bar graphs show levels of plasma adiponectin (top), 25 kDa SOGA (middle) and glucose (bottom). Calorie restriction, a nutritional intervention that doubled plasma adiponectin, resulted in a 2-fold elevation of circulating SOGA (FIG. 14B). The concentration of plasma glucose in calorie restricted mice compared to ad libitum fed mice was 80±7 mg/dl and 131±10 mg/dl, respectively (FIG. 14B). The complex oligomeric structure, high turnover rate and abundance of circulating adiponectin prevented us from using recombinant adiponectin to study the regulation of SOGA in vivo (Shetty et al., *Trends Pharmacol. Sci.* 30:234 (2009)). Therefore, oral pioglitazone treatment was used to elevate adiponectin in ob/ob mice, an obese model of type II diabetes. FIG. 14C shows the effect of pioglitazone treatment on liver SOGA mRNA and circulating adiponectin, SOGA and glucose in diabetic ob/ob mice. Mice received a daily dose of pioglitazone (TZD) or placebo (CTL) by oral gavage. Bar graphs show the levels of plasma adiponectin (top), liver SOGA mRNA/18S RNA (second), plasma 25 kDa SOGA (third) and plasma glucose (bottom) after 4 days of treatment. Pioglitazone treatment caused a 40% increase of SOGA mRNA in the liver and a 3-fold elevation of circulating adiponectin and SOGA (FIG. 14C). The concentration of plasma glucose was 155±8 mg/dl in pioglitazone treated ob/ob mice compared to 450±18 mg/dl in untreated ob/ob mice ($p<0.05$) (FIG. 14C). These results support the hypothesis that adiponectin elevation of SOGA increases insulin sensitivity. Both calorie restriction and pioglitazone treatment have pleiotropic effects beyond the elevation of circulating adiponectin making it difficult to draw any conclusions about the linkage between adiponectin and SOGA. Hence, circulating levels of SOGA between wild-type and adiponectin transgenic mice were compared. FIG. 14D shows circulating levels of adiponectin and SOGA in male adiponectin transgenic mice and their wild type litter mates on a high fat diet. Bars in panels B, C and D represent mean±SEM for n=4-5 per group where "*" indicates a significant difference ($p<0.05$) by nonparametric Student's t-test. Previous studies have shown that the 3-fold elevation of adiponectin in transgenic mice exerts a protective effect against diabetogenic high fat diet (Combs et al., *Endocrinology* 145:367 (2004); Brooks et al., *J. Biol. Chem.* 282: 35069 (2007)). Consistent with a stimulatory effect of adiponectin, circulating levels of SOGA were higher in adiponectin transgenic mice than their wild type litter mates on a high fat diet (FIG. 14D). These results support the hypothesis that the increase of SOGA in response to adiponectin contributes to the reduction of glucose production in vivo.

EXAMPLE 8

Correlation Between Circulating Insulin and SOGA

Figure 15A:
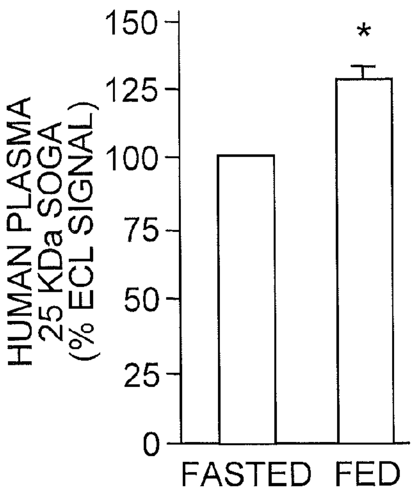
FIGS. 15A-15B show the circulating levels of SOGA in relation to insulin in humans and mice.
Figure 15B:
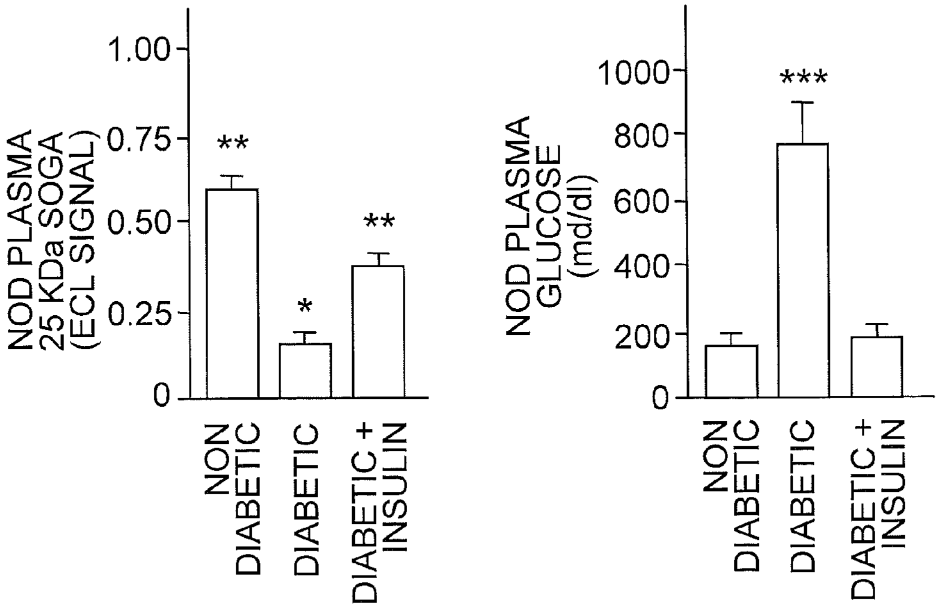

Because adiponectin is an insulin sensitizer and the inhibition of the insulin signaling intermediate PI3K blocked the induction of SOGA in isolated hepatocytes (FIG. 11D), we sought to determine whether there is a correlation between circulating insulin and SOGA during (a) feeding and fasting in humans and (b) insulin withdrawal in NOD mice, a model of type I diabetes. FIG. 15A shows the percent change in circulating levels of SOGA in healthy human volunteers (20-43 years old) measured at 8-11 AM, within 2 hours of feeding or following an overnight (10-12 hour) fast. Bars represent mean values±SEM for n=5 and "*" indicates a significant difference at $p<0.05$ by nonparametric Student's t-test. Consistent with the theory that insulin stimulates SOGA, a 12-hour fast in healthy human volunteers was associated with a 25% decrease in circulating SOGA (FIG. 15A). The reduction of SOGA in the fasted state is consistent with the induction of SOGA by insulin and the role of SOGA in the inhibition of autophagy and glucose production. FIG. 15B shows the effect of insulin withdrawal and insulin injection on SOGA and glucose in NOD mice. Circulating levels of 25 kDa SOGA and glucose in NOD mice without diabetes (Group I), NOD mice with diabetes (Group 2) and NOD mice with diabetes treated by a single injection of insulin 24 hours earlier (Group 3) were measured. Bar graphs show the levels of plasma SOGA (top) and glucose (bottom). Bars show mean±SEM for n=5 per group where "*" indicates significantly lower than Groups 1 and 3, "" indicates significantly greater than Group 2 and "*" indicates significantly greater than Groups 1 and 3. Statistical significance was determined by Student's t-test where $p<0.05$. A 3-fold reduction of circulating SOGA in hyperglycemic NOD mice, in comparison to euglycemic NOD mice, also suggests that insulin induces SOGA in vivo (FIG. 15B). In support of the theory that the increase of SOGA in response to insulin contributes to the reduction of plasma glucose, the treatment of type I diabetes by insulin injection was associated with a 2-fold induction of SOGA (FIG. 15B).

The results of this study suggest that the elevation of SOGA in response to adiponectin and insulin can lower liver glucose production through the inhibition of autophagy resulting in a decrease of plasma glucose. The observation that knockdown of SOGA elevated glucose production in primary hepatocytes suggested that SOGA is an inhibitor of glucose production. The elevation of glucose production during the reduction of SOGA was linked to changes in primary hepatocytes that suggested an increase in autophagy such as the reduction in protein content and the elevation of lysosome staining and the secretion of valine, a branched chain amino acid that cannot be synthesized or metabolized in hepatocytes.

The hypothesis that SOGA may interfere with autophagy is supported by the identification of conserved domains found in Atg16 and Rab5-binding proteins (Longatti et al., *Cell Death Differ.* 16:956 (2009)). Both Atg16 and the Rab5-binding proteins contribute to the early stages of autophagy. Although Atg16 is an essential component of the autophagic machinery, adenoviral overexpression of Atg16 inhibits autophagy in mammalian cells (Matsushita et al., *J. Biol. Chem.* 282:6763 (2007)); Fujita et al., *Mol. Biol. Cell* 19:2092 (2008)). The disruption of autophagy by overexpression of Atg16 provides a paradigm that may explain how elevated SOGA inhibits glucose production. Although the current study focuses on the role of SOGA in the liver, it is important to point out that SOGA is also expressed in the other gluconeogenic organs like the kidney and tissues that are rich sources of gluconeogenic substrates like skeletal and cardiac muscle. The elevation of SOGA in extrahepatic tissues may play a critical role in the reduction of glucose production and the amelioration of glucose homeostasis.

Intracellular levels of SOGA in isolated hepatocytes were proportional to the levels of SOGA in hepatocyte conditioned media leading us to propose that circulating levels of SOGA can be used as a biomarker of intracellular SOGA levels. This hypothesis was supported by the elevation of liver SOGA mRNA and circulating SOGA in pioglitazone treated ob/ob mice. Our in vitro experiments suggest that the elevation of circulating SOGA indicates a decrease in glucose production. This interpretation is consistent with the elevation of circulating SOGA after calorie restriction, oral pioglitazone, transgenic elevation of adiponectin, feeding and insulin injection. Although glucose production was not measured in the present study, previous reports in mice, rats and humans show that glucose production is reduced by the elevation of adiponectin in transgenic mice, the implementation of calorie restriction, the treatment of type II diabetes by oral insulin sensitizers and the treatment of type I diabetes by insulin (Wahren et al., *Annu. Rev. Nutr.* 27:329 (2007); Combs et al., *J. Clin. Invest.* 108:1875 (2001); Combs et al., *Endocrinology* 145:367 (2004); Barzilai et al., *J. Clin. Invest.* 101:1353 (2998); Miyazaki et al., *J. Clin. Endocrinol. Metab.* 89:4312 (2004)).

The elevation of SOGA in calorie restricted, pioglitazone and adiponectin transgenic mice supports the hypothesis that adiponectin induces SOGA. The elevation of SOGA in response to adiponectin was not impaired by pharmacologic inhibition of AMPK in isolated hepatocytes suggesting that the induction of SOGA is an insulin sensitizing effect of adiponectin that is mediated independent of AMPK. Adiponectin mediated increases in SOGA were impaired by pharmacologic inhibition of the insulin signaling intermediate PI3K suggesting that the expression of SOGA is regulated by the insulin signaling pathway. The reduction of circulating SOGA by a 12-hour fast in humans or hyperglycemic NOD mice and the elevation of circulating SOGA by insulin injection support the hypothesis that SOGA is induced by the insulin signaling pathway. Adiponectin could increase SOGA through the insulin signaling pathway via APPL1, an adaptor protein that binds to the intracellular domain of the adiponectin receptors and the catalytic subunit of PI3K (Mao et al., *Nat. Cell Biol.* 8:516 (2006); Mitsuuchi et al., *Oncogene* 18:4891 (1999); Yang et al., *J. Biol. Chem.* 278:16820 (2003)).

Antibodies recognizing the C-terminal region of murine SOGA show that cultured hepatocytes as well as liver samples incubated ex vivo secrete an 80 kDa SOGA fragment rather than a 161 kDa protein predicted by the 4.7 kb cDNA. The size discrepancy is explained by the location of an internal secretory signal peptide, also seen in chicken ovalbumin (Lingappa et al., *Nature* 281:117 (1979)). The presence of repeated LXXXXXL sequences in the amino terminal portion of the SOGA (amino acids 222-250 and 288-314) suggests a potential feedback mechanism through protein-protein interactions of leucine zipper motifs in SOGA and APPL1. The absence of 25 kDa SOGA in hepatocytes and liver conditioned media suggests that proteolytic cleavage of 80 kDa SOGA depends on an extracellular factor that is inactive or absent in vitro. The incubation of mouse hepatocyte conditioned media containing 80 kDa SOGA with endothelial cells (HUVECs) or human plasma did not yield a 25 kDa fragment. Circulating SOGA may play a physiologic role in glucose homeostasis.

The discovery that circulating levels of adiponectin and SOGA were highly correlated in humans suggests that the measurement of SOGA may be clinically relevant. For example, while TZD drug treatment is almost always effective in the induction of adiponectin, it is only effective in lowering glucose in 70% of type II diabetics (Snitlter et al., *Diabetes Care* 27:1365 (2004)). Insulin treatment in type I diabetics is also not completely effective 100% of the time. Based on the results presented here, it would not be surprising if specific cases of poor clinical outcomes were associated with poor induction of SOGA.

The foregoing is illustrative of the present invention, and is not to be construed as limiting thereof. The invention is defined by the following claims, with equivalents of the claims to be included therein.

That which is claimed is:

1. An antibody or antibody fragment that specifically binds to a polypeptide encoded by a polynucleotide selected from the group consisting of:

(a) a polynucleotide comprising a nucleotide sequence at least 95% identical to a nucleotide sequence selected from the group consisting of SEQ ID NOS:1 and 3 and encoding a functional Suppressor of Glucose by Autophagy (SOGA) polypeptide;

(b) a polynucleotide encoding a functional SOGA polypeptide comprising an amino acid sequence at least 95% identical to an amino acid sequence selected from the group consisting of SEQ ID NOS:2 and 4;

(c) a polynucleotide of (a) or (b) encoding a C-terminal functional fragment of a SOGA polypeptide of about 80 kDa; and (d) a polynucleotide of (a) or (b) encoding a C-terminal functional fragment of a SOGA polypeptide of about 25 kDa.

2. The antibody or antibody fragment of claim 1, wherein said polynucleotide is selected from the group consisting of:

(a) a polynucleotide comprising a nucleotide sequence selected from the group consisting of SEQ ID NOS:1 and 3;

(b) a polynucleotide encoding a functional SOGA polypeptide comprising an amino acid sequence selected from the group consisting of SEQ ID NOS:2 and 4;

(c) a polynucleotide of (a) or (b) encoding a C-terminal functional fragment of a SOGA polypeptide of about 80 kDa;

(d) a polynucleotide of (a) or (b) encoding a C-terminal functional fragment of a SOGA polypeptide of about 25 kDa; and (e) a polynucleotide comprising a nucleotide sequence that differs from the nucleotide sequences of any of (a) to (d) above due to the degeneracy of the genetic code.

3. The antibody or antibody fragment of claim 1, wherein the polynucleotide encodes a C-terminal functional fragment of a SOGA polypeptide of about 80 kDa.

4. The antibody or antibody fragment of claim 1, wherein the polynucleotide encodes a C-terminal functional fragment of a SOGA polypeptide of about 25 kDa.

5. The antibody or antibody fragment of claim 1, wherein the antibody or antibody fragment is a polyclonal antibody or antibody fragment.

6. The antibody or antibody fragment of claim 1, wherein the antibody or antibody fragment is a monoclonal antibody or antibody fragment.

7. The antibody or antibody fragment of claim 1, wherein the antibody or antibody fragment specifically binds to a human SOGA polypeptide.

8. An antibody or antibody fragment that specifically recognizes an epitope within the amino acid sequence STQSLTSCFARSSRSAIRHSPSKC (SEQ ID NO:5).

9. The antibody or antibody fragment of claim 1, wherein the antibody or antibody fragment specifically binds to a mouse SOGA polypeptide.

10. An antibody or antibody fragment that specifically recognizes an epitope within the amino acid sequence CSAQSLASCFIRPSRN (SEQ ID NO:6) or SAQSLASCFIRPSRNPIRHSPSKC (SEQ ID NO:7).

11. A pharmaceutical composition comprising the antibody or antibody fragment of claim 1 and a pharmaceutically acceptable carrier.

12. A kit comprising the antibody or antibody fragment of claim 1.

13. A method of increasing glucose production in a cell in vitro comprising contacting said cell with the antibody or antibody fragment of claim 1 in an amount effective to increase glucose production in said cell.

14. A method of increasing autophagy in a cell in vitro comprising contacting said cell with the antibody or antibody fragment of claim 1 in an amount effective to increase autophagy in said cell.

* * * * *

UNITED STATES PATENT AND TRADEMARK OFFICE

CERTIFICATE OF CORRECTION

PATENT NO. : 9,102,719 B2
APPLICATION NO. : 14/019925
DATED : August 11, 2015
INVENTOR(S) : Combs et al.

It is certified that error appears in the above-identified patent and that said Letters Patent is hereby corrected as shown below:

In the Specification:

Column 23, Line 29: delete "lysine (+3.0);"
and insert -- lysine (±3.0); --

Column 35, Line 24: delete "a Mouse and,"
and insert -- a mouse and, --

Column 39, Line 25: delete "Ultralente" and insert -- ultralente --

Column 47, Line 48: delete "DNA in the cell;"
and insert -- DNA in the cell. --

Column 55, Line 58: delete "CFARSSRSAIRHSPSKC"
and insert -- CFARSSRSAIRHSPSKC --

Signed and Sealed this
Tenth Day of May, 2016

Michelle K. Lee
*Director of the United States Patent and Trademark Office*

UNITED STATES PATENT AND TRADEMARK OFFICE

CERTIFICATE OF CORRECTION

PATENT NO. : 9,102,719 B2
APPLICATION NO. : 14/019925
DATED : August 11, 2015
INVENTOR(S) : Combs et al.

It is certified that error appears in the above-identified patent and that said Letters Patent is hereby corrected as shown below:

In the Specification:
Column 1, Lines 15-21, STATEMENT OF FEDERAL SUPPORT:
Please replace with:

This invention was made with government support under Grant Nos. DK075573, DK056350 and ES010126 awarded by the National Institutes of Health. The government has certain rights in the invention.

Signed and Sealed this
Fourteenth Day of June, 2016

Michelle K. Lee
*Director of the United States Patent and Trademark Office*

SEQUENCE LISTING

<160> NUMBER OF SEQ ID NOS: 11

<210> SEQ ID NO 1
<211> LENGTH: 4716
<212> TYPE: DNA
<213> ORGANISM: Mus musculus

<400> SEQUENCE: 1

```
agttgggcct ggagctggcg ctgagcagcg acgccgagtc tgcggcgggc ggcccggcgg      60

ggacccgcac cgggcagccg ccccagccag cgcagtcggg gcagcagcct ccgcggcctc     120

ccgcctcccc ggatgagccg tcggtggccg catcgtcggt gggcagcagc cgcttgccat     180

tcagcgcctc gctagccttc tccgacctca ccgaggagat gctggactgt gggcccggag     240

gcttggtgcg ggagctggaa gagctgcgtt ccgagaacga ctatctcaag gatgagattg     300

aggagctacg ggctgagatg ctggagatgc gggatgtcta catggaggaa gacgtgtatc     360

agctgcagta ccgactgcgt aaggctgagc gccgcagcct ccgcgctgcc cagacaggcc     420

aggttgatgg ggaactcatc cgaggtctgg aacaggacgt caaggtctct aaggacatct     480

ccatgcggct tcacaaggag ctggaggtgg tggagaagaa gcggatgagg ctggaggagg     540

agaacgaggg gcttcgacag aggctcattg agacagagct ggccaagcag gtgctacaga     600

cggagctgga tcgtcccaga gagcattcct tgaagaaaag aggaacccgg tctctgggga     660

agacagataa gaagcctact gcacaggagg atagtgcaga cctgaagtgc cagctgcatt     720

ttgcaaagga ggagtcggcc ctcatgtgca agaagctcac caagttggct aaggagaacg     780
```

-continued

```
acagcatgaa ggaggagctg ctcaagtaca gatcgctcta tggggacctg gatgcagccc    840
tgtcggcaga ggagctggcg gatgctccgc actcccgtga gactgagctg aaggtgcacc    900
tgaagctggt ggaggaggag gccaacctgc tgagccggcg catagtggag ctggaggtgg    960
agaaccgtgg cctgcgagcc gagatggacg acatgaagga ccacgggggt ggcgggggtc   1020
ccgaggccag gctggccttc tcttctctgg gtggtgagtg cggggagagc ctagccgagt   1080
tgcggcgcca cctgcagttc gtggaagagg aggctgagct gctgaggcgc tcctcagctg   1140
agctggagga ccagaacaag ttgctgctga acgagctggc caaataccgc tcggagcacg   1200
agctggacgt gacgctgtcg gaggacagct gctccgtgct cagcgagccc tcgcaggagg   1260
agctggcagc cgccaagctg cagatcggcg agctcagcgg caaggtcaag aagctgcagt   1320
atgagaaccg cgtgctcctc tccaatctgc agcgctgtga cctggcctcc tgccagagca   1380
cacgccccat gctggagacg gacgctgagg ctggggactc tgcgcagtgc gtgcctgccc   1440
ctctgggtga gacgctggag ccccacgccg cccggctgtg cagggcccgt gaagccgagg   1500
cgctgcccgg cctacgggag caggccgctt tggtcagcaa ggccatcgac gtcctggtgg   1560
ctgatgccaa tggcttctca gtcggcctcc gcctgtgcct ggacaatgag tgtgctgact   1620
tgcgactgca cgaggcgcct gacaacagcg agggccccag ggatgccaag ctcatccacg   1680
ccatcctggt gcggctgagt gtgttgcaac aggagctgaa cgccttcacc cgcaaggcag   1740
atgtggcctt ggggagctct ggcaaggagc agcctgagcc cttccctgct ctgcctgcct   1800
tgggctccca gggccctgct aaggagatca tgctgtccaa agaccttggc tctgacttcc   1860
agccacctga cttcagagac ctgcttgagt gggagcccag gatccgagag gccttccgta   1920
ccggggactt ggagtccaag cctgacccta gtcggaactt caggccctac cgagctgaag   1980
ataacgattc ttatgcctct gagatcaagg atcttcagct ggtcctggcc gaggcccacg   2040
acagcctccg gggcttgcaa gagcagctgt cccaggagcg gcagctccgg aaggaggagg   2100
ctgacagctt caaccagaaa atggtccagc tgaaggaaga ccagcagagg gcgctgctga   2160
gacgggagtt tgagctgcag agtctgagcc tccagcggcg actggagcag aagttctgga   2220
gccaagagaa gaacatcctg gtgcaggagt cccagcagtt caagcacaac tttctgctgc   2280
tcttcatgaa gctccggtgg ttcctgaagc gctggcggca gggcaaggtt ctgcccagcg   2340
aagaggatga cttcctggag gtgaacagca tgaaggaact gtacctgctg atggaggaag   2400
aggagatgaa cgcccagcac tcggataaca aggcctgcac aggggagagc tggacccaga   2460
acacgcctaa tgagtgcatc aagaccctgg ccgacatgaa ggtcaccctg aaggagctgt   2520
gctggctgct ccaggacgag cgtcggggtc tgactgaact tcagcagcag ttcgcaaagg   2580
ccaaggccac ctgggagaca gagcgtgcag agctcaaggg ccacgcctcg cagatggagc   2640
tgaaggctgg gaagggtgcc agtgagaggc ccgggcctga ctggaaggct gcactgcaga   2700
gagagcggga ggagcagcaa cacctcctgg cagagtccta cagcgccgtc atggagctga   2760
cgaggcagct gcagctgagc gagcgccact ggagccagga gaagctgcag ctggtggagc   2820
ggctgcaggg agaaaagcag caggtggagc agcaggtgaa ggagctgcag aaccgcctca   2880
gtcagttgca gaaggctgcc gagccctggg tcctgaagca ctcagacatg gagaagcaag   2940
acaacagctg gaaagaggca cgaagtgaga agacccatga caaggagggt gtctctgaag   3000
ctgagctcgg gggaactggc ttaaagagga ccaaatcagt ctcctccatg tctgagtttg   3060
aaagtttgct cgactgctcc ccgtaccttg ctggcgggga tgcccggaac aagaagctgc   3120
ccaacggccc tgcttttgcc tttgtgagta ctgagccagt ggagcctgag aaagacgcca   3180
```

```
aggagaaggc ggggctttcc acccgggact gtagccacat tggtagcttg gcctgtcagg   3240

aacctgcagg gagacagatg cagcgcagct acacggctcc agacaagacg ggaatccgag   3300

tctactatag tccgccagtg gctcggcgcc tgggtgtccc tgtggtccat gacaaggagg   3360

gcaagatcct cattgagcca ggcttcctct tcactaccgc caagcccaag gagtcagccg   3420

aggctgacgg gctggccgag agctcctaca gccggtggct ttgcaatttc tcccggcagc   3480

ggctggatgg aggatccggg gccagcacct cgggttccgg acctgctttc cccgccttgc   3540

atgactttga gatgtcgggc aacatgagtg acgacatgaa ggagatcacc aactgcgtgc   3600

ggcaggccat gcgctccggc tctctggaga ggaaggtaaa gaacacatcc agccagacgg   3660

taggcgtggc caccgtgggc acccagacca ttcggacggt cagtgtaggt cttcagaccg   3720

acccaccccg cagcagcctc cacagcaaga gctggtcacc ccgcagctcc tcgcttgtgt   3780

ctgtgcgcag caagcagatc tcttcctccc tggacaaggt ccattctcgc attgagcggc   3840

catgttgctc gcccaagtac ggctcaccca agctccagag acgatcggtg tccaagctgg   3900

atagcaccaa ggaccgcagc ctgtggaacc tgcaccaggg caagcaaaat ggctccgcct   3960

gggctcgctc caccaccaca cgggatagcc ctgtactgag gaacatcaat gatgggcttt   4020

ctagcctctt tagtgtggtg gagcactctg ggagcaccga gtctgtgtgg aaactgggca   4080

tgtctgaggc ccgaaccaaa cctgagcctc ccaagtatgg cattgttcag gagttcttcc   4140

ggaacgtgtg tggccgggca ccgagcccca ctactgcagc aggcgaggaa agctgcaaga   4200

aaccagagcc cctttcgcca gccagctacc atcaacccga gggtgtatcc aggatcctga   4260

acaagaaggc ggccaaggca ggtggtagcg aagaggtcag acccaccatg ctgtcccagg   4320

tggggaagga tggcatcctt cgggatggag atggatcctt gatccttccc agtgaggatg   4380

ccgtatgtga ctgtagcgcc cagtcacttg cctcctgctt catccggcca tcccgcaaca   4440

ccatccggca ctctccttcc aagtgcaggc tgcacccttc agagtcaggc tggggcgggg   4500

aggagagggc agctccccag tgagtccctg agcaaccaag cacccacctc aagcagccca   4560

gaccctggag atgaggcaag ggctcgtgtc ctcagcctca gtccatccag gaggaatggc   4620

agctgtgcca ctgccacaga agagctttca cattaaggta aagcaaggtg tcttgctgac   4680

tgctgggcag tgacctctga tttccagggg aagaca                             4716
```

```
<210> SEQ ID NO 2
<211> LENGTH: 1434
<212> TYPE: PRT
<213> ORGANISM: Mus musculus

<400> SEQUENCE: 2

Met Leu Asp Cys Gly Pro Gly Gly Leu Val Arg Glu Leu Glu Glu Leu
1               5                   10                  15

Arg Ser Glu Asn Asp Tyr Leu Lys Asp Glu Ile Glu Glu Leu Arg Ala
            20                  25                  30

Glu Met Leu Glu Met Arg Asp Val Tyr Met Glu Glu Asp Val Tyr Gln
        35                  40                  45

Leu Gln Tyr Arg Leu Arg Lys Ala Glu Arg Arg Ser Leu Arg Ala Ala
    50                  55                  60

Gln Thr Gly Gln Val Asp Gly Glu Leu Ile Arg Gly Leu Glu Gln Asp
65                  70                  75                  80

Val Lys Val Ser Lys Asp Ile Ser Met Arg Leu His Lys Glu Leu Glu
                85                  90                  95
```

-continued

```
Val Val Glu Lys Lys Arg Met Arg Leu Glu Glu Glu Asn Glu Gly Leu
            100                 105                 110

Arg Gln Arg Leu Ile Glu Thr Glu Leu Ala Lys Gln Val Leu Gln Thr
        115                 120                 125

Glu Leu Asp Arg Pro Arg Glu His Ser Leu Lys Lys Arg Gly Thr Arg
    130                 135                 140

Ser Leu Gly Lys Thr Asp Lys Lys Pro Thr Ala Gln Glu Asp Ser Ala
145                 150                 155                 160

Asp Leu Lys Cys Gln Leu His Phe Ala Lys Glu Glu Ser Ala Leu Met
                165                 170                 175

Cys Lys Lys Leu Thr Lys Leu Ala Lys Glu Asn Asp Ser Met Lys Glu
            180                 185                 190

Glu Leu Leu Lys Tyr Arg Ser Leu Tyr Gly Asp Leu Asp Ala Ala Leu
        195                 200                 205

Ser Ala Glu Glu Leu Ala Asp Ala Pro His Ser Arg Glu Thr Glu Leu
    210                 215                 220

Lys Val His Leu Lys Leu Val Glu Glu Glu Ala Asn Leu Leu Ser Arg
225                 230                 235                 240

Arg Ile Val Glu Leu Glu Val Glu Asn Arg Gly Leu Arg Ala Glu Met
                245                 250                 255

Asp Asp Met Lys Asp His Gly Gly Gly Gly Gly Pro Glu Ala Arg Leu
            260                 265                 270

Ala Phe Ser Ser Leu Gly Gly Glu Cys Gly Glu Ser Leu Ala Glu Leu
        275                 280                 285

Arg Arg His Leu Gln Phe Val Glu Glu Glu Ala Glu Leu Leu Arg Arg
    290                 295                 300

Ser Ser Ala Glu Leu Glu Asp Gln Asn Lys Leu Leu Leu Asn Glu Leu
305                 310                 315                 320

Ala Lys Tyr Arg Ser Glu His Glu Leu Asp Val Thr Leu Ser Glu Asp
                325                 330                 335

Ser Cys Ser Val Leu Ser Glu Pro Ser Gln Glu Glu Leu Ala Ala Ala
            340                 345                 350

Lys Leu Gln Ile Gly Glu Leu Ser Gly Lys Val Lys Lys Leu Gln Tyr
        355                 360                 365

Glu Asn Arg Val Leu Leu Ser Asn Leu Gln Arg Cys Asp Leu Ala Ser
    370                 375                 380

Cys Gln Ser Thr Arg Pro Met Leu Glu Thr Asp Ala Glu Ala Gly Asp
385                 390                 395                 400

Ser Ala Gln Cys Val Pro Ala Pro Leu Gly Glu Thr Leu Glu Pro His
                405                 410                 415

Ala Ala Arg Leu Cys Arg Ala Arg Glu Ala Glu Ala Leu Pro Gly Leu
            420                 425                 430

Arg Glu Gln Ala Ala Leu Val Ser Lys Ala Ile Asp Val Leu Val Ala
        435                 440                 445

Asp Ala Asn Gly Phe Ser Val Gly Leu Arg Leu Cys Leu Asp Asn Glu
    450                 455                 460

Cys Ala Asp Leu Arg Leu His Glu Ala Pro Asp Asn Ser Glu Gly Pro
465                 470                 475                 480

Arg Asp Ala Lys Leu Ile His Ala Ile Leu Val Arg Leu Ser Val Leu
                485                 490                 495

Gln Gln Glu Leu Asn Ala Phe Thr Arg Lys Ala Asp Val Ala Leu Gly
            500                 505                 510

Ser Ser Gly Lys Glu Gln Pro Glu Pro Phe Pro Ala Leu Pro Ala Leu
```

-continued

```
        515                 520                 525

Gly Ser Gln Gly Pro Ala Lys Glu Ile Met Leu Ser Lys Asp Leu Gly
    530                 535                 540

Ser Asp Phe Gln Pro Pro Asp Phe Arg Asp Leu Leu Glu Trp Glu Pro
545                 550                 555                 560

Arg Ile Arg Glu Ala Phe Arg Thr Gly Asp Leu Glu Ser Lys Pro Asp
                565                 570                 575

Pro Ser Arg Asn Phe Arg Pro Tyr Arg Ala Glu Asp Asn Asp Ser Tyr
            580                 585                 590

Ala Ser Glu Ile Lys Asp Leu Gln Leu Val Leu Ala Glu Ala His Asp
        595                 600                 605

Ser Leu Arg Gly Leu Gln Glu Gln Leu Ser Gln Glu Arg Gln Leu Arg
    610                 615                 620

Lys Glu Glu Ala Asp Ser Phe Asn Gln Lys Met Val Gln Leu Lys Glu
625                 630                 635                 640

Asp Gln Gln Arg Ala Leu Leu Arg Arg Glu Phe Glu Leu Gln Ser Leu
                645                 650                 655

Ser Leu Gln Arg Arg Leu Glu Gln Lys Phe Trp Ser Gln Glu Lys Asn
            660                 665                 670

Ile Leu Val Gln Glu Ser Gln Gln Phe Lys His Asn Phe Leu Leu Leu
        675                 680                 685

Phe Met Lys Leu Arg Trp Phe Leu Lys Arg Trp Arg Gln Gly Lys Val
    690                 695                 700

Leu Pro Ser Glu Glu Asp Asp Phe Leu Glu Val Asn Ser Met Lys Glu
705                 710                 715                 720

Leu Tyr Leu Leu Met Glu Glu Glu Glu Met Asn Ala Gln His Ser Asp
                725                 730                 735

Asn Lys Ala Cys Thr Gly Glu Ser Trp Thr Gln Asn Thr Pro Asn Glu
            740                 745                 750

Cys Ile Lys Thr Leu Ala Asp Met Lys Val Thr Leu Lys Glu Leu Cys
        755                 760                 765

Trp Leu Leu Gln Asp Glu Arg Arg Gly Leu Thr Glu Leu Gln Gln Gln
    770                 775                 780

Phe Ala Lys Ala Lys Ala Thr Trp Glu Thr Glu Arg Ala Glu Leu Lys
785                 790                 795                 800

Gly His Ala Ser Gln Met Glu Leu Lys Ala Gly Lys Gly Ala Ser Glu
                805                 810                 815

Arg Pro Gly Pro Asp Trp Lys Ala Ala Leu Gln Arg Glu Arg Glu Glu
            820                 825                 830

Gln Gln His Leu Leu Ala Glu Ser Tyr Ser Ala Val Met Glu Leu Thr
        835                 840                 845

Arg Gln Leu Gln Leu Ser Glu Arg His Trp Ser Gln Glu Lys Leu Gln
    850                 855                 860

Leu Val Glu Arg Leu Gln Gly Glu Lys Gln Gln Val Glu Gln Gln Val
865                 870                 875                 880

Lys Glu Leu Gln Asn Arg Leu Ser Gln Leu Gln Lys Ala Ala Glu Pro
                885                 890                 895

Trp Val Leu Lys His Ser Asp Met Glu Lys Gln Asp Asn Ser Trp Lys
            900                 905                 910

Glu Ala Arg Ser Glu Lys Thr His Asp Lys Glu Gly Val Ser Glu Ala
        915                 920                 925

Glu Leu Gly Gly Thr Gly Leu Lys Arg Thr Lys Ser Val Ser Ser Met
    930                 935                 940
```

-continued

```
Ser Glu Phe Glu Ser Leu Leu Asp Cys Ser Pro Tyr Leu Ala Gly Gly
945                 950                 955                 960

Asp Ala Arg Asn Lys Lys Leu Pro Asn Gly Pro Ala Phe Ala Phe Val
                965                 970                 975

Ser Thr Glu Pro Val Glu Pro Glu Lys Asp Ala Lys Glu Lys Ala Gly
            980                 985                 990

Leu Ser Thr Arg Asp Cys Ser His  Ile Gly Ser Leu Ala  Cys Gln Glu
        995                 1000                1005

Pro Ala  Gly Arg Gln Met Gln  Arg Ser Tyr Thr Ala  Pro Asp Lys
    1010                1015                1020

Thr Gly  Ile Arg Val Tyr Tyr  Ser Pro Pro Val Ala  Arg Arg Leu
    1025                1030                1035

Gly Val  Pro Val Val His Asp  Lys Glu Gly Lys Ile  Leu Ile Glu
    1040                1045                1050

Pro Gly  Phe Leu Phe Thr Thr  Ala Lys Pro Lys Glu  Ser Ala Glu
    1055                1060                1065

Ala Asp  Gly Leu Ala Glu Ser  Ser Tyr Ser Arg Trp  Leu Cys Asn
    1070                1075                1080

Phe Ser  Arg Gln Arg Leu Asp  Gly Gly Ser Gly Ala  Ser Thr Ser
    1085                1090                1095

Gly Ser  Gly Pro Ala Phe Pro  Ala Leu His Asp Phe  Glu Met Ser
    1100                1105                1110

Gly Asn  Met Ser Asp Asp Met  Lys Glu Ile Thr Asn  Cys Val Arg
    1115                1120                1125

Gln Ala  Met Arg Ser Gly Ser  Leu Glu Arg Lys Val  Lys Asn Thr
    1130                1135                1140

Ser Ser  Gln Thr Val Gly Val  Ala Thr Val Gly Thr  Gln Thr Ile
    1145                1150                1155

Arg Thr  Val Ser Val Gly Leu  Gln Thr Asp Pro Pro  Arg Ser Ser
    1160                1165                1170

Leu His  Ser Lys Ser Trp Ser  Pro Arg Ser Ser Ser  Leu Val Ser
    1175                1180                1185

Val Arg  Ser Lys Gln Ile Ser  Ser Ser Leu Asp Lys  Val His Ser
    1190                1195                1200

Arg Ile  Glu Arg Pro Cys Cys  Ser Pro Lys Tyr Gly  Ser Pro Lys
    1205                1210                1215

Leu Gln  Arg Arg Ser Val Ser  Lys Leu Asp Ser Thr  Lys Asp Arg
    1220                1225                1230

Ser Leu  Trp Asn Leu His Gln  Gly Lys Gln Asn Gly  Ser Ala Trp
    1235                1240                1245

Ala Arg  Ser Thr Thr Thr Arg  Asp Ser Pro Val Leu  Arg Asn Ile
    1250                1255                1260

Asn Asp  Gly Leu Ser Ser Leu  Phe Ser Val Val Glu  His Ser Gly
    1265                1270                1275

Ser Thr  Glu Ser Val Trp Lys  Leu Gly Met Ser Glu  Ala Arg Thr
    1280                1285                1290

Lys Pro  Glu Pro Pro Lys Tyr  Gly Ile Val Gln Glu  Phe Phe Arg
    1295                1300                1305

Asn Val  Cys Gly Arg Ala Pro  Ser Pro Thr Thr Ala  Ala Gly Glu
    1310                1315                1320

Glu Ser  Cys Lys Lys Pro Glu  Pro Leu Ser Pro Ala  Ser Tyr His
    1325                1330                1335
```

-continued

Gln Pro Glu Gly Val Ser Arg Ile Leu Asn Lys Lys Ala Ala Lys
1340 1345 1350

Ala Gly Gly Ser Glu Glu Val Arg Pro Thr Met Leu Ser Gln Val
1355 1360 1365

Gly Lys Asp Gly Ile Leu Arg Asp Gly Asp Gly Ser Leu Ile Leu
1370 1375 1380

Pro Ser Glu Asp Ala Val Cys Asp Cys Ser Ala Gln Ser Leu Ala
1385 1390 1395

Ser Cys Phe Ile Arg Pro Ser Arg Asn Thr Ile Arg His Ser Pro
1400 1405 1410

Ser Lys Cys Arg Leu His Pro Ser Glu Ser Gly Trp Gly Gly Glu
1415 1420 1425

Glu Arg Ala Ala Pro Gln
1430

<210> SEQ ID NO 3
<211> LENGTH: 4862
<212> TYPE: DNA
<213> ORGANISM: Homo sapiens

<400> SEQUENCE: 3
cgctgagcag cgacgccgag tccgcggccg ggggcccggc gggggtccgt acggggcagc 60
cggcccagcc cgcgccctcc gcgcagcagc ccccgcggcc gcccgcctcc ccggacgagc 120
cgtcggtggc cgcgtcgtcg gtgggcagca gccgcttgcc gctcagcgcc tcgcttgcct 180
tctccgacct caccgaggag atgctggact gcgggcccag cggcttggtg cgggagctgg 240
aggagctgcg ctcggagaac gactatctca aggacgagat tgaggagctg cgggccgaga 300
tgctggagat gcgggacgtc tatatggagg aggacgtgta tcagctgcag taccggctgc 360
gcaaagccga gcgccgcagt ctccgtgccg cccagaccgg ccaggtggac ggcgagctta 420
tccgtggtct ggagcaggat gtcaaggtct ctaaggacat ctccatgcgg ctgcataagg 480
agctcgaggt ggtggagaag aaacgggcgc ggctggagga ggagaacgaa gagcttcgtc 540
agcggctcat cgagactgag ctggctaagc aggtgctgca gacggagctg gagcgaccga 600
gagagcattc cttgaagaaa agaggaaccc gctccctggg gaaggccgat aagaagactt 660
tggtgcagga ggacagtgca gacctgaagt gccagttgca ctttgcaaag gaggagtcag 720
ccctcatgtg caagaagctc actaagcttg ccaaggagaa tgacagcatg aaggaggagc 780
tgctgaagta ccgctcgctc tatggggacc tggacagcgc gctgtcagcc gaggagctgg 840
ccgatgcccc ccactcgcgg gagaccgagc tgaaggtgca cctgaagctg gtggaggagg 900
aagccaacct gctgagccgc cgcatcgtgg agctggaggt ggagaaccga ggcctgcggg 960
ctgagatgga cgacatgaag gatcatggag gtggctgtgg gggtcctgag gcacgcctgg 1020
ccttctccgc gctgggtggc ggagagtgcg gggagagctt ggcagagctg cggcgacacc 1080
tgcagtttgt cgaagaggag gccgagctgc tgcggcgctc ctctgccgag ctcgaggacc 1140
agaacaagct gctgctgaac gagctggcca agttccgctc ggagcacgag ctggacgtgg 1200
cgctgtcgga ggacagttgt tctgtgctca gcgaaccttc acaggaggag ctggcggccg 1260
ccaagctgca gatcggcgag ctcagcggca aggtcaagaa gctgcagtac gagaaccgcg 1320
tgctcctctc caacctccag cgctgtgacc tcgcctcctg ccagagtacg cggcccatgc 1380
tggagacgga cgccgaggcc ggggactctg cccagtgtgt gcctgctccc ctgggcgaga 1440
cacacgagtc ccatgcggtc cgactctgca gagccaggga ggccgaggtg ctgcctgggc 1500

-continued

```
tgagagagca ggccgccctg gtcagtaagg ccatcgatgt cctggtggct gatgccaatg   1560
gcttcacggc tggcctccgg ctgtgtctgg acaacgagtg tgctgacttc cggctgcatg   1620
aggcccccga caacagcgag ggccccaggg acaccaagct catccatgcc atcctggtgc   1680
gcctgagcgt gctgcagcag gagctgaatg ccttcacgcg gaaggcagat gcagtcctcg   1740
ggtgctctgt caaggaacag caggagtcct tctcatcact gccccccttg ggctcccagg   1800
ggctctctaa ggagattctt ctggcaaaag accttggctc agactttcag ccacctgact   1860
tcagggacct gccggaatgg gagcccagga tccgagaggc tttccgcact ggtgacttgg   1920
actctaagcc cgaccccagc cggagcttca ggccttaccg agctgaagac aatgattcct   1980
atgcctctga gatcaaggag ctgcagctgg tgctggctga ggcccacgac agcctccggg   2040
gcttgcaaga gcagctctcc caggagcggc agctacgaaa ggaggaggcc gacaatttca   2100
accagaaaat ggtccagctg aaggaggacc agcagagggc gctcctgagg cgggagtttg   2160
agctgcagag tctgagcctc cagcggaggc tggagcagaa attctggagc caggagaaga   2220
acatgctggt gcaggagtcc cagcaattca agcacaactt cctgctgctc ttcatgaagc   2280
tcaggtggtt cctcaagcgc tggcggcagg gcaaggtttt gcccagcgaa ggggatgact   2340
tcctcgaggt gaacagcatg aaggagctgt acttgctgat ggaggaagag gagataaacg   2400
ctcagcattc tgataacaag gcctgcacgg gggacagctg gacccagaac acgcccaatg   2460
agtacatcaa gacactggcc gacatgaagg tgacgctgaa ggagctgtgc tggctgctcc   2520
gggatgaacg ccgtggtctg acggagcttc agcaacagtt tgccaaggcc aaggctacct   2580
gggagacaga gcgggcagag ctcaagggcc atacctccca gatggagctg aagacaggga   2640
agggggccgg ggagcgggca gggcccgact ggaaggcagc cctacagcgg gagcgtgagg   2700
agcagcagca cctcctagct gagtcctaca gcgctgtcat ggagctgact cggcagctgc   2760
agatcagtga gcgcaactgg agccaggaaa agctgcagct ggtggagcgg ctgcagggtg   2820
agaagcagca ggtggagcag caggtgaagg agctgcagaa ccgcctaagc cagctgcaga   2880
aggctgccga cccctgggtc ctgaagcact cggagctgga gaagcaggac aacagctgga   2940
aggagacacg cagtgagaag atccacgaca aggaggctgt ttccgaagtt gagcttggag   3000
gaaatggttt aaagagaacc aaatctgttt cttccatgtc tgagtttgaa agtttgctcg   3060
actgttcccc ttaccttgct ggcggagatg cccggggcaa gaagctgcct aacaaccctg   3120
cctttggctt tgtgagctcc gagccagggg atccagagaa agacaccaag gagaagcctg   3180
ggctctcgtc gagggactgc aaccacctgg gtgccctggc ctgccaggac cccccaggga   3240
ggcagatgca gcgcagctac acggctcctg acaagacggg catccgagtc tactatagtc   3300
ccccggtggc ccggcgcctc ggagtccctg tggttcatga caaagagggc aagatcatta   3360
tcgagcccgg cttcctcttc accacagcca agcccaaaga gtcggccgag gctgatgggc   3420
tggctgagag ctcctatggt cggtggctct gcaacttctc acggcagcgc ctggacggag   3480
gctcagcggg cagcccctcg gcggccgggc ctggcttccc agcggccctg catgactttg   3540
agatgtcagg caacatgagt gatgacatga aggagatcac caactgtgtg cgccaggcca   3600
tgcgctccgg ctcactggag aggaaagtga agagcacatc cagccagacg gtgggcctgg   3660
ccagtgtggg cacacagacc atccgcacgg tcagcgtggg cctgcagacc gacccacccc   3720
gcagcagcct ccatggcaag gcctggtcac cccgcagctc ttcgctcgtg tctgtgcgca   3780
gcaagcagat ctcctcctcc ctggacaagg tccattcgcg catcgagcgg ccctgctgct   3840
cccccaagta tggctcacca aagctccaga ggcggtctgt gtccaagctg gacagcagca   3900
```

```
aggaccgcag cctgtggaac ctgcaccagg gcaagcagaa cggctcggcc tgggcccgct   3960

ccaccaccac gcgggacagc cctgtattga gaaacatcaa cgatggactc tccagcctct   4020

tcagtgtggt ggagcactca gggagcacgg agtctgtctg gaaactaggc atgtctgaga   4080

cgcgggccaa gcccgagcct cccaagtacg gcattgtgca ggaattcttc cgtaatgtgt   4140

gtggccgggc accgagcccc acctcatcag caggagagga gggcaccaag aagccagagc   4200

ccctctcccc agccagctac catcagccag agggtgtggc caggatcctg aacaagaagg   4260

cagccaagtt gggcagcagt gaggaggtca gactcaccat gctcccccag gtggggaagg   4320

atggtgtcct ccgggacgga gatggagccg tggtccttcc caatgaggac gctgtttgtg   4380

actgtagtac ccagtctctc acctcctgct tcgcccgatc gtcccgctct gccatccgcc   4440

actctccttc caagtgcagg ctgcaccctt cagagtccag ctggggtggg gaggagaggg   4500

cactcccccc cagcgagtga cagagcagcc aagctccccg cctcaaccag cccagcccct   4560

ggatagcaga agggaaccag cagagacgag acgaggtgag gcgaggggct gtgtcctcag   4620

cattgcctgg ccctggaggg acagcagtga tgccactgcc agaatgcagc tttcacatca   4680

aggtaaagcc gggtctcctg ctggcccctg ggtggtgagc ttcgacttcc caggggaagg   4740

cagtgagtgg gagagagacc aaacctgggc ttcccaagca tccactgaga gatctgtcaa   4800

gagccgatcc ctgggtccta agagagagcc ttgcctggtt ctgcccatgc caccctcttg   4860

ga                                                                  4862
```

<210> SEQ ID NO 4
<211> LENGTH: 1439
<212> TYPE: PRT
<213> ORGANISM: Homo sapiens

<400> SEQUENCE: 4

```
Met Leu Asp Cys Gly Pro Ser Gly Leu Val Arg Glu Leu Glu Glu Leu
1               5                   10                  15

Arg Ser Glu Asn Asp Tyr Leu Lys Asp Glu Ile Glu Glu Leu Arg Ala
            20                  25                  30

Glu Met Leu Glu Met Arg Asp Val Tyr Met Glu Glu Asp Val Tyr Gln
        35                  40                  45

Leu Gln Tyr Arg Leu Arg Lys Ala Glu Arg Arg Ser Leu Arg Ala Ala
    50                  55                  60

Gln Thr Gly Gln Val Asp Gly Glu Leu Ile Arg Gly Leu Glu Gln Asp
65                  70                  75                  80

Val Lys Val Ser Lys Asp Ile Ser Met Arg Leu His Lys Glu Leu Glu
                85                  90                  95

Val Val Glu Lys Lys Arg Ala Arg Leu Glu Glu Glu Asn Glu Glu Leu
            100                 105                 110

Arg Gln Arg Leu Ile Glu Thr Glu Leu Ala Lys Gln Val Leu Gln Thr
        115                 120                 125

Glu Leu Glu Arg Pro Arg Glu His Ser Leu Lys Lys Arg Gly Thr Arg
    130                 135                 140

Ser Leu Gly Lys Ala Asp Lys Lys Thr Leu Val Gln Glu Asp Ser Ala
145                 150                 155                 160

Asp Leu Lys Cys Gln Leu His Phe Ala Lys Glu Glu Ser Ala Leu Met
                165                 170                 175

Cys Lys Lys Leu Thr Lys Leu Ala Lys Glu Asn Asp Ser Met Lys Glu
            180                 185                 190
```

-continued

```
Glu Leu Leu Lys Tyr Arg Ser Leu Tyr Gly Asp Leu Asp Ser Ala Leu
        195                 200                 205

Ser Ala Glu Glu Leu Ala Asp Ala Pro His Ser Arg Glu Thr Glu Leu
    210                 215                 220

Lys Val His Leu Lys Leu Val Glu Glu Glu Ala Asn Leu Leu Ser Arg
225                 230                 235                 240

Arg Ile Val Glu Leu Glu Val Glu Asn Arg Gly Leu Arg Ala Glu Met
                245                 250                 255

Asp Asp Met Lys Asp His Gly Gly Gly Cys Gly Gly Pro Glu Ala Arg
            260                 265                 270

Leu Ala Phe Ser Ala Leu Gly Gly Gly Glu Cys Gly Glu Ser Leu Ala
        275                 280                 285

Glu Leu Arg Arg His Leu Gln Phe Val Glu Glu Glu Ala Glu Leu Leu
    290                 295                 300

Arg Arg Ser Ser Ala Glu Leu Glu Asp Gln Asn Lys Leu Leu Leu Asn
305                 310                 315                 320

Glu Leu Ala Lys Phe Arg Ser Glu His Glu Leu Asp Val Ala Leu Ser
                325                 330                 335

Glu Asp Ser Cys Ser Val Leu Ser Glu Pro Ser Gln Glu Glu Leu Ala
            340                 345                 350

Ala Ala Lys Leu Gln Ile Gly Glu Leu Ser Gly Lys Val Lys Lys Leu
        355                 360                 365

Gln Tyr Glu Asn Arg Val Leu Leu Ser Asn Leu Gln Arg Cys Asp Leu
    370                 375                 380

Ala Ser Cys Gln Ser Thr Arg Pro Met Leu Glu Thr Asp Ala Glu Ala
385                 390                 395                 400

Gly Asp Ser Ala Gln Cys Val Pro Ala Pro Leu Gly Glu Thr His Glu
                405                 410                 415

Ser His Ala Val Arg Leu Cys Arg Ala Arg Glu Ala Glu Val Leu Pro
            420                 425                 430

Gly Leu Arg Glu Gln Ala Ala Leu Val Ser Lys Ala Ile Asp Val Leu
        435                 440                 445

Val Ala Asp Ala Asn Gly Phe Thr Ala Gly Leu Arg Leu Cys Leu Asp
    450                 455                 460

Asn Glu Cys Ala Asp Phe Arg Leu His Glu Ala Pro Asp Asn Ser Glu
465                 470                 475                 480

Gly Pro Arg Asp Thr Lys Leu Ile His Ala Ile Leu Val Arg Leu Ser
                485                 490                 495

Val Leu Gln Gln Glu Leu Asn Ala Phe Thr Arg Lys Ala Asp Ala Val
            500                 505                 510

Leu Gly Cys Ser Val Lys Glu Gln Gln Glu Ser Phe Ser Ser Leu Pro
        515                 520                 525

Pro Leu Gly Ser Gln Gly Leu Ser Lys Glu Ile Leu Leu Ala Lys Asp
    530                 535                 540

Leu Gly Ser Asp Phe Gln Pro Pro Asp Phe Arg Asp Leu Pro Glu Trp
545                 550                 555                 560

Glu Pro Arg Ile Arg Glu Ala Phe Arg Thr Gly Asp Leu Asp Ser Lys
                565                 570                 575

Pro Asp Pro Ser Arg Ser Phe Arg Pro Tyr Arg Ala Glu Asp Asn Asp
            580                 585                 590

Ser Tyr Ala Ser Glu Ile Lys Glu Leu Gln Leu Val Leu Ala Glu Ala
        595                 600                 605

His Asp Ser Leu Arg Gly Leu Gln Glu Gln Leu Ser Gln Glu Arg Gln
```

```
    610                 615                 620

Leu Arg Lys Glu Glu Ala Asp Asn Phe Asn Gln Lys Met Val Gln Leu
625                 630                 635                 640

Lys Glu Asp Gln Gln Arg Ala Leu Leu Arg Arg Glu Phe Glu Leu Gln
                645                 650                 655

Ser Leu Ser Leu Gln Arg Arg Leu Glu Gln Lys Phe Trp Ser Gln Glu
            660                 665                 670

Lys Asn Met Leu Val Gln Glu Ser Gln Gln Phe Lys His Asn Phe Leu
        675                 680                 685

Leu Leu Phe Met Lys Leu Arg Trp Phe Leu Lys Arg Trp Arg Gln Gly
    690                 695                 700

Lys Val Leu Pro Ser Glu Gly Asp Asp Phe Leu Glu Val Asn Ser Met
705                 710                 715                 720

Lys Glu Leu Tyr Leu Leu Met Glu Glu Glu Glu Ile Asn Ala Gln His
                725                 730                 735

Ser Asp Asn Lys Ala Cys Thr Gly Asp Ser Trp Thr Gln Asn Thr Pro
            740                 745                 750

Asn Glu Tyr Ile Lys Thr Leu Ala Asp Met Lys Val Thr Leu Lys Glu
        755                 760                 765

Leu Cys Trp Leu Leu Arg Asp Glu Arg Arg Gly Leu Thr Glu Leu Gln
    770                 775                 780

Gln Gln Phe Ala Lys Ala Lys Ala Thr Trp Glu Thr Glu Arg Ala Glu
785                 790                 795                 800

Leu Lys Gly His Thr Ser Gln Met Glu Leu Lys Thr Gly Lys Gly Ala
                805                 810                 815

Gly Glu Arg Ala Gly Pro Asp Trp Lys Ala Ala Leu Gln Arg Glu Arg
            820                 825                 830

Glu Glu Gln Gln His Leu Leu Ala Glu Ser Tyr Ser Ala Val Met Glu
        835                 840                 845

Leu Thr Arg Gln Leu Gln Ile Ser Glu Arg Asn Trp Ser Gln Glu Lys
    850                 855                 860

Leu Gln Leu Val Glu Arg Leu Gln Gly Glu Lys Gln Gln Val Glu Gln
865                 870                 875                 880

Gln Val Lys Glu Leu Gln Asn Arg Leu Ser Gln Leu Gln Lys Ala Ala
                885                 890                 895

Asp Pro Trp Val Leu Lys His Ser Glu Leu Glu Lys Gln Asp Asn Ser
            900                 905                 910

Trp Lys Glu Thr Arg Ser Glu Lys Ile His Asp Lys Glu Ala Val Ser
        915                 920                 925

Glu Val Glu Leu Gly Gly Asn Gly Leu Lys Arg Thr Lys Ser Val Ser
    930                 935                 940

Ser Met Ser Glu Phe Glu Ser Leu Leu Asp Cys Ser Pro Tyr Leu Ala
945                 950                 955                 960

Gly Gly Asp Ala Arg Gly Lys Lys Leu Pro Asn Asn Pro Ala Phe Gly
                965                 970                 975

Phe Val Ser Ser Glu Pro Gly Asp Pro Glu Lys Asp Thr Lys Glu Lys
            980                 985                 990

Pro Gly Leu Ser Ser Arg Asp Cys  Asn His Leu Gly Ala  Leu Ala Cys
        995                 1000                1005

Gln Asp  Pro Pro Gly Arg Gln  Met Gln Arg Ser Tyr  Thr Ala Pro
    1010                1015                1020

Asp Lys  Thr Gly Ile Arg Val  Tyr Tyr Ser Pro Pro  Val Ala Arg
    1025                1030                1035
```

```
Arg Leu Gly Val Pro Val Val His Asp Lys Glu Gly Lys Ile Ile
    1040                1045                1050

Ile Glu Pro Gly Phe Leu Phe Thr Thr Ala Lys Pro Lys Glu Ser
    1055                1060                1065

Ala Glu Ala Asp Gly Leu Ala Glu Ser Ser Tyr Gly Arg Trp Leu
    1070                1075                1080

Cys Asn Phe Ser Arg Gln Arg Leu Asp Gly Gly Ser Ala Gly Ser
    1085                1090                1095

Pro Ser Ala Ala Gly Pro Gly Phe Pro Ala Ala Leu His Asp Phe
    1100                1105                1110

Glu Met Ser Gly Asn Met Ser Asp Asp Met Lys Glu Ile Thr Asn
    1115                1120                1125

Cys Val Arg Gln Ala Met Arg Ser Gly Ser Leu Glu Arg Lys Val
    1130                1135                1140

Lys Ser Thr Ser Ser Gln Thr Val Gly Leu Ala Ser Val Gly Thr
    1145                1150                1155

Gln Thr Ile Arg Thr Val Ser Val Gly Leu Gln Thr Asp Pro Pro
    1160                1165                1170

Arg Ser Ser Leu His Gly Lys Ala Trp Ser Pro Arg Ser Ser Ser
    1175                1180                1185

Leu Val Ser Val Arg Ser Lys Gln Ile Ser Ser Ser Leu Asp Lys
    1190                1195                1200

Val His Ser Arg Ile Glu Arg Pro Cys Cys Ser Pro Lys Tyr Gly
    1205                1210                1215

Ser Pro Lys Leu Gln Arg Arg Ser Val Ser Lys Leu Asp Ser Ser
    1220                1225                1230

Lys Asp Arg Ser Leu Trp Asn Leu His Gln Gly Lys Gln Asn Gly
    1235                1240                1245

Ser Ala Trp Ala Arg Ser Thr Thr Thr Arg Asp Ser Pro Val Leu
    1250                1255                1260

Arg Asn Ile Asn Asp Gly Leu Ser Ser Leu Phe Ser Val Val Glu
    1265                1270                1275

His Ser Gly Ser Thr Glu Ser Val Trp Lys Leu Gly Met Ser Glu
    1280                1285                1290

Thr Arg Ala Lys Pro Glu Pro Pro Lys Tyr Gly Ile Val Gln Glu
    1295                1300                1305

Phe Phe Arg Asn Val Cys Gly Arg Ala Pro Ser Pro Thr Ser Ser
    1310                1315                1320

Ala Gly Glu Glu Gly Thr Lys Lys Pro Glu Pro Leu Ser Pro Ala
    1325                1330                1335

Ser Tyr His Gln Pro Glu Gly Val Ala Arg Ile Leu Asn Lys Lys
    1340                1345                1350

Ala Ala Lys Leu Gly Ser Ser Glu Glu Val Arg Leu Thr Met Leu
    1355                1360                1365

Pro Gln Val Gly Lys Asp Gly Val Leu Arg Asp Gly Asp Gly Ala
    1370                1375                1380

Val Val Leu Pro Asn Glu Asp Ala Val Cys Asp Cys Ser Thr Gln
    1385                1390                1395

Ser Leu Thr Ser Cys Phe Ala Arg Ser Ser Arg Ser Ala Ile Arg
    1400                1405                1410

His Ser Pro Ser Lys Cys Arg Leu His Pro Ser Glu Ser Ser Trp
    1415                1420                1425
```

```
Gly Gly  Glu Glu Arg Ala Leu  Pro Pro Ser Glu
    1430                 1435


<210> SEQ ID NO 5
<211> LENGTH: 23
<212> TYPE: PRT
<213> ORGANISM: Artificial
<220> FEATURE:
<223> OTHER INFORMATION: Synthetic human-specific peptide antigen

<400> SEQUENCE: 5

Ser Thr Gln Ser Leu Thr Ser Phe Ala Arg Ser Ser Arg Ser Ala Ile
1               5                   10                  15

Arg His Ser Pro Ser Lys Cys
            20


<210> SEQ ID NO 6
<211> LENGTH: 16
<212> TYPE: PRT
<213> ORGANISM: Artificial
<220> FEATURE:
<223> OTHER INFORMATION: Synthetic murine-specific peptide antigen

<400> SEQUENCE: 6

Cys Ser Ala Gln Ser Leu Ala Ser Cys Phe Ile Arg Pro Ser Arg Asn
1               5                   10                  15


<210> SEQ ID NO 7
<211> LENGTH: 24
<212> TYPE: PRT
<213> ORGANISM: Artificial
<220> FEATURE:
<223> OTHER INFORMATION: Synthetic overlapping murine-specific peptide
      antigens
<220> FEATURE:
<221> NAME/KEY: MISC_FEATURE
<222> LOCATION: (8)..(8)
<223> OTHER INFORMATION: Xaa is acemidomethyl cysteine

<400> SEQUENCE: 7

Ser Ala Gln Ser Leu Ala Ser Xaa Phe Ile Arg Pro Ser Arg Asn Pro
1               5                   10                  15

Ile Arg His Ser Pro Ser Lys Cys
            20


<210> SEQ ID NO 8
<211> LENGTH: 16
<212> TYPE: PRT
<213> ORGANISM: Artificial
<220> FEATURE:
<223> OTHER INFORMATION: SOGA peptide fragment sequence

<400> SEQUENCE: 8

Lys Val Leu Pro Ser Glu Glu Asp Asp Phe Leu Glu Val Asn Ser Met
1               5                   10                  15


<210> SEQ ID NO 9
<211> LENGTH: 22
<212> TYPE: PRT
<213> ORGANISM: Mus musculus

<400> SEQUENCE: 9

Phe Lys His Asn Phe Leu Leu Leu Phe Met Lys Leu Arg Trp Phe Leu
1               5                   10                  15

Lys Arg Trp Arg Gln Gly
            20
```

<210> SEQ ID NO 10
<211> LENGTH: 60359
<212> TYPE: DNA
<213> ORGANISM: Mus musculus

<400> SEQUENCE: 10
agttgggcct ggagctggcg ctgagcagcg acgccgagtc tgcggcgggc ggcccggcgg 60
ggacccgcac cgggcagccg ccccagccag cgcagtcggg gcagcagcct ccgcggcctc 120
ccgcctcccc ggatgagccg tcggtggccg catcgtcggt gggcagcagc cgcttgccac 180
tcagcgcctc gctagccttc tccgacctca ccgaggagat gctggactgt gggcccggag 240
gcttggtgcg ggagctggaa gagctgcgtt ccgagaacga ctatctcaag gtggggacct 300 ggggggatg ggggaggcgc aggggcggga gaggactggt catccgggct caagagtcca 360
gggcgctgac caagcaggga gagtgcccca ccttctcttc ccacttttcc ggtgaggagg 420
attatggata agacaccgag taaaggaccc caatgtgcac tttcccaccc gcggtaaaac 480
tgttttagag gacacgttct gatgggtgag tggggatagt cagccaaggc tgaccttccc 540
cccctctaac ctgcccagga ccccggtccc agatcagcag gctttctcgg ctctctgttc 600
tggaaccaat gtccgtgtgt taggctgcca gggaaaccgt gctatcccct ggcaaggaga 660
ggcagaacac catcctaagt ccttacccag ggcttccccg gcaggcctgt cctcgcctgc 720
cttttggggc ggatccagtt tgaaagcgtg acatctggga acatcccctt ggctcgagtc 780
cacttccgcc cagtctaacg gtcccacagc ctgggaggat gatgtcgtgg gagaactggt 840
tcagaggcca cttcctcaat cccaggatat tgtcttctgt cccctctgag agaggtttgg 900
gcagacttgg cccgtgctcc ctgtgggaag agggaaactg tcctgctggt taggggtatt 960
ccctctgtgt gtgggcctgg agagctgtct gggagaagca atcgtcggtg actgggcacc 1020
taggtgcagc ccatgctctg gctgcctctt ctttgacatg gtggcagcta tggggacagt 1080
cctgccctgg cttcttgacc ttggtgtggg aagctgggat cttcacgggc tgcactgccg 1140
ctgctggaag aggctacagt attgtctgca cttgacagtt gatggcctgg cacaacaccc 1200
agagtgccct ggccaggagc cattgagttg acagcactct aatgacatgt ctgccctgtg 1260
gcacttaact gcctcttgct tctactgtcg gggggagtctt ccttaggatg ttggggtgtc 1320
cctcttgctt tcctttgggt cctctatcca gcatgttctc aggaaactcc tgtacactag 1380
aggacacagg tctatctgac aaaggattat ttaccacctg tttgtagcct gggccttccc 1440
caaaccaggc ctccattttt tttttttttc agttaaatgg gagtgtaagt cttcacaaag 1500
gtgttactca ctgttgacat ttgggagctg gggttcagtt agagggcgaa gtcttctgaa 1560
gtcagtggtt agagtgcagg ccctgaggat ggagtcagtc ttccgagatg ctcctcgtgg 1620
cttcctgaat tcccagcctg agctactcca gacctggacc cgagcaccag atgagcacaa 1680
ctcacagttc ttggtttggt ttcttcctgc ccagatcccg ggccctttcc tgtgctccca 1740
ggaagtggtc agacagagtc cctaactcca tctgaagcta cccatgagta tgtagatggg 1800
aaagtggtcc caggaggctg gggtcgagt ccaggttctc ctagagacca agactgggtt 1860
gagttccagt tccagggcca gactgagcct cactttctgc caaccattca gttgagtttt 1920
tgggcgaaag cttcaggccc ctgttggatc tgtagcttcc tggctgtgta atcttgggca 1980
cattacttac catgtttgga cctgagtttt ctcatcttaa gacttgaata agtacacaca 2040
gatcatcctt aaagattaaa tgtgcacgta gctagagcat ttggcacggt aggaaacttc 2100

-continued

```
agatgcggtg gctgagatct cctgctgctc tcaggatgga gagcatggtg ccttgtgcat   2160
ctgtcacatt cttttgtgga ttctatggga tcaggctggg gtcttcctcc ttacctcgag   2220
gccatccatc catccatcca tccagtcagt cactgtttgc ttagagcaga ttttggagta   2280
tgagtgaact agggagagcc tctgtgacac caagagttaa acaatagtca caacaaaaca   2340
caatgcgcct ggtgataagg gtgagctttg tggaggtggg gcagaggact catggaggcc   2400
aggagttggg agatgatgta gacagccaaa tgaggagctg caagaaaaac attctagact   2460
gaagaaagtt gggcgagtga ggaagggagc catgccaact cttgctgcat gcattcaggc   2520
agtacccaca ctgctctgca gggctgtttt ccacagtgtc tgccctcacg gagatacagt   2580
aaaagccctg ggagtgtgga ctgtacacct acagggcagc ttcttactgg aggtgttatg   2640
ttgtcacagt gccaggggct ggcttagcca gagcaggaag gcgacctgct ccaggcagcc   2700
agggctggga gtcagggaga agcagtctcc tgagtgtttc ctgtttctct aaactacttt   2760
acatctgagg tacagaaact gggttagaag gaaaatgact ccaaatcccc agggtgtgca   2820
ctgcagactg accttctgag tccagggaat gccctggact ctagctggct ctctcgtcag   2880
gttcacctcc ctgtgtgtgt gtgtgtgtgt gtgtgtgtgt gtgtgtgcgc taggggtggc   2940
acggtgtggg taaactgtca accaggaagg acccttgggt aactgcatat ctcctgtctt   3000
aagaacccct gctctaggac ctaagttaga gaggtagcag aacctctagc ctctgccagt   3060
gaaaagacag aaagcacttc tgcagggaag gtggtgagct tggtgtcact tgaactatgc   3120
agagaggcct ggatacaggc atagggttgg tgggagcatc atgtaaatgg ttcttagtgt   3180
tggttgtgat ccctggggtg caactgggga ggtatgtgtg gtggctacag tctgacatga   3240
ggtcccttct agtcaaggtg tctgcggggg gtgggggggt gggggggtca tccgatgtgg   3300
tttttaggac ccagaaatac aactttagct gtagagcagc caggttaact gggtctgact   3360
ttgacccagt ggcctgaggt ccctatgacc actaaccgtt ccccttgtcc ccctgggcca   3420
tgttgtatct cagagtactg gagctcaaag atctggcttg gagccctgat tctacctttg   3480
ctgtgtggtc atggtcaagg gctggacctc tccgcgatgc tcttgttttt gttttgtttt   3540
gttttgtttg tttcatttgt ataatggaga tgacggatgg ggtgtgcctg gacactctcc   3600
aaggatttc tcagtaatca gggtagatgt aaatagtgaa gaaagcatct gaaagtgaga   3660
tccttgtatt gtgaggaact gttaggattt caagccaatg agcagacagg atgtctgttt   3720
gttcattttc ggaggaactg ggaggagtcg ggagggtggg catcctcagc ccttgagggt   3780
taataaaccc tcccgcttca ggcaggatag acaggcaaga tcacattccc ccctgcacag   3840
gctggcagtg gggagactag gcccctgcct gggggttcca gctgggagtc acaggtccca   3900
gagaaaagcc cttactgact ggcgattgcc attatataga tgggcaagtg gagactccag   3960
gattctgtca tacagcccat attccaacct tgctgttcac tcttggtcca tatccttctg   4020
ccatgtggcc ggcgagactg tgcttttgat cgctactggc gtgtctggtc ttggatagag   4080
gttggtgaga ggagtcctgt gggccaggtg ccaggccaag atttgtaggc agccatggtg   4140
agtaagctca gttggggcag tgtctgctca gcatgcacaa agccctggct ccatccctag   4200
atccgaataa gcctggaatg ctggcacacg cccgtctgta atcctgccat ttgggaggca   4260
gaggaaggct atcctcggca gtgtagtgag ttcaaggcca gcttgggcta agactgagtc   4320
tcaaaaaaca aaaacctaaa aggctgattg atatctatct aagcctgtag gtgggggtgt   4380
gcctctgggg cattttatac atgtctgtaa aatggggatt gaattgtcat ggacctctta   4440
attgtgagga tgcagtgtcc attgctcagt aaatgtgcca acccaatcac catcctttcc   4500
```

```
ctctcttcct ccctcccttc ctctgatgta gcccagagtc ttgtgagtgg catgcctgag   4560
gcagttcctt caaagctcct gggagatagg agaggaggga cccagcctgt caccatgtca   4620
gcgatgtccc ctggttcctg ccctgagttg tagcttctgg ggaggggggg tgcagcaggg   4680
cttggaggtt gggggagcag ctccagcagg atggaaaatg tgggcggcag ctgctgtggc   4740
cagaggatac cacagagctc ggcgcactct gcaaggggct gggcctgtgt ccctggacac   4800
agccctgtac acataaacac atgcacactt cttcagagct caagcctaga gacccacagt   4860
tactcatgcc tggctgatgt atacattcag tgactcactt atgctatatg cttccagaaa   4920
ccagcctcca gacacgttca ctgtggatcc acatggaaag tgacagacag acccttcatg   4980
ccacacacta ccaaacacaa cacttagcag caggagacgc caggctggga agtacacact   5040
ccctcacaca gcctgaagac actctcagac acaggaagtc catatacacg ggaaagtgtg   5100
cacatacgtg cacacagaca ttatctatac gcaccagcat ccataggatc ccagagactt   5160
gtcaggggac acagacacca tccactccag tacccagtgc cacctcttcc tcagagagca   5220
agcaaccttt gcacaagtac ctggggttca acagatgtca catgaatacc cacaaagagg   5280
ttcgcaggca ggatggaccc aacctccgca cacattagca ccaacacaag ggttgatcat   5340
gcagatgtca gacatggtgt ttgcttaacc agggcaccca gacatacatg ctcatgcaca   5400
cgcacgtcta tttacactga cggtgacatt tcacctacgc acataaacac aggaactctt   5460
ggtcagtgtt ccccggagct actgtgtatg actcttctgt ttccagctgt ttcataaggc   5520
ttcttgtctt gctgccggga ccataagtgg cgtcaggact gggtttgtaa ctgtctggat   5580
ctggggtccc aggggcccag ctgaggaggg ctgcaggtgg agtctggagg tctccataac   5640
tggagaaact gcatctaagt tgcccaggct ccagagccac gccctgtggg actaagggaa   5700
atagacacat gtcaagcctg ccacagaagg aacggtgcct cagggtaact cttctaatcc   5760
ctttggaatt tcctgcatac cctgcctccc tctgctgcaa gtcacagagg ccgcaatgcc   5820
ctgatctgta gagggtgccc atgcctagtc tagaactagt ctagaagtga gaagaggtat   5880
acgcacctaa gagcagctga gcaggcttcc tggaggagga ggtgtcacag ctggggattt   5940
gcctgattgg ctgcctcagt gctcagcttc tggataaggg cctgccgcct tgcaggggct   6000
cactaagtag atgtgtatgc ttaattgatc agctatggtt ctggcctaga aatggatagt   6060
aggtttggaa aggagggctg gagccaggtg tggaggtatg tacgctcagt ccttgtactc   6120
aggaggctgg ggcaggagtt caaggccagc tggttactac atagtgagac ctgtcaggaa   6180
aggacagagc gagagggagg aaagaatagt tgagtcatgg gtgtgagagt catggaacta   6240
ggggttgggg ttgaggagta gtagaaggtc aggaggactt aggaaggaca ctaggtacct   6300
gagcagtaga cccttggctg gaagatagtt ttgttggttt gtagcagggc tggggccagg   6360
tggccctagc actaggcaca aaattgctgc tatctcaggg tgccaatgaa ggcaaaagca   6420
aggaagactg tgaggtccca caggcacact ccgtctttag aatcaggtcc gaggccaagc   6480
cacaccttgt tatgtccctt cctgtgcatg ttgcctcttg gaacctcagt cttccagtct   6540
gtatagaggg aattcaatcc ctttcttgca gatactctgg gagataagag ttcagacaca   6600
tgagagccca tttctgtcct gtatacagaa gatgggaggg actccaggct ctaggtagcc   6660
tctgtggcag agggacactc cagaaaaggg cttggttaag ttcaaggcaa agggctggct   6720
gtcagccagg gttctaactg tggccagccc ctagcctcca acatatgaca tcatctgtag   6780
tctatacaca cccctctggt gcaggaaggt ggggcccctg cggtcagcac tgtggctgcc   6840
```

-continued

```
tttgctggct ttccaagctg gggcaggagt cggaggaggt agaagctact gttcatccct   6900
cccttgtctc agtctaaagg tctgaaagct tgggatctgg accaagcctg ggctgcatct   6960
gggcctgtgc tttgctccct gttccccctc caggaaatgt tctgcagtgt caccatgatc   7020
attcaacagg agggagccgg tgtgtgagga gttggtcccc tctgtgtttc actcatcctg   7080
gttgtcagcc cttacccttc aacagctcca gaaatgtgta gacacatttc tccttggcag   7140
ctcacttacc ctaagtcact cctcccctga tggccaaaac ctgtgtctca tttgcaacct   7200
ggtgatgctc gcttagtggt gaaggaccac ccttgggggc ccattccaag atagtggtaa   7260
aacatctcct gcctgggcta cagatgaaaa taaaggtgac tggtgtgtgt gtgtgtgtgt   7320
gtgtgtgtgt gtgtgtgtgt atgtgtgtgt gtgtgtatgt gtgtgtgctg tgattcccca   7380
actgctggtg tgtatgtgtg tgtgtgtgtg tgtgtgtgtg tgtgtgtgtg tgtgtgtgta   7440
tgtgtgtgta tgtgtttgtg ctgtgattcc ccaactgcct gagcctccgt ggctctttgg   7500
gactcttcag tagcaccaga ctttgtttgg tcacccctcc ctggtctgcc ttgcctaggc   7560
accatcctcc tgtcccagcc catggctaag tgcgcggctg agctgccttt aagtcttgct   7620
tccccagcct tttcacccag acgcccccag tgtcctcttt gccctttcat tatggatcca   7680
ttcccctgtc ccctttccat gatctcctgg ggactgctcc aggcctggtt tcctgtgtta   7740
ggtactagga gctgtgggga ctcctcggtg ggacatttag ctcacagtga ctagacttgt   7800
taacaggaca tttctggctt cgcagcagcc actcctgctt ctgcatgcag tgtggcgctt   7860
ccagggtgct tagccccttc cttctaacca ggcttaaact gcagcccgag cattacgtca   7920
ccttgcttgc tagtcacatt agctgtaaag gacaagaggg attcaggccg tgtggttctc   7980
ggtgattctg caagcctcga ctccctgccc ttttctgtta cagacttggc tgaagcccag   8040
aggttggggg atgttgtcaa caaaccctga tccaaagctg ccttccttcc tgggcaggac   8100
aggagagaca gtgtctgtgc ttccttgagt gtgcccagca gcccagggcc tcggggcgct   8160
gcccctaggc tacacacaca cacacacaca cacacacaca cacacacaga gagagagaga   8220
gagagagaga gagagagaga gagagagacc tggagacaac ctcacttccc tccctcagcc   8280
tcagttggtt cccctgggaa gtgggcaggg taagaataga gcttgccaca aagtatcacc   8340
aatgagaaag agagaatagc ttctcacctc tgctggtgtc tggcacatgc catacccttg   8400
gaagtgccca gctgttgtta cttctgttgt cccatttatg agcctcaaaa tgagcctaag   8460
tcctgactcc tgacgcctct gctttcaggc ttcttgccta ctggggaggg agggactaac   8520
tgtgtgctgt tggcatgagc ctgccgtggt cagtctgtct gctctctctg gtgttggaga   8580
ggcagggccc agagaagtgg gacctcatag atctctaggg tcagatatcc ccagtgccaa   8640
tggaacagga gcattgagat cctgtaactc ggtgatgcat ggctggatgt gacttcctct   8700
gtgacactta accctgattc ccccaaacct ctgcccacag aggctaagct gggttgagct   8760
tgaacaggag gcaggaaccc agagtccttc ttggcctcac tgcgcgttct gtaaaggaca   8820
aggagtcttt gagttcccct tctcctggag tgtttgcatt caaactggga gggaagtgaa   8880
gctctttgca gccttctcct ggggtctgac tgtgatgatc tcatctggag ccctgtcaga   8940
gtcccgggga ggaggaggga cagcagatgg cttttctggc cttttgggtg gggctggcct   9000
gctgtccctg tggccactgc tggtcagctc ttccatagct ggggtaggtt gccagggcca   9060
gagtgggtga caagtggtct ggagccaggg tggcagatgg gtaggcagcc tgggccttgg   9120
cccaggggag gaccatggta gccaagtggt gtgggaggag gagggcaaag cggagcccct   9180
ggtcctttgt agagtggttg attagagtga agtccctggc cccatataga gcatagcttt   9240
```

-continued

```
tcctgtccat ccctaagtct gcttttgagc tgggcaggaa atgatccatt tgggtaagat   9300
ttggaatatg tcacggctgc ggtcgggtgt catggtgctg ggagttgaag cctccgtgga   9360
gattggcctc ggagtctaaa cagttgctgc agctgctcag tgggatggtg gtcctccctt   9420
cagcctggct gttctgttcc ctcatggcta tttcttgagc ccctctatat gtgcccgttc   9480
tctggtgact gaagtgggtc ttccacaacc aagcagacaa atgagtaaaa tacccgtcac   9540
taatagaact gtgtcgtgca gtgtgaggga aggagaaggg taggctgcac ggcttggcag   9600
gaggcctgac aggaggtgcc ataggccacc cacacaggaa tggcagaggc tgaaggctgt   9660
gacaggccag gtgatttctg ctggtgcagg aagactcggg tggctgagtg tggcccacgt   9720
gaggggtggt taagggacat ggaggtgaag ggagtcaggg ttgggcctgg tggagcctga   9780
gctcctagga taggtttgct ctgcgtgatg aacgagaccc cccggaggtt ctgtttctgc   9840
tttgctttat gtctatttga aaaaaaggtc tcactgtaaa ataagttttg ataaatgtac   9900
tataactgtt aaccccagtc aagataaggg ctaacgccta taaactaggt acattaggat   9960
tgtatttctt cttcaatcta tttatctatc tacttagtta attaattaat gtgagtgtgg  10020
gcgtgcatgt gggggtcctt gtggaacttg gttctcccct cccatcaagt gggttcttgg  10080
aattaaagtc aaatcgtcaa gcttggtggt aagggtcttt gctccctgaa ccagctcaca  10140
ggcccctaat tggatacatt aatttttttt aaatttaatt ttatttttac tgtatataag  10200
ttatacctga gagctaggga tgtagtagct cagggccaga gcctggactt cacatgtgag  10260
agatgctggg tttaatcctt agcaatcaaa aaagaaaggg agtgggggat tagaagtgtt  10320
cattgttcag ccaaacttcc tctacaacca gagccctccc tcgactactg atctgttctc  10380
tgtcccttag cctcacccat tcacagtgtc acatgcatgg caccctcagc atctcctgtg  10440
gctggcttcc ttcgaggagt caaagcccgg ctgctccagg cttccagagc accccacccc  10500
cacccccacc cctcgctgct gctggtgtta catggtgggg tcacagctta gccatttgtg  10560
agtcaggagt cacgtgggct gtccccacgt tttgattatc attggagggc ttaaagcagg  10620
gaacatttaa acagttttaa tcacatttta agtattaaaa aaaaaatcac aggctggaga  10680
gatggcttag ggttaagag cactgactgc tcttccagag gtcctgagtt caattcccag  10740
cgaccacatg gtggctcaca accatctgta acggaatctg acgccctctt ctggtccgta  10800
ctcacataca taaaataaat aaatagttca ttaaaaaaaa atcactcttt gggagctggg  10860
gtacagagca agcactaata tgcaaggtgc tgagttcaat ccccggagct ggagaagcga  10920
tgggggtggg gggagaaaga gagggaggga gaattactgt gtcttgtact aagttgggag  10980
cagcttactg aggtcaagga agggtcacca tgacaagaat ctgggcccgg ccaccaggcc  11040
tgctgtaggc actcactaag tattcaaaca cctggatgtg cccaaggaag tctgtgtttc  11100
tgaggtaaag agttaggagg cagtgacaga gcaggaggcc caggtgtgct gtctgtgggc  11160
tcactgcgat aggctgtcag ttcccagctt ctgaccctgc ctgggcacaa ctgggatctc  11220
agatgtggtc attaggcttc cagggtggca ctgggagtta ttctccagtg ggagggagtt  11280
gagggtctcc acatatcatc ctcttgtctt caggaacttt atgtcccctt ggctccttct  11340
tggttgggac tgtctctggg gtcagactac ccactgccac ttgctgtgtg tctgcaaagg  11400
gatgtcgtgt ccagtcctca tttcccacag gccagatcca tcatgcacac agtctgcact  11460
cctgtacaag gaaggacttc accaaagcca ttcccctctg tgttctcagg gacagtcaat  11520
catcttacat ccatgtaggc ggcacagaat caatccttgg atctgaagtc agggctggcc  11580
```

-continued aggaagttca gggatctgcc tgtctccacg cctggcttta tccatgggtg ccggatgacc 11640
tcagatctgt gtgcttgcac agcgagtact ttgcccgccc agccatctcc ccagtgttgt 11700
ttctcccttt tgatgctctg agctatcagg ggctggggta ataacccagg ctttgcagat 11760
catggtgctc ccaagagaat agaggctctg gcattgtatt ctatgcatgg accctattac 11820
tgttataagt tatactgtta taggacccta ttataggtta taacctctgc tgagaccctc 11880
aggataatgt ctttcagtgt taacctccaa atccaaggag attcaagcta gattgaaaca 11940
attactaaag tatgctacaa ctatgatata gttatgtgct tgttaactct tggattctga 12000
tagctgcttt aactactgta attacaaggt actgatgagt ataaacaata ttttgacatt 12060
tttgcaacaa ccgttatagg atatgaagat attagcaatt tctttggtgt ccaagtcttg 12120
agtgcttctg atacaacctc actttgttct tgagtccaca atggaaggag atgcaaattt 12180
caagaggttg ttgcaaataa agatgcaact ttgttgagta gccaacagag aggaggggac 12240
ctgagggaag catcccttca gggctctgcc tgttggggta ggctcagcag gcccggtccc 12300
ttgatgcaca cagctctctc tgtacaacgg attcctggct tgccttgctt tctgcaggac 12360
tcatgaggtg attcaccagg aatgtctgta taaactgtgg agtcccttgc aaccctgcaa 12420
gcctattatt agcaatattg tgagttcatg ttgggtcctc gagcccagcc tgaacttaga 12480
gactcttccg ggccagtttc ccaggagtcc tgggaactgg ccatctctga gaggttgctt 12540
cctgccggca gccctcacgg aggtacttga catgtaggag atgtgtggga agcttgcggt 12600
tccctgggca ggcagacctt gctatcctcc tgaggtggca ctggagtcag cctgggctct 12660
ccctgccctt tcacacaagc cctagatctg gggtcaaaag gacagaaggc tccaggctat 12720
ggaaagagac caggcaggcc aatagccttt ctcttttgtt cacacctgcc catggtgcct 12780
gttgcattcc acatcctagg gatgttgggg agcagaagtg ggtgagaccc agcctcactc 12840
tgccctgccc ttcctcaggc agttagaggt agaacgacga ggagcaagcc gatgtaaccg 12900
taagtcgtta ccaccaggga cctgcagttc agggtgtagg ttctgaacag ggaagagaga 12960
gaggaatgtt ctggaaagcc gagagagctg ggagttctcg tggtgaaggt cagtagagca 13020
tagcacacgg cctgcgtaaa gctggaagaa tgcagttcgc atgccctggc ccagggccac 13080
tgccttgtat gtaatccagc ttcacccctc cctagcttga acagctctgg gaaacttctg 13140
agcctcagat gccccctctg caaaatggga gcattttcga tgcctctcac agggttagca 13200
agagatttaa cactcagaag tgcgtggatg agcctgtgtt tgtgagcctc cctgtagggc 13260
cagggtcagc cattcagtcc tagtatagct gggtgcaggt gcaagataga atagggaaca 13320
gattggcaag gggtcagagg ttaggggctt ggacctgagg tggaagccag gggaatgagc 13380
ctgaaagcca cctgctttta ttcagactag tcaacagaca ctgccttccg aacagagcca 13440
aggagccttg caaagggacg atcatggcag gctgcactgt ccctagaccc tgccctccct 13500
tctactccct gtctgcaacc tggacttaga tgttgtctaa gggacagagg gcagcaggga 13560
gtcagagcct ggcggggctg cttgactcct ttcttcagct tccttaggct tgataacagt 13620
ctaggggtct aatttatttc agggtgtagg gttgagaact gggggcccct cagactccag 13680
ggtgggcact gcacagtgtg gccttttaca tctgaggtag agggtgagat ttggagtgcc 13740
cccatgctgg gaagggggaa cctcagaacc ttgttctatg agattgatcc ctctttcttg 13800
atgtcctata gaagagttca agaggtggca tctctgtggg gcctctggac tgtctgtgaa 13860
gaaaccagga ggcctgtgtc tcagctctct ccaactggac ctgtcacccc agagcctcca 13920
aaggcaaaac tctgactgta gggcccaggt gcccagaaga tctctgggct gggtgtggac 13980

-continued

```
accgagcctc tgtcttttcc ctgccccctc ctcagaccca gatacccaga gtctctgcct  14040
aagcactaca gtgtccagcc catgtgggct acaagcctgc ttttgtcaac tcaagccgtg  14100
ccaggagggg ctggtgggtg ttttgcccgc agctggggca agcccccaga ggcttcagcg  14160
ccccaacccc ctcagataca gaactggcat gcccacaaca gcctgcactg tggtgagggc  14220
agttccccccg agagacagct gttggggata gccattcagt cacttcttcc ctagacgcct  14280
gtgtcaggct cagagccagg gacttgtgcc gtgagatggg gctcttgtct tctgtgggga  14340
agaaagtggg aaggaagttc cttgcctcgg aatcacttgg ggaacccacc cctgaagttt  14400
ctgcttagta ggtgtggatt gggaatatgt gtggggtggg ggttgcatag ccctggggta  14460
gaaccacacc cctgagcatg tttggcagac actgccagtg agctatacca tcctggggaa  14520
cacttgtcat tcagaaccag atagagaaat tgtgattgat gttttctgta tttttcaaaa  14580
ctttctgttt gaccgtggtg gactaccttc acaaaagccc gttacttaaa atatagaggg  14640
atgtcacctc ctgtgatctg tatggagcga catctccacc tgtgatccca tcagcctgag  14700
cttgagtatg tctgtgttcc ccttgactca ttctgaccta gagtcacttg gaccctcaca  14760
tcctcccagt taccgtgttg tcaggataac agggtaacat gtgagctgct cgtggttggc  14820
aaggccctgc agcctgggcc atggatgtag ctgtctgcct tcacttcctg ccccttcctt  14880
cctgccccct tccctgccag ctgagctggt tcatgggctc ctcacttccc catttctccc  14940
accgactgtc tcacttcctc cctgtccacg ctggtctgcc cagttggcat ggtgtggggt  15000
ggtgactctg ggtactttga gatgactgct cctctgcagc cagtaggcag ggtcacccac  15060
tccggttgct ggtgaacaca ccctctggac acagtctggt gctgcacagg gatacttgga  15120
tcagttgtga gttgagagag acagcatgtg gtggggtgga gccgccaatt tgtcacttct  15180
gtcttccttt cctgggttct gagaaatagt tccagaagtt aggcagatgg atgggagggc  15240
ccctggagtg tgctgtggcc tggatagttt ggcttcttac ctgtccatca atccagcaag  15300
ccacaccctt tcccctcaca gggagccatt gcagccagga catattctgg tcccactgca  15360
gtgtggaccc acagcctgtg ctcggcccag tggaggctgg caggcaggtg tgaggagagg  15420
tctccgtgtt tccttttcca gactatcaga tccctggggc gagcacaggg tgtggggagc  15480
agaggggatc ccacccctac accctcccct ttattcccat cttctttagg ggactccagc  15540
cctccagagt agcctttctg ttctggttgt ctccctgctt ccatcagtac caaccttgtg  15600
agcttctcct gggagcagag ccttcgtcag ggcctggtcc ctggtgactc agtttccctt  15660
ctgtgtgtaa tctcgttaaa gctaacagca aatattattc atgtttgtga ctcagtttcc  15720
acatttctta tgagacataa ttatgtgttt cctctgggag gcgtccacat ccccccctctg  15780
tgtagtgtct gggagtcacg tcccatcttt cacagtgaga agtctctctt attctctctt  15840
ccttagctag gcatgttttc gttcgttctg ttagtacctg ttgagagtgt gcaggaggct  15900
aagcaggtgc tgggtgtgtg tgtggggggg gtaggggcag gcaggtaggg cgacctgaag  15960
attcccacag tcactgggag agcaactgcc aaacagcttc agatgagctg aggtgggtga  16020
ggcaccgata ggagctgtga cagaggtggc agtagctggg cttcctgagc gaggtcacct  16080
gaagatcccc cactcaaaac tccaaccaga ccttccaggc ctgcaaggct gatccctcca  16140
tatccccagc cttgtgggtt ttggacagtc tcacatagat gaggctggtt ttgaaatcat  16200
gatcttctta attccatatc cccgtgcctg acccttgctc gatctttaaa acaaacaaac  16260
aaaagctttt ttagacaata gtcccactat gtataagact tggctggcct gcagctttct  16320
```

-continued ctatagacca gactggcctg gtctgaaatc aagtcactct gctctgagat cctgcctttt 16380
tgtctctgcc tttttcaga tgctgagatt aaaggtatgc accattatta aataaatatg 16440
tttttgatta aaaaaatttt ttttcaagac agggttctct ctgggtagtc ctgtctgtcc 16500
tggaactcac tctgtagacc aggctggcct tgaactcaga gatccttctg cctctgtctg 16560
tctcttgagt gctgggatca aaggcgtgca gcacactacc tgaccaatat acttttaaaa 16620
tgacatttct ttgtacatgt atgtgccaca gaatacatga ggagatcaga ggacagctta 16680
cagaagtggg ttctctcctc tcttctacca cgtgggtccc aaggaccaaa ctcaagccac 16740
taggcttggt gggcagcacc ctgacccatc ttacctgtcc cattgatgtg tctttgtttt 16800
ctcagctgag acagggcctt actgtgtagc cctggctatc tcagaactta ctctgtagac 16860
caggctgccc ttgacatctg cttgcctctg cctcccaagt gctgggcttc aaggcatgca 16920
ccactacact caacgtcttg cagtgtctgg atacattgag ttctacttct aagcctttgt 16980
acacactgtt ccctcttcct ggaactcctc tggatgttgc ttcttgcctt ggcttagatg 17040
tcccttcttt agagatggcc cccttcctcg ctcactgcca tgtaacccac attgttactt 17100
tgttattttt gcctccatga tacttactta acagtatctg aatttgcttt ttgtttactt 17160
tgttttccaa acaaggctgc gctaacatcc ttccctggtt ttgtgtgcta cacagtgtcg 17220
gttatgtagc agacactcat gaatgtttgt ggagtggatc cctggtgtat gtttcccatt 17280
gcttctgtct gcgacaagcc tctactgttc cctctgtcgc tatgacaaga gaaggaaggc 17340
tgtgtttccc atgcttttgg aggcctccgt tcaagatcat tttgttcctc ctgtgacaca 17400
gagccatcaa ggcagggaga gcgtgacgca ggaggctgtc acctcatggt gaccaggaag 17460
caaggcacag ggtatcaata gcctttcaag ggccctttcc aaagatgtct ctcccttgcc 17520
tcctgaaaat ggtccactgc ttcacagtag aaccatgagg aatactcagc ccatagcaag 17580
tgactttggg gggggggggc gctttaagat ccaaatcgta agagtggtgt ggctgtaaat 17640
tatcttccag gtctttgaga ctcgagtcct ggtggctcac atgtctgctg agtgttctga 17700
gacaaacagc atcctctcct gggccttttg gcccttgtgg atggttcaca ctgtggaggc 17760
cacctgtact ccctggctgg tggccctttc tctacctgca caacctgtca gtatttcccc 17820
tatttctccc tcacattgct cgctcccact aacttccctc tcatggccca cccagatggt 17880
caagaataat actcccatct agagaccctt ctcttagtct cgtttgcaaa gccccctttg 17940
ctgtggaagg catatattta ggatcccctg aatttagctg tggctgtctt tgggtggtgg 18000
tattcagcct gtaaccccag ctggctttct gagtgtggcc agcattcagg caccctggct 18060
actgccatga catctgtagg tctgaccctt tcttttcacc cctcaggatg agattgagga 18120
gctacgggct gagatgctgg agatgcggga tgtctacatg gaggaagacg tgtatcagct 18180
gcaggagttg cggcagcagc tggaccaagc cagcaaaacc tgtcgcatcc tgcagtaccg 18240
actgcgtaag gctgagcgcc gcagcctccg cgctgcccag acaggccagg ttgatgggga 18300
actcatccga ggtctggaac aggacgtcaa ggtcagtctg gggtcactgc caaccttcac 18360
aggtgccctc gttgggtggt tggatcataa accccattgg ggatccaggt taggcctgtg 18420
gcttactgct tgccttgagc aaattatcct gcctctctgg gcctcagttt ttccatcttc 18480
aaagtgggga cccctggtgg atcaacacat cctccaaaca ggatagccag gaaatggtat 18540
gacaagaacc cttctgaagc agcaagaggc cgtttcttgt atgtctgctt tgtatgtggc 18600
tttggcctct gagtaggccc tacttatggt ccctgctcag caccacaggc ttcttatggg 18660
aagactgcag ctgaaccagg atggttcaga gctgggctcc aggatacttg ggctttgagg 18720

-continued

```
ttttaatcaa gtcttctata tttcaatgtc ctcatctgca aaatgggtat aagaacctac  18780
aatccagaat attaaaaccc tggctaagac accagaggga ctgacagtga gtagctatta  18840
ttactgcatc cgttttctgg aggagggggc tgggcctcag aggagagaag cacctatcca  18900
gggtcaagac gtcaggccca tccacctctc agacctcact gctggaacct gctgcttctc  18960
tgcctaagga gaaagcctga atggcgccac ttaggtcggg gatggaggag agaagtcccc  19020
attgccagtc tgtcttatgt aagcccccaa aatgtgggga ccctgagcca gcctccgctc  19080
tcagaactca gtccagtgtg aacaaggaac tcagggtgct gcgaccggta cagaactggg  19140
aggagcctag gagttctgca ggtagcccaa gggggaagag ggcgtgagcc tgggaaagat  19200
ccaggacttc cttggggaaa gatcccaagg gccccggagg gcaggcaggt gctgagcaag  19260
ccacacacct gctgctggaa agccctgaga atccagccct gcagggcatt cagaaaggac  19320
actgttcatt ctgtgaccag cgttgagact ctatgcaagc ctgtgaacct gtgtggagcc  19380
agtttccttg actgcacact aagatcttgt tatccaaaaa atcataaaca aaacacgatt  19440
taaaaaaaaa acaacctaac aactccccgg ttccctcatc ggtaggagac agagcaggga  19500
gggaaagagc ggagcgagcc gttcaggcga atctgcggtt gggccctggt ctttgaatct  19560
gggagggacc ctagacaagc aagaccgaga agagaggtgg ggagcaggct ggtgggcggg  19620
gccagagcag ctgggatggg ggtggggctc agccctccag gaggagggga agggcccctt  19680
ctgttaggat ttgaacgagc caatctgcat gcccgcgctg ctcctgccca cccccgcagc  19740
tgcaacgctg agctcatgtt ctggctctgt cttagcgggc cgcacagttt tgccatcacc  19800
cttcctccca gtgtgctggg gatgttagag gcaattatgg aggtcctcag aatgctgact  19860
tccctgtctt cccctaggca cctctcaacc aggtggagag ggactggggg cggggacgga  19920
ggtgggggt atgcctaggg attcctctcc tgctcagcag gctccttggc cctgtgccct  19980
gcagggcttt tgagctccgg tggtttttatt gagctggtat gttattagtg agattcccca  20040
gccgccaccc cagaacaacc ctcccaggct ccttttgctg gtccacacag ttaacaagat  20100
ctccgaccct caacagggag acccgctagc atgaggatgg tctggccact ttatggccgt  20160
gtgggcttgg gtaagctgct tcaatctctg atcctgtttc cactgtggaa catggagata  20220
agtttagtat cctatagaga ctttaaaaaa aaaacacaca aacaaacctt tatttactat  20280
gtctgtagct ttctgcttac atatatgcct caacaccaga agaggcacca gatttcagta  20340
cagatggttg tgagccacca tgtggttgct gggaattgaa ctcaggacct ctggtagagc  20400
agccagtgct cttaaccgct gagccatctc tccagccccc tatagagact ttcatgacta  20460
taaaatgaaa ttacaaaata gagtcctgtg tggtaggcat ggcaccaatc ataggagcac  20520
gtgatgggag gagcctcggc tgggggactc tgggatccac tgcttttcct gtagagagcc  20580
ccagaacatg tcagtaacat gtaccccatc cttctataag gatgctctgg ccttggctct  20640
gtgtcctggg tgacctgcat cacttcctcc ttggagcctc agtttccctc tgtcaaatgg  20700
cgtgacaaca cccatcatgt gatttttgag tttggtcaca catgcctcag gatgcttgcc  20760
tggcctgagg tactgcttat gatttccatc tctctccttg aagatcagag ccacagggtc  20820
gcactgcaat cccaggttca gagcccagag actgatctac ccaggagctg ggggccaccg  20880
ctgctgctgg cctttggcag ggaccagcac tgtgaatagt gacctcatgg atgagcacat  20940
ttgtttgtgc tttaggcatt tgctgtgtgt ccaaggctgc ctctcctctt tgtctccctg  21000
cttataactt cggggctcaa tgagacaggc acacaaggcc cttcaggctc tttggacata  21060
```

-continued

```
gaaagttgtg ttgggacttg ctgttgacag gccattgtta atcattgtag tccttcaagc  21120
ttgcccttct tcggcatcat cagcttcata gttgacccat gctaccttcc tagtcatgtg  21180
accttgggca actgcccttt cctttctggg attcaaagct gtcatgaaac atgtcctgag  21240
ggtgagaaga gcctatggtt atagcctgga gaggctataa gtgacccgtg agagcccagg  21300
gccctgggac cactggaaat ctgggcctgg atatgggcgg tggtaccctt ttcttccgga  21360
ctctaatgga ggcttcaagg cactggatgc agggatctaa gcttgtaggc tcttctgttt  21420
agaatgctgc agcttcccag gggatgggtg ctttctttct ttttatttat ttttattttt  21480
ttggtttttc gagacagtgt ttctctgtgt agtcctggct gtcctggaac tcactttgta  21540
gatcaggctg gccttgaact cagaaatccg cctgcctctg cctcctgagt gctgggatta  21600
aaggcgtgcg ccaccatgcc cggccttttt tttttttaa agaattattt atttattata  21660
tgtaagtaca ctgtagctgt cttcagacac accagaggag gtgtacttat gtcagatctc  21720
attacgggtg gttgtgagcc accatgtggt tgctgggatt tgaactcagg acctccagaa  21780
gaggagtcag tgctcttaac tgcccagccc gatgggtgct ttcttttttt tttttttttt  21840
taaagattta tttatttatt tattatatgt aagtacactg tagctgtctt cagacacacc  21900
agaagagggc atcagatctc attacagatg gttgtgagcc accatgtggt tgctgggatt  21960
tgaactctgg acctctggaa gagcagtcgg gtgctcttac ccactgagcc atctcaccag  22020
cccggatggg tgctttctta acatgtggcc ctggggacag ggaattcatg gagaaggaag  22080
aggatccagg aactctgatg gtgaccagat gggcttccca ggtaggccat ggtggagaca  22140
gagcccttcc tatcccaatg gaagcatgtt tgggagacga cccttggccc cagtgaccct  22200
ctttggacaa tggggtaggg gctgtggagg agagtgcctg acaccttgct agggcaggtt  22260
ccgctcccac atgtattcca ccagccactc ctcctttttc ttgttctggg tcttgatttg  22320
tttgtccacc caacaagtat ttctaggcat tcagtgtgtg gtgagccctg ggctgctgct  22380
ggaacacaaa tctaaatgaa tccagatagg cgtggcccta ggtttaccac ttctacccca  22440
gtaccaaggc gagatgaatg aatgaatgaa tgagtgaatg gaatgttggt gaggacagag  22500
cttcctgagt gacctagtag cccaaaattg ggcctgggcc aaggtgaata aaaccaatac  22560
aaagaggcaa agcagtagga atgcattaaa caacaacaac aacaacaaca acaacaacgc  22620
ttttgtgact cagctggcag ggtgcttacc tagcaggcac gaagccctgg ggttggtctt  22680
gagtgctgca tagactaagc aagacggcat agactaagca agatggcata ggattagcac  22740
agcgcttggg agacagagac aggaagatca gaagttcaag gctatccctg actagtagca  22800
agctcaagtc cctcctggag aggaaaactt ttttgtgtcc ctggagatgt agttgagtgg  22860
gcgagtactt gcctagtgtg cacaaaagtc taaccattcc cagcacaggc taaaagtcaa  22920
aatccctgtg tggatggctc cttgacctcg tgcctttgag ctgcccagtg agcccttaaa  22980
tattttacac aatcaaaaac aggtcaagaa actatgaaat caatacaact tttgtaatac  23040
actaaataga ctgaattatt taaaaataat agtaaataag aagccttgtg tttttttgagc  23100
acctcctgga ttccagccac cactcaagca cccatgatgg catttgctcc ctcttgccac  23160
cacgggaaca gtgtatccat gtaatggtga ccagatgtag gctccagatg ttcagggctc  23220
tggcactggg tttgaatcga gtttcttct ctgcaaaatc ttttctttgc tattgaaggg  23280
tggggagagc tttgtggccc acagtggcca caggggaggc ttgtgggcct ctgcctggcg  23340
tcctcagaga gctccaggct agagggggca gtgggccgag gagagagtag agctgtgccc  23400
agtttccttt caactattat ttttcctggc cttccctgca cattgccaaa ggggtctgtg  23460
```

-continued

```
ctaagttggg cttgggccca ggcagagggc agagccaggg agggcctctt cccttccaga  23520
gggaggagac acgtggtcat ttccgacatt ggcagccttg agtgctaggt tgtctgtgcc  23580
acacaggtct ggctgaccag gcttttgggc tcctcagggg gctctgacta tgcaggctcc  23640
tccaaacccc agggagtcct agcccagccc aggcatgccc gatgtacagg accctgagaa  23700
agtcactcct gctctgacct tcagtaaagc ctagcatcta gtgggtagga gttagcagga  23760
cccagcctac gtggggagtg gcacctattt gcatatatct gctctgtagg gcttccttca  23820
ccccacctca gccccccttgc cctgctttcc cacgcccagc agcagggcca ggactgaggg  23880
gatcttccca attttggggt gcttttcctg ctgagcctgg acctgaaatt ggagactgct  23940
gttctgtgag ctgcatctaa gggatggctt ggacactagc ccagcctgtg tcattctagc  24000
atgttcttta tcccagaaca ggcctcaggg tcactgtgac ctccagcaaa tcatgcccgt  24060
ctctggacct cggttccggg gagcagcagc cacgagtcac cagacactca ctgtggcagg  24120
cactgggtga aggctttgta agcaatagcc gatgtgatcc tgctgtcggc cctgagagtg  24180
ttctgctact gctgtgccca ttttatacgt caggaacact gaggcacaag gccaggaaat  24240
gacttgccga gaagcacaca ctgcccgctt tgtgctggcc ttccaaacca gttctctttc  24300
ctttcaggct cttgtgaaga cagggctggg agtactgctt agtggaagag tgattgtcag  24360
agagaagcaa ggctgggttc agactccagc acagctctgg cggaacataa aggctacttt  24420
aagaactaaa ccagaggggt tggtgagatg gctcattggt taagagccac tgctattcca  24480
gaggtcctga gttcaatccc cagcaaccgc atggtggctc acaaccatct ctagggaagt  24540
ctgatgccct cttcaggcag gcgaatgtat atgcagctga gcactcatac aataaataaa  24600
attaaaaaga aaaaaaataa agatcatcac agctttgggg gggcaacata ttgggagctg  24660
gagtgcctgg gatcggatct gataatcctt agattcatgg ctcttggtga gactttagac  24720
ctctctgctg agtgagggtg aagaggtgac actgtaacca aggagagatg ctcactgaga  24780
ctcgaggtgt gtcctcctcc tgcttgacca tgccctctgt ctctctccca ccctggctca  24840
ggtctctaag gacatctcca tgcggcttca caaggagctg gaggtggtgg agaagaagcg  24900
gatgaggctg gaggaggaga acgaggggct tcgacagagg ctcattgaga cagagctggc  24960
caagcaggtg ctacagacgg agctggatcg tcccagagag gtgagggcgg cagcccagct  25020
ggggctggtg tgatgcatat ccctgcctgg ttgcttgtgg actgaagacg ggcacccttg  25080
tgccttgaca gcgctgtttc tccatccacc cttccagcat ttgctgagca cctaatctgt  25140
attcagccct ggttactctc tctgggacta actgaggcta tgttcagcaa tgcccagcat  25200
gggcctggcc ctgtgcctca gtttccttgt ctataagact tggcagttgt tccctggtca  25260
tcgacagggc cactgactgg cttgtgtgga gatgttttag ggactagtgt gctgtggcca  25320
cttggtttaa gaaggatgct agggccgggc agtagtggct catgccttta atcccagcac  25380
ttgggaggca gaggcaggtg ggtttctgag ttcgaggaca gcctgctaca cagagaaacc  25440
aaggctatac agagaaaccc catcttgaaa aaccaaaaaa aaaaaaaaaa aaaaggatgc  25500
taggcttggg tctcccactt ttgtctctga atgtgacttt cagatccatg tccccagtca  25560
tggtgatgtc agcccttcct cctactgtaa ccttctccag ctgtgtgtta ggctcacata  25620
aagacagttt atctcagaaa cctccgcaaa ggcccaacaa agctgtggac attccatggc  25680
cgagtgagca gcagccggcc aggaagagtg aggcagattc tcaaggtcat gcagggtgca  25740
ggggacttca cagtggaaag ccatcagccc gggtgatgct taaagcctgg gtaactcctg  25800
```

-continued

```
attcctggtg gggtcagcag ttcaaacact aggtggcctc tggccccaga ggcatagctg  25860
gccctcagct ggttggttgc tcatgaggcg aaccgggctg cattcttctg gggcacccac  25920
ctgcttccca agaggcccgg catgccagac gttcaggact gagacatcag tgtccccggg  25980
gcagagcagt cctttggctg ttcttcctac tgggcatgtt ggtgctatgg gccagtgcca  26040
tgtagggtgg agaggggagg acctgccctg tgggcttctg tggagggcac catgctgtgg  26100
agctgggtgg gaggcttcct gctggcttcg ggctgcctat gcactgcgaa ctgtcgcaca  26160
caaccttgtc gctttcatct ctgatggtga aaaggagggg cattacaaag cctgttcttg  26220
cacagctagg gagactgagg cactcggctg cagcttgttg agtttgcccc agcctttcct  26280
cagcagagac atgtctgcag ccacttcccc ctccaagtcc cggcttcttc ctctgtgatg  26340
tcagccaata gtagcagctt aagaggatgt tttggatcac taagaagttt gtggaacgca  26400
gcccagaggt agagcatgtg cttggcacat gggaggccct gggttcaagc cttagggccg  26460
gaaagcaaag gatcaatatt gtaaagttcc ctttatctga gattccccag agtagtgaat  26520
gagattcata agacagggag cagagctact gggcggggga ggagggagcg aggctcactg  26580
ggggtgggaa tagagtttca gtttgggctg atgaaagggt ttggaggcaa actgtgcctg  26640
tgatctaagc agggtgtgtt gttgctacca acacctggga ggcaaaagca aaagacttag  26700
gaattcaggc caccctgggg tctgtgagac cctgtcttta aaaaaaaaaa ggcctggttc  26760
aagccgggca gtgatggtgc atgcctttaa tcccagtact caggaggcag aggcaggcga  26820
atttctgagt tcgagaccag cctggtctac aaagtgagtt ccaggacagc cagagctaca  26880
cagagaaaca ctgtctcgaa aaaaaacaac acaaaacaaa atagaatgtt taaaatgata  26940
catttatatc atctaacctt taccacatgt taaaaagtag aaaaatgtgt attgatatga  27000
caagctcccc aaggtgttct gtaaaccaga gaaggaaatt aagaaactag gcctggtggt  27060
tgaaggggga ggttctaggc ctgcttgagc tgcagtgtgt ctgtctgtct gtctgtctgc  27120
ctgcctctct gtatgtgtgt atatttgtgt gtgtatgtgt atgtatgtgt gtatgggggg  27180
ggtatatgtg tgtgcctgct tgtctgactg tgcaccacat gtgtcccggt gcctgcagag  27240
gccagaagat ggcattggaa tccctggaac ttgagctatc gtgtttgtaa gctgctcagt  27300
gagggagctg ggacgagagc tagtcctctg caagagcagc aagtgttcct acctgccaag  27360
ccatctcttc aggtccctgg cggttaaata agaagaatgt acagtcccag tagttaggaa  27420
ccaactgggc tctgtgatgt gaggccagcc tgggctacaa cgtaagactt tctcaaaaca  27480
caaagaataa aataaaaatg gattggcact gtagctcaga tggtagagcg cttgcctagg  27540
atgagtgagc tcctggactc aatatgcagt tcccaataaa atgggcgtgg ctccacacat  27600
ctctacccca gcacccagga gatagagaca tgacctacag tagaagcttg gggtcatcct  27660
ttgtgtggaa atcctgggct acatgaggca gtgccccaag agaaagtcct taaacaggac  27720
atgatgagaa cgtctacagt cccgttacag ggaagcctga gggagaagat ggctgatgtc  27780
taggtatcta aaagctgctg ggatagcata gcaagaccct gtcttacaac aaacaaacaa  27840
acaaccccat gatttactta ggaattactt gtgagattaa aattttacaa catttgaaaa  27900
ctttatttca tgtctgtgtg tgtgtgtgtg tgtgtgtctg ttcgtctgtc tgtctgtctc  27960
tgtctgcata tgtgctccac tgtaggcatg tggcaatcag aggacaactt gaagcacttg  28020
gttctcttct tctacactct ggatcctagg gatccaactc aggtcatcag ggttggtagc  28080
aggcgccttt tgcccactga cttctcacca tgcctctttg tggaccttta aatgtagatt  28140
ttagggtttt aatgtaaaga tcccacaatg gaccctgaca ccgagtaggc gctgaagata  28200
```

ttggttctca ctcctgggaa gcctgatgga gcctcccagt gtttagtgct ggctccagag 28260
cctgtttatt tgctgtttgc cctctcctcc tccctctcct tcctgacatg gttgctatgg 28320
agacaagggt ccctcagcac ttctgccaga gctacagtct tatccttggg atctgccttt 28380
tccatcctga cagatgatga ggtgatgctg tcacccgact gggaatggga gctgatgctg 28440
ttgccgtgga gacagctcct ggcgagacag aagggaggtg gcatgtcctc actgctgtct 28500
gcagtggcac cgtggcccag ctgggttgcc gcttcagaat ctaacggcag ctgccccttc 28560
attcccacta tcatctccct tgtctgcagg cagagagcca gtgtgagagt gtgattcgtc 28620
ctaacacagc cgctgtgtct gagagcttac cctgtaccag gcaccactgc cagccttgcc 28680
catgtgccgt catgccgttt aaccccccgt tgtccctgct ttgtaggtac tactccttgg 28740
acattttaaa atcacagttt ttaattcagt gatcacagaa tgcaccattt tacagttcag 28800
ttgcatagat tggggtgctg ttatcagcat gaccgaattc cagaaagctc cctttactct 28860
tgtgagtaac cccacacctg ttagcagtca ctcctcactc cccgtagccc ctggcaactg 28920
ctggcctgtt ttctgtctct aatgatttct ccaatcagga gactgcatta aaatgggatc 28980
aagcaatgcg tgatcattgg tggtgggcgc tactacttag aacaaggctt tcagagtttg 29040
gacatccatg ttgaaggacc tcgttgtttt tttttgtttt ttgctttttt tccccatagc 29100
tgggtaatgc tgcattgtgt gggcagagtg ccttatattt gatatttggg tggcttctgc 29160
ttttccgctg tcataaataa tgctgtggtg gacatgttca agtttttgtg attctgtatg 29220
tgtttttctt gggtatgtac acaggagtag aattgtctgt gaatgagacc gggggaaaga 29280
tacgtaaggg attcaaaccc cggccctgg ctctcccaca ctcacactca ctcctaacag 29340
agttgccgat cggctccgga ctcatcaagg ggctttccag agcctgcatc tgtggttcct 29400
catctggctt tccttcttga tgggtggggc gagcacctcc agccacttgg ggttgagcct 29460
ggttctcctg ctgtgcagtg tgttctggcc ccagtgtgtg agctgcagag caaacccagc 29520
caaggagcca cgtagacctg ggcatggaat cttggctttg ctgtttcctt gagagtgact 29580
gccaccttgg gcagatggca cagcagctca atgctcactt gctctgttta cagaaaggga 29640
aaatcagccc ctacagcttg tgggtgtttg tgaagattaa atgaggctgg gaagtgctca 29700
gcatagaata ggcgcttgct aaacacagtg tgtaccatta tcgttaccat ctcaaccagc 29760
cactggctgt gggcctggag aagcctttgc tgcctccctc gcacaggggt tccccccaca 29820
gagctggcag ctgtacgtgg aaggaacagc tacgctgaaa actgttgggt ctaaacttat 29880
tttttgctgg ctttggggtg actgtaatgc tcagagacct tgctgactca gcatgatgat 29940
ctgagttcag atctccgcag cccacataaa aagctgggca tgatcccaag cagacctata 30000
actccagcac tttgcttgcc tccaggctca gtggaaaacc ttgtctcaaa ggagcaagga 30060
gacaaagcag gacacccgac atcctggctt ccatgtgtgt acaagtgtgt gcgcatacac 30120
cacatctgca tacatacaca cactatacaa tttaaaatta aaaataaaaa aattaaaaat 30180
ttttttctcc acccaagtgg tggtctctcc aggggactat atggcttgtc tgcatggcat 30240
tttggccatg gtgcaaagag catacctcac tctagagatg ctcccccaac ccaggtccca 30300
ttcatggtca gttctgtgca catagcaatc tggtttcagt aagacttaca tggacaccct 30360
ccacatttgc tgagtcggca gccaggaagc tcaggagata ttggggacag aggggacaga 30420
gtttagacag ctctctcctg aacttagggc actgcctgga ggcttctggg gaagacagac 30480
cccaggctca tgctgggaag ggttgggcca gggattctca gagctatcac ccaggctgct 30540
aatagtggct tgaggagtgg ggaatctgcc ttggggctgg gtcctcctgg accttagacc 30600
tggagaatcc ttttgaggtt cttgcaattt accactctag gattcctact tgagaggtga 30660
acacacactt cccataggat tttctgtgta ttcacacaca ttattttcta tgtatatgtg 30720
tgtgtaatgc ttccttaaat ttaaaaatgc agtataaact taatgaggca aaaatcctgc 30780
cacaaaagcc cataaacgca tacctgacat gaccctgagg aaagttccag caaattccga 30840
ggcaggaatc cgggacctgc tccatctctc tgttcctctt gtgtactctc tgaatcttca 30900
ccacgtgact gaggaatctt attcaaaatg acagatctag cttaaacata tacaaaataa 30960
tgaaagcctt cccaggccac ccccctgctc atctgcctaa cctgaggata acagtttgct 31020
ttgtgttttt ctggatcttt ctctgtgctt gacaatgtgc ttttctgtgt ctttaaaaaa 31080
taaagatggg cttcgtttgc acacagggtt tctgtaatgt gcaggatcat gttgcataga 31140
tatagtcctt taaaatgcca gatgctttgg gggttttctt cagtctgaag tgcttattat 31200
agaaacaaac aaacaaacaa aacaaaaacc acggaatcaa ataagcatag gaaggaaaga 31260
aagtcataaa tagcactctc tatttcaacc ttaaacaggg ggctgaaggt ttagagtcag 31320
ctcctgaagc atcagttggc aaagatccct cggggagggg aggaggatgg gacagcatga 31380
ggggcgtggc tttagctacc tgacttatgg ctttgctggg ttttttgttt gtttagttgg 31440
ttggttggtt ggcttgggga ggggagttgt tttaatttat gtttttcgag acagggtttc 31500
actgtgtatc cctgactgcc cttgaactca ctctgtagag caggctgacc tcgatctcag 31560
agatctgcct gcctctgcct cttgagtgtc agtaccacca cccagcaaca tatgtgtttt 31620
ctgatgaggc ttccctggaa ctaactgcac accaggttgg actggacttt gcgatgcaca 31680
caagctggcc ttgaacttcc ggcatccttc cagtttctat ttccaggtgc tggaattaca 31740
gatgtgtgct gctgtgctca gcaatccagt tttggattga gatgtaattc acatactatg 31800
aagtctgcct tcgtcctttt tatttgcagt gctgagaact gaacccgtgc cagccagatg 31860
ctctactatt gagctacatt actggcccaa gtttgccctt ttaagctgca tagttagtgg 31920
gttgcacagt tgtatatcca tccctactgc ctaattccag aaccttttg tttcaccctt 31980
aaaaaaaacc ctcacacata ttagcagcct cttcccatct ccccaccaca ctccctcctc 32040
agctctgaga tatcagtaat atattttcca tctttgagaa tttgcatggt ctggacattt 32100
tgtagaaatg aaatctgatt ctatgtgcct gttgtgtgac aaaactttta ctggggagac 32160
aaaacacata catctgttca cctcagatag ggatcccatg ataagccaaa ggatggatac 32220
caccatagtc caacattgtg aaaaaacagg ttttatggga gttacttaca ggaacagaaa 32280
tgactcacag acagctgctt accccagcac aggtgacagc tcacaaaagc tgggaacctg 32340
gaacacacag cacagcctgt aggcagctca acaggttaga gcgtgttctt tcttagcaac 32400
tctggtctaa gcctcttcca ggcaggtgat cagctctcag agtcttctgt gcagctttcc 32460
tcctctaaga atccttggaa ttcagtttca tgtcacgtga gaaggactct cagctcttaa 32520
tacttattct ggcagaaaag gagcctagtg aatctggtca gtttcaggaa cttcctgaat 32580
caatttgagt tgtcttcctg cgtaaggaac ttccaatagg gtggaatgtt ttaagctagg 32640
aggagattgt tacacaacat gtcaggatgt cctggctcac atggtgtctt cacggcgccc 32700
atgctgcctg ggcatcagga tcttgttcct ttcatgactg aataagtttt taccacgtgg 32760
ccaccccata gtttgttcct ctgttcctca tctggaggcc atattgggtt ggaggtttta 32820
tttgtaaatt acttccttct cttcacagag tgttccggct ttgtgtcagc cactatcatg 32880
acccccagtt gttcctactg gctttttata tcatctcatg ggtgcgtgtg atagcttgaa 32940

```
cctcttgagg tccttagata gcctaggctc ttcaatcctt ggtggagctg ggatcaccta  33000
agtcatggat tcttcaatgt gtgggttcac cagaactgat accacagcca aggcaccagt  33060
caacctgtga tggcaagccc agttctctta ggctgagtct gacccagagc accacatcac  33120
tctgtggtag tctccctctg agctcccttc cagggccctt accctggtgt agcagctcct  33180
gtgaagggct tgttgtgtgg ccccctttcc aagatctctt taggtagcct ggtgtattca  33240
aactcatctc caccttcctg cctcatttgt gttcccaaag ttctcactta gagtaggccg  33300
agaagatgtg aagacaccag acacttcagg tgatggtggt gctcgcctct aatctcagca  33360
ctggcagaca aagacagttg aatttctgag ttcaaggcca gcctgatata tagagtgagt  33420
tccaggatgg ccagggctat acagagaaac cctgtgtcat gagaaatcaa ccaaccaacc  33480
aaaaatgaaa agcaaccacc accaacaaaa cagaaacaaa tcaacaacaa caacaacccc  33540
cagactcagt aaggaactcc ctggatcctt agcagttagc ctagcataat ccaggcaaat  33600
gaacaaccat gactcagaaa aacaggatga aatgatggag gtgttctgaa cacagaccta  33660
aggttgtcct ctagtctcca catacatgaa aacatatgca cacatgcaca catggatttg  33720
tgcatgacac ataaatgctc acacacatgt acacacacat gtgcacccat gcggacacac  33780
ttacacacat gataaagctg acctgctttc ctgggaagct actttaaatt tcagtggctg  33840
agacataacc caggccagtt attccagaat ctttgacgtg gtacctggtc attggtattt  33900
tcttaaatcc cccaggaaat tcttctctgc gtgcaggttg aaaaccacta caccactagg  33960
gtccatgctg gccctaatca tagatgcgtt ttctcctacc aagcctttgg aactcagtca  34020
agagctaggt caagaattgg tctcaggagc cgggtggtgg cggcgcacgc ctttctttaa  34080
tcccagcact cgggaggcag aggcaggtga atttctgagt tcaaggccag cctggtctac  34140
aaagtgaaaa aaaaaaaaaa ttggtctcag gttggctttg tatttgctat agaattctgg  34200
tcaagttcct tccctcctct gtttgagcaa aacagggctc acagagatgg agagatgact  34260
cagcaattaa gagccctggc tgctcttcca gaggatccaa gttcaattcc cagtaccaca  34320
tggcagctca gagccaactc ttaactccag gtccaggaga tctagtgccc tcttctggct  34380
tccataggca ctgcacacac tgcacactat gtgatataca aagatatatg tgggcaaaac  34440
acccatacac ataaaataca aataaatttt aagcaaagtt tgtgttatgt cagtggtttg  34500
cctacaaggg tggggagtga gaggtgaggg ttggtggtga gcatgtattt aaagtcaact  34560
gggagcattt tcagaaatcc aagtgggcag ctcaactcag aaagttgaga gcaacctgtg  34620
gtttccaacg ctgccagcgt gaattatcct ctctcggtag gaagcgttca gtggaatctt  34680
gtgtcgaagt gaatgatttt ttttttaaa caagtaactg cagcactaat tattgtggca  34740
tttcctcaaa ttcccatctg tgcggcttac gctgttttgc actcatgcca gcaacaacta  34800
aaccttcttg tttagcaaga gcctcaccag taggatatac tgtgaggtgg ctcagggttt  34860
cgctagtctg atcagtgaga ggctcagccc agtagcattg ctctgggtgt ctccctcctg  34920
agaagggctg agtgtcttct cagggttaag atctgtttgt tttcctccca taaaccattt  34980
tgtttggttt tggtttttc cttctctgaa cctagagtcc catgcacact gggcaagctc  35040
taaaagtgaa ctgcgtccct tagtctttca tttgtctttt tattatgaga caaggtcaaa  35100
atctgtcagg tgggccttgg gttacgattc tcctgcctca ctgggcctga cttctatgct  35160
ctttcttgta ttcctaaccc gctttcctat tgcagatatt tcccccagct cattgcctat  35220
tttttaatgc acgcgcgcgt gtatgtgtgt gtgtgtgtct gtgtctgtct gtctctggga  35280
```

-continued

```
tgggaactgg ggctttgtgc tctgcccctg agctgcacag catggattgc tgtcctgttt  35340
tgtgttccat gcagtgttta cccgtgtaat caatgcattg attcccctcc ctccaacgct  35400
tctgggtttt tcaatcctcg tttgttgcta gtctctctca gtcattttca gaaatgatcg  35460
agtctcctgt gctgtttata gttttctacc cgtattttgt ttgttagtta gtcttcatcc  35520
tgtgttcagg gtcctacgaa atgtcacttc ccgtgaggcg gagacttgca tgcagtttta  35580
gagacaagcc cctttggctg tgagggagtg agtcacatca catagatggc ctcagctgga  35640
gctagtgggg acctgggata gtctttagat gtgtattcca cacaagaaga gcatataaag  35700
cgaccccctt ggccagcaag caccactaag aatggtcctc agcctggagg gctttctgcc  35760
cacagcatcc ttagcatctc atctgtctag ctcactgcta tgtgctctac cctctgagat  35820
ttgcccggga aacctctgat gagcggatga aagacaagcg tcagccatga aaacatacat  35880
acatgtgaca tctggagtga gcaggatgta tttatatatt taggaacaca catatatgta  35940
gcaacattta aagaccataa atttgcatga gaacagggaa ggggatacat gagaagggtc  36000
agagggaaga aagtgaaggg agaagatgat gtaattgtag tataattggg ggggggataa  36060
aagccccaaa catcaaagat gaacaagagc acaaattctg atttccagcc aacaggacca  36120
cagaggccag atgggtgcag tggggtactg cacccctgtg ccggtgtcta atcatttctt  36180
tcttttcttt tcttttcttt tcttttcttt tcttttcttt tcttttttttt ttttttgaga  36240
cagggtttac ctgtgtagcc ctggctgtcc tggaactcat tctgtagacc aggctggcct  36300
cgaactcaga aattcgcctg cctctgcctc ccaagtgctg ggattaaagg cgtgcgccac  36360
catacccggc ctagtcattt cttccagtac ttgtggtcat tctctcctgc acaaggtgct  36420
cggtgatccc tggttccgct gtgggtaacg gttagcacag acaggctgag tggggaccct  36480
cagtatgact ctgttttatg acacctcttt ggatgtgtgt catctttgtg acccttcagt  36540
ttgctttctt ctttcccttt agcattcctt gaagaaaaga ggaacccggt ctctggggaa  36600
gacagataag aagcctactg cacaggtagg acctctgtac ccatcacact ccctgcagtt  36660
ggtagtttgg atgcccatac caacttcaag tgtcctgagt agtcccccag aggtccctat  36720
cccttcccaa tgtctctcct gccctccttc ccctatgcat ttttttggct tccccattta  36780
gttcctccaa gcccactccg accccatcct tacacactcc tggacccaca agttgataac  36840
ccaacatagg gacggataga cccaagggga gtcggtccct ccgcagcttg actgccaccc  36900
gactgagaca aatcagcttt ccagtctgtt tcctcatgcc ttcctgttct gtgggtttgt  36960
tggaagaact ggataaaaat gtcatgtcgt gcacaggcca gaatcctgtt agcagccaag  37020
gcaccttttg aacggtttcc catttagcag tcatcatatg acaacaatgt ttctccccac  37080
ttttttttt gtttgtttgt ttgttttttt cccgagacag tgtttctctg tatagctccg  37140
gctgtcctag agctcacttt gtagaccaag ctggcctcga actcagaaat ccacctgcct  37200
ctgcctccca agtgctggga ttaaaggcat gcgccaccac gcccggctct gcccactttt  37260
agagatgggg caggaatggc catagtcaca tgtctgaagg tcacctgctc ccagacttcc  37320
agattgtagg tagtgtgtct tgggctctca atattgatgt ccctgctctc tatcctgtgg  37380
cctccaggcc ttgagagcca agctgattca cccctgtgtt ctccgacagt cagggcaccc  37440
cagaatcctg tggctgggtc caagctgaca ctaaccttcc ttgttgttgc ctgtctccgt  37500
gtccattggg ctgcaggagg atagtgcaga cctgaagtgc cagctgcatt ttgcaaagga  37560
ggagtcggcc ctcatgtgca agaagctcac caagttggct aaggagaacg acagcatgaa  37620
ggaggagctg ctcaagtaca gatcgctcta tggggacctg gatgcagccc tgtcggcaga  37680
```

ggagctggcg gatgctccgc actcccgtga gactgagctg aaggtgcacc tgaagctggt 37740
ggaggaggag gccaacctgc tgagccggcg catagtggag ctggaggtgg agaaccgtgg 37800
cctgcgagcc gagatggacg acatgaagga ccacgggggt ggcgggggtc ccgaggccag 37860
gctggccttc tcttctctgg gtggtgagtg cggggagagc ctagccgagt tgcggcgcca 37920
cctgcagttc gtggaagagg aggctgagct gctgaggcgc tcctcagctg agctggagga 37980
ccagaacaag ttgctgctga acgagctggc caaataccgc tcggagcacg agctggacgt 38040
gacgctgtcg gaggacagct gctccgtgct cagcgagccc tcgcaggagg agctggcagc 38100
cgccaagctg cagatcggcg agctcagcgg caaggtcaag aagctgcagt atgagaaccg 38160
cgtgctcctc tccaatctgc agcgctgtga cctggcctcc tgccagagca cacgccccat 38220
gctggagacg gacgctgagg ctggggactc tgcgcagtgc gtgcctgccc ctctgggtga 38280
gacgctggag ccccacgccg cccggctgtg cagggcccgt gaagccgagg cgctgcccgg 38340
cctacgggag caggccgctt tggtcagcaa ggccatcgac gtcctggtgg ctgatgccaa 38400
tggcttctca gtcggcctcc gcctgtgcct ggacaatgag tgtgctgact tgcgactgca 38460
cgaggcgcct gacaacagcg agggccccag ggatgccaag ctcatccacg ccatcctggt 38520
gcggctgagt gtgttgcaac aggagctgaa cgccttcacc cgcaaggcag atgtggcctt 38580
ggggagctct ggcaaggagc agcctgagcc cttccctgct ctgcctgcct tgggctccca 38640
gggccctgct aaggagatca tgctgtccaa agaccttggc tctgacttcc aggtaagatg 38700
ctacatgttc tgaaccaggc acatgacaga aggacacaaa gccccaggta cacaacttca 38760
caactgccct gcagggagca gtcctggtca tcacctagaa cataaccagc cctaaggcag 38820
ccatggttca tctccctgtt ctctggtttt attcgtcttt gagctttata taaattctat 38880
agactaaaca cagcagtgcc tggctgtgtt ctctcagcca actatttgct gttacaggta 38940
ggaaaaacaa ttatttattc tcacctaact aggaataagc ctgccgactc agcaaactgc 39000
ctggtatgcg tttactatgg atagggatta attctgaggt cccatctttt tgctagactt 39060
cccgtttttc tccctttccc tctcctcttc cagtgctggg gacacaacgc aggacctcat 39120
acatgtaagg caagaaccct accattgagc cacatccctg gccccttctt tttaaaaaca 39180
tttttgagcc aggcgtggtg gcacacgcct ttaatcccag tacttgggag gcagaaccag 39240
gcagatttct gagttcgagg ccagcctggt ctacagagtg agttccagga cagccagggc 39300
tatacagaga aaccctgtct taaaaaacgg gaaaaaaaag aaaaagaaaa aaaaaaaaaa 39360
aaagaaagtt tgcatatgtg tgtgcaggtg tgtgtgtgtg tgtgtgtgtg tgtgtgtgtg 39420
tgtgtaccca cagaaggcag agcaaagtgc tggagccccc agagctagag ttgaaggtgg 39480
ttgtgagctc cttgattagg gtgctagaag ctgaactcgg gtccttttaa agagcattaa 39540
tgtatcttaa ctgttgagcc atttctctag ggtagccccc tcctttttcc atctcttttg 39600
taactaaaat tattacacgt atttggtggg gttcaggggg agccgttgtg cacatgtggt 39660
ggtcacagga gtcagtctca gatggtcctg gggatcagct caggcttggt agcaagtacc 39720
tttacctggt cagctcgctt gccagatccc cacatcccac ttctttttgg ttttttcgag 39780
gcagggtttc actgtgtagt cctgctgtcc tggaactcac tctgtaggcc aagctaaccc 39840
tgaactcata tagagatctg cctgcctctg cccccccac cccccacaaa tgctgggatt 39900
aaaggtgtgt gtcatcaccg cccaccacca gtccataata ttaaatttaa aaaaatattt 39960
taaacttttt gatcaacttt tgagaagctt agccttgata cccatgacag gctacccaga 40020

```
aaaactaaaa cggaaaagac acttgttgaa aaatttaaaa tgcattagtg caaaagcaaa  40080
acgtaaacat ttgacgcaaa tataaaaata aacgaacacc tcgtgtgcct acctaccact  40140
tcctgccgat gtctctgtac accgtcttga ctggtgacgt tcagtgcagc agccatgtgg  40200
ggatgtgccg cgatggtaaa ggatcagcct tagttggcgg cacaggttct atccccagta  40260
cagaacagaa acaacccaaa actcccaaga caaattttaa aaattaaatt aacgaagcat  40320
aggattgagc tgcagttcct tcgttgtagt tacacatcgc agatgcttga ggctggctgc  40380
gtgctgggag cgccccctct gatccttccc acacagcctt tcctgggcct gggcttcatg  40440
ttatggctac tgtcgctggg cagtgtgctt cctcacaccc tgcattccct gtccgcaggc  40500
tgggatacct tgtggatggt ccccaccctt cgtgcttaac acgggatggg tggtgatctg  40560
cagaaccagg gagggatagg agccccactc gaaaggtccc accgcctagc gagggggaat  40620
taattagtca atctgtcaag cctgtgaatg tgacatgaga aatggttttt atcaaccagg  40680
aacttgtcct agatcttgaa ggggctcaga tcattgagag aaggaacacg gtaggtcgaa  40740
ggaacaggac agagttgtga ggctgggctg cagagagcgt ggagtggtgt ggttttcatc  40800
ctgagagaat ggcgggagat tgctgtgtgt ggccctgcac tgcatgggac cgggcgggta  40860
gtggcttcag ctgtgctgct gtggcttcag atcgcttctt gaaaggggag gcccgtgttg  40920
agtctccctc ttcctgaagt aagagtgagc agggaccaca cgggtcaccg acagggtgat  40980
agaattgttt cagagggctt tgcgtaagag ccattcacaa aattaatgtt tccacttgcc  41040
ccactgctcg ttatgcaata agcaaatgag ttgtggcctc gcaccctggg aaggccaatt  41100
cacccaggct ccctctcatg tggacaaagc ccattatatg gcagaggcct ggtggggacc  41160
tttgttgcac tccttgggcc tctccctatg gatctcttct gcttttagcc acctgacttc  41220
agagacctgc ttgagtggga gcccaggatc cgagaggcct tccgtaccgg ggacttggag  41280
tccaagcctg accctagtcg gaacttcagg ccctaccgag ctgaagataa cgattcttat  41340
gcctctgagg tgggtctagg cctaagcagg ctgttgggtg gaagccgatt gcctcctgaa  41400
agcaggcagg gtggcccttg gaggaggatg gtataggttt taagcattta aacttctgac  41460
agccaaggca aaaaaagaaa gaaagaaaga aagagagaga gagagagaga gagagagaga  41520
gagagagaga gagagagaga gaaagagaaa agggaatttg aatcaatccc gtggtttagt  41580
tagaggaagc ttagctggat atgggacatg atatcaaact gtaatcccag tgtcaggacg  41640
ctgaggcagc ctgaatgctg agctggaggc catcttgaaa tgactaactt atgtagcaga  41700
gaagcaatgg cctctccatt taggctgttt gagttcatgc tgtgactttc tgggtgctgg  41760
ctgtgagatc tcgggtacgt catttcactc tcgaaaattg tcaggtttgc cacagacaag  41820
tacagagcct cataggattg ttggcctggc ctccacgggt tgaggatgag gtcggtgtcc  41880
gtgacaagtc acatggactc agggatcctg agtgctgagt cactctgctg gtctggtggt  41940
gtgaccttcg acatgtccac tcccatgggc ccggctttcc caccacaaca gttataatcc  42000
ctagagttgc taagattctc tgatctttga gaagttccct gtcctcctga gcctgggaaa  42060
ctccctggaa ctgaagggtc caactgccta gtgaggtggt ctggatgtcc tcataaccat  42120
ggcgaaggag gaagaggaag agcgttgtct ggggctggag agatggctca gtggttaaga  42180
gcaccgactg ctcttccaaa ggtcgtgagt tcaaatccca gcaaccacat ggtggctcac  42240
aaccatctgt aatgggatct gatgccctct tctggggtgt ctgaagacag ctacagcgta  42300
cttacatata ataaataaat ctttaaaaag aaaaaagaaa agaaaagcac tgtctggaca  42360
aggagctaag ctgtagtgct gtgtagcctt agctttgatc cccagtcagg agatggatag  42420
```

acagagagaa ggggagggag agaggaagaa gaggaggagg aggaagaaga ggaagaagag 42480
gaggacgatg actacgttga agcaacctga gatgcttaga tctcgttttc tgagaagaaa 42540
ataggcttgt ttgtttgtgt tggctcattt acaccttgac tccgtttcct tcattcttac 42600
cgattagcta tgactaagca cagcgccaac ccccagttca agagcgatgt gcaggggcag 42660
gcgcctgact tctatttaag aggttttttt tttttgtttc tttgttgagc cagggtctca 42720
gtaattatat tatgcttact tcaaacttac catcctcctg cctacaactt ccaagtgctg 42780
ggattacagg cacatgacag tttgcccaga tctgcagaga tttttaatac agaacaggtg 42840
tacaagacac gcctcgtatc actgcagaga cggccaaatt atattattgg ccacattttt 42900
tttcacagca ggaacctgct atgcctggga ccatgtccac tcttctgttc ctgtgcagcg 42960
tgttagagtc aacattcctg ttaccagaaa tacttaacac ttgtcttttg cgatggagtc 43020
ttactgtgtt gctcaggctg gcctcagact cacaggttcc ggtgatccgc ctgcttcatg 43080
cccacttcat ctcatctaaa aaatgttgtt actggggaat aacagcaaag tagtgatgga 43140
tggggctgca gctcagtgat gaggcacttg ctcagcacgt gtgaggcctt gtgcccacac 43200
aaggcagggt cttgctatgt aacccagcac cagtgcacac acatggactc acatgcacac 43260
acaagcagac acgtgtgtac acacacatgc actgcacatg gacacaccca tgtaccacac 43320
atgcatacac attcatacat gcctgcacac atatgcacac atacatgcat gtattagtca 43380
gggttctcta gagtcacaga acttatggat agtctctaga tagtaaagga atttattgat 43440
gacttacagt cggcagccca attcccaaca atggttcagt cgcagctgtg aatggaagtc 43500
caaggatcta gcagttactc agtctcacgc agcaagcagg cgaaggagca agagcaagag 43560
ctagactccc ttcttccaat gtccctatat tgtctccagc agaaggtgta gcccagatta 43620
aaggtgtgtc ccaccacacc tttaatccca gatgaaaggc gtagcccaga ttaaaggtgt 43680
gttccttaaa ctccgagatt caatcttctg gaatccatag ccactatggc tcaagatctt 43740
caaaccaaga tctagataag gatctccaag cctccagata agggtcactg gtgagccttc 43800
caattctgga ttgtagttca ttccaaatat agtcaagttg acaaccagga atagccacta 43860
caatgcatta cacatggata cacacatgca ccacacatgc atgcacatac atgcacatac 43920
acacacacgg ggaagggcag agatggagaa aggaaggaga atgggtgcct atggcttttg 43980
acaaactgaa cacttctctc ccctttggtg ctttgggcag ggtcttgcta tgtaacccac 44040
gctggcctca agctcatgac ttcctgtttt gtaagtaaca tctagaatca taagaagact 44100
ctagacatct gtgttcccta ctagtctgct gtctgtctgt ctgtctatct atctatctat 44160
ctatctatct atctatctat ctatctatct tgtgtgtggg tatgtgcaca tggtatataa 44220
gtcagcggac agtttatagg agttggttct ctcctcccac catgtgggtc ccagggatca 44280
aacccaggtc ctgacgcttg gctgcaagca cctttatctg ctgagccatc ttgacagccc 44340
aagaacaaat taacttcatt tagctctaaa tgcttttaaa acacaatttc ccccagaaaa 44400
tggagaattt ggttagcttt tttaaaatga tcttactcca tagttactga aatccacaaa 44460
taatcacaat taaacttctg ggcagcatta ttacatgaag aaacaaagaa aagcaagatc 44520
attctgtagt taaccacacc gacgttcacc gtagttctgt tacgtaacaa cgctcaaaga 44580
cagcatctgt gacggaacat ctggatggaa cttaacacat acagatccac taaacacatc 44640
tgaaacctca tttatctttt aaactgcgtc taaatttgta attatagaca gtgccctagc 44700
ttgggagtgg caagcaccta tagccccagc tacctggggg agctgaagta gggggatacc 44760

-continued

```
ttgagctcag gagtttgcca ccagcctgtg agactctaca tcagaaataa gtaatcaatt  44820
acatttaatc agttaatttg atcaattaaa gagactatga acaacgttgt gacttacatt  44880
gagtttgcac aggatttttc ttttctgcag ctacgtttgc aagagagaaa tgttaaaatt  44940
atattgggaa gatttgacac gtactgtttt gtgtaattgt cctgatgacc cgctaggcaa  45000
ggacagtgct gtgcctcgta gaggtgactc ccatccagtt ttctgttgac tccttactgc  45060
ttctgttctt tgaccacagc ctgtgtcttc tccttcctcc ttgtctgtcc cctccaccct  45120
acctccctcc tgcagatcaa ggatcttcag ctggtcctgg ccgaggccca cgacagcctc  45180
cggggcttgc aagagcagct gtcccaggag cggcagctcc ggaaggagga ggctgacagc  45240
ttcaaccaga aaatggtcca ggtgggtttg taccacaggt ttgtgttttt tgttttttta  45300
ctgactatag cttgtctcag aagggaaggt aaaggggcca tgggatagct ctttggtaga  45360
acacttgacc agcgcgtgag aagctctggg ttctgttccc agcataggaa gaaatcaaac  45420
actactaaaa agaaggggac aacactgggg aaacccaagc ttccccaccc ctgcgctctg  45480
ccagtttgtg gttgtcagca gctacactga gctggagcca atcacatggt aatagttttc  45540
tgggtgacgg tgagcctgct taatatttct gggtcttgct tggttgtgtt tgtttgagaa  45600
agggtttctc cgtgtagccc tggttatcca cttgatatgt tgactgggtt gattttaact  45660
cacagaaatc ctcctgcttc tgtctcccgg gtgctgggat taaagacata cagcaccacg  45720
cctgtctctg tttcatgtct ttttttaaaa aaattttttt taaagaattt ttacttttaa  45780
ttacatgtag atgtgtatgt aaatgtgcat gcctgtgtag gtatgtgtgt atgtatgtgt  45840
atatatatat atatatgcat gtttgtgtaa gtgtatgtgc atagatgcat gtctgtgtag  45900
gtgtctgcag aaaccagaag tgtcaggttt cctttgatct gcctaatgtg ggtgctagga  45960
attgaatccg ggtcctagta ctcttaacca ctgagccatt tctccagctc ttgtttcatc  46020
tcttggcctc agtttcctgt ctgtgaaatg gtgcccgtat caaacctggc tgtggatcag  46080
atctataata gcatttcttt ctttaaaaaa aaaagattca ttttatttta tatatatgag  46140
tacactgtag cggtcttcag acacaccaga agagggcatc agatctcatt acagatggtg  46200
gtgagccacc gtgtgggtgc tgggaattga acacaggacc tctggaagag cagtcagtgc  46260
ttttaaccgc tgagccatct ctccagcccc tgtaataaca tttcttttct tttcttttct  46320
tttcttttct tttcttttct tttcttttct tttcttttct tttcttttct tttcttttct  46380
tttcctttct ttctttcttt ctttctttct ttctttcttt ctttctttct ttctttcttt  46440
ctcttctttc gagacagggt ttctctgtgt agccctggct gtcctggaac tcactttgta  46500
gaccaggctg gcctcgaact cagaagtccc cctgcctctg cctcctgagt gctgggatta  46560
aaggtgtatg ccaccatacc cggctataac atttcttaaa ccttaatgtt gaggctggtg  46620
agatgggtaa agacacttgc caccaagcct cacaacttgg gtttgatccc caggacccac  46680
acagggagag agagctaacc tgcctgagtc ttctgaccag cacacacatg ccacggcagc  46740
catgcccacc catacacata caaaacagta agagagtgta aaaattaaaa agcacctcat  46800
tggacggccc gtggaaccca ccgtgaacac atgatagcct gcaggcctca tactcctccc  46860
ttataagata ccctcacttt accgattggt ggtgcgtggt aggatgaact gaagaggcag  46920
gcagactgca gacaggagca cagagcagtc cagtcgtgct ttgctcagag ctgtacatcc  46980
caggctccct tagctgtgaa ccagtgttac ttactccctg gggtgcttct tgtttctcag  47040
ccttctttaa cccagcatgc cttgctctgc acccaccctc tctctgccgt ccccactcac  47100
cagtgtgagc acgtgggaaa cacctgctgc tctgtgggtg ctcagagtat ggtgtccaga  47160
```

```
gatcgttcct caggctgttt gctcagggtt ttgagatggg atccctccct ggcacctggg  47220
ctcacctatg agactacgct gggcggctga gctttcatag gtgggttctg gagagtgaac  47280
tctggtcttt gtgcttgtct agagggcact ttagtgactg ctctctccag cccactgctg  47340
ctgcttgtga gagttcttct tcccaggata caatgggctg ctggtagtag aagccctggc  47400
ggggggtccc cagtaggcac ttgccatcag tgttcccctc tacccttgtc tggttctgca  47460
atcaactggg gcctcccttg ctcacccctg tcaatgacag ctgaaggaag accagcagag  47520
ggcgctgctg agacgggagt ttgagctgca gagtctgagc ctccagcggc gactggagca  47580
gaagttctgg agccaagaga agaacatcct ggtgcaggag tcccagcagt tcaagcacaa  47640
ctttctgctg ctcttcatga agctccggtg gttcctgaag cgctggcggc agggcaaggt  47700
tctgcccagc gaagaggatg acttcctgga ggtatggctg agcatagcct tagcgcgggg  47760
ctggaagaat gggagcgtgg cacctgagtt ctgcctcttg tccctaacag tacctggttg  47820
ggagtaggtc acatgctatc tggactgctt gccgccgggg tctcccggtt tgttgaatgt  47880
ggtttctcaa accaggtgaa cagcatgaag gaactgtacc tgctgatgga ggaagaggag  47940
atgaacgccc agcactcgga taacaaggcc tgcacagggg agagctggac ccagaacacg  48000
gtgtgtttaa ccccttcggg tcctacctta actgtgtgta actcgttcat taatgagcgc  48060
ttcctgctat cttctcagcc ctgacaggac acagggtctg tggatgctta ttgcttggat  48120
tctggcccac cagtttctca gtgctagggg gacatgccag ggtagtgaca gaaggccaat  48180
gtcacaagta agggaagcag ttcgcccgtt tgttttatag gaaacagtgt tagagaatgg  48240
gggtcccgtg tccgtgcgtt tccatggatg aataggggct tgtccaattc agaataggga  48300
aaaaaggcca tattgaaccc agaggacagc atgtgctgag gtgtggcaag atgtgctgga  48360
gtgctgctgg ccagtgggac attgtgggag ggtgaggata taccaggcca gggacatacg  48420
aagagagacc ttaagtaaga actgtcaaat caagccacag gttggagagg gcggtggagt  48480
caccccctag ggttctatag tgagctagag tgagggcgag cagtgtgaaa ggcaccagga  48540
aagaggtttg ggatccagtc tggcgccatt tgagggacat cagtcagaga ggagagacct  48600
gcagcctgga gcccgctaag cctaggtgag gttgtttctc tgcgtttggg cagagtagct  48660
gctcctggaa tagacttcat tgtgtatgag acttgctgct cagctgagct atttaggaca  48720
ggccttcagc cccattttac tggtgagagg acctgaggag agctctctgg agctggtagg  48780
gccccagctg gactcctggg tgagtctgct atgccagggc tgccctttct gccttcataa  48840
agttcctgac caggccttac tctgccggca gcctaatgag tgcatcaaga ccctggccga  48900
catgaaggtc accctgaagg agctgtgctg gctgctccag gacgagcgtc ggggtctgac  48960
tgaacttcag cagcagttcg caaaggccaa ggccacctgg gagacagagc gtgcagagct  49020
caagggccac gcctcgcagg taagcctccc tgcttgttag ggacggtccc ttccttttc   49080
ccggcccagc tctagacagg caggtctcgg aggaggatgc taaggatgca cagggtcccc  49140
tgcacctcac cgtgtgcccc agagagattg acaggaatgt aggctgcact gtggactcac  49200
agaacgcttc cacgccagcc tgcgcgtcat atcctgcatg gctcctaata gaccggacta  49260
gggtgttgag agggtgaaga aaagacagac agacacaagg atacacagat agctgggatc  49320
aggcgatctg gactctctat ggagctctgg aaactcagcc tatttaccat gaagttggtg  49380
gtcattaatg cagataaccc gggtggtggg gattatggtg taccacagta tcaggggaca  49440
agctcagcaa atctgagcag gagcgctctg taggggagct gtctccaggc tgcgaatgtt  49500
```

ggagggggct gctgtggcgg acatcttcat acactaataa catcgcccac acacagagga 49560
aggctttgcc gtttccctct gagtctcacc ctggtgggac aaatggcttt gccatgtctc 49620
cctgggtccc acggtcgcca ggtatctgtg acgtgactgt acccatttca agagtacaca 49680
taagctcagg acctgactca cgagggcgtc ctctgccctc acacctgtac ttggtaacag 49740
gctgcacact cctgtctggg ctctgctggc tgccaccctc atttgttttc ttctttcttc 49800
ctaaggactc ccagcccctg ctacctggct ctaatgtgtt cctcatactc aaattgggtc 49860
tcccctcaca gccacccagc ctgactaaca gcgctctcac cagcatcccc agggggctgg 49920
catctgctgt gtgcctgggg gcaagttgtt tccccactct gatctgacaa ataggaaggt 49980
agaaatgctg tctctgcttc tctggactgg gcccctggcc gcctccagca catcttggct 50040
tccgggtgcc ttccttgcca tctgtggcca tgggagacag gcatgctgaa ggtctctgct 50100
ggccagatgg ccaagcaggc ccagaggagt taggtttctc tcctaggtat taagtagcag 50160
gcttgctctt gccccccagg cttctgacct tcttgttccc atgggtgcat ttccaccctc 50220
gcctggtgtg tggagactcc ttgagtttcc ctgagccctg cgctcttcct caccctgtgg 50280
gtatccatct tcttccagcg ttccccgctg cccctcactg ctccccaggc ccagccgtcc 50340
caggagctct ggctctcgga ccagcctcat aaggatcagc gttctagatc catgggcagt 50400
gagtcttgag gctgtatgtt tctttcctgc ctccccatga tgaggtcgag gctgagaaaa 50460
atatgctgga ccattcctgc gccagcgtat tatgtgactg tgtgtacatc tccctgtgca 50520
gggcctctgg gacaaggtga ggcccagctt tcaaggggta gcagtgggga ataaagaatg 50580
tcttccaccc gtggaagctg gtgctcctgg taagaactga taaatgtttg gttatcagta 50640
gccggggctc tccctttgt agcaggatgt ggaatgctta tctagcccct tggagccacg 50700
gtgagggaca ggaagtggtg ctttgcttac agaggcttag gaagagaaca ttgggttcgg 50760
ggtcagtctt gtatgtagaa aggggtccat agcacagaga gtccctgaag acctccccag 50820
tatgggtttg gagccagtgt cccctgccac tatccagcta gctggtgctt cttcctgcag 50880
atggagctga aggctgggaa gggtgccagt gagaggcccg ggcctgactg gaaggctgca 50940
ctgcagagag agcgggagga gcagcaacac ctcctggcag agtcctacag cgccgtcatg 51000
gagctgacga ggcagctgca gctgagcgag cgccactgga gccaggagaa gctgcagctg 51060
gtggagcggc tgcagggaga aaagcagcag gtggagcagc aggtgaagga gctgcagaac 51120
cgcctcagtc aggtgaggag gctctggtgc agtgatagct ggagcccagg gcacagggga 51180
agccgccaga gtcgggccct tcccttccca gcacaccaca tggcagcctc ggtgatcgca 51240
tcttacatct tagcagttgc aataaggaag tgatcttgtc tcacgagttc tcactgagca 51300
ggtgtcgatc ttgtgcccat tggtggggcc tgtcgagacc caggacccaa aagggaagag 51360
ccaagagtgg tttccatagg aaagcgagag tcctcagacc agaatgggaa accaagacct 51420
aagtattaca aaatccttat tccgtccggc tccctccctt tgctctgcag gtatacatct 51480
gtggagagat ctctgtctgg tttggttttc actaattgag tcattgtctt ccgaggagag 51540
ccttgctcgg tttaactgct gtttgactcc cactcattcc gcgtggacag agtccaggct 51600
ccatgtttga tttggagcag gtgacgtcac tcagttggta cagcactgcc ctagcacgca 51660
tgaagccctg ggctggattc ccagcaccac aggaacaatg tgtggcagct catggctgtc 51720
agtttttggt aggtaaaggc agaaaggtta gaggttcaag gtcatcaccc tcagctactt 51780
agtgagtttg aagccagcct ggtttacatg aaaccttgtc tcaaaaaacc aaaccaaaca 51840
aacacaccag cagaaagcag ccctctactg tcctgtgcac aggtgtatat gtgaacagta 51900

-continued

```
tttacaatgc tgtagtcaca ggctctcaca tggatagaga gtgagagaaa gagaacttca  51960
gggggctttc cccactgttc tcgtgtctgt ctgtctgtct gtgtgcagtg cgcagactcg  52020
ctttgcttct ttcttgccag ttcttatgac tctccagtct ttggactcac ctaatccccc  52080
tgagagccac catctttgtc ttgtcagccc gccattttaa accctctcag tcctgtaagg  52140
ccacttccca gaagagaaga acgagccaaa atgtcctgtt aatgacagga cagaaacatg  52200
ccagctcctc acatctgttg gatttttttt ttttaaagat ttacttgttt ttatgtagat  52260
gcgtgttttg cttgcttact tacatgtaca cacaccatat tcctgttcat attctctggc  52320
tagtgtcaga tttctcagtt atagatggtt gtgagctgcc gtgtgggtcc tgggaactga  52380
gcctgagtcc tctggaaaca agtgctttta actgctgagc catctctgta gccctaacat  52440
ctgatagatt cttttttttt tttttttggt tttttttttt ttgagacaag gtttctctgt  52500
gtagctctaa gtgtcctgga atttgctgtg tgtagaccgg gctgacttca aactcacaga  52560
gatcctcctg cctctgcctc ccaaatgctg ggattgtagg catgcaccac cactgcccaa  52620
cttttaatat catttttttaa tgatttggaa atcattaacc aaatcaatgc cctgctgaat  52680
gaggtgtgag cacaccgctg ggacctgcca gctcgtgggt gctcgctctt gtgcttaatt  52740
tcccagcagc gcccacctat ggaatttgct gacttcctag ctcggctcct gcaacctttt  52800
gatgctgatt tgtttccctg cattcaagcc caagctgcat cctgtatttc ttattttctt  52860
cctccttttt cccttccccc tgtcctttct ttctttgttt gtttgttttg agactacata  52920
tctcaatatt tggcccagac tagcctggca tgctcagttc tcctgagcta ggatgacaga  52980
ggtcagcccc aacatctgta taagctgtgc tctagatgaa accagcttgg tcaagcaacc  53040
agcagagcaa cagataggaa gagtatcttt agtcagtgtt cttccccacg aagagtcacc  53100
ttgaccatcg cagctcttaa aaggaaacat ttaatcgggg ctggttggct gttccagagg  53160
tttcctccct tttcgtcatg ttgagcagct tggtggcctg caggcagact tggtgctggt  53220
gaggtggctg agagttctac atccagatcc aaaggcagca cgaagagaga gtgacaatgg  53280
gcctggcttg agcatttgaa agttcaaatg ccccgccccc cagtgacaca cttcctccaa  53340
tgaggccacg cctcctaata gtgccactcc ctataagcct atgggtctca tttttttttt  53400
tttaaatatt tgtctttctt tttttttttt taatttatta tatgtaagta taagtacact  53460
gtagctgtct tcagacactc cagaagaggg catcagattt cattatggat ggttgtgagc  53520
taccatgtgg ttgctgggat ttgaactcgg gacttttgga agagcagtcc gtgctcttaa  53580
ccactgagcc atctcgccag cccctatggg tctcattttt attcaaacta ccacaaaggg  53640
gctcctagcg ctaatcaaat cccctctgat ctctgggctt cctctacaca aggaggatgg  53700
ctgttcaatc ttcttatctc tcaggacagc caagggaata aaagagctag ccacaagaat  53760
ggtgcgttgc tcctaggtcc ccccctccc cccactgggc cttggcttac atcttcatct  53820
gtgattgctg ttcattcatg ctgagatgac ttttgttgct gccctcccac ccccattctg  53880
tttgtcttac attgggttcc aagtaagcag agcttgagat gggggttcag gtgcaaacag  53940
gtagccagcc tgtcctggtg ttgcttagga cttcattgca cctctgggaa atggaaggca  54000
aagcctactt gctttttcag aactgaaagg gtttggggtg gggggagcct tactaacact  54060
ggggaagctg ggggggcggg gggtggggaa ctagggcgag tcgtcccctg tgggagcgaa  54120
gtggtgatgc ggcgcccgtc atctcagctg ctgtctgaac tgctccacat ctgggccctc  54180
cttctgttga ctttatcctc tcacctgcta cttggaaata atctcagttg tactggctcc  54240
```

-continued

```
tatgtctgct atgaggacta attgagctga tgagcacatg caaatgggcc ccctggaatt  54300
gtggtactcc agggaacacc tcaggactca gcaggttcgc agcatggtcc ccgagtgaaa  54360
tagctactgc ttgtctgccg ccctagctgt tctgtgaact gccgtgcaga gtaatgtagc  54420
aacagctcct gttaactcta tcagccaggt cagcaagatg cctgccagta gctgtttgta  54480
ttactggttt ccaaatccac cttgtgcggg gctcagaggt actatctatt gagaagccaa  54540
tgccggacat atgttgtggg tgggtcatgt ggcttataga attgagactg gggagtggcc  54600
ctgctcagag taaccctgcc cgccagcata cacacttttc tctttctcag ttgcagaagg  54660
ctgccgagcc ctgggtcctg aagcactcag acatggagaa gcaagacaac agctggaaag  54720
aggtgagagc atccctgcta cccacatcct attggcccgg actgtaccag aaaattcctt  54780
gcttgtgaga aatgtaacag agggatgcta actctgtccc agaagccaca ccctcactac  54840
accctgggct cccgagcccc agagtcacta ccccatgact gctgtccatg aatgtggact  54900
tgggaagggt tctctgctgt ggaagaaacc ccaggccagt tcagtcatac ctcaacagaa  54960
agcaggcctt ctaagtagct gtgtggtctt gggtgagtca ctctccatct ccgggcccca  55020
tttcctcatt gccctggcct catcctgagt gggtcggtgg ggtgacactg gaggaattca  55080
cacataaggt caggggggact gttaatagaa cacagagctg aggaacaaag ggtacataca  55140
ggtccctcat gtcgtccctc ctcatgatgg cgtgaagaaa tggcacccca ctcaggatat  55200
ggggctacaa aagcctattc tggagaactg aagcagagag gattttgagg ggctcacagg  55260
gctagtgatg cgcttctggt tactcatggg ccccgagggc tgcgtctcta gacccagagt  55320
gggaaaatct cacaatcact gtcatggcca tcaactgtac agtggctgtc atggaaaaag  55380
ttctgtctca agtggtccct ctttctctgg tccctctttg cactgcagat atctgagcct  55440
ggctcccatt gccattgtaa gggggtgaga ggtaacggtc cagacagtta gattgctact  55500
gacggcgtct taccctccag aggagacaac tcacgtgtgg agtcttgggc tcagttccca  55560
cgtgggtctg atgtcatcac ccatcacaca ctggtcacca gaactgatct tcttgtctct  55620
tcctttgaca ggcacgaagt gagaagaccc atgacaagga gggtgtctct gaagctgagc  55680
tcgggggaac tggcttaaag aggtgctggc cactcatccc ccaattctgt cctctacccc  55740
acagctctgg cccatgccct atagactttt ggctttgact ctctctactc ccctgctccg  55800
tgtgtccact cccaccccca tgagagttgg gagaaccacc agatgttccc ccctcccttg  55860
ggaccccagg cactcgggaa ctggagagcc tggggtcaca aggattgcag gctgcagttt  55920
aatgttgatt ctgggtatgg aaaactggag cctcagctgc acttgctgac aaagaagcca  55980
tttggctcct ttgagggttc tctttttctc cctggaattt gaatcatggt agatatccat  56040
ttgggggatt attaggcagt gtctattagg cctactacta tgctatggcc aagaggatat  56100
gcaagaatag cattctcatc attaagaccc tccatgacct gggcagtggc agtgcacacc  56160
tttaatcgca gcactcagga ggcagaggca ggcggatttc tgagttcgag gccagcctgg  56220
tctacagagt gagttccagg acagccaggg ctacacagag aaaccctgtc ttgaaaaaaa  56280
accaaaaaat aaaaaaattt taaaaagacc cttcatgaaa gaagagagga atagtacaga  56340
acagaacatt ctagagtgag gggctcactg gagtcagaag gccaggtgta gatctaactc  56400
tgccattcct agcacagggg ccttgggtgc ctccctctct ctagtgggtg aattggagat  56460
gcccacagag ccgtgcagtg accagtcatg tgtggtagag gattccagta gcaaaccaaa  56520
cctggatgtg aaatagggaa tgaaggcagc cagcggatca aaggaatttc aaatgatcca  56580
tgggggtggg aagagggggg tggggggggag aggcagctgg gatcctatca agatgtcatg  56640
```

gggtagctgg aactcaggat tgctgaggaa cctggaagcc agcagaggcc gaacccctca 56700
gagatccccc agcacaggtg tgaggaagcc aggtacttaa ctccagattc caccattgtg 56760
tgctaagggc tgtgttctgg ggattgaaag agctgtttct gccttcctct gcccagaggc 56820
caaccatgat cctagcattt gtgctactta agcgtgtaaa gagggtttga ggaggcagca 56880
gccagatgtc tacaagagat aggcaagaca ggcttggtcc ccacggcatg tccactttgt 56940
tatttcccac taaccccatt ttcttccttt acttttccca ggaccaaatc agtctcctcc 57000
atgtctgagt ttgaaagttt gctcgactgc tccccgtacc ttgctggcgg ggatgcccgg 57060
aacaagaagc tgcccaacgg ccctgctttt gcctttgtga gtactgagcc agtggagcct 57120
gagaaagacg ccaaggagaa ggcggggctt tccacccggg actgtagcca cattggtagc 57180
ttggcctgtc aggaacctgc agggagacag atgcagcgca gctacacggc tccagacaag 57240
acgggaatcc gagtctacta tagtccgcca gtggcccggc gcctgggtgt ccctgtggtc 57300
catgacaagg agggcaagat cctcattgag ccaggcttcc tcttcactac cgccaagccc 57360
aaggagtcag ccgaggctga cgggctggcc gagagctcct acagccggtg gctttgcaat 57420
ttctcccggc agcggctgga tggaggatcc ggggccagca cctcgggttc cggacctgct 57480
ttccccgcct tgcatgactt tgagatgtcg ggcaacatga gtgacgacat gaaggagatc 57540
accaactgcg tgcggcaggc catgcgctcc ggctctctgg agaggaaggt aaagaacaca 57600
tccagccaga cggtaggcgt ggccaccgtg ggcacccaga ccattcggac ggtcagtgta 57660
ggtcttcaga ccgacccacc ccgcagcagc ctccacagca agagctggtc accccgcagc 57720
tcctcgcttg tgtctgtgcg cagcaagcag atctcttcct ccctggacaa ggtccattct 57780
cgcattgagc ggccatgttg ctcgcccaag tacggctcac ccaagctcca gagacgatcg 57840
gtgtccaagc tggatagcac caaggaccgc agcctgtgga acctgcacca gggcaagcaa 57900
aatggctccg cctgggctcg ctccaccacc acacgggata gccctgtact gaggaacatc 57960
aatgatgggc tttctagcct ctttagtgtg gtggagcact ctgggagcac cgagtctgtg 58020
tggaaactgg gcatgtctga ggcccgaacc aaacctgagc ctcccaagta tggcattgtt 58080
caggagttct tccggaacgt gtgtggccgg gcaccgagcc ccactactgc agcaggcgag 58140
gaaagctgca agaaaccaga gcccctttcg ccagccagct accatcaacc cgagggtgta 58200
tccaggatcc tgaacaagaa ggcggccaag gcaggtggta gcgaagaggt cagacccacc 58260
atgctgtccc aggtggggaa ggatggcatc cttcgggatg gagatggatc cttgatcctt 58320
cccagtgagg tatgggtgga ctttaccctt cattcagaat gggggattag cctagaaagt 58380
tcaaattctt ctgttttgtg ctgttctgtg ttttgcttct cttctgtaaa gtttcatgta 58440
gcccaggcta gccttgaact ttctgtgtgt gtgtgtgtgt gtgtgtgtgt gtgtgtgtgt 58500
gtgtgtgtgt gtgtgtattt aaatatgtcc tttttgtttg gtttggcttt tgtttttgtt 58560
ttttttcaag acagagtttc tctgtggagc cctggctgtc ctagaactca ctctgttgac 58620
caggctggcc ttgaactcag aaatcctcct gcctctgcct cccaagtgcc caagtgctgg 58680
gattaaaggc atgcaccaaa aatatgtcct tttttatttt ttagaaggaa agcaacagca 58740
gttcagggct agagtgtggt ttgatggtaa aaacacatgc gtagcacagg gaagccctga 58800
attcaatccc aacacttcaa aagagataga aaggagaaag gagtgtgtta ctgagacatg 58860
ttaggtgctt agtgggcacc atgtcacatc ctttacatgc cctgtttgat cggatcctca 58920
cgacactgag aaacacaata catttttcat tgttgagaag aggagagaaa gattcttcgt 58980
agagtgtcac ttgcctagca agtggcagag ctgagagagt gtttgggttc tacagcaagg 59040
cttttcacca tctctttgtt cttatgataa ttaaaaaatg aataatccca gcaggtggga 59100
ggcaaaggca ggtggatctt tgaggcaagt ctggtctaca gccagggtta cacagagaaa 59160
ccttgtttca agaacaaaca aacaccaacc cccccaccca cccactcaca aataataaag 59220
aaaaagaatg aatgtaccta aatacacatc aaaagtgtat ctggaatcct cagtactccg 59280
gatatgatag cacatgccct tagtcccagc acttgaatag ctgagactga agcaccacgg 59340
gttgaggcca gcctggacta catcgtgaat tcaaaggcca gctggagcta cacagtgtga 59400
ccctgacaca aagaagcaaa cagagagtaa attggaacta aggatgtagc tcagtggtag 59460
agcacctgcc tggcttgctc aagcccctaa attccatcac tatggggtgg gggtgggggt 59520
gttggaaaat acgtatttcc attcagtaga acaccataga gcctttaaga ctaagaccca 59580
ggagctgggg agatggctca gccgttaaga gcactggctg cttttccaga ggacctgggt 59640
tcaattctca gcacccacat gatggctcac aactgtctat agctctactt ccagggcatc 59700
tgacaccttc ttccaaactc tacgggcact ccatacttgc ggtgcacaaa cacgcgtgca 59760
ggcaaacttc ccaaacacaa gccaagctgg tcgtgtctgc gtagagtgtt gagaatctca 59820
acctcggaca gcgtctgcct tctctgtgcc ttgcagactt tattagaatg tggatccatt 59880
gttgccctaa taggagtaat atggtctaga gcagagttgc agctcctgcc tcagcatgag 59940
acatggctga attctggtgc ctgggtggct gtagcccagg cttcaggctg ctgctgatct 60000
cttctctgtc tctccccagg atgccgtatg tgactgtagc gcccagtcac ttgcctcctg 60060
cttcatccgg ccatcccgca acaccatccg gcactctcct tccaagtgca ggctgcaccc 60120
ttcagagtca ggctggggcg gggaggagag ggcagctccc cagtgagtcc ctgagcaacc 60180
aagcacccac ctcaagcagc ccagaccctg gagatgaggc aagggctcgt gtcctcagcc 60240
tcagtccatc caggaggaat ggcagctgtg ccactgccac agaagagctt tcacattaag 60300
gtaaagcaag gtgtcttgct gactgctggg cagtgacctc tgatttccag gggaagaca 60359

<210> SEQ ID NO 11
<211> LENGTH: 76771
<212> TYPE: DNA
<213> ORGANISM: Homo sapiens

<400> SEQUENCE: 11
cgctgagcag cgacgccgag tccgcggccg gggcccggc gggggtccgt acggggcagc 60
cggcccagcc cgcgccctcc gcgcagcagc ccccgcggcc gcccgcctcc ccggacgagc 120
cgtcggtggc cgcgtcgtcg gtgggcagca gccgcttgcc gctcagcgcc tcgcttgcct 180
tctccgacct caccgaggag atgctggact gcgggcccag cggcttggtg cgggagctgg 240
aggagctgcg ctcggagaac gactatctca aggtgggggc gcccgggtag aaagggaggt 300
cgcaggggtc gccggctgtc acagtcccgc gggcctgagg caccagccgg ccctccttcc 360
cactgaacaa tccggagaaa ggggcccaag ccctctgggg accactctga ggtggatctg 420
gggctccctc attccccccg ccccctctca actttatttg ggaagcgcgc tcctgaaaaa 480
gaccttggaa ctggctacag ggccctaacc tgggagcggg gacttgagaa agctttggag 540
cgttctggga ggcgttgctg aggtgggggt gggtagccag ggaagggatg gatctctgcc 600
ttcagctgcc cagaacctcc acgcccaggc tctccttctt gggacgggat tgatagacac 660
cgccgccagg gaaacctgtg gccatcccct gcccaggaaa ggcctgaatg ccatcctgag 720
tcgttaccca gggctttccc gggcgcaggc ctgtctctgc ctgcctttct gggcgggtcc 780

-continued agtttgaaag catgacatct gggaacatcc ccttggctgg agtccacttc cgcccagcct 840
aacggtccca cagcctggag gatgatgtcg tgggagaacc ggttcagagg cagcttccta 900
aatcccagga cagtgtcttt tgccctccct ggggcagacc ttgtgcacac aacagcccca 960
ttggcccctc gtggccagtg cctttccatg ttcgcagtga gaggagggca actgcccacc 1020
tggaacagga cttccctgtg gccatgtggg gaccctaggg cttcccccgg acagcaggct 1080
ttgcctttgc tttttcagtg gacatgagca cctactgggt gccagccggg ctccatctgc 1140
acgcttccag gtgccatggc agctttaggg acagcccagc ttgcacgtgt tgacctctcc 1200
ctgggaggct ggaagcttcc tgagctctcc tgccgctggc tgggcacggt tttggaggag 1260
gctgaaatgt tgccgactct tgtcagtgga tgatggcctg gcacaacacc cagagtgccc 1320
ctggctgtgg agctcacagc atgctgctgg tttatgtctg ccctcagcac ttaggtttta 1380
acttttcctt gtggctcttc tgaccaaatg ggcttctccc tcattagagt gttggtgtct 1440
tgctcaacta tgtctctgtc tccccatttt ccccgggatc tgctctccag cctgagttct 1500
gtaaatgctt gtagtatgga aggacaaggt ctgtctgaat caagagacac ctttccccaa 1560
gccaggcctc agtctcctca tccgttaaat gggaggatgt cttcccaagg gccgggttcg 1620
gtgttggcaa ctgggagttc agtcggctct ttgagtcttc agaagccggt ggtaaggaga 1680
gggcaagtgg aaggtgagga ggaggaggga ggtgacgagc caggacaagg gtcttttgct 1740
cctgccctct tggtgctctg agctgcttcc agtgagtgct gcctgaattg gccttaaccg 1800
aaactctgag ttcctcaccc ctgcctcccg gttcctgcta ctcactctgg tgaaggggga 1860
tgggttgcag agctttgctt cagggctcct aggcacccat ctccatgggc ccctgtccat 1920
cccaggaagt catcaggctc tgacccaaag tctgtttgag gcacccatga ctgtttaaag 1980
gggaaaacag tcccaggagg ctgggggttg agcccgggat ctcacagggg ccggggtcca 2040
gctggggaca tcccacgttt gggccaagat ggaaccgtaa tttccaccat tcattcagtg 2100
gctcaggctt cgtgctgcta ttggatctgg ggtctgtcgc ttcctgacgg cgtgatcttt 2160
ggcaagttac ttaaaggccc tggacctttg ctttctcatt tgtaaaaatg ggacagtaac 2220
acgctttcca acctcaacgg ttaaatgagc tgattcctgc aaacaccatt agagcacctg 2280
gtatgtagta aacctctgat cactgctctt gtcagaggca cgggacatgt ttccatgtgc 2340
acccagcctg ttctcttgtg gattctgtga gggcagaata gatcctcttc atcacccaag 2400
gcaggctggg ctctttctcc tggcccctca ttggttcatt cggcagctgt ttatttagaa 2460
cctgccgtgt gctagggcag atctgggata cagctgtgga caagggagga tgaggtgtct 2520
gttttcatag agcttttggg gagaccagaa ttaaacaata gtcatacaag aaatcacaac 2580
acagatcata atgagggtaa aggggacagt ttgccaggag cacacgaagg tgggggctgg 2640
ggtgcacagg gaggctgagg gctgcaggat gccgtggagc caactgagtg agggtctgga 2700
gtaagaagat ttcaggctaa gggaaattgg aatgctcgtt gagttcaaga acagcgctaa 2760
ggccagagag gggaaggagt gtgggtaaga gaggagagca aggccagccc atgccacttc 2820
tcactgtgta catttgggtt agtcccttaa cttctctgta tatctgttta tcccagccgc 2880
cagcctcaca gaggcagggt caaaatccag agactaaatg tggaccataa atagaggggt 2940
tattactgga ggtgttgtgt tgtttattcc acagatggga aaactgtggc cagagtgggt 3000
cccagagcag ggtcgctagg ctgccagggc ttggagtaag catgtgttag actcttgatg 3060
tgttttctgc ctttctggac tactttgcct ctaagatgca gaaactgagt acaagggaaa 3120

-continued

```
ggactccaaa tccccagtat gtcccctgca ggagcagagt tgaaggaggt cccaccaggt   3180
ctggtgggtg gccctgctca ggcttacctc cccctgtag gggtcactgg gaactgtcaa    3240
ctgcgaagga ctgtgatctc cagtctggta tggtctgctc tggggtccaa gtgaggaaag   3300
cataaatcgg gcaactctct cccagtgaga agatagaagg agcttctaca gagaaggtag   3360
tgagctcact gtcactttaa ttattcagag agaggcggga tgaccttgca tgcttggata   3420
aagatagagg gtttgtggaa tgattgcttg agaagggttc agagggagat tgatgtggtg   3480
gctgcagttg agctgcctga ccttgggtcc cttctagcca aggaagtctg aaggttatta   3540
actactgagg tgccaggatt ctaagatgca gctttagctg ccgagcagac acgtcacctg   3600
agaccttcaa agacccggtg atctgaggtc ttccagcctt tcatcaccac taaccattaa   3660
gcacgtacca tgtggccaga acatgtagga acccactggg tgtggatgga ggaatctgag   3720
agttggagtc tgaagacctg actttgaaac ctgactctcc cgtttactgt gtggccatgg   3780
gcaagttacc tggcttctct gagctgcttt ttttctcatc tgtataataa aggtgatggg   3840
gcctggcgca gtgactcacg cctgtaatcc cagcactttg ggaggccaag gcgggcggat   3900
cacctaaggt caggagttcg aaaccagtct ggccaacgtg gcgaaacccc atctctacta   3960
aaaatacaaa aattacccag gcgtggtcgt gggcgcctgt aatcccagct actcaggagg   4020
ctgaggcagg agaatcactt gaccctggga ggcagaagtt gcagtgatcc gagatggcgc   4080
cactgcactc tagcctgggc aacagagtga aactcttgtc tcaaaaaaaa ataagtaaag   4140
gtgatggaac ctgcctggac aacctcatac gatggtcatc aggaatcagg gaagtgtgaa   4200
tagacaagaa aacattttgc aagcagtgaa cccaagtcgc ctgaggaatt gttattattc   4260
atagccaata ggcagacagg atgtctgtgt cttcattctt ggaggaactg ggagaatgca   4320
ggagggtgga tttccttagt tttagaatgt taatacatca gtagctgccc cagggagaac   4380
ggaaaggtgt gatcaccttc cctgccgtgt gtgtgtgtgt gtgtgtgtgt gtgtgtgtgt   4440
gtgtgtgtgt gtgtgtgtgt gtgtgttttc cctccttggt gattctagat gtgagtgaag   4500
tgcagccagt gtgtgtgtgt gtgtgtgtgt gtgtgttttc cctccttggt gattctagat   4560
gtgagtgaag tgcagccagt gtgtgtgtgt gtgtgtgtgt gtgtgtgtgt gtgtgtgttt   4620
tccctccttg gtgattctag atgtgagtga agtgcagcca gtctagatgt cagctcagaa   4680
gggcctggag gaagcaccta atccatcccc acttgccatt ttacagatca gtaaatggag   4740
gctctaaatt acatagccag gattccaacc caggtttgtc taactctggg cctgttcttt   4800
ctgcagtgtg accagagcag tgagcttttg gttgttaact agcgtgtcta ggctgagaca   4860
catttggtga gaggaatcct gtcatgggcc aggctctagg ctaaggcatg ctgggggccc   4920
ggagcctggg ggaggtgggg gttagtggag gatgtttgtg tgtgcatgtg tgtgagattg   4980
ttccttctgt aacatggggg acaagcacgc ccgcccaggg ccgtgaggac ccttttcaat   5040
gtgaggacgc agatggagtg cacagtgagt gttagtgtgt cccagtcatt gccgatccct   5100
tatccgttcc tccaggcatt cattcattca ttcaacacat atttccccag tggctcctgg   5160
gtaccaggcc ctgtgctggg tgtctggacc cagtggccac gtagtaggct tctgcatgta   5220
gctcttctct tcttggctcc caggagctac agggggagga ctctagtctg tcactgggtg   5280
gaggagagga ggtcaccaca gtcagcaaag ctcttggctg ctccttaccc tgagtcccag   5340
ccgcagcctc cttggggctg agcctgtgtc cctgggcata ctctgtcttg cacatacaaa   5400
tgcacatata ctgttcacag ctcaagctca gagacacaca gccacttgca cacatctcac   5460
agacccatcc agtgactcgc tggtgttgga tgctttcaga agcacgcctc cagacagatt   5520
```

agagaggata ctcactcaga gaagtgcaca aacccatgca gccacacaac tcccattcta 5580
tcacacgcac acatcaccaa acagacacaa cggaggctca gaccctgctg caaccccccac 5640
gtcagaaaca cattctcata tacacatctt acaccccctag acacacccgg atatgtccca 5700
gagacagact gacatcctgc agacacactc agacttatca gaagtacaca tgtaggcgga 5760
gacacaaacc cacacagacg ttatacacac acactagcat ccacagaagt ctgcacatct 5820
acccttgcca ggctggccca ggcacaagct caccacccgg gtacctcccc tgcctcttct 5880
acaaagagag cagcagagac ttgcacacct acccgaggct tacagacacc caccaagggg 5940
actcccacat gcacatcagc agggacacag cacagtctgg catgcaaaca ttaggcatgt 6000
agcatttgcc cacaggagcc agaggctctc aaaccaggga acctagacac acgcacacac 6060
gtgcgcgcac gcacacacac acacacacac gctgtgacat ttcatccaca cacagaaaca 6120
ggaaatcctg gtctgtgtct ccctggagct aatgtgtaca aactactact gttttcagtg 6180
gctcactaga cttacttcta caaggctgct gggaacacta aggagtgtgg ccagggcctt 6240
gactttgtaa ccttctggag ctgggggtct tggggtcctg ggtggtgggt ggatgggggt 6300
ggtaggtctt gaagtcagaa gaagctacac cgaagtcccc caggtccctg atgcccagct 6360
cctgggccca gggccagtgg ggctgagtga agtggaccga ttgtcgagct gcccacagaa 6420
gaaacactgc ccgggggcaa ctcccttcta atctccttgg aatttcctgc tggccctatc 6480
tccccccttct cccccctgttc ccttgctggg ggctgcagag ggccatgcca ctcccatcta 6540
taaagggtgc cccattctgg ctggggaatg atggaggcaa gggtagaggt ggctagagga 6600
gctatgggag ctcagaggag ggacttggca gacttcctgg aggaggaggt gtccttggag 6660
ctggggagtt agcctcaagt ggctgtctct gtgcccagct cttagaacag tgcctgccat 6720
gttgtagggg ctcaataaat atgtgtacaa ttaagtgaaa ggcagtaggc agggcctgga 6780
ggtggaccac aggcttgaaa cggaaaagct ggagggagtg gtgggagctg gcagggatgg 6840
ggagagtctg ggaaggggcg ttgggctggc ttgggaaggg cattgaatgc caagccaagg 6900
gagcaccttg ctgggagtgg tcttgttgca gcaaagctgc agccacctcc ttttatgtgt 6960
ctgcagccct gggcctgagg cctgccctgc cggagaggcc tggggaggga ggagagccag 7020
gctgtgtggt ctaggggcca actccacctc tggagtcaag tctggagcca aacctcactg 7080
tgtcacctcc tccgtgtgca tgctgtccct gtgcaaaccc ctcaccaaga ctccgtcttc 7140
ctcctgtaaa atggggatgt gatcctttct agtggggcac ttgggaggct gacagctcag 7200
atgttctgtg cacctagcac catcctggca cagaggaggg gaggaggccc cgtgtcttgc 7260
atagcctccg gggcagagag agtcccctag gaaaggggcg cagctaagtt caagcaaggg 7320
cctgcccagc agccaaggtt ttcactgagg tcattcccct agtccccaca tgcatgacct 7380
catccatggt cacgttcact ccccttggtg ccggaaggaa cttggagctg gggtgctcca 7440
tgccaggctg accctggcat cactggaggc ctcagtcagc actgcatcta cctgctttgc 7500
ggtagtgagg cacagcaggg gtcagagcag gtggaagcag caggccagcc ctttgttctc 7560
cgaggtccag ggtggttggg agagagcact gtgatctgga gccaagctga ctgggctgga 7620
atcccagctc tgccttttcc tttctgagct ttccctttct gagcctcggt ctcgtcatct 7680
gtagaatggg gatgtggatg tccttgcccc gcacgttgcc gtgagggttc cgtaagagaa 7740
agtgtgcagg tgtgggtccc attagccagg tctggctcct gggaaggacc cgacagcact 7800
tggcgcttgc ctgttatatc tggctctggt gtgacccccg tgaccccagg ttaagctggg 7860

-continued

```
tgcttgatga caggggctgt gcttggctct gggtgtccct ctgtgggtgt tggcttgggg   7920
catcagtctg agtgttatgc acagagctgc actgcatttt gggcaccccc aaacgtatat   7980
ccctgtctgt gtcccccctt ccctccccca cggcgtcgtg tcactcttcc ctgaatggcc   8040
caggctagtg cctccagctt agtaactggt gatacacatt tgctaatgga aggacacctt   8100
tggcggcccc tcattctcaa atggaggtga atcatctctc actgcctgag ccacaaggaa   8160
aagctcagcc tctatgaaaa aaattctggg gttccctagc taggctggat cagctgaaca   8220
tctttactct ggttggggcc caggcctgct ttgggtcttc tgggctcgag tcagttgcac   8280
cagcctctcc cctccccgcc tctccttgac cctaccccat ggtggagcag cctgtgtggt   8340
cctgcctccc acagcctcac ccacccctgc cccgcccaag ctctgcgggt gctggacaca   8400
ccccggcctc tgtcccgtgc tcttgctctt cccatccggc ctttgtgctt gcagttcccg   8460
gctccttccc ttggtttctt cctccacctt tgagcgctca gccccagcag cagctcccca   8520
ggtcaggctc ctgtgtcaga caccttggag ctccctggag cttcctttgg ggcatttacc   8580
acgatgttga ttagattatt aatggggtaa tgataggttt catgccatca ctgccccacc   8640
tttccctgca tgagggcagg gaccttccag ggtaattagc tccttccttt tacaaaggga   8700
gaaactaagg cccagagagg ttaaggggct tgttagaggt catgcagcct gtaagtggca   8760
agaggcaaga ctggggtctt gtgcttctct ccaggatgcc aggcaggggg aatggcaggg   8820
gtgtgaagtg ctggggtgtc ctggagcttc aggctttgtg gccttgggcc actctctttg   8880
gagctttgcc ttctatccct aaagacctca gacccctgct ctgagttttt gagatttcgc   8940
tgcaacccag agggtgtttg gggatgttt taaacacatc caggtccaga tgctgccttc   9000
cttcctgttc acatggaaag gatgggagga aactgtcagg cgcttcctga cacgaatgcc   9060
ccagaggccg tagggcctgt ggatatctcc ctgctctgcc aggtaaggcc ttgaatggga   9120
gagtgacaac agtgacaagc cagatgtggc cttggtgggc agtggtctct taccaacaac   9180
aaccaccaca cacacacaca cacacacaca cacacacaca cacacacccc tccctgatag   9240
agcatctgta gtgtctcttg tgcagaactg taccagacgg atctgggagg ctcactcctg   9300
actggctgcg tagaccttat cttcctgggc ctccgtttgc ttgtctgtga aatggggata   9360
aaataataat agtgcctgcc tctaaggatc atcactgagc aagagataat ggcttttctg   9420
tctcagtccg gtgtctggaa cgcattaaac gcttgtcaat gttagctatt gttatcgtca   9480
ccattgttca ttataagact gtctagtcca gcttatagga gctccaactg gacctgaatc   9540
ctggctgtgc cacttagtgt gtgaccctgg gcaacatact tgacctctgt gaggttcctc   9600
tcccatcggg gattgctcgg gctgcagtga gagaatgtgc actccctggc ggggatcagg   9660
ggtgcacagg gagcatctca tttcttggca ttggagaggc gggtccaggc cccagtcttc   9720
cctcattatt cccaaccaga ggagcaggac gtggtgagtc tccagggcca ggcagcctct   9780
gtgttgtctg gagtggggac atcatgtggc acggtgatgc caggctgcgt gtcctggcct   9840
tctttccccg ggaccttttt tttttttttt ttggagacga agtctcactc tgtcgcccaa   9900
gctggagtgc agtggcgtga tcttggctca ctgcaacctc cgtctcctgg gttcaagtga   9960
ttctcctgcc tcagcctccc gagtagctgg gactacaggc atgtgccatc atgcctggct  10020
aatttttgta tttttagtag agacggggtt tcatcatgtt ggccaggctg gtctcgaact  10080
cctgacctca ggtgatccac ccgcctcagc ctcccaaagt gctgggatta caggtgtgag  10140
ccaccatgcc cggcctcatc aggacctttg atgcaacttc ctgaaaactg gaccctagct  10200
tcttcgcaag gatgctaagc tagattgagc tctggggtgg gagacaggtg cccagagtcc  10260
```

```
cccctcccac tcagtgctat cccctccagg gactgtggga ttgtcccctg tccttctcaa  10320
ggcctttctg tccctgggta tgaagggatt gagtctttgg tttccctccc ctgctgctgt  10380
gcccagagtg tttgcatttg ggctgagaag tggagctctg cggagttttt tgcatatcct  10440
tttttggggt ccaagtgtga tgatctcatc tggagccttg acagactcct gggggaccgg  10500
cagaagggac ggcagatggc tgccctggcc tcttgggtgg ggctggcatg ccgcccctgt  10560
ggccactgcc ggcccactcc acagagcagc ccttccgggg ctggggtgag tggcccgggc  10620
ccgggcagga gacgagtggc ccagagccag ggtggcagat gggaggcagc ccaggcctcg  10680
gcctgaggga gggaccatgg tggccagggc agtatgggag caggcgggcc aggcggaggc  10740
tcccgttcct ctgtagtgtg gttgctgcct cgcagagtga aggttctggg cctctcagct  10800
cagctctgtc attcttctgg gttggtctgc ccgtcggagg gcttgttggg cccctggaac  10860
ctggggagga ggtggtacat ttgggtaagg tttggaatct ggcagggctg tggcctgggt  10920
gttgctgggc tgggacttga gccccaccac tggggtctga agcacccatg ggcattagct  10980
tcacagaatc aaggaattag attcaaacac aggagcgctg actagaagta gttttctgta  11040
ggggagtaga acagggggat tctcctcccc tctgagggcc tgtgtattca ttcagcacct  11100
ctttattgag ctgttctgtg tgtcccaggc actgtgctgg gctctgtcct cctgacatca  11160
catcctggtg gtagagactg acattctgca ggcaaacaga caaataaaac gctgagtatc  11220
acaaataagc ctatgatata tgccaagaaa gaaacaaggg attaagatgg acgtaatggg  11280
cctggaggag catggaaggc ttctcagagg aggtggcatt tcagtggaga cttgaggcag  11340
aaggcaagcc agcagggcag agatgggggg cagggaaatc caggcagagg aaactgcaag  11400
gccaaaggct ttgaggtggg acaggtgagg tggctgctgg ttgcctacga cccaagtggc  11460
tgctgtgttg ccagtgagag gaggcgtcga gggagatgaa gatggagaag tggacggggc  11520
ttaggccagg cagggcctgt atgctgtacg atgggatttg ggttttcttt tgtatgtgat  11580
gaaaagtcac tggaggtttt gttttgcttt gctttttgct ttttggggtt ttaggtcagg  11640
tgtactgggt atatatatac aatatactgt acaatatact gtacaactat atacaatata  11700
ctgtataata tattgtacaa atatatacaa tatactgtac aatatattat acaaatacat  11760
acaataaaat gaattttggc aaatgcatcc agttctgtag ccaccaccac aaccaagata  11820
tagaacagtt ccttcacacc ccaaatttca ccctgtgagg tcagttcctc tctcgatttc  11880
agaccctgac aaccaccggg actgttttct gtccctagag ccttgccgtt tccagagtgt  11940
caaaaacaga ctcatacagt gtgtagccta ctcagtctgg cttccttccc taagcttcct  12000
gcatgtgagc ttcctccatg ttgcaggtgt cagcagttct ttccttttca tcgctgagta  12060
gtattctatt gcgtggacgt accacagttt atcattcacc agctgaggga catttgggtg  12120
attcccaggt tttggtgatc attggagaat tttaaacagg agaaaatttt aaacagtttt  12180
aaccacattt taaacatggt tttagaaaaa atcactcact gtactgaatg gagaacaaat  12240
tagttgggag cagagtgacc atcataagga ttaaatccaa taatttggtg atggatctgg  12300
cccaccatag gcactcacta attgttcaaa caaaagggct gtgccctggg acagtcaggg  12360
aggcttttgg tggaggtggc ttttttttt cttttttttt tggtcaaaca cagtctcatt  12420
ctgtcatccc ggctggagta tagtggtgcc atcttggctc actgcaacct ccacctcctg  12480
ggttcaagca attctccgcc ttagcctcct gagcagctgg gattacaggc gtgcaccacc  12540
acgcccggct aattttttgt atttttatag agacggtttc gccatgttga ccaggctggt  12600
```

-continued

```
cttgaagtcc tgacctcaag taatccgtcc gtctcggcct cccaaagtgc tgggattaca  12660
ggtgtgagcc actgcgctct gctggaggtg gcttttgagg tgggaaacag gtgtggagta  12720
ggagtcccag gcagtacaga gtcccatggg agtgggtggg ctcagattcc agctccccgc  12780
ccctgagcca gccttggcat atgtagagtt gctagaatat ggtctgtagg ggtcatatca  12840
gagttcccca gggacactag gggctgactc ttgggtggga ggtagctgag ggacttccgc  12900
tctggaagtc tcttccttgg tggctggcaa gaggcaacct gctcctgcct ttgggagcct  12960
catgtcccct tggttctctc cgtgtcctcc cagctgggag ctgttgctgg gttcagacca  13020
catgctgcca cttgtgtttc tgcagagggt cctggtgttt ggtcactttc atctccagcc  13080
ccacagctca ccagctgctg caggccaatt ccgtcatagc catgcatctg gagccacgtg  13140
caaaggttcc agtgggcccc aaatctaaac ttcccccgc tgtcctcagt gtacaaacgt  13200
aaatcatttt atatctgcgt gggtttctga tagaaagtaa tctttcttag aacacttaaa  13260
gtgtgattta ccagcccagg ctggtaaatc actaaagcaa gaccccctct ctacaaaaaa  13320
tacaacattc agccaggcat ggtggtgtgt gccagtagtc ccagctactc aggaggctga  13380
agtgggagga tgactttagt ccaagaggtc aaggctacag tgagctgtga tcaagccact  13440
gtgctccagc ctgggtgaca cagagggacc ctgtcttaaa gaataaaata agtaaaaagt  13500
gtgatttgaa agtggagctc tgcttctccc gcctgtattt catttcaaca tttaaagtta  13560
tatcttattt tggctgggtg cggtggctca cacctgtaat cccagcactt tgggaggccg  13620
aggcgggtgg attacctgtc aggagttcaa gaccagactg tctaacgagg cgaaaccccg  13680
tctctactaa aaatacaaaa attagccaag cgtggtgctg catgcctgta atcccagcta  13740
ctcgggaggc tgaggtggga gaatcgtttg aaccccagag gcagaggttg cagtgagctg  13800
agattgcacc attgcactcc agcctgggta acaagagtga aactccgtca caaaaaaaaa  13860
aaaaaaaaag gaaaccaact atattgaaac acagttatta aagtattttt aaattacaac  13920
atagtaatat gtgtgcttat taactcataa attctggtga cagatctaac tagcataatt  13980
tcaaactact gatgagtgta aataatattt tgacattttt gcagcaactg ttatatgata  14040
tgaaaatacc tgtgattttt ttttggtggc aaagtcacag atattactca tataatgatg  14100
atttgttcat aggcccagaa tagaaggaaa tgctacattt tacttagagg tcagtgaaaa  14160
ggaagatgtg attttccaag ttcatggact ccctgagttc tggttccaag gaaagatctt  14220
gaagttggtg gttggacttt gagtcctgct tggaggtctc accccctccc cctgcctgtt  14280
tgcgtgtgct tgggcaccac ccaccttccc tgtgcttctc tgaagttctt catctgtaga  14340
acatggatga tggttcctgt ctttccttac tgggagtggg gggttcagtg aggatctgtg  14400
agatgattca gatggaatgt ctttgtaaac tgtgaagccc tctgctgctg tgcaagatct  14460
tgctattatt agcagtagtg tgagctcatg tttggctgtc cggcccagcc gggaccaaga  14520
ggctcttcct ggacaattct cccaggattc ttgggaatca gtccatcgag gggagcaggt  14580
ttgcctttga gaggctgctt cctgcaggct gagctcatgg tttggcaggg ggtggacaga  14640
gatgcacctt gtgggcaggg agtgggtggg tgagcaggag gttccctacg tagacagacc  14700
ctgcctaccc tccttgggtg gcatagggat ctgcgaccag ttctgatctg cccaggctct  14760
ccctctctca tttttattta gagacagggg tctcactctg tcacctagcc tggagtgcag  14820
tggtgcactc atggctcaca gcagcctgga actcctgggc tcaagtgaac ctcctgcctc  14880
agcctcctga gtagctgggg actacaggca catgcccagc taagttttta aaattttttta  14940
ttttttgta gagacggaga ctcactgtgt tgccaaggct ggtcttgaac tcctgtcttc  15000
```

ctaactcttt gcagctggct gggagttgtg gactgggcag gacagaagct atactctttt 15060
ttttttttt ttttttgagt cagactgtct ctgtgtcact caggctggag tgtagtggtg 15120
caatccttgc ttattgcagc ctcaacctcc caagctcaag tgatcctcct gttgcagcct 15180
cctgagtatc tgaggctaca ggtgtacagc accatgcctg gctaattttt aatttttttg 15240
tagagatggg gtctcgctat gttgtccagg ctggtctcaa actcctgagc tcaagggatc 15300
ttccctcttt ggcctctgca aagtgttgcg attacaggcg tgagccaccg cgcctggccc 15360
catactcatt ctttaattcc tacatctacc catagacagt gacaggtacc tgctctgtgc 15420
cacggtctgc cctgggtgat gctgaggact agacacaaac cagcccctgc ccttctccct 15480
agctcttggg gaagattgac atgaaaacag acaaatacaa cctaaaatta ccagcacaac 15540
ggaccataga tttcagagtg tggggtttga atcagagtct gggaaggaaa tgttctggaa 15600
ggatgagata gtcaggagtc agcctggcaa aggccgttct agcagaggga atagctgaac 15660
aaattggaag agcacagtta tgacgcactg acccagggcc acgtggcttg tttggaatcc 15720
agccccgcag gtcccttgct caagcagctc tgcgaagctt ctgagcctcg tctcctcatc 15780
tgcaaaacag gaacgttttc agcacctacc tcacagggtc ggtaagagga ttaaactgtc 15840
aactgataat gcacgtactg cctgtgcggg ggcctggtaa ttagtgagcc tcctaatagg 15900
tggtagccgt gttttgtttg ttgaaacagt ctgtctctgt cgcccaggct ggagtgcatt 15960
gttgcaatct cagctcactg caacctctgc ctctgggttt caagcgattc tcctgcctca 16020
gcctcccgag tagctgggat tacaggcaca cgccaccaag cctggctaat ttttttgtat 16080
tttttgtag agatggggtt tcaccatgtt ggtcaggcaa gtctcaaact cctgacctca 16140
ggtaatccat ccgcctcggc ctcccaaagt gctgggatta caggcgtgag ccgccgtgcc 16200
tggccaatgg tagccatttc taaagtcaca gcctatttgg acgctggagg gctggggtaa 16260
ggcgggagta gggaggagac caggggctgg ctcaggaccc ggtaagggga cttggaccta 16320
ctgcagaagc tggtgagaac cggtggaaga gatagaaagc cgtctacctt cttcagattt 16380
tctccaaaaa cagctattaa ctgtaatcag agcaaaaaag cattctctag aaagggaagc 16440
actgcctatc ctggcagcag tgtgggtgcc ctggtccccc atcctccccc atgctcctat 16500
tccccgtttc tagtccagct aaaaaatctg ggttagcttc aagagtagcc tttaaggtga 16560
agaggtcaac ttgaaggagg tggccaggcc gtggtggggc tgagggtcag gggccccaag 16620
gctctgaggt gggcactacc aggcactgtg ccctttgtt gtctggcaga ggatgaggct 16680
tggggtttcc ccagtggtgt tgaggggatt ttttttttt ttttgagaca cagtctcgct 16740
ctgttgccca ggccggagtg cagtggtgcg atcttggctc actacaacct ctgcctccca 16800
aattcaagca attctcttgc ctcagcctcc caaacagctg ggattacagt cgtgagccac 16860
cacagctggc taatttttat atttttagta gagacaaggt ttcaccatgt ctacaacttt 16920
gttccatagc cacgaggcct actgagtcca gtggagctgg gcctctccct ccccacttcc 16980
acacagttag ggggtctggg agctgggaga ggctcttcag aaccactgag ctgtctgtga 17040
aggagctggg aagcctgtgc tcctcacccc cacctcccag ggccccccac ccccagctcc 17100
ttcagttgga tctgtcactg gagagctctc ctgggatgga ggcccagact gcatgaccac 17160
agagccccag aacattctta ggctccctga ggactgtgaa cctctggaac agaacaaagg 17220
cctgccctct gggtcccctc cccaagcccc agcagcacct ctcctagccc cacctcgggc 17280
ccggaaagcc cagcgcccct gcctaagtcc tgcattcgcc agcctctccc gcccacgtcc 17340

-continued

```
ctgcagaccc agcctggggc cacaagcctg cctttgtcag ctcaccctct cacgtggggc  17400
cgtgccagca ggggctaacg ggcattctgc ctgcagctgg gactagcccc ctgagaggcc  17460
taggcccccc tggagagatg gaactggcgt gaatgcaaca tcttgggctg tcacaaattg  17520
actgtggtga agggcaggcc ttggggagac agctgctcat gtgagaacta tcattcattc  17580
attcacttat tcaaaggatg cttgctgaga tcctgctctg tgtcaggccc tggcatgggg  17640
acttgtgctc agagacctga ctcttgccct tttagggggg gaaataacta gaaggaaacg  17700
cccttcatca gaatcccttg gggggctcac cctaggagtt tctgattcag caagtctggg  17760
ttgggacatg agaatttctc acaaattcac cagtgatgct gatgttactg gtccaggaac  17820
tgcactttga gagccactgt aattcaggta ttgtaattat gcatggatta tgttttcttt  17880
ttcttttctt cttcttcttc ttcttttttt tttttttttg agacagaatc ttgctctgtc  17940
acccagggtg gagtgcagtg gtgtgatctc agctcactgc aatgtccatc tcctgggttc  18000
aagcaattct cctgccttag tagctggtat tacaggcacc tgccaccatg cctggctaat  18060
tttatatttt tagtaaagac agggtttcac caagttgccc aggctggtct cgaactcctg  18120
acctcaaatg gtccgcccgc ctcggtctcc ccatagtgct gggattacag gcgtgagcca  18180
ctgcacctgg cctgttttct ctattttcaa aactgtctct atgatcatgt tttactttta  18240
gagacaggtt cttgctctgt tacccaggct ggagtgcagt ggtgcaatca tagttcaaca  18300
gaaccccaac ctcctgggct caaacaatcc tcccacccca gcctcccaag tagctggggc  18360
cacaggtgca ctaccagacc aggtaatcca tccacctcag cctcccaaag tgctgggatt  18420
acaggcatga gccaccgcac ctggccaatg atagccattt ttaaagtcac ggcctatttg  18480
gatgtaatac attattatta ttgttgttat tattattatt attattattt tttttttgta  18540
gagatgaggt cttactgtgt tgcccaggct ggtcttcaac tcctgggctc aagtgatcct  18600
cctgcctcag cctctcagag tgctggggtt acaggggtga gccactgtgc cctgccagtg  18660
ctttatttta ttttatttta ttttattttt ttctgagaca gagtctcgct ctgttaccca  18720
ggctggagtg cagtggcatg atctcagctc actgcaacct ccgcctcctg ggttcaagca  18780
attctcctgc ctcagcctcc tgaatagctg ggattacagg cgtgcaccac cacgcccggc  18840
taattcttat atttttagta gagatggggt ttcaccatgt tggccaggct ggtctcaaac  18900
tcctgacatc gtgatctgcc ggccttggcc tcccaaagtg ctgggattac aggcgtgagc  18960
catcgtgccc gacctggcct gttttataaa taagaaaatc agtcatttaa aagttaaaaa  19020
aaatgatttc caaaaatgac tctagtgctc tgggtgtgat cttgtgtaag agatgttacc  19080
tcccatgatc taaatgtcat gcatttgtta atgtagccca gcatcatagg gttgtgtgca  19140
tttcccccttg gttcaacctg agcttggggt ccacttagac cctcctattc tttccatcac  19200
catatcctgt cattttaact ttctagagat aataagtgag gtgctggtaa ccggcatggc  19260
taggatttga acacagatcc atctggaggc tggcctagcc taccggcttg cacttcctga  19320
gtgatctttc cttcatgctt ccttcaccgg ctgcctgaaa cagcgcgtgg atccttcact  19380
tcctcatttt tttaactggt gtgatcattt actgttccac ttcctcctct ccactctggt  19440
tctgtccacg tggtatgctg gtggggtggt gagtctatga gggtggaggt gggggtgggg  19500
ggctggcaaa gtgactgttc tctgcagccc caggagtcaa accgatgggc aggaaaacct  19560
ctcgagcttg tgagaactgg cctggagggc agggctccct aaccctgact ctgagttaaa  19620
tccatccagc ctcagggggc gctggcaacc ccagtcgtac ccccttcctc acagggagcc  19680
atcctaccag gctgaccatt ggaagagcag agcagtcctc cccatctggg caggcaggag  19740
```

tgaagagaga gaaccccatg tttgttcctt tcacaggcac aaaatcagat ccccccttcct 19800 cccagcccca gcgagggtgt ggtgaggggt gctcggacag aagccagagg tgtccctctg 19860
acgggagcag agtggacact ccctcctccc agtggcagca tgaggaggga ggaatacgag 19920
accccacttc ccagtccctt cctttccgtt ttctttgggg aaagacgggt agggagagct 19980
gaggaatccg gctctccaga tctgccctct ccagggccca cagaggcctt cttgcccctt 20040 ggaccccccca cccctgcttc catcactgcc atcctcggtg cttcccctgg ctcctcaggg 20100
atgcctttag caggtcattc atccctggtg actctgtttc tcttttttttt tattttgtga 20160 gacagaggct cgctctgctg cccaggctgg agtgcagtgg tatgatcttg ggtcactgca 20220
acctctgcct cccaggttca aatgattctc ctgcttcagc ctcccgagta gctgggatta 20280
caggtgccca ccaccatgcc tggctaattt ttgtattttt agtagagacg ggatttcacc 20340
atgttggcca ggctggtctt gaactcctgg cctcaggcga tctgaccgcc ttggcctccc 20400
aaagcgctgg gattacaggc gtgagccacc gcacctggcc agtttccctt cttagtatac 20460
aatcttattt aaatcattcg gtcacattaa gagtaggtat tatcattccc atttgtgact 20520
aggttttcac atttgtatga gacataataa ttatgcattt cttctgcgta attctacttc 20580
cctccccctt acacttagta tctaatgatt gttgcacatt cgtatgtctt ttttgttgtt 20640
tttgacctga ctaaacatgc atgcatccat tcagttaata tttgttggga ggctaccacc 20700
tgctaggcca aatggggttg cctccaggca ctcatggttt ggctgggaga caaactatta 20760
aacatagaat tgcaaatttg ctaataatga ttacaaagga gaagtgagga acagctggaa 20820
gctgatgaca gcggtagcag aagctgcctt caggaagtga ggtcatactc ttaccctctc 20880
tgcttaaaac ccaaacccag gccaggcatg gtggcttatg cctgtaatcc cagcactttg 20940
ggatgctgag ctaggcagat tgcttgagct cagttcatga gcaacctggg caacatggca 21000
aaaccctgta tacacacaca cacacacaca cacacacaca cacacacaca cacaccccac 21060
cccccacccc cgatgtgggg ttgtgtgtct ttggtcccaa ctacttggga ggctaaggtg 21120
ggagggtggc ttgagcctgg gaggcagagg ttgcagcgag ctgagatttt gccaccgcac 21180
tccagcctgg gtgacagagt gagaccccat ctcaaaacaa aagcaagcaa acaaatccca 21240
aacccaaatt ctatttggcc cttcacagta ccatgtggtt gactcctgtc agtttcctca 21300
gcctcaaatt aacccagtag ctgccctggc ctccttgctg taccttgaca cactgagctc 21360
tttcctgcct ctgagccttg gcacacactg ttccctctgc ctggaataac ctctcccccct 21420 agctttctcg gctgttcctt cttgtctcag ctcaaatgtc tcttttgtag agatggcctc 21480
cctgatcatg tcccctaaca tagcaccccc cctcacccta tcatataact catgttgttt 21540
ggtttcattt tggctttgtc tttatagcac ttaacagtat ctgaggtttg tttttgtttt 21600
tttttcttgg agatagggtc tcactctgtc acccaatggt gcaatctcgg ctcactgcat 21660
cctctgcctc ctaggttcaa gtgattctca tgcctcggcc tcccgagtag ctgggattac 21720
aggcgtgaac caccacgctg ggctcatttt tttttttttt tttttttttt ttttgtattt 21780
ttagtagaga cagggtttca ccatgttggc caggctggtc tcaaactcct gacctcaaat 21840
gatccaccca cctcggcctc ccaaagtgcc gggattagag gtgcgagcca ctgcgcccag 21900
ccaggtgtct tttgttatta ttattttctg gtttactgtg tatcttcctg gtgaagcttg 21960
gggctccata cagagtatat agaaggggct ggacccaccc cattgtccct ccctgcccct 22020
gcgcttagca cagggcctac ctaggacgta catagttgat gctcatccat gtttcttttt 22080
ttttgagacg gagtctcgct ctgtcgccca ggctggggtg cagtggtgcg atctcggctc 22140
actgcaagct ccgcctcctg ggttcacgcc attctcctgc ctcagcctcc cgagtagctg 22200
ggactacagg cacccgccac catgcccagc taattttttg tatttttaat agagacggat 22260
tttcaccatg ttagccagga tggtcttgat ccaacctcgt gatccgccca tctcagcctc 22320
ccaaagttct gggattacag gcatgagcca ccgtgcccaa cctcatccat gtttcttaaa 22380
tggcctctcc tgcttcccca gtgtgttcct gttgcttctg taacaaatca ctacaaattt 22440
agtggcttaa aagaacacca ggccaagggc acggtggctc atgcctgtaa tcccagcaat 22500
ttgggaggcc gaggcaggct gattacgagg tcaggagatg gagaccatcc tggctaacac 22560
ggtgaaaccc cgtctctact aaaaataaaa aaaaaaaatt agccaggcgt ggtggcgggt 22620
gcctgtagtc ccagctactc aggaggctga ggcgggagaa tggcgtgaac ccaggagggg 22680
gagtttgcag tgagccgaga tagcgccact gcactccagc ctgggcgaca gagcgagact 22740
ccgtctcaaa aaaaaaaaaa aaacaccagg ctgggcaggg tggctcatac ctgttcccag 22800
cactttggga ggccaaggcg ggcagatcgc ttgaggtcag gagttcaaga ccaacctggc 22860
caacatggtg aaaccccgtc tccactaaaa atataaaaaa tcagctgggt gtggtggtgg 22920
gcacctgtaa tcccaactac ttgggaggct aaggcaggga gaatcgcttg aagtagggag 22980
gaggaggttg cagtgagctg agattgtgcc actacactcc agcctgggca acagagtgag 23040
actccgtctc aaaaacaaca aaaaaatgaa caccagatta ttatcttctg atcctggagg 23100
tcaaaggtct agaaatcaag gtttgggcag ggctgcattc ctcgggaagg ctccagggga 23160
gaaacctttt ccttgccttg agaggcaccc ccttcctccg tcatcacagc cccttcctcc 23220
aacatcaaag catctcactc cagcctctgc ttctgtttcc ctgtcttggg atccttaatt 23280
tactcatatt tgcaaagtct cttttgccat gtaaggcaac attcacagat cctgggaatg 23340
tgaacatgga cgtctttgga ggtctgtcat tcagcctgcc acatccaggt cccccacggt 23400
gcttcattca gtcctaggtg tggccagtac tccggcctcc tagctgctac tgtgggccca 23460
gtgacctgac tcttccttcc ctccgcagga cgagattgag gagctgcggg ccgagatgct 23520
ggagatgcgg gacgtctata tggaggagga cgtgtatcag ctgcaggagc tgcgacagca 23580
gctggaccag gccagcaaga cctgccgcat cctgcagtac cggctgcgca aagccgagcg 23640
ccgcagtctc cgtgccgccc agaccggcca ggtggacggc gagcttatcc gtggtctgga 23700
gcaggatgtc aaggtcagcc tgggctcggg tgcccttgtt gctgggatgg gaccacaagt 23760
ctaagtgggg cccaggttgg ccttgcatct catttccgtg tgtccatggc caagttctac 23820
cacctctctg ggcctcagtt tcctcatcta agtaggaatt cctggtgaac ccacagggct 23880
tctatcaagg gtatcccaaa atgatatcat aatatgaatc cttcctacta gcagcagcta 23940
ctgttttttt tttttccttt gagacagagt ttctctcttg ttgcccaggc tggaatgcaa 24000
tggcgcgatc tcagctcact gcaacttctg cctcccggga tcaagcgatt tctcttgcct 24060
cagcctccca agtagctggg attacaggca cctgccacca cacccggcta atttttgtat 24120
ttttagtaga gacagggttt caccatgttg gccagcctgg tttcgaactc ctgacctcag 24180
gtgatctgcc caccttggcc tcccaaagtg ctggggttac aggcatgagc cactgcgcct 24240
ggctgagaag ctactgttta ttgagtatca accaccacct ggtgctagcc tctaattgtc 24300
cccgcacagt tccatggggg tttctttttc ttcttgtttt tttagagaca aggtcttgct 24360
ctgttgccta ggtatcaggc agtgatgtga tcatagctca ctgtagcctc cacctcctgg 24420
gctacccccca cctcagcttc ctgagtagct gggactacag gcacacacca ccacacctgg 24480 ctaattttc tatatgttgt agagatgggg tctcattatg ttgcccaggc tggtctcaaa 24540
cttctgggct caagtgatcc tcctgccttg gcctcccaaa gtgctgggat tacaggatg 24600
agccacggtg tcaggcagag gttccttaat tatgctaatg aaaagtagtg aaggcctcga 24660
gaccatcctg gctaatacag tgaaaccctg tctctactga aaacacaaaa aattagccag 24720
gtgtggtggc aggcatgtgt agtcccagct actcgggagg ctgaggcagg agaatggcgt 24780
gaacccacga ggcggagctt gcagtgagcc aagatcgtgt caccactgca ctccagcctg 24840
ggcgacagag cgagactccg tctcaaaaaa aaaaaaacaa agagaagtag tgaaggccta 24900
gagttggtca aggctggttt aaatcttggc tccaatatac ctgaacttta ttattttgag 24960
caaagtcatc aatttcagtg tcctcatctg taaaatgggt ttgcagcaat ctctatctca 25020
cagggttata tgaggattaa atgaaataat gcgggctggg cacagtggct catgcctgta 25080
atcccagcac tttgggaggc cgaggcgggc agatcacctg aggtcaggag ttcgagacca 25140
gcctggccaa catggtgaaa ccccatctct actaaaaata cacaaattag ccgagtgtgg 25200
tggttcccgc ctgtaatccc agctactcag ggctgagac aggagaatcg cttgaacccg 25260
ggaggcggag gttgcagtga gctgagatcg cgccactgca ctccagccag ggtgacagag 25320
tgagactccg tctcaaaaat aataataata ataataataa taataataat aataataata 25380
atgtgggtaa aatgccagca taaggactca aaaatgttag ctatcattat ttccattttc 25440
ttgatgaaga atctgaggtt cagagaaaag caatacctgc cgaaggtcaa ggggcgctca 25500
gtgtgttggt ggcagagccc aggctcatga gcctcccaag cctccagctt ggcctcactg 25560
ctctctgctt caggaagcag gggaagggtg ggtgggaggt tggcaggtgg gatgtccccc 25620
tgcctgtctt cggaagctct ggtctggtgg tgagaactcc agggccccca ggcccggccc 25680
tctgccctca gaactcagcc cagtgtgatc tggtgacacg aggagctggg atggggccct 25740
agggaggctt cctgcagggg tgacttctga gtgaaggccc aagggagaag tgggcctgag 25800
ccaggaaggg ggaaagagga aggtggcaga agatggctcc tgtgaggacc caggggagcg 25860
gcaggatgcg agtcagccac acacttacct ggggagaagt cccttctgtt ggaagacact 25920
ggcaaactca agccctatag cctttccagt ggaatataaa agaaaaacct ttgttaaggg 25980
accagggaga gccatggttt caaaggccag cagaaccagg ggaggtaaac aggagtgcct 26040
gttccaggaa gctgctggcg ccccctgtgg tcttgttggt gcacaatggg attgtagtgc 26100
tgtcctacac atgaggcaac caatggttgt gtctccgcca gaggtggagg ctcatgcctg 26160
taatcccaga atcccagcgc tttgggaggc tgaagtggga ggatcgctag aggccaatag 26220
ttggaaatca ggctgggcaa catagcaaga ccctatctct acaaaaaaat aaaaaaaatt 26280
agcagaggct gggggtggtg gctcacacct gtaatcctag cactttggca ggccgaggcg 26340
gatggatcac ctgaggtcag gagttcgaga ccagcctggc caacatggtg aaaccccggc 26400
tctactaaaa atacaaaatg agccgggtgt ggtggtacac gcctgtactc ccagctactc 26460
aggaggctga ggcagatgaa tcgcttgaac ctgggaggcc gaggttgcag tgagctcaca 26520
ccattgcagt ccagcctggg tgacagagtg aaactctgtc tcaaaaaaaa aaaaaaaaaa 26580
aaaaaaaatt agctgggcgt ggtggcaagt gcctatagtc ccagctatat gggaggccaa 26640
ggccagagga ttgcttgagt ccaggagtta aaggtttcag tgagctatga ttgcagcact 26700
gcactccagc ctgggcgaca gagcgacaag gtctctctct aaaagaaaaa aaagaatgag 26760
ttagtttcca agttcaaagc gtacctctac ttgacagggc agctcccggg catattcaga 26820
ttccaatcac tgggttggga ggggtggggg gtggtggggg aaggcagtag ggaggagatg 26880
gggaggggga gggaatagct ggagaagctc agaggaatct gcgtttgggc atatagtgga 26940
ggatttctgg gagggacaca aaaaaatgtc agacttcaga aagatgagga agaggcggag 27000
gagaggctgg gacctggagc tagctgccgg ctgcggcgcc tccgtgggtg gagctagagc 27060
agcggcggcg gcggcgggga ggcgggtgtg gggagcgggt gtgtggctct ccggagtctg 27120
ggcggagagg aggggccgtt tctgttgggg tttgaattag ccaatcagca tccctcttgc 27180
ccttccctcc ctcctctccc cacgctgcag ctggagcgct gagctcatct gcgggcctgg 27240
ggcctgagct ggatggacac ctctggccac caccctgagc cccatgtgct ggggtcgttc 27300
tggggggttt tgggaagtta tcagaatgct gctttccctg gcatcgtctt ggagggcttg 27360
atggacccga gtggggaggg ggcgggcgct gcctaggagg gtacctctgg gacttcccca 27420
acttgctctg ccagctccgt ggtccatgcc ctgacttgcc cctaccgctt ggtgcctcat 27480
tttccccttc tgttaaatgt ggcttttgac cagctgaatc ctcagggctt ttgagctcct 27540
gtggttttat ggagcagagg ggtattggtg gggtggggtg gggggtcatg aataaaacca 27600
caggcctcag tgcccccccc caacccccag ctctccctct ctgctggtcc tcaccgttga 27660
caggacctac agaacctcgg tggggccttt gcccagcatg aggagggcaa ggtcacgggg 27720
cggagagctg ctgtgccacg tttgctgtgt ggccttgggt aagttccttc acatctctga 27780
gcttgtttcc tcatggaaaa tggagataaa atgagtccct ccctctagag gtttttgtga 27840
ggataaaatg aaataattca agtgaagaga gtattaaata ctaggtctgg aaataaacat 27900
gtattggttg tggttttctt tttcttttt tttttaaggc agggtctcac tctgtcaccc 27960
aggctggagt gcagtggtgt gatctcagca acctctgcct cctgggttcc agcaattctc 28020
ctacctcagc ctcccaagta gctgggatta caggcatgcg ccaccatgtc cagctaattt 28080
tcgtattttt agtagagatg gggtttctct gtgttggcca ggctggtctc taactcctga 28140
cctcaggtga tctacccacg tcggcctccc aaagtgctgg gattacaggt gtgagccacc 28200
atgcctggtc tggttgtggt tttcttattg ctgagaagaa ctcacacagc aagtataagt 28260
tcttctgagc aatacatcag taggactact agtagtagta ggctagtagg actggttggt 28320
agtagtagta gactagtagt ctgggggcga gggtaggcca ggatctcagc ctcccagggt 28380
ggataaaaat caccaggagg gcttgttcac aacatacatt cccaggaccc gtgaggagct 28440
gagaccggat acaaggaggt caggtccagg gaatctggga tctaaactct ggtctaaagt 28500
gactcctgtg ggaagccaag gacacaccag gagcacgccc ccttcctcag atacagatgt 28560
tgctggagaa aatgttctgg ctttgggttt cattcctagg tgacctgtgc aggttacctc 28620
ccttctttga gcctcacttt cctcatctgt agagtggggg tgacattcct accctcctgg 28680
ggtttgtagg aggattcagc cacacggagt ccagaatgct gcctggccag gggatgctct 28740
tcctttttc tttttttttt tttttttgag atgaagtctt gctctgtcac ccaggctgga 28800
gtacagtagc gtgatcgctg ctcactgcaa cttccacctc ccgggttcaa gcaattctcc 28860
tgcctcagcc ttccgagtag ctgggattac aggcatgcca ccatacccag ctaatttttg 28920
tattttttta gtagagacgg ggtttcaccg tgttgaccgg tctggtctcg aactcctgac 28980
ctcaagtgat ctgccggcct cggcctccca aagggccaga attacaggca tgagccacca 29040
tgcccggcct tgtttctttg tttctttctt tctttcttga aacatagtct ctctttgtca 29100
cccaggctgc agtacggtgg ctgatcacag ctcactgcag ccttgacctc ctgggctctc 29160
aagggatcct cctgtctcag cttcctgagt agctgatact gcaggcacac accatcatgc 29220

```
cctgctaatt ttaaaaagtt tttatagaga tgggggtctc cctattttgc tcaggctggt  29280
cttgaactcc tggcctcaag cagtcttcct acctcgacct cccaaagtat tggaattaca  29340
ggcgtcagcc accatgcccg gccaggagct gctctttcgt gagagctccc atccctctcc  29400
ctgaggatca ggatgacaga ggcccaggag ccgaggggcc tgatgcctgg ggagcagggg  29460
ctggaggctg ctagttgcac ttggcaggag ccaggcccta gcgctgtaaa cagtgacctc  29520
atggctgagt gcatttgttt atggtttagg gatttgccct ggttttcgga agccgcagct  29580
gccgcgcctc ccttagtatc tcagcccccc taccttgagg gtagctggga ggatcaaatg  29640
ggatagacac gtggggccct tcaaatgcct gacacagtaa gcccactgtt ggggtttatt  29700
attaatactt gtattgttga tgttaatgta atgtgttttc acgcattggg cctatacggc  29760
aaaatcagcc tgagagtgag actttagagt tgacccactc gatttcaaac cttagttcta  29820
tagccttcct agctgtgtga ccttgggaag tgacctttcc tttctgagcc tcagaatggg  29880
gataataatc aaagtgcttc ccaacgggat gaaaagcacg tggtgagcac ccgggggatg  29940
ttccagctga ttctgtaaat cacttgtgag ggccgagggg gcccaggacc actgaggctc  30000
actgaggagc agggacaagc ccaggccaca gggctcctgc ctcccagtct ggctgcctgg  30060
agttgtgatt tttttttttc tttttctgag acaaagtatt gctctgtcac ccaggctgga  30120
gtgcagtggt gcaatctcag ctcactgcaa cctccgtctc ctgggttcaa gcaattctcc  30180
tgcctcagct tctcaagaag ctgggattat aggcatgtgc caccacgcct ggctaatttt  30240
tgtattttta gtagagacag caaagacggg gttttaccat gttggccagg ctggtcctga  30300
actcctgacc tcaagtgatc tgcccgtctc agcctcccaa agtgttggga ttataggcgt  30360
gagtcatcgt gcctggcctg tgctttcttt tgatacagca gccatcaggg aaagggagta  30420
aataggaaag ggattccatg gagaatgggg cagaagggaa ctggggaatc atggagagga  30480
tgggagggga tgaaatccat agagttgttc atgaacccca gaggatccag aaatccacat  30540
ggattgtgac ttcttgatgg ggactggtag cctccccagg tggaggacat ggtggagatg  30600
gggcatcccc gcaggtggag aggagctggc ccagatggga gctcatttga gagaggagcc  30660
ctcaccccag ccaggggtgc agcccttcct ggatagtggg tggggttggc atttgagggc  30720
agcctcttca gccctgcgag ggcaggtacc actccccatg tatattcagt cattcactca  30780
ttcatctccc tcccttttca cttgttggac ccttggattt atttgttcat ccaacaagca  30840
tttattaggc acttagtgtg tgcctgacgc tgcgctgctg ctgggacaca tagatatgaa  30900
tgaggccaag tatgtctgcg gccttgatct ctgtacccca ccactcctgc ctccagtgcc  30960
taagcaggat gagtgagtga gtgagttagt gagtgagtat gagtgagtta atgaatggaa  31020
tgttgatcag gacaggggct tactgggtga cctaacagcc ccaaactggg gaccatgttt  31080
aaataactta acctgggtca catagccagt aaatgctgga actgggcttg aatctagttt  31140
tcctatctgc aaagcccttg ttctgatact gaggggttgt tctccccact tcgtggatga  31200
ggaaggtctg gtacccagag aggctgtggg aggagcctca tgggcccgct cctggctgtc  31260
ctacgagatc ctcgggcaga aacaggcagt ggcagtgcag ggagggagag gccatgcctg  31320
gtttcctttc tggtcgttgt ttttcctggc ctgcctcata cattgccaag gggtccgtgc  31380
cgagctgggc ttcggcccag gcagaggtca gagccaggga gggccctctt cccttctggc  31440
aaggaggagg cacaacagtc atttccgaga ccagcaggca tgggttgctg ggctctctgc  31500
cccacatgga gttcctgctg gcgaaacctg ggcacccctg ggaaaccctg ggctatactg  31560
```

gcccctcagc caaacccctg gggctcccag cccagctcaa cccacactgg ctttgcgtga 31620
ccctgagtga gtcacttctg ctctgagctc cagtttcctt gtaaaatggg gacaggattg 31680
gggtgaagat gggtgagttt ggcatgcagt aggtattcac caaacagtag ttcccaatgt 31740
acatagagat ggagtctggt tgcaatttcc cagcccagaa gggccttcct tcctcatccc 31800
tgcaggcctc ctttcctggc ttccctcaac cagccagcag gggacagaac agagggtgtc 31860
taccaggaat ggggtgctgt tgctacagag tcctggacca ggatcagaga ttgcagctcc 31920
tctagcttct ttctgtaggg atgacttgga catctgccca ccctttgtca ttttgggcct 31980
gttctacatc ccagacaact agatataggt ctcagggtca cactgtgacc tccagcgatc 32040
atgcccttct ctgggcttca gttccttgga gcagcagcta ccagtcaccc agaactcact 32100
gtgtgcaggc cccaggccaa ggcttttgtg taatagctgg ttcagttatc ctgtcgggcc 32160
tgtaaggttg accctgttat cactgcgttc attttatagt tgaggagact gaggtacaga 32220
gaggaaaatt gccttgccca ggactacatg ctggtcactg gcagagatgg gattcagtgg 32280
tctagggccc atcttctctg ggtttccact gcagctcaat cccctctctg ttttgttttg 32340
ctttgctttg ttttgttttt aggagacagg gtctcgctct gttgcctagg ctggagtgca 32400
gtggcacaat catagctcac tgcaacctcg aactccaggg cccaggtgat tcttccatgt 32460
tggcctcctg agtagttggg cctgtaggtg tgtgccacca tgccaagcta actttttttgg 32520
gtttttgta gaggtggggt cttgctatgt tccccaggca catctcgaat tcctgggctc 32580
aagcgatccc cctgcctcgg cctctcaaag tgtgggattc caggtgtgag ctaccgtgtc 32640
cagcccctca aagtgttggg attacaggtg tgagctactg tacccagttc ctcagtctcc 32700
tccctttaag atgagcttct ggccctccca caggcttttg tgaggactgg gcaagtggtg 32760
gctgggagag gctttggaag tgtgaagagc ccaggtaggc aggcacagtg gctcatgcct 32820
gtaatctcag ctactcggga agctgaggca ggaggatccc ttgaggccac aagttcaaga 32880
ctctcctgga ccacatagtg agaccccgtt tctttttatt tatttattta tagacaaagt 32940
tttgctctta ttgcccaggc tggagtgcag tggcatgatt ttggctcacc gcagcctctg 33000
cctccctggt tcaagcaatt ctcctgcttc agcctcccaa agtgctggga ttacaggcac 33060
ctgccaccac gcctggctaa ttttttgtat ttttagtaga gatggggttt caccatgttg 33120
gccagtctgg tctcgaactc ttgacctgag gtgatccacc tgtctcgacc tcccaaagtg 33180
ctgggattac aggtgtgagc cactgcgccc ggctgagacc ccgtgtctac ataaaaaatgc 33240
aaaaattagc cagttgtggt tatgcatacc tgtagtccca gctactcagg aggctgaggt 33300
gagaggattg cttgagccct ggagttcaag cctgcagtga gacatgattg caccactgca 33360
ctccagcctg ggagacatag tgagaccctg tctcaaaaaa aaaaaaaaaa aaaaaagcct 33420
caggtaaatg aaaaggcatt cctgagaaca gggtcttccc agctttctgg ggctgtgctg 33480
tgatacagat gctgagagct tgcggtacct aggtttgggt tttggttcta ctgcttcctt 33540
catgagtttc ttggtctctt tgtgcctcag tttgctcatc tgcagcgtgg cagtgatgcg 33600
ataggaacct gcctgtctct agggttgccc tgctgtgaaa gtcgggtggt cagtgggact 33660
tgcagtgggg gctctcctca gcctgctcac atccttctct ctcccacccc tgcacaggtc 33720
tctaaggaca tctccatgcg gctgcataag gagctcgagg tggtggagaa gaaacgggcg 33780
cggctggagg aggagaacga agagcttcgt cagcggctca tcgagactga gctggctaag 33840
caggtgctgc agacggagct ggagcgaccg agagaggtga ggacctcatg catccagcag 33900
ggccagccta gggcaggtgg gcacatgcaa gcccccccaa gccagtgtct ctgtgagccc 33960
ccgcttgtgg gaaatgggca gcttatgcct ccctggcaag gttgtttatt cattcattcc 34020
tccaacatgc atttcctgag cacctactgt gtaaattgtg tgctggacac taaggttaca 34080
atggtgaaca aaacacaccc agttcctgtc ctcagggagc tcacggggta atgagagaga 34140
gagtcattca tcaaagaacc acagccgctg tgggaggatt aactgagaaa acatgcaaca 34200
atgtcaggca tggggctcag ccctctgtgc ctcagtttcc ttacctatac aatggggcag 34260
tggtgccctg agtcattgtg aggaccaaca ggaataacgc atgtggagtg gctgcaagag 34320
actgcgagat cctgccattt ggtgtgaagt cagtgcaggg gctgggtctc aggccagtgt 34380
ctctggggta ctggtgcttc ccgaatgtga ccctgagaca cattcctgtc tgtgtttgtt 34440
catgccagtt cctcccctgg cagaccttct cctcctgttg tgtgttgggt atacagtgtg 34500
ttatgcgccc tgcttgacag tttatctcaa acattttcat gctaacaagg ttgcgatcat 34560
gcccattttg tggatgagca aacagcccct gagagagagg gagggacaac ctcaaggcca 34620
tgcagggctc agggggttct gcagaatgcc ggctagaaac catcagccta ggtgtccctt 34680
aaaggctgga atccccccat tccagggttc tgtgttccaa atggcctggg gtggcttctg 34740
gccctagagg cagagccagg ccttagctct ctgcctgctg atgagatatg aggatcgtgc 34800
attcttctag ggcacactcc tcgctgcagg cgctgcctgc cttcctcccc cgagggcgag 34860
cctgccagtg tccttggact gagacaccac agcccaaggc cagaacattc ctccagccat 34920
ccttcccact gggtgtgttg gtgtgatgtg ccaatgccct ctcagtgtgc agggagagga 34980
ggcgtttgct gctaagggtg gctagccccc tcccttcatt cagctgccca cccccatggc 35040
ctggcccata acacggagca ccatcttcac accgtcttgc tgctgcaacc cttgatagtg 35100
aaaaggggag acaatttctg aaagcatctt aaggtcacgg tacaagtaat gaaactgagg 35160
ctcaggagga acagcttgcc tgagttcacc cagcctctcc ttagcagaga tgtggctgga 35220
accctgaagc cacttcccct ctctaagtct cagtttcttt atctgtgaca tcaggataag 35280
caagcaaaca aacaagcaaa gcctgcacgg tggctcacac ctataatccc agcactttgg 35340
gaggccaagg tgggcagatc tcttgagcct aggagttcga gaccagcctg ggcaacatag 35400
tgaaactctg tctctataaa gaatgcaaaa attatccagg tgtggtggtg cctgcctgta 35460
gtcccagcta cttaggaagt ggaggctgca gtgaggtgag atcgcaccac tgcactccag 35520
cctgggagac agagtgagac cctatctcca aaaaaaaaaa aaaaaaaaaa aagggggtc 35580
caggcacagt ggctcacgcc tgtaatccca gcactttggg aggctgaggt gggtggatca 35640
cctgaggtta ggagttcaag accagcctgg ccaacatggc gaaaccccat gtctactaaa 35700
aatacaaaaa aaaattagct gggtgtggtg gcgggcacct gtaatcccag gtacttggga 35760
ggctgaggca ggagcatctc ttgaacctgg gaggtggagg ttgcagtgag ccgagattgc 35820
gccactgcat tcattccagc ctgggcgaca aaagtgaaac tccatctcaa ataaataaat 35880
aaataaataa ataaataaat aaataaagca ggatgataac tgtacgcagc ctatgaggtt 35940
gtttaggatc attaataaga ttatgtagcc atagaatact atgaagaaat taaaaagaat 36000
aagatagtat ggcagttcct caaaaattaa acatagaaca atcatatgat ccagcaatct 36060
cacttctagg tatatcccaa aagaattgaa agcagagact caaagagata tttacacacc 36120
cgtgttcata gcagcataac tcacaatagc cagagggtag aagcaaccca aatgttcatc 36180
aacagaggaa tggataaaca aagtgtagta cacatgtata atggaaaact attcaacctt 36240
aagaaggaat gaggctgggt gtggtggctc atgcttgtaa ccccagcatt ctgggaggca 36300

-continued

```
gaggtgggca gattggttgg ggctaggagt tcaagaccag cctgagcaac atggcaaaac  36360
cccgtctcta caaaaaatac gaaatttagc caggcatctt tgtgcatgcc tgtagtccca  36420
gctactaggg aggttgaggt gggaggatca cttgagccca agaggttgag gctgcagtga  36480
gctatgatgg tgccactgga ctctagcctg ggctatagag tgagaccctg catcgagagg  36540
gagagggaga aggagaggga gggggggaggg ggaggggggga gggggaggga gagggggagg  36600
gggagggaga gggggagggg gagggggagg ggggaaacag aaaagaaaag accagcactt  36660
tgggaagcca aggcaggcgg atcatgaggt caggagatca agaccatcct ggctaacacg  36720
gtgaaacccc gtctctacta aaaatacaaa aaaaaattag ccaggagtga tggcgggcac  36780
ctgtagtccc agctactcag gaggctgagg caggagaatg gcatgaaccc cggaggtgaa  36840
gcttgcagtg agctgagatt gtgccactgc actccagcct gggcgacaga acgggactcc  36900
gtctcaaaga aaaaaaaaaa agaaaagaaa gtatttggaa tttatttgtg aaatttttaa  36960
aagaggtaaa gcttgtaaag agccctttgt ggtgcctggt acagagtagg tgctcaagaa  37020
acactggttc acatcctttt gcagctggtg tcagtgaggc tggtctagct ctcctcgcgt  37080
gccctgtggt gtctcaggct tgtgcacagg aggcgggagc ctgtgtttat tatttgctgt  37140
ttatcctctc cctcctccgt ctctttcctg acatggtttc tatggagacg agggtccctg  37200
agcaattctt ctgccagagc ctcagtccca tcatcaagat ctgccgttgc catcctgaca  37260
ggctgccgag gtggtgctgt cacccggctg ggaacaggag cccctggcct gagctgatgt  37320
ggttgccatg gagacagctc tccgctagag agaagggagg tggcagaccc tggccgaggg  37380
ctgcggtggc actgttgccc agctaccctc tcttccagtg tcacacccct ccttgtgttt  37440
taggcagaaa gccaatacga gtgttgacgt gatttattat ggtatagctg ctgtgtttga  37500
gccctcactc tgtgccaggc accacagaag ccttgaccac accagcacat tgtttaaccc  37560
tccaacagcc ttcccacgga catggtgtgg ttgtcttatt ttataggtgc cactgtttgt  37620
tggcaatttt aaaatcatga tttaattccc atatcataca actcaccatt taaaagtgta  37680
cagtttgggc tgggcacagt ggctcacacc tgtaatccca gcactttggg aggccaaggc  37740
gggtggatca cctgaggtca ggagttcgag accagcctga ccaacatggt gaaaccccac  37800
ttctactaca aatacaaaaa ttagccaagt gtggtggtgg gcgcctgtaa tcccagctac  37860
ctgggaggtt gaaataggag gagaattgct tgaacccggg agctggaggt tgcagtgagc  37920
cgacatccca tcattgcact ccagcctagg caacaaagcg agactctgtc tcaaaaaaaa  37980
aaaaaagtgt acaattcaga ccagacacag cactttggga ggccgaggca gcaggattgc  38040
ttgagcccag gagtttgaga ccagcctggg caatatattg agacccttgt ctctacaaaa  38100
atttaaaaaa ttagctggac ctgatgacac aagcctgtgg ttccagctac ccaagaggtt  38160
gaggtgggag aattgcttga gcctgggaaa cggaggttgc agtgagccaa gatcacgcca  38220
gtgtactcca gcctgggtga cagagcgaga ccctgtctga aaaaaaaaat taaaataaaa  38280
acaacaaaaa ataaaagtgt ataatttagt gatttttagt atattcatga tgttttgtag  38340
cgtcaccatt atctaattcc agaacatttc catggcccca aaaagtaacc tcatgcctat  38400
gaacagtcac tccccactcc ccctttccct cttgccccca gcaaccactc atccgctttc  38460
tgtctctgga tttgcctgtt ctggatgctt catccaaatg gagtctttgg tgactggcct  38520
cttttactta gcatcaggtt ttcaaggttt atccatccat gttgaagaat gtagcaggac  38580
ctcattcctc tttatggctg agtaatcatc cattgtgtgg gtatatgacc acattagatt  38640
tgtccattta tctgggttgt tttggctact atgaataatg ctgctgggaa cattcatgtg  38700
```

cacgtttctg agattctgtg ttagttctct tgtgtagatc ccagggagta gaactgcagg 38760
atgtagacgt gactggggaa agacaaagat gggattcaaa cccaggactc cacatctctc 38820
aaacccgcac tgactcttct ggtgttgccc ctatgctcct tgccccaccc ttgctctcct 38880
aggaccctgt tgtgtcttca gaaacctgga agaggctgcc cactcctgtg actgcttcct 38940
tccctggcac agccttctca tccggaattc ctacctggtg ggctaggaag ggctgatag 39000
ttcaaagccc ggttctgcct tttttccaga cttggcactt acttgcaagt gactgtaacc 39060
ttgcggaaat gatataactg ctctagcgct tagtttattt attttattat tatttttggg 39120
ggagacaaga gtcttgctgt gtcactcagg ctagagtgta gtggcacgat catggttcat 39180
tgcagcctca aacttccggg ctcaagagat cctcctgcct cagcatccca agttgttggg 39240
actataggcg cacgccacca cacctggcta atttcgtatt tttgaaagag atggggtctc 39300
tcactatgtt gcccaggctg gtctcaaact cctgggctca agctatctgc ccttctcagc 39360
ttcccaaagt gctgggatta caggcatgag ccatcgtacc cagcctagtt tgtttataaa 39420
attggaatat tatccctact tctcagaggt gtttgtgaaa attaaacaag acaagcaagt 39480
aaagtgctta acacagacta aggacttatt attttcatta gtgtcacaac caccgtgagg 39540
gctgcgggtc tggagaagca tttgtcttag ttaaataaat acatttctgc ttcctctggc 39600
aaggagctct gtgtctagag ctgccagttg cccgggaaag gagcagctac gttgccaatc 39660
ttcacgtgca gttggctcca tctgtccttg tgacatttga tttggggcca atgtttaaaa 39720
cactctttgt tttctccccc aagtgatctc tccctaatca agagccacat ggcctctctc 39780
tgtggccatt tcagccactc aggaggaaga atgaatgcct aaatctttga ggtacacccc 39840
caaccccaag ttccttctag aatctacagt aggccgggca cagtggctca cgcctgtaat 39900
cccaacactt tgggaggtca aggcgggtgg atcacttggg ttcaggagtt cgagaccagc 39960
ctgggcaaca tggcgaaatc ccatttctac aaaaaataca aaaaattagc cagatatggt 40020
ggtgcacacc tgtagtctcg gctactcagg aggctgaggc atgagaattg cttgaacctg 40080
ggaggcggag gttgcagtga gccgagatca tgccactgca ctccagcctg ggcgacagag 40140
tgagaccctg tctcaaaaaa aaaaaaaaaa gaatctagag taaattttgt acctgaagca 40200
cagtctgtgc tttcagtgag acctttccaa acatctcctc cagatttggt gaaaatctgc 40260
cctgctgttt tggcagaaga ttcattttgt tccttggaag gttggccttt gtttcttggc 40320
caaagtgggg caggaaggtg tttgagtgca gaggcccctc cagagctgtg ctcaggcagc 40380
tctctcctgg gctgaaggaa agacaaggga ggacatagct caggcttctc ctagaagcct 40440
gtagacaggg agatgcttag aggtaccaca ctggctgctc aaagatggcc ttgtgagttg 40500
ctggcgagtg gggaagcccc tgttgcatgc caggccacag agtttgtcct cagggctggg 40560
catgtcccca ggccttgcgg ctgcattcct gctggggcct aggcaccgcc ctgccttgtc 40620
ctgccctccc aaggcccaga gccagaacat ctgcctcttg ggcagagact ggcttcatcc 40680
ctgggggctc cacaaagggg ctctgacagg ccctggcttt cttgcggggt gcagcccccc 40740
agccacctgg ccagctgctg ccgtgcagag gggaggaagg tctttgtgca ctctgagccc 40800
gccttgtttt ccctccagaa tggcagggct gtgtgggagc ccacatggct tagataaggt 40860
gggggaagtg tcaggtccta ccagaaaagg gtggaactcg tctcctctgc ccccaaccct 40920
gctttctggt gagattcaag ccactcagct cattcacacc ttttctctgc ctgctggaaa 40980
ggtgtttggt gacttcttgg ggaaagtata ttttaaaaac cttttataat gacttttccc 41040

```
ttccccccag caggtagtag tatgtgctta gcagaaaaag attagaagat tcgaataagc  41100
catagggaat ttctgtgtgg atggggaggt gcatatactt ccaataagtt tttctatgta  41160
tacatatatg tgtatttaaa tgtaaacgtg aatatgcttt ttttcttttt tggagacaag  41220
gtctggctct gttgcccagg ctggagtgca gggacgtgat cttggctcaa tgtaacctcc  41280
accttgcggg ctcaagcaat tctcccacct cagcctccca agtagctagg actacagaca  41340
catgccacaa cacccggcta agaatatgca ttttgtctgt tttgtttttg ttcttgtttt  41400
tgagacagag tttctctctt gttgcccagg ctacagtgca gtggtgtgat ctcggctcac  41460
tgcaacctct gcctcctggg ttcaagtgat cctcctgcct cagcctcccg agtagctggg  41520
attacaggca tgcaccacca tgcccggcta attttttttt ttgtattttt agtagagacg  41580
gggtttctcc atgttggtta ggctggtctt gaactcccga cctcaggtga tccacccacc  41640
tcggcctccc aaagtgctgg gattataggc gtgagccact gcatccagcc agaatatgta  41700
tttttaatc taaaaaagta atataaactc agtgaagcaa aaatatcatt agaaaagcac  41760
acagatgcat gcctagcata cctccaagga caagctgcag tgctctggtt acgttggttg  41820
ccttggggcg ggataactgg gtgactgggt tcactgtatt cttctatgtc ctttttgaat  41880
gttgaaccat gcaactttgt tatctattca aaaataatag aaataataaa acccataaat  41940
taaagaagaa agccttccct aactgcctcc ttcaattcta ctcctcagcc tgacccagca  42000
tcagcagttt gctttgtatc tttccaggtc tttctctagt ctcatacaat gcaggtttct  42060
atatattttt aaactctttt ttttttttga gacagagtct tactcttttg cccaggctgg  42120
agtgcagtgg tgtgatctcg gctcactgca accactgcct catgggttca accgattctc  42180
ctgccccagt ctccctagta gctgggatta caggtgcctg ccaccacacc tggctaattt  42240
ttgtattttt agtagagaca gggtttcact atgttggcca ggctggtctc aaactcctgg  42300
cctcaggtga tccaactgcc tcagcctccc caaaagctgg aattacaggc atgagccacc  42360
acacccagcc atttctttct tctttctgtg gctgagtaaa tattctgttg tgtggataga  42420
ccacattttt ttaatccatt ctaaagttgg tggacatatt tgggttatag gctttgtttt  42480
gctggtcact tctttccctt aacagagtgt ctgagagact ttaccatgtc agtgaatctc  42540
atgatccctt agtactttga atggctttag gtgatctcat tcattcacat gtgatgcctg  42600
acccccttggt acctatgcag acccctggct ctcctctctg tcacttcact tccttcctcc  42660
agggagtctg cagtcattgg tggggctctg gtcacctaat ccatggccca gtgttataaa  42720
tgagaaaatg gaatttcagg gagaggaaag ggttcaccca gggatcataa actcagcgtt  42780
gcaagggccc cagagttcaa ctcccagctg aggccacagc ccttcccact cagcttgtaa  42840
taggtgggcc tagatccttc catagcctga tggtctgagc ccacagcacc cccttgcatg  42900
ctatacgggg gtctgcttct gtgtgccccg tccagggccc cactggctgc ccttgtctgc  42960
tgcctcctgg ctcttgtgga aggactcgtt ttctgaccca tagccctgtt tcctcctctt  43020
cccttccagc ttttgaaagc tcccaggtca gcacttctca aatactggct cctggctctt  43080
ggcacccagc gtctgaaata tcagcctctg cctccctgcc tcatttgcat ttcaaaaggt  43140
ctctttagga tttgattgag ctctaagata ttctgtactt aggagtccat ctggagctct  43200
ccttgcctgg cacagaggat ccgacctgca cttcagaatc acctgaaagc atttgaaaaa  43260
tactgatgtc tcagacctac ctcagaccac cagtattttt tctttttttt ttttttttg  43320
agtaattctg atgtgtacca ggttgagaac cactgtgctg gctacactct ggccctcatc  43380
agagaagaca cattttctcc taccaactct ttggaatttg gtcaagagct atgtcaagaa  43440
```

-continued

```
ctggtcccag gtcagctgtg ggtgtactgt gagaccttgg acaagtccct gcccctctgt  43500
cttggtttca gaaaaatggg actcagatta gatcagtggc tgtcactttc agggatgggg  43560
tgtgagaggt gggggatgga gcaagcatgt atccaaatca cctggggcca ttttcaaaaa  43620
tataccagcc caccttgaaa agtcaaaaca acctaagcaa ggttttatac atacaccacc  43680
accaggaatc acccctcctc tcttgggagg aagcgctcaa aagaatcgtg catctaattg  43740
aatgacttct ttaaacattg agaaatttca gtaattgtta ttgtaacatt tcctccaatt  43800
ccctctgtag ggcttgtgcc atttggcatt cttgccagca atttatgaac ctttttgttt  43860
ctctatagct tcaccaatag aatatgtcgt cagatatttg gatttttgcc aatctgatag  43920
gtgagaaacg gtatctcagt gtaattttaa tttgcattta tctaacagga gtggggttga  43980
atatcatcat gtgccttgat gtcttcatgt gccatgatcc atttgccttt cttttcctgt  44040
gaactgtttt tcatatctct agcctatttt cctacaggtc tgctggcctt ttaatgctct  44100
gtttgtgaaa ctctttccat atttaggata tcaacccttt gttggtgttg tacattgcag  44160
atattttttc agagtttgtc atttatgttt ttacttttct taaggtgttt ttatttccat  44220
gcagaatttg cttgtataat caaatgtatc tatttttttcc cctattgctt ctggatttta  44280
aacatcttat ttttttgagg tggagtcttg ctatgttgcc taggctagtc tcaaactcct  44340
caatgcaagc aatcctctca cctcagcctc ccaaagtact gggattacag gcatgagcca  44400
ctatgccaga ccagcttctg gatttttgaa tcactgtttg ccatcagtct cttatgacca  44460
tttctaagcc tcatgtgtaa ttacgatttg ttatattcat tttattgttg ttgtttgttc  44520
tttgagacag ggtcttgcta tgttggccag gctggtctca aactcttggc ctcaggcaat  44580
cctcctgtct tggcctccca aagtgttggg attacaggca tgaactacca catccagcct  44640
ccatattcat tttatccatt agtattcatt ctgaattaca gttcccacta gatgtcagtt  44700
tcatgaagac aggattttct ctgagatgga gatttgcatg cagaggttta tggaagagtc  44760
tccttgggaa caacaccaca gggagtgagg cagagctgga agctgaatta caccagtgat  44820
ctcaggcgat cccatgggga gctctggagc taggatggcc ctccctgtag agctgaggca  44880
aggggtcatg gacccatccc tggatgtggg ctccatccac ggatagcacc tgcccttgga  44940
caaggtggtt ctcctcaacc aatggctgtc gctgggagag gtactcagct ttgaggtctc  45000
agctctggga atgagtgtct cagttccgaa ggggaatctg ggcaaagcac cacaacatcc  45060
tccctggttc actgctgtgt tctctacacc tacctacctg gcgcttgata ggtgctcagg  45120
aaatcctttg atgaaagaca aatgagaaca gaaacacagc tttccaagtc ttcgccgagg  45180
ccaactgggt cacacatggg agcaggctgg aggggaggag ccctgagcag gtgtttttag  45240
aatcatcttc tccaatgctt ctggcctatc tcccattgct gctcactggg tgatctggag  45300
ggctcctctt actcaacagt cagtgccatc agggtggggt ggcctgggga ctggggccct  45360
ccctggaccc tgggcactgt gacagctctc tgcatgtgca tcattctgtg agctttcagt  45420
cctgactttt tttttttttt ttaattaaat ctcacttcag cattccttga agaaaagagg  45480
aacccgctcc ctggggaagg ccgataagaa gactttggtg caggtaattc ccagcagccc  45540
ccgtaggaag gttttattct gaagacctga gcctgactct aagtggcctg gggatcccag  45600
attctgccct gtcctcccct tgctcatttt cctttttttc ttttcttttt tttttttttt  45660
tttgagacgg agtcacactc tcttgcccag gctgcagtgc agtggcacaa tctcagctca  45720
ctgcaacctc tacctcccag gttcaagcaa ttttcatgcc tcagcctccc gagtagctgg  45780
```

gactacaggc gtgcaccacc acacctggct aatttttgta tttttagtag agacagggtt 45840
tcaccgtgtt gaccaggctg gtcttgaact cctggcctca agcaatccac ctgcctcggc 45900
ctcccaaagt tctgggatta caggtgtgag ccactgcgcc cggcccccctt gctcattttc 45960 ttagtttcac tgcccacttt atttcccaaa accacatcct gagcccatgg ttcttagatg 46020
cttagatgct cgctccccac cccagccagg aacttagcaa gcagcactac agtcaaatcc 46080
aaaggtctag agttggagac ccaggcttga atcttggctc tgccacttga ctgccatgtg 46140
attggagcga gtcattttga gtttctgggc tccatttcct atctatccct gtcttggggg 46200
ttcattggaa gaattggatg aagtactata tgcagcaaag gccacatacc gttagctcct 46260
agtggtatgg gattgtcaga gtgccaggcc cttttcatcc ttagctcatt taatcccgtc 46320
tgtggctctg ggagggaggt aatgttaccg ccccatttta ctgatgaaac tgtagtggca 46380
gcagttgctc atcagtatgt cacctgttcc tgtactccca ggctatgtgt ggcgccccat 46440
ccttgctgtc atttcaacat ctacccctct gcgtctcccc cggaccctta gctccttgag 46500
ggtctggctg tgtctgattc atccctgtgt tcccagcaca tagtgctccc caaaatgcca 46560
tggctggtac tgagactccc agcactaacc ttcctgggtt gtgtctgtct ctgtggtccc 46620
aggaggacag tgcagacctg aagtgccagt tgcactttgc aaaggaggag tcagccctca 46680
tgtgcaagaa gctcactaag cttgccaagg agaatgacag catgaaggag gagctgctga 46740
agtaccgctc gctctatggg gacctggaca gcgcgctgtc agccgaggag ctggccgatg 46800
ccccccactc gcgggagacc gagctgaagg tgcacctgaa gctggtggag gaggaagcca 46860
acctgctgag ccgccgcatc gtggagctgg aggtggagaa ccgaggcctg cgggctgaga 46920
tggacgacat gaaggatcat ggaggtggct gtgggggtcc tgaggcacgc ctggccttct 46980
ccgcgctggg tggcggagag tgcggggaga gcttggcaga gctgcggcga cacctgcagt 47040
ttgtcgaaga ggaggccgag ctgctgcggc gctcctctgc cgagctcgag gaccagaaca 47100
agctgctgct gaacgagctg gccaagttcc gctcggagca cgagctggac gtggcgctgt 47160
cggaggacag ttgttctgtg ctcagcgaac cttcacagga ggagctggcg gccgccaagc 47220
tgcagatcgg cgagctcagc ggcaaggtca agaagctgca gtacgagaac cgcgtgctcc 47280
tctccaacct ccagcgctgt gacctcgcct cctgccagag tacgcggccc atgctggaga 47340
cggacgccga ggccggggac tctgcccagt gtgtgcctgc tcccctgggc gagacacacg 47400
agtcccatgc ggtccgactc tgcagagcca gggaggccga ggtgctgcct gggctgagag 47460
agcaggccgc cctggtcagt aaggccatcg atgtcctggt ggctgatgcc aatggcttca 47520
cggctggcct ccggctgtgt ctggacaacg agtgtgctga cttccggctg catgaggccc 47580
ccgacaacag cgagggcccc agggacacca agctcatcca tgccatcctg gtgcgcctga 47640
gcgtgctgca gcaggagctg aatgccttca cgcggaaggc agatgcagtc ctcgggtgct 47700
ctgtcaagga acagcaggag tccttctcat cactgccccc cttgggctcc caggggctct 47760
ctaaggagat tcttctggca aaagaccttg gctcagactt tcaggtaagg tgcctcatgc 47820
acagatccta ttatttattt ttttcctttg ttttgttttg tttttcttga gatagggtct 47880
ctccccgctg gccaggctga agtgcagtgg tgcaatctca gttcactgca gcctcgatat 47940
cctgggctct agccattctc cccccctcac tctcctgagt acctgggact acaagtgagc 48000
accaccacac ccagctaatt tttatttatt ttttattttt tttgagacgg agtctcgctc 48060
tgtcacccag gctggaatgc agtggcgcaa tctcggctca ctgtaacctc caactcccag 48120
gttcaagcga ttctcctctc ttagcctccc aagtagccag gattacaggc gccctccatc 48180

-continued

```
atgcctggct aatttttgta tttttagtag agatggggtt tcaccatgtt ggccaggctg  48240
gtctcgaact cctgacttca agtgatccga ccgcctttgt ctcccaaagt tctgggatta  48300
caggtgtgag ccactgtgcc tggccataat ttttaaattt ttttgtagag atggaatctt  48360
gccatattgc ccaggctggt cttgaactcc tgagcttaag tgatccacca gcctcagcct  48420
cccaaagtgc taggactata ggtgtgagcc actgtgtgtg gcctaatagt cacattttaa  48480
atgttcagta tttgtgtgtg tctagtagag tggatctaga atatttcatc cttgcagctt  48540
gtccttctaa atccttctct acacatctat catatatttg tttttccacc cagattgctt  48600
tatatctatt gttactacac aacttatatt tttaacgcaa tgtatcagtt tgttaattta  48660
tgatgccttg tctgttgttc acacagtttt tgtgctcact gctgaagatg tcatgattag  48720
caaaaacaga tatgattccc cctctcatgg tccttatcat ctagtggggc agagtcaccc  48780
aaaatatcat gtcagtgaat gtgcaattag acactgagag aggaatctga aggaagcgta  48840
catggtttta tgaacaagga acttgaccta gaccctatgc tgagggaagg cctctgatct  48900
gaccagaggt cagagggatg gatggctggg ggaacacagt gttttcagca gagcaaatag  48960
cctgtgcaaa gacacagctc agatcagagg cggaaggagc gtggtgtgtc caggacactg  49020
agtgaagaga caatgtgaag ctggactgca ctgagcatgc gggaggtttg atcttcatcc  49080
tcagagcaat ggcagggaat ttttcatttc cagggaaaga gagcgattta gcactttctt  49140
tttttctttt atcttttttt tttttttttt tttttttgag acagagtctt actctgtcgc  49200
ccaggctgga gtgcggtggc acgatctcag ctcactgcaa cctccgcctc ctgtctccgc  49260
cttccgggta gctgaaatta caattctcct gtctccgtct cctgggtagc tggaattaga  49320
ggcatgcccc accacacctg gctaattttt gtatttttaa tagagatggg gtttcacgat  49380
gttggccagg ctggtcttga actcctgacc tcaggtgatc cacctgcctc ggcctcccaa  49440
agtgttggga ttgcaggtgt gagccatcgt gcccttctga gatttagcac tttcttttta  49500
acaactatac agtggatatg tgccataatt tctttaactc aagacctgtt gatccggttt  49560
catcttgctt ttttaagcaa gcacattgcc tttttttttt tttttttttt ttttttaaag  49620
aaacagtctt gctctgttgc ccacgctgga gggcaatggt atgatcacag ctcgctgtag  49680
cctcaaattg tagatggaat tacaggcaca tgccactgtg cccatagact gctctatgtt  49740
atctcccttt tggttcttct tgaaagaggg atgaacagag gtcacacatg tgataggaca  49800
gtttgggctg actcaaaagg tttgtgcaca aggcacacat tcagaaaatc acttcgcact  49860
tacctactca ttcatccttt cagcaaacat tcattaaacg gcagcagtgc ccccagctgg  49920
ggctgggtct gggttgcaga ggtgaatcta ccagggtccc agccctcagg tgggtggttc  49980
aagcctctta gggagcgcag aggcctgggg tgggtgtttc tggcacccct cgggcccctc  50040
cccatggtga tctttggttt gttctgcctg tgcctctggg tgcagccacc tgacttcagg  50100
gacctgccgg aatgggagcc caggatccga gaggctttcc gcactggtga cttggactct  50160
aagcccgacc ccagccggag cttcaggcct taccgagctg aagacaatga ttcctatgcc  50220
tctgaggtgg gtctaggcct gagcaagcat gggattgggt aggaggagag tgactgagcc  50280
ctgtcaaaag cagagtggtc catatatcac ttagctggtg aggatatggg tttggggcat  50340
tccatttggt tccaggcttc ttggcagcca aggccagaag ggaaataagg aagtttggga  50400
cattctcatg gcctgatcca aggaaactta taaactcatc tgcataaatt atttttttctt  50460
ctgtactaaa ttccactggg aatttaacaa tttatgtaat ttaatggaac tactcatgta  50520
```

-continued

```
tgtagcagga aggcagcagt ctctatagcc aggcagtttg ggtttcaatt gtggatccac  50580
tctattctgg ctgtgagatc ttggataagt cattttacct ctctgattct cagttttctc  50640
acatgtaaaa tgaaggtgcc tcacagggtt gttgaaagga ttaaatacat gaaaagccat  50700
agcttaaggc atggtccaca ttgggtgagg atgaggagga ggaggaggat gattatgatg  50760
ataatgacac atctctggga ctcaggggac ctgagttcaa gtctcagttc taccagtgtt  50820
cctgtgtgac cttggacaga tttctacctt ctggccacag cttccccatc tgtaacggga  50880
gggttagagt gaatggtagt tattgaattg ctaggattct ttgatcctca gggaattctg  50940
ggtagttctg agccccttct aagcctgctg agcttctcct tgctcttcat aatgagcctg  51000
aagcaggaaa aggctcctac ggactgggtg gagtatccct gaaaccctga accttgcaga  51060
gtcctatgta ttttccagcc tgagcacctt tctgagcatc tcttggaaga caactctgta  51120
gtcccaggaa ggtcagccca tgactatgtg ggaaggagaa gctcacttga agctgatgga  51180
tcagactctc taagtgagct tcctggaagc catggcaaaa agagaaaaaa ctgagataac  51240
ttagttgtca ttttctaaga aaaggaaata ggcctattct tttttttgtt tttttttttt  51300
tagactgagt ctcgctctgt tgcccagtct ggagtgcagt agtgcgatct tggctcactg  51360
taacctccat ttcctgagtt caagcgaatc tcgagcctca gccctcccag ttaggtggga  51420
ctataggcgt gcgccaccat gcccagctaa ttttcgtatt tttagtagag acagggtttt  51480
gtcatgtcac ctaggctggc ctcaaactct ggggctcaag tgatcttccc gtctcagcct  51540
tccaaagtgc tggtattaca ggcgtgagcc actgtgccct gccaggaaat aggcctattc  51600
tataggctta cctgtagaaa aaatgatttc ctgcacacat tcaattattt gtttcattca  51660
gccactcttt attgagtagt gacaattgcc cagtgctgtt gaccactgag ttcagggagg  51720
aaaccaggga cagcagacag tatgtagccc tgcaaaaatt tttaatgcaa aacagatata  51780
gaagatatac ctcaagtcac tgtgccttcc actgccaaat catcatatta ttgaccatat  51840
aatgaatgtt tactttctca cagagggaca tttgccatgc ctaggaaggt tttatgtagg  51900
agttctgggg ccaggcacgg tgactcacac ctgtaatttc agcactttgg gaggcccagg  51960
tgggcagatt gcttaagcct aggagttcga gatgagcctg ggcaacatgg caaaatcctg  52020
tctctatcaa aaatatacaa aaattagcca ggcgtggtgg cgggtgcctg taatcccagt  52080
taattgagag gctgaggcag gataatcgct tgaacctggg aggcagaggt tgcagtgagc  52140
caagatcacg ctcaaagctg gcgaaactcc gttgaaagag agagagagag agagagagag  52200
agagagagag agggagagag agaaggaggg gagggtgggt gaaggttgga ggtcagaagg  52260
tcttcacata gttcccactg gttacattta ttgtgtgtgt ccatgtcctt tgtatgtttt  52320
tttatggagg cctatagcgt ttttggtttt gtttttctac tttctgttgt agtataacat  52380
aataacatac atacaataaa ggacactgtc cttaagggta ccactgaatg gattgttaca  52440
tatgtataga tccattaagc atcttttaag tcccatcatt tagtatctaa gttgtttcta  52500
aaatattgca attataaaca atgaaacaat gaacatcttt gtgaatcaaa cttagttttc  52560
ccagtacctt attaagataa atttcagaga gaaaagaaca agttccaatg gtaacaaaag  52620
ccagatttga tatgtactgt ttcatttaat catcatgacg accctcagag gtggggacag  52680
tcattctgcc tgatttgtat ttggacagct tgggtccaac atcccatcgt tcccctacca  52740
ctgtcatcct tagatcacaa tttctatcca cttcttcctc tctctccctc ctcattatct  52800
gtgtcccctg tctgtaccac agatcaagga gctgcagctg gtgctggctg aggcccacga  52860
cagcctccgg ggcttgcaag agcagctctc ccaggagcgg cagctacgaa aggaggaggc  52920
```

cgacaatttc aaccagaaaa tggtccaggt gcgtggtgcc cagcgctttc caggcagcta 52980
ttcctacagc ctctctgagc tggaagcaga ggccttgagg atctatgggc cctctgaagt 53040
caagaaagtc aggggaggct gggtgtggtg gctcacgcct gtaatcccag cactttggga 53100
ggccaaggca ggcagatcac ttgaggccag gagtttgaga ccagcctggc caacatggaa 53160
accccgcctc tactaaaaat acaaaaatta gccaggcgtg cactagcacg cctgtaatcc 53220
cagctactca ggaggctgag gcaagagaac cgcttgaacc caggaggcgg aggttacagt 53280
gagccgagat catcccactg tattctagcc tgggtgacag agtgatatct aaaaaaaaaa 53340
aaaaaaaaaa agaatgaaag aatgtcaagg gaaacctgag tcttcagccc ctgtgccctg 53400
ctgggatgtt attgtccttg ccattgtgca ttagttgtgt aacagggctg tcattggcgg 53460
cctgtgggac ctggggccag tcctgttttc tctcaggacc tcagtttccc atttatgaaa 53520
tggtgccctc atcaggcctg gcttctaatc aagataatag ttctggaata acatttgtta 53580
agcccttact gtatggtggg cctgtccaat gcactttcta cccattatgt cttttaatcc 53640
ttgtgccctc ccttatcacc attttgcaga tggggaaact gatgcccaga gagctggagt 53700
gctctgccca gggttgcaca tccagagtgt ggcagggctg ggcctctaat ccaggtccct 53760
ctgttaggca tgacactgca ttgcttccta gggtgttgcc tagtcatcag ctgtcctcaa 53820
ccctggcacg ccctttgctc tccatgcgtc acccctccct gctatcatcg ctcaccctcg 53880
caggttcctc attgaacatg agcattcgtg tgagacattt ggtgcccagg aggtgctcag 53940
tatatgatgt catggttttt tagagccagg gtcaaatccc agctccttca atgatgtgtc 54000
actgtttttg caggagcaga gggcagtgct catctgaata gattgcgcca cgtgtggtgg 54060
gatccccggc agggatcact cacaggcacc acccagactt tcctccctgc ccctgtccag 54120
gggcccagaa aggggtgggg gagaggacag ggccctgggg ttgctcaagc tcttgtcccc 54180
cggcagctga aggaggacca gcagagggcg ctcctgaggc gggagtttga gctgcagagt 54240
ctgagcctcc agcggaggct ggagcagaaa ttctggagcc aggagaagaa catgctggtg 54300
caggagtccc agcaattcaa gcacaacttc ctgctgctct tcatgaagct caggtggttc 54360
ctcaagcgct ggcggcaggg caaggttttg cccagcgaag gggatgactt cctcgaggta 54420
agattgggcc agggactggg actgggagtg tgggctgggg agagagggac agggaaggga 54480
cgcccagctg gtattgacac aactcctagg ctcacatacc tgccatcagc atgcaggctt 54540
ccttcctgca ttcgttgctt tttttttttt ttttccgaga tggagtctca ctccagccca 54600
ggctagagtg cagtggtgca atctcagcct gctgcaatct ccatctcccg ggttcaagca 54660
attctcctgc ctcagcctcc cgagtagctg ggattacagg cacatgccac catgcccagc 54720
taatttttgt attttaagta aagacagggt ttcttggccg ggtgcggtgg ctcacacctg 54780
taatcccagc actttgggag gccgaggcgg gtggatcacg aggtcaggag atcgagacca 54840
tcctggctaa catggtgaaa ccccgtctct actaaaaata caaaaaatta gccaggtgtg 54900
gtggcgggtg cctgtagtcc cagctactcg ggaggctgag gcgggagaat ggcgtgaacc 54960
caggaggcgg agcttgcagt gagcctagat tgtgccactg cactccagag tgggagagag 55020
agcaagactc cttctcaaaa aaaaaaaaaa aaaaaaaaaa aaaagacagg gtttctccat 55080
gttggccagg ctgatctctc aaactcctga cctcaagtaa tccacctgcc ttggcctccc 55140
aaagtgctgg gattacaggc atgagccacc atgcctggcc aaaagatatg tttacttaac 55200
aagagggagt aggctggctt aaaaacattg gtgatagtac aggtggtatt aggatgtggc 55260
aggaaacgtg ggggcggagc tctgggaatg taagaagctt agaaaggacc cacctgaccc 55320
attcatgccc cagtctatgc aggacccttt gctgctcaaa gcccttgcgt cctgtcatca 55380
gcacagcagc acacatcaac acatcaggga agagaagggg acttacaagg atgtcagacc 55440
ttggtcacac tcatcttagt tgacattgtt cactttggcc gtgtcctttt gggttcaggt 55500
acctcgagtc tagcccaggc ttggccctcc tctagtccag gctgctctct gtagtcccct 55560
gtccagatcc agtagggagc attggcatgc ctcaagttgc cacttacgcc atcaggggta 55620
ctccagagga gcccagatgc cccaggagcc aggcaagaca gttagacctg agtgtgtagc 55680
aagaccctgc atcaccctat ctcagtgggg ctcatcattc tcgcaggcca ccagctcctc 55740
cccagggcct catgggagag tcactaccgc cattccatag gcccacaccc tgctgccctg 55800
gccctgcagt gcctgacaca gggccgcccc tgggagcatt cgcctcggtc ctcctgtccg 55860
aagctgtctc ttctgtgacg tttggaaaca taggagccct ctcacctgtt tggaagtctc 55920
acaggcctct ggatgaagcc cagtttaagg gaatgacctg caggccacac agtctatatt 55980
ttaagtcagt ttgtctcaga cgaaccctcc acatttggtg aaaacctttc tagccatttc 56040
catatcctag agtaaaagag agagaaactt actttaggga aaaaaaatta gggcataaac 56100
atagaaaatt ggctaggtgc agtggctcac acctgtaatc tcagcacttt gggaggttaa 56160
ggtgggcaga tcacttgaga tcaggagttc gagaccagtc tggtcaacgt gatgaaaccc 56220
tgtctctact aaaaatacaa aaattagctg ggaacggtgg tgcacactgg tagtcccagc 56280
tactcaggag cctgaagcaa gagaatctct tgaacctgca aggcagaggt tgcagtgagc 56340
taagagcatg ccattgcact ctagcctgga tgacacagtg agactccatc tcaaaaaaaa 56400
aataaagaga cacagaaaat tacataacat atataattaa gaaatatata catttaccaa 56460
aataagcata attaataaga tataaacata atcatgctgg gcatggtggc tcgcgcctgt 56520
aatcccagca ttttgggagg ctgaggcagg aggattgctt gagcacagaa ggtgactcgc 56580
tccctttttgt cttatttcca tcctgaacta ggtccctgat ctccttggct ggccctggac 56640
tcttgcccag aatctatcag caagcagtcc aaccccccag caaggtccct tctgtccacc 56700
caaacctttg gtcaccctta tgtagcattg tgggagtgcg tgtggccttt tcatttcaac 56760
cacagtgcct gccttgaccc agcctgtcaa catggttatt tcagagtgac tctcagggat 56820
gcttcctggt ctttggggca gaatagatgt cgtgggaggc taggagggcc tgactatcca 56880
gccgtgctcc tcgacctaca tggtgcccaa ggttggaatt aaaatttggg aaaacttccc 56940
acctgctgtt aagcatggtt tttaaaaaac aggtgaacag catgaaggag ctgtacttgc 57000
tgatggagga agaggagata aacgctcagc attctgataa caaggcctgc acgggggaca 57060
gctggaccca gaacacggtg tgtttccagc cccttcccgg tcctgttgtg tccattcatt 57120
cctttgtctg ctcagtaatc aattcctact gctttctctg accccattcc tggacattga 57180
agttgcaagt tattgcctgg tcatcccagg gcagtaacag agtccagatg atggactgtg 57240
gggtcatagg caagacagca agtaattctc tttgcagtat aggggacaat atcacggtga 57300
aggggtcatg gatgatgggt tttgaaggat gtataggagt ttacctaata gagaataggg 57360
gaaagactat tctggaccaa gagaactctg tgtgccaagg tgtggcaagg tgttctggta 57420
ttgagtatgg cttgggaggt acatggtaag ggtaaggata tcaggctaga gtcatctgaa 57480
gaggggcctt gtggtctagg gtcaggaacc ttcaaatcaa gccataagtc agagagaaca 57540
gtggggtcag gatcccaggg tcacacacgg tgagctgggg tagggatggg aaatgagggc 57600
atgggcccag gagagaagat ttgggacaga atcaggcaaa ctgagggagt ctccatgaat 57660
tagaccccac atctggcctg cagcgggtca gagaggcaga tcctgagtga ggagaaggac 57720
ccacggcaca gacgctgcag agccttgaag aagccagatg attcagctca gagttaggct 57780
gaataattat tactgtaact gcagggtttt ttcttggtgt cagatttggg cctcatgtca 57840
gcctaggagg tagccagggc tgggcctgtc attcccattt tatgggtgag atgacctagg 57900
gaggttgtgg gacttgcctg aggcctcgtg aagtcccaag ctggactcct aggtgagttc 57960
tctgaaccca ggttcccctc cctaccccac agaggctctt gactcaggtt ttgcctcctg 58020
tctgcagccc aatgagtaca tcaagacact ggccgacatg aaggtgacgc tgaaggagct 58080
gtgctggctg ctccgggatg aacgccgtgg tctgacggag cttcagcaac agtttgccaa 58140
ggccaaggct acctgggaga cagagcgggc agagctcaag ggccatacct cccaggtgag 58200
ccccccacct gtcagacgcc tctcccctta ctctcagcca agcctttagc tgtcagatct 58260
gggagtagaa taccaaggcc atgctcctag aggaataaga atgccgttgc ttcacctgtg 58320
gcccagagag ggcaagagac ttgcctaaag tcacacagca agggtatcag aaacggtggg 58380
gaatgggagt cacagaggaa gggaaggaag gtgggggatt gcgccctggg ctcacaggtg 58440
aggctggtgc acatccccac tgcctgctgt cctcatttgc tccttcattt cctcataagc 58500
actccctcag ccccaactgc ctggctctat tttgctccct ccacgcaaaa tgggggcctc 58560
ccctcccaac tccccagcgt gcccccaaag gagccttaac caggagccct gggggtttgg 58620
tgtctgctgt gtgcctgagg gtgacttgct gcctcctttg gcctgaaaag tgagagggtg 58680
ggcttcttcc cactcagaga gaatgctctg accctgcagc ttgggctcca gcttcttcca 58740
tccagcctgc ccctgctgca agctgccttc ccaggcgtca gcagcctctg ggaggcaggc 58800
actccgatgg tctctgctgg acagatgaca aaactggcac agaggagtta aatttatctc 58860
ccaaggtcac ccggctaata agtgtcagac tggcccttgc tcccccaaac ctctaacccc 58920
tggctccctg tgaccccaat tccacctcct tttttttttt tttttttttt tttgagacgg 58980
catctcactg tgtcactcag gctggagtgc agtggtgcaa tcttggatca ctgcaacctc 59040
cgcctcccgg gttcaagaga ttctcctgcc tcagcctgca aagcaactgg aattatagat 59100
ggcacaccac catgcccagc taatttttgt atttttagta gagatggggc tgcaccatgt 59160
tggccaggct agtcttgaac ttctgatctc aagtgatctg ccggcctcag cctcccaaag 59220
cgctgggagt actggcgtga gccaccactc ccggccccaa ttccaccttc ttcccactgc 59280
tcacagtctc ctggctactt cctggggcca ctactctccc ctcctaaccc tcttccagat 59340
ctcacagctc cctccatctg catattccac ggtgtcccct gcacctgctg cccccaaaga 59400
cctgggcatt tcaggtgctc ctcccaccaa gaacctgacc agctcatggg ggttaatggg 59460
gggcattgag tctaaaggtt gcacattccc tttcctgcca ctctgaggtt tgaggccaag 59520
aaaaccatct tgctggaatg accactagta atctttctga gtttttatga ggatactgac 59580
atcatgcctg aaaagcccac agaagagcat ggcttataga aagagctctt caaaccctta 59640
ttgtgtggag gggttagggg ttagttctga gtggggagga ctaagctggg ttagtcccta 59700
gtgaggggtc ttctgagggg acctctcccc ttttccccgc tggcacccag gagggaagga 59760
gagagaaggg ccaagaggag tggcctcctg ctgccagctg cttagtctgc ttctttccgc 59820
agatggagct gaagacaggg aagggggccg gggagcgggc agggcccgac tggaaggcag 59880
ccctacagcg ggagcgtgag gagcagcagc acctcctagc tgagtcctac agcgctgtca 59940
tggagctgac tcggcagctg cagatcagtg agcgcaactg gagccaggaa aagctgcagc 60000

-continued

```
tggtggagcg gctgcagggt gagaagcagc aggtggagca gcaggtgaag gagctgcaga  60060
accgcctaag ccaggtgagg cccacccctg ccaagccgct tccacccgca agggagagtt  60120
gctacagaaa tgattcagaa gcaggaactc cttcaggtat agctggatct aggtgctcat  60180
ccagtgaggt ctggcacacc atctccttca ggtatagctg gatccaggca cttagagaat  60240
gcagtgggaa ctagattttt ctttctgctt cagcctgtca ggcctgcttt cctctgtgtt  60300
agctttactc ttaaacaagc tattcccaaa tatggccact gttagtttca tgctcatatc  60360
ttacagctta gcaagtacag tggattggcc agatatgagt catgtgccca cccctggagc  60420
ctacccaaac ccaggaacca agagggagga actaagagtg gttcccatgg gaaaattggg  60480
aggcctccaa tcaaaagaag gaggaaagga aaagcaatca ttgaccctca ctccccatta  60540
tagttcactt catgcagcca ggcaccacct accataggct gctctgctcc actcttgatt  60600
ttgacttttc cctttctttc acttttattt ttatttactt atctatttat ttgagacaga  60660
gtctcactct gtcacccagg ctagagagca ctctcggctc actgcagcct ccgcctccca  60720
ggttcaagtg attcatgtgc ttcagcctcc tcagtagctg ggattacagg cgtgtgctac  60780
cacagccggc taatttttat atttttagta gagatagggt ttcaccatgt tggccaggct  60840
ggtctcaaac tcctggcctc aagtgatcct cccgcctcag cctcccaaag tgctgggatt  60900
acaggagtga gccaccatgc ccggccttac ttttatttta tttattttta tttatttatt  60960
ttttctttga gacagtctta ctctgtcgcc caggctggag tacagtggtg tgatctcagc  61020
tcactgcaac ctccacctcc cgggttcaag tgattctcct gcctcagcct cccgagtagc  61080
tgggattaca ggcacgtgcc accacacccg gctaattttt tatttttagt agagatgggg  61140
ttcaccatgt tggccaggct ggtctcgaac tcctgacctc aggtgatccg cccgcctcgg  61200
tcttccaaag tgctgggatt acaggcatga accaccgcgc ctggccttac ttttaatttt  61260
aattacgtaa atcaggactt catctttata taatgttcac atattacaaa ggtacatttc  61320
agcctactcc ctccctttct tgtcattttt ttttaatgaa aaaaagttgt ttttttttt  61380
tatgagagat gaggtcttac tgtatggccc aggctggact tgagctcctg gtctcaagcc  61440
atcctcctac ctcagcctcc cgagtcgctg ggcctttctt tctatttaaa tttatattta  61500
cagggttttg ttttgtttgt tttttaatca tcaatcaaat tttaatgtcc atttatttat  61560
actttgtgtc tttcctggag agctgttcac aagagtatgg aggccttcct tattcagtgt  61620
gactggtgcc tggtgttcct agtgtggaga tactatgatt tgttatctac agtgattaaa  61680
tctagattgt ttccagtttt tcactattga aagttgtgac ctgaagctgg ttgtggcaat  61740
gtgtgcctgt agtcccagct acatgagagg ctaaggtggg aggattgctt gagctcagga  61800
aatcaaggct gcagtgagcc atgatcatgc cactgcactc cagcctgggc aacagagtga  61860
gacttcgtat ctaaaaaaag aaaaaaaaag ttcaagttgt gcctcagtga acatctccac  61920
acatatattt ctgcacacgc atgaatattt cagtaggata gattcctaga ggtgaaattg  61980
ctaaatccaa gggcatatgc atttatagtt gatggtaact gccaggccgc cttctagaaa  62040
ggctttgccc atgtaccctc ctgccagctg cacagtgaga aggacaagaa ggcccttttt  62100
gctttatctt tgccagttcc tgtgattacc aatctttgaa atgtctgccc aagttagggt  62160
gtgaaatgct atctcattgc tttactttgc atttctctga cttctactga aggtgagcat  62220
ttttcatgag tttatggatc ttaggtattt cctcttccta atgttctctt cagtacttca  62280
acagccttgc aaggtcacgt tcatgaaacc cctttttcag atgaggagac tgaggcaaag  62340
tgatttgccc aaggtcataa agtgagtaag ggagaggacc agaatctggc agaactccca  62400
```

gatctggaaa gttcctggtc ctgggccatg cccactttcc tgcaggtaaa gagctccttt 62460
gaggttcaca cttgctagga ggctgtgctt ggggagtgca ggatggcagg ctgactaaca 62520
aatcccagaa ccatccaggt accatgtgga aagcaggtca gatgcatgca tctgtttgca 62580
ccatcaaacc aaattcctgt ctataaaaga ataattcctt cttattatat taacaacaaa 62640
atgtttctaa aatgattctg aaattatgaa acaagcttca tgtcatccct ggggaacatg 62700
tcagcccaca ggcgtgtctt gtcagctcat cagggcacgg gttccatgtt ctgctgttgt 62760
tctcacatca gagacttgcc ggccctctag ctccagcctc ttgtgtctct gacattcttc 62820
tgcctcctgc actttaaacc aaatccccca aagcagcatt cttctttaca ctggactgac 62880
gattaagcca gactggtgaa agcaacagag tggctggtgg gaaagagctt ctgaccagga 62940
gtccccagtc cttacctggc tccaccaggt acaaccccag tcaagtcacc tctgatctct 63000
gggcctcatc tgtaaaataa ggatgaccat tcttgacctt ctcatcttgc aaggcagcta 63060
tggaaataaa gtgagatagc cagaagattc aaagtgcttc ttaagcccac ccctgtctgg 63120
ggcttggttt gattctatgg tcttcatctc tcattgctgt ttgctgatgt tagtgttatt 63180
tccctccttc ccttccctcc cttcctccct cccttcttct ttcttcgttt ctttcttttc 63240
ttattttgag acaaggtctt gctctgtcac ctaggctgga gtgcagtggc accatctcag 63300
ctcactgcaa cctccgcctc ccaggctcaa gtgatcctcc cacctcaacc tctcgtgcag 63360
ctgggagcac actctaccat gcctggctaa cttttattta tttatttatt tatttattta 63420
tttatttatt tatttttgag atggagtttc actcttgttg cccagactag agtgcaatgg 63480
cgcgatcttg gctcaccgca acctctgcct cccgcgttca aacgattctc ctgcctcagc 63540
ctcctgagca gctgggatta caggcttata ccaccacgcc tgtctaattt tttgtatttt 63600
tagtagagac agggtttctc catgttggtc aggctggtct cgaactccca acctcaggtg 63660
atccacctgc cttggcctcc caaagtgctg ggattacagg tgtgagccac cgtgcccggc 63720
aacttttgta ttttttgta gagatggggt ttcgccgtgt tgcccaggct gatcttaaac 63780
tgctaggctc aagtgatcct cccacctcag cctcccaaag tgctgggatt atagttgtga 63840
gctgccacac ctggcctagt gttattttca ttgttgccct tattactgtt tgtctcatgt 63900
tgagtttctt agaagcaaag ccctagacat gaattcaagt acaagtaagg tgaccaaccc 63960
atgctggctt gcctgggact gagcgcgttc ctgggacttt gacttttaaa actagaatag 64020
tcctagccgt agcctactag ttttttttag aactgagggt tctgggacat gggactttca 64080
atgcaaacac tgagaaagtc ctgggcaaac caagatgagt tggttaccct gtgtgcaagt 64140
gatttgttaa cggatggagt caggatgggg aaggggaaga aaccacgtaa gatatgcttt 64200
cagatgaagt ctgccctcgg cctgacccca tgacatgccc aggagtgtaa acagtaaatc 64260
accccacagt ttggtccacc ttaaggcaag gggtctgcct tttgggccgg tcttttggac 64320
ccctgtcttt gtctgtcatt ggcagtgatt cggttctaat tgcccaaggc aatcctccag 64380
agaaggctgt agtgtcagat ggtacagatg gagccaccaa caatgggaag tgctacacga 64440
tcattcactc agtcagctgc ccaacctctt ctctcagtct tgatcctctc atctgccaaa 64500
tggaaataac cacaagaaca cctatcatac actgtttctg tgaggattaa atcaactaat 64560
gcggccagac gcggtgcctc acacctgtaa tcccagcatt ttaggaagtc gaggcaggcg 64620
gatcacctga gtcaggagtt caagaccagg ctggccaaca tgtgaaaccc gtctctacta 64680
aaaacacaaa aattagccag gcgaggtggc tcatccctgt aaatgccagc cactcgggag 64740

-continued

```
gctgaggcag gagaattgct tgaacctggg aggcagagtt tgcagtgagc tgcgatcgta  64800
ccacagcact ccagtctgga caacagagta agaccctgtc tcaaaaaaaa aaaaaaatta  64860
actaatgtgt gcataggaga taggttccat cacaagccac ctggaagtga tggagctcca  64920
aagaggggag agaagcagag gcccctcaag gcccagcagg aaaaagtgcc gagatccata  64980
aatgacggcc actgtggatg gagcagtggg ggtgcctgga tcttacattt gccactctga  65040
tgggatgtag ctgctgctta gctagtctag ctgttctgtg aattgtaaca tgaattcaca  65100
tagtcatggc tgttactata ttaggtataa tgacatctag aaggatgcct gcaagtagtt  65160
ccttttatta tcattttcca aatccaccag gcagagtggg gcgctctgag ctgctaccca  65220
ctgagaaggt ggccccttgt ccatgatgta ggttctgtgg gctgcagagt ggagtctggg  65280
gaatggcctt gcttagagca gggtcctgca taccagcttt gcccattacc gacccaccct  65340
ctctgccctt gcccagctgc agaaggctgc cgacccctgg gtcctgaagc actcggagct  65400
ggagaagcag gacaacagct ggaaggaggt gagtggggcg gctgctgcca tgctatcttg  65460
gctcctggct gcaccataaa ggtccctgct tgtgggggac atgagaggaa gttgctaacc  65520
ctgtctcata ggtcacaccc ttgcaccttg ggctcctcag ccctggagtc tgtatctcat  65580
ggttcctgcc tcaaaaaaat aaaaaaaaaa cccaaccacc cagggactgg gctaagtgag  65640
ggggtagggt tgaggaggaa gaagacaagc ccaccaccag ctgagcagtg gaccactgga  65700
tgctttgttg cagtcaccac atttggatta aattttaagt ggtccctttc cttgggtggg  65760
tcactcttgg agctctgatt ggcccagcct ggatcacata tggtggggga gttggatgca  65820
gggcagccag aaactgacca tgctagatca ttgatgacat cattcctgct ctccggatga  65880
ggagattcaa gcactgaggt cggggctggt ctcttgttcc atgcccttag tgctctggtg  65940
gccagaactg acccttcctg tctctcttcc ttgacagaca cgcagtgaga agatccacga  66000
caaggaggct gtttccgaag ttgagcttgg aggaaatggt ttaaagaggt gcttgcatgc  66060
tggtcccctg ctctgcctct ctgaccggcc ccacagcctc gcccctctcc acctcctgct  66120
gcgccctgca cccactctac ctgctttcac cgcagccctg ccccgcccct ttgccctctt  66180
cctgccgcca ccccaccgca tccaagttgg gagagcatcg ggatatggtt tctctggaac  66240
ccgagccact caggagctgg aaggcttggg gcagtgggaa ttccaggctg ctgcatgttg  66300
tttgagtccg ggaatggaac acaggtggaa acaaaacatt ttgctcctct tgggattctt  66360
ttctcctgcc tctggagtta ggagagtcaa gattgacctc tattcctggg attattgagc  66420
agcatccttt gggcccagcc ctgtgctatg gccaaggaga cccccacccc aagaccataa  66480
ggaccacgtc tccactgtta ggaaacccat gaaaggagtc agggaaacag aacccccagc  66540
cgctatcaga ccagcccaga agcaaggcag gcgggacagg ctgtggagcc agagggccag  66600
gtttgaatgc cagccctgcc agttctagct ctatgacctt gaccttgagc agtacttccc  66660
atctctgtct agtggggatg ataggagctg cctcttgaag ttaatcagag tggtctgaca  66720
cgtgcatttc catatgcctg gtgtgttcag tgattcaggc aataggtgtg ccaggagctt  66780
catggcgtct tagtttgggt tcccccataa gcaaaccctg agacaaagat ttaagtgcaa  66840
atggtttatt tgggacagaa tttcaggaaa cacttggaag tgagacaggg aagggaaagc  66900
agccgataaa aggagcttca accaggttat tccacgggca actggagttc aggctgtcgg  66960
aggaactcag ggagccagag gagaacatgc agcttagagt catcccacca caaggaggct  67020
ggggcacttg ttcaccatat cccacctatt gtttgttgag ggctgtgttt aggggtgtga  67080
actcattaac tctgtgctat ctctagcttc ggtttgggcg tgtgttttgt ttttttgtt   67140
```

```
tttgtttttt ttttgaggca gagttttgct ctgtctccca gggtggagtg caatggcaca  67200
atcttagttt actgcaacct ccacctccca ggttcaagca attctcctgc ctcagcctcc  67260
tgagtagctg ggttacagg ctaacgccac cacgcttggc taatttttgt atttttacta  67320
agagataggg ttttaccatc ttggtcaggc tagtctcaaa ctcctgacct caggtgatct  67380
gcctgcctca gcatcccaaa gtgctgggtc tagcttcttc tatgtgtagg acagccaagt  67440
atgatcccac aggcagaaaa aaaaaccatc agatagagaa tggtggagta tgcagttcag  67500
agtatgcagt tttaggtgta taggtgaaag tgcaaagaga ggccaggtgc agtggctcat  67560
gcctctaatc ccagcatttt gagaggcaga ggcaggaaga tctcttgagg ccagaagttt  67620
gagaccagcc tgggcaacat agggagatcc ccatctctac aaaaaatttt ttaaaaatta  67680
gccaggtgtt aggctgggca cagtggctca catctgtaat cccagcactt tgggaggctg  67740
aggcgggtgg atcacctgag gtcaggagtt ccagaccagc ctggccaaca tggtgaaacc  67800
ccgtctctac taaaaataca aaaattagct gggcgtggtg gcgcacgcct gtaatttcat  67860
ctgctccgga tgctgagaca ggagaatctc ttgaacctgg agggtggaag ttgtagtgag  67920
ccgagatcat gccactgcac tccagcctgg gtgacagaac aagactctgt ctcaagaaaa  67980
aaaaaagaaa aaaaaaagcc aggtttggtg gtgcacacct gtagtcccag ctactctgga  68040
ggctgaaatg ggaggatcac ttgagcccag gagtttgagg ctgcagtgag ctattattgc  68100
actactgcat tccagcctgg gtgacatatc aagacctgtt tgggagaaaa aaaaaaaaaa  68160
gaaaatgcag acagaatgtg ggactgggca ccaacaacat ctctacaaga ggtgaacaag  68220
acggtcctgg tctttgccct cacgcagcac acggaccagg gtggtagacc agagtgtgcc  68280
ctcagtgtta tttccactaa taacgacgtt tcctcctctg tccttcgcag aaccaaatct  68340
gtttcttcca tgtctgagtt tgaaagtttg ctcgactgtt ccccttacct tgctggcgga  68400
gatgcccggg gcaagaagct gcctaacaac cctgcctttg gctttgtgag ctccgagcca  68460
ggggatccag agaaagacac caaggagaag cctgggctct cgtcgaggga ctgcaaccac  68520
ctgggtgccc tggcctgcca ggaccccccca gggaggcaga tgcagcgcag ctacacggct  68580
cctgacaaga cgggcatccg agtctactat agtcccccgg tggcccggcg cctcggagtc  68640
cctgtggttc atgacaaaga gggcaagatc attatcgagc ccggcttcct cttcaccaca  68700
gccaagccca aagagtcggc cgaggctgat gggctggctg agagctccta tggtcggtgg  68760
ctctgcaact tctcacggca gcgcctggac ggaggctcag cgggcagccc ctcggcggcc  68820
gggcctggct tcccagcggc cctgcatgac tttgagatgt caggcaacat gagtgatgac  68880
atgaaggaga tcaccaactg tgtgcgccag gccatgcgct ccggctcact ggagaggaaa  68940
gtgaagagca catccagcca gacggtgggc ctggccagtg tgggcacaca gaccatccgc  69000
acggtcagcg tgggcctgca gaccgaccca ccccgcagca gcctccatgg caaggcctgg  69060
tcaccccgca gctcttcgct cgtgtctgtg cgcagcaagc agatctcctc ctccctggac  69120
aaggtccatt cgcgcatcga gcggccctgc tgctccccca agtatggctc accaaagctc  69180
cagaggcggt ctgtgtccaa gctggacagc agcaaggacc gcagcctgtg gaacctgcac  69240
cagggcaagc agaacggctc ggcctgggcc cgctccacca ccacgcggga cagccctgta  69300
ttgagaaaca tcaacgatgg actctccagc ctcttcagtg tggtggagca ctcagggagc  69360
acggagtctg tctggaaact aggcatgtct gagacgcggg ccaagcccga gcctcccaag  69420
tacggcattg tgcaggaatt cttccgtaat gtgtgtggcc gggcaccgag ccccacctca  69480
```

tcagcaggag aggagggcac caagaagcca gagcccctct ccccagccag ctaccatcag 69540
ccagagggtg tggccaggat cctgaacaag aaggcagcca agttgggcag cagtgaggag 69600
gtcagactca ccatgctccc ccaggtgggg aaggatggtg tcctccggga cggagatgga 69660
gccgtggtcc ttcccaatga ggtaggtggg tgggatctgt cctttctctt agtaggtgga 69720
gttagtatat aaggtccaag ctcttttggt ttttaagttc agagatatgg gccgaggtgg 69780
gtggatcgcc tgagatcagg agttcaagac cagtctggcc aacatggtga aaccccatct 69840
ctactaaaaa tacaaaaatt ggccaggcgt ggtggcatgc acctgttgtc ccagctgctc 69900
tggaggctga ggtaggagaa tcacttgaac ccagtaggcg gaagttgcag tgagctgaaa 69960
ttgtgctatt gcactccagc ctgggtgaca gactaagact ccgtctcacc aaaaaaaaaa 70020
aattatctat ctgtctgtct gtctgtctgt ctgtctgtct gtctgtctgt ctatctatct 70080
atctatctat ctatatatct atatatataa aataaaaatt cagggatatg gccatgtgtt 70140
ccaggaagtt cttatgctgg tctaggatag agttggaagg tcccagacct ggaacaacac 70200
agacctgatg gtcacatggt ctgaattcca agagactagt gagcatggct taactagcag 70260
cttttgctcc acccaccaga gactgccagc atcccctcca gggaaggggc cttactgctc 70320
tcctgccacc cagtggtgtg ctagagccag cttgtttggc ttgcaggagc caattgtcag 70380
catctctgtg ggtttttttt tttttattgt ttttgttttt gttttgagag aagtctcgtt 70440
cttgtccccc aggcttgagt gcaatgactc aatctcggct cactgtaacc tccgcctcct 70500
gggttcaaac aattctgtct ctgcctccca agtagctggg attaaggcac ctgccaccat 70560
gcccggctaa tttttgtatt ttttagtaga gacggggttt caccatgttg gccaggctgg 70620
tctcgaactc ccgacctcaa gtgatccgcc caccttggcc tcccaaagtg ttaggattac 70680
aggcgtgagc caccgcgcct ggccacatct ctgtgtttaa catcaccttg gtaccttgag 70740
attggccaca gtgggaggat ttacagcata aaaattggta aacactacaa atcggggctc 70800
ctcctatcac tcctggaaaa ctaattgtta aacattagcg ggcataccac ttctccaccc 70860
catcaagact tcacacctaa gtgctcacat ttcctctgag aatctttcac accccactcc 70920
tgctatcagt ttcttataag ttaattagta aaccttattt gaatgttagt gagcattatt 70980
tgaatgtgtt agaatgtgca taagttaact ttgcagaaag ggaaggaaat gtatttgaag 71040
gatggcatgt tttataaaac ccaagagtag gaacctgaca acctcagcag cttctccctg 71100
tcttcctctc ctctctttaa gcttcaccct ctctgatatc atattcctcc tttttctctg 71160
tttctctctc tgttgcattt gcacaaggac tgggtgggct gtcccagctc tgactttaca 71220
acatcttcca gttcaagccc ctaggagaga ctgacacaaa tccctgtctc ccaattccac 71280
atttctgaaa gaaggaaact ctgattggtg cagctagagg cgagtgtacc ccttggtcca 71340
gtctatggct gggagtggta ccatgtggtc tgctgtgggg cacagagaca tgagaagggc 71400
tgtgtgtgga atgggctgtg atagactcaa acattctact tttctattat tgtacgttta 71460
ggtggtttct agtttgtccc tactgcaaat aatgctgtgg tgaacatctt ggtgcaaaat 71520
catttttta catttcagac tatttcctta ggtataagtt gcagaaatga gattaaagga 71580
taatagaata taaatgtggc cgggcgcggt ggctcatgcc tgtaatccca gcactttggg 71640
aggccgaggc gggtggatca caaggtcagg agtttgagat cagcctggcc aatatggtga 71700
aaccctgtct gtactaaaaa tacaaaaatt agccgggcat agtggtggtc acctgtagtc 71760
ctagctactc aggaggctga ggcaggagaa tcgcgtgaac ccaggaggcg gaggctgcag 71820
tgagctgaga tggtaccact gcactccagc ctgggtgaca gagtgagact ccatctccac 71880

-continued

```
acaaaaaaaa aaatataaat gttttaaagt tatttgataa atactgccaa attgtttttc  71940
aaaagtgtgc catatctaca gcttccagca gtgtgtggcg agtgcgttac ttttctatac  72000
tctcactcag ctggctgaca tttaaaaaca tcttttaaat atttattcct tttttggcca  72060
ggtgcaatgg ctcatgtctc taatcccagc actttgggag actgaggtgg gcagatcact  72120
tgagctagga gttcaagacc agtctgagca acatggtgag agctcatctc tacattaaaa  72180
aaaaaaaaaa agaggccagg catggtggct tacgcctgta atcctagcac tttgggaggc  72240
cgaggcaggt ggattgcctg agctcaggaa tttaagacca gcctgggcaa cacagtgaaa  72300
ccccatctct actaaaaaat acaaaaaatt agccaggcgt ggcagcatgc gcctatagtc  72360
ccagctactc gggaggctga ggcaggagaa ttgcttgaag ccgggaggtg gaggttgcaa  72420
caagctgaga ccacgccact gcactctagc ctgggcaaca gagcaagact ccatctttta  72480
aaaaaaaaaa aaaaaaaaaa agggccaggc gtggtggctc acacctgtaa tcccagcact  72540
ttgggaggcc gagagaggtg gattgcttga agccaggagt ttgagaccag cctggccaac  72600
gtagcaaaac cctgtctcta cttaaaaaat acaaaaattg gccgggcgca gtggctcacg  72660
cctgtaatcc cagcactttg ggaggctgag gtgggtggat catgaggtca ggagatcgag  72720
accatcctgg ctaacacagt gaaaccccgt ctctactaaa aatacaaaaa gttagccagg  72780
cgtggtggca ggcgcctgta gtcccagcta ctcgggaagc tgaggcagga gaatggcatg  72840
aacccgggag gcggagcttg cagtgagccg agatcgcgcc actgcactcc agcctgggtg  72900
acagagcgag actccatctc aaaaaaaaaa aaaaaaaaaa atacaaaaat tagctgggca  72960
tggtggcaca tgcttacagt tccagccact tgggtgattg aggcatgaga attgctggaa  73020
cccaggaggc agtgagccaa tatcgcacca ctgcactcca gcctgagcaa cagagtgaga  73080
ctctgtctca aaaataaata aataataaag tctcaaggca ggaaaaaagc aagtgtctca  73140
gtctgaaggc tgtcaggcag gaagaattct cttacttgag ggagagtaag ccctcttgtt  73200
ctgttcaagc ctttaactga ctggatgggg tccatgttag ggagaattcg cttttttttt  73260
tttttgagac ggagcctcac tctgtcaccc aggttggaat gcagtggtgt gatctcggct  73320
cactgcaacc tctgcctccc aggctcaagc gattcttgta cctcagcttc ccaaccaagt  73380
agctgggatt acaggcacat gccaccacgc ccggctactt ttttattttt agtagaaata  73440
gggtttcacc atgttggcca ggctggtctc gaactgctaa tctcaagtga tccgcctgcc  73500
tcagtctccc aaagtggtgg gataacagac gtgagccact gcgcctggct gagaatttac  73560
atgttaatct catctcaaag cactctgaca gaaacaccca gaacaatgtt ttacgtaata  73620
tctcggcacc tgtggcccag tcatattgaa tataaaatta accatcactt ccatataacc  73680
agcaccacat caagaaacaa cagcacaaag ctggctggat tttgaatgtt gattttaaag  73740
ttgatccaaa tattgttcag tatgtaaaat gtgcgtgcta cccattgacc cagtagttct  73800
tcttttacga aggtagccta tggaaatatt cacagagatg gataaagaaa aataaaaaga  73860
ggctgggcgc agtggctcac ccaatcacct gaggtcggga gtttgagacc agcctgacca  73920
atgccgagaa accccatctc tactaaaaat acacaattag ccgggcgtgg tggcacatgc  73980
ctgtaatccc agctactcgg gaggctgagg caggagaatc gctcgaaccc gggaggcaga  74040
ggttgctgtg agctgagatc gcatcattgc actccagcct gggcaacaag agctaaactc  74100
tgtctcaaaa aaaaaaaaaa aaagaaaaga aaagaaaaag aaaaaaagag agaggggagg  74160
aaatcaaagc tcaagagagg ttaagtaaat ctcccaaggt cacacagcta gtaattggca  74220
```

-continued aagctgggat ttaaccaagc agtttggctc tatcacagca cttttatttt atttatttat 74280
ttatttattt ttgagacgga gtctcgctct gttgcctagg ctggagtgca gtggcacgat 74340
cttggctcac tgcaagctcc gcctcccagg ttcacgccat tctcctgcct cagcctccta 74400
agtagctggg actacaggca cctgccaccg cgcccggcta atttttgta tttttagtag 74460 agacggggtt tcagatggtc tcgatctcct gacctcgtga tccacccgcc ttggcctccc 74520
aaagtgctgg gattacaggc atgagccacc gcgcccgggc cattttattt attttttaaa 74580
gagatggggt cttgctctat tgctcaagcc agagcccagt gacacaatca tagctcactg 74640
ctgccttgac ctcctgggct caaaggatcc tcctgtctca gcctcccaca tggcccagcc 74700
cagcagcact ttttttttt ttttttttg agatggagtc tcactctgtc cccaggctg 74760 gagtgcagtg atgtgatctc ggctcactgc aacctccgcc tcctgagttc aagccgttct 74820
gctgcttcgg tctcccaagt agctgggact gcaggaatgt gccaccatgc ccgggtaatt 74880
tttgtatttt gagtagagat ggggtttcac catgttggcc agcctggtct tgaactcctg 74940
acctcaggtg atccacctgc catagcctcc caaagtgctg gcattacagg tgtgagccac 75000
catggccagc tgtccagcag cacttttttt tttttttttt ttttcagatg gagtcttgct 75060
ctttcaccca ggctggagtg cagtggcaca atctcagctc actgcaacct ccgcaccctg 75120
ggtttaagcg attctcctgc cctagcctcc cgagtagctg ggactacagg cgcatgccac 75180
catgcccagc taatttttgt atttttagta gagatggggt ttcaccatgt tggccaggat 75240
ggtctcgatc tcctgacctc gtgatccacc tgcctcagcc tcccaaagtg ctaggattac 75300
aggcatgagc caccgtgcct ggcagcagca cttttgatca ttatttctgt ttattggtaa 75360
tagtaaaaaa ttagaaacta cccagatgta cataaaaagt gaattggggc caggcacagt 75420
ggctcacacc tgcaatccca ccactttgga aggccgaggc gggcagatca ctagaggtca 75480
ggagtttgag cctgaccaac atgctaaaat cccctctcta ctaaaaatac aaaaattagc 75540
taggcatggt ggcacacgct tgtaatctta gctacttggg aggctgaggc acaagaatca 75600
cttgaatccg tgaggtggag gttgtagtga gtcaagatcg taccactgca ctccagcctg 75660
gggaacagag caagattctg tctaaaaaat aaaaaaataa aaaaagcgaa ttgggtatat 75720
aaatcagtta tttctatcta gtgaaatggt acagagacac taaaaaagaa ggcgatcagc 75780
caggcatggt ggctcatgcc tttgggaggc atgagcaccc aaaggtgcta attccagcag 75840
tttgggaggc tgaggcagga ggatcgcttg agcccaggag ttcaagacca gcctgagcaa 75900
catagtgaga ccctgtctca aacgaaaaaa aaggataaaa aggaaggaga tctagacata 75960
cctagtgaca gaaaagtgtt cgtgttttac agttgcaaaa taagctgtca ttttggtaaa 76020
tgtatgttaa gaatctcttt ggcgtgcagg accatggaca gtgtccactg tcctctctgt 76080
atagcctaga atatattaca atgaacttcc attaccgctc taatgggaga agaacaacag 76140
aaagaaaaaa ttggtccagt gaggagcttc agcccctggg aactggttta tggccgagtc 76200
tcagttcctt gcctggcata ccacacagct catggtggtc catgtctcct ggctcctctt 76260
gacttcctgc ctccctgcct ccctcttcct aggacgctgt ttgtgactgt agtacccagt 76320
ctctcacctc ctgcttcgcc cgatcgtccc gctctgccat ccgccactct ccttccaagt 76380
gcaggctgca cccttcagag tccagctggg gtggggagga gagggcactc ccccccagcg 76440
agtgacagag cagccaagct ccccgcctca accagcccag cccctggata gcagaaggga 76500
accagcagag acgagacgag gtgaggcgag gggctgtgtc ctcagcattg cctggccctg 76560
gagggacagc agtgatgcca ctgccagaat gcagctttca catcaaggta aagccgggtc 76620

-continued

| | |
|---|---|
| tcctgctggc ccctgggtgg tgagcttcga cttcccaggg gaaggcagtg agtgggagag | 76680 |
| agaccaaacc tgggcttccc aagcatccac tgagagatct gtcaagagcc gatccctggg | 76740 |
| tcctaagaga gagccttgcc tggttctgcc c | 76771 |